US011167025B2

(12) United States Patent
Pavlakis et al.

(10) Patent No.: US 11,167,025 B2
(45) Date of Patent: *Nov. 9, 2021

(54) ALTERING THE IMMUNDOMINANCE HIERARCHY USING A DNA VACCINE EXPRESSING CONSERVED REGIONS

(71) Applicants: THE UNITED STATES OF AMERICA, AS REPRESENTED BY THE SECRETARY, DEPARTMENT OF HEALTH AND HUMAN SERVICES, Rockville, MD (US); UNIVERSITY OF WASHINGTON THROUGH ITS CENTER FOR COMMERCIALIZATION, Seattle, WA (US)

(72) Inventors: George Pavlakis, Rockville, MD (US); Barbara Felber, Rockville, MD (US); James Mullins, Seattle, WA (US)

(73) Assignees: THE UNITED STATES OF AMERICA, AS REPRESENTED BY THE SECRETARY, DEPARTMENT OF HEALTH AND HUMAN SERVICES, Rockville, MD (US); UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/554,133

(22) Filed: Aug. 28, 2019

(65) Prior Publication Data

US 2019/0381166 A1 Dec. 19, 2019

Related U.S. Application Data

(60) Division of application No. 15/235,430, filed on Aug. 12, 2016, now Pat. No. 10,426,830, which is a continuation of application No. 14/382,281, filed as application No. PCT/US2013/028932 on Mar. 4, 2014, now Pat. No. 9,415,099.

(60) Provisional application No. 61/606,265, filed on Mar. 2, 2012.

(51) Int. Cl.

| | |
|---|---|
| ***A61K 39/21*** | (2006.01) |
| ***A61K 39/12*** | (2006.01) |
| ***C07K 14/005*** | (2006.01) |
| ***A61N 1/32*** | (2006.01) |
| ***C12N 7/00*** | (2006.01) |
| *A61K 39/00* | (2006.01) |

(52) U.S. Cl.

CPC .............. *A61K 39/21* (2013.01); *A61K 39/12* (2013.01); *A61N 1/327* (2013.01); *C07K 14/005* (2013.01); *C12N 7/00* (2013.01); *A61K 2039/53* (2013.01); *A61K 2039/545* (2013.01); *C12N 2740/16222* (2013.01); *C12N 2740/16234* (2013.01); *C12N 2740/16271* (2013.01)

(58) Field of Classification Search

None

See application file for complete search history.

(56) References Cited

U.S. PATENT DOCUMENTS

| | | | |
|---|---|---|---|
| 5,616,477 A | 4/1997 | Price | |
| 7,981,430 B2 | 7/2011 | Hanke et al. | |
| 8,071,107 B2 | 12/2011 | Haynes et al. | |
| 9,415,099 B2 | 8/2016 | Pavlakis | |
| 2011/0269937 A1 | 11/2011 | Mullins et al. | |

FOREIGN PATENT DOCUMENTS

| | | |
|---|---|---|
| WO | 2002036806 A2 | 5/2002 |
| WO | 2007136585 A2 | 11/2007 |
| WO | 2013131099 A2 | 9/2013 |

OTHER PUBLICATIONS

Chikhlikar et al., "Inverted Terminal Repeat Sequences of Adeno-Associated Virus Enhance the Antibody and CD8 <+> Responses to a HIV-1 p55Gag/Lamp DNA Vaccine Chimera", Virology, vol. 323, No. 2, Jun. 1, 2004, pp. 220-232.

Ferrari et al., "Identification of Highly Conserved and Broadly Cross-Reactive HIV tupe 1 Cytotoxic T Lymphocyte Epitopes as Candidate Immunogens for Inclusion in *Mycobacterium bovis* BCG-Vectored HIV Vaccines", AIDS Research and Human Retroviruses, vol. 16, No. 14, Aug. 20, 2000, pp. 1433-1443.

Koup et al., "Priming immunization with DNA augments immunogenicity of recombinant adenoviral vectors for both HIV-1 specific antibody and T-cell responses.", PLoS One, vol. 5, No. 2, Feb. 2, 2010, pp. 1-15.

Kulkarni et al., "Comparison of Immune Responses Generated by Optomized DNA Vaccination Against SIV Antigens in Mice and Macaques", Vaccine, vol. 29, No. 39, Dec. 30, 2010, pp. 6742-6754.

Kulkarni et al., "HIV-1 p242 (gag) Derived Conserved Element DNA Vaccine Increases the Breadth of Immune Response in Mice", Plos One, vol. 8, No. 3; XP002701148, Mar. 2013.

Letoumeau et al., "Design and Pre-Cinical Evaluation of a Universal HIV-1 Vaccine", *PlosOne*, vol. 2, No. 10, e984, 11 pages (2007).

Mothe et al., "CTL Responses of High Functional AVIDITY and Broad Variant Cross-Reactivity Are Associated with HIV Control", *Plos OneU*, vol. 7, No. 1, pp. e29717 (2012).

Mullins et al., "A Global Aids Vaccine Based on Conserved Elements of the Viral Proteome", Abstracts from AIDS Vaccines, vol. 26, No. 10 XP002701146; Retrieved from the Internet: URL: http://online.liebertpub.com/doi/pdf/10.1089/aid.2010.9998, 2010, p. A2.

Mullins et al., "Conserved Elements (CE) Vaccine", Retrieved from the Internet: URL: http://www.vaccineenterprise.org/conference/2011/sites/default/files/Mulins_CEposter_AIDSvax2011.pdf, 2011.

(Continued)

*Primary Examiner* — Benjamin P Blumel

(74) *Attorney, Agent, or Firm* — Mintz Levin Cohn Ferris Glovsky and Popeo, P.C.; Peter F. Corless

(57) ABSTRACT

The invention provides methods and compositions for eliciting broad immune responses. The methods employ nucleic acid vaccines that encodes highly conserved elements from a virus.

19 Claims, 34 Drawing Sheets

Specification includes a Sequence Listing.

(56) References Cited

OTHER PUBLICATIONS

Niu et al., "Preclinical Evaluation of HIV-1 Therapeutic Ex Vivo Dendritic Cell Vaccines Expressing Consensus Gag Antigens and Conserved Gag Epitopes", Vaccine, Elsevier Ltd.; vol. 29, No. 11, Dec. 24, 2010, pp. 2110-2119.
Pavlakis et al., "DNA Vaccines Expressing Conserved Elements Provide Potent and Broad Immune Responses", Retrovirology, Biomed Central Ltd, vol. 9, No. Suppl 2; XP021116304, Sep. 13, 2012, p. 067.
Pavlakis et al., "Conserved Elements (CE) Vaccine", AIDS Research and Human Retroviruses, vol. 27, No. 10, XP002700142 & Conference on AIDS Vaccine; Bangkok, Thailand; Sep. 12-15, 2011, Oct. 2011, p. A110.
International Patent Application No. PCT/US2013/028932, International Search Report & Written Opinion, dated Aug. 7, 2013, 16 pages.
Rolland et al., "HIV-1 Group M Conserved Elements Vaccine", Plos Pathogens, vol. 3, No. 11, Nov. 2007, pp. 1551-1555.
Shiver , "Adenoviral Vector as a Potential HIV Vaccine", The Body Pro, Retrieved from the Internet: URL: http://www.thebodypro.com/content/art34193.html, 2003.
Wilson et al., "Development of a DNA Vaccine Designed to Induce Cytotoxic T Lymphocyte Responses to Multiple Conserved Epitopes in HIV-1", The Journal of Immunology, The American Association of Immunologists, vol. 171, No. 10, Nov. 15, 2003, pp. 5611-5623.
Yang, "Candidate Vaccine Sequences to Represent Intra- and Inter-Clade HIV-1 Variation", *Plos One*, vol. 4, No. 10, e7388, 14 pages (2009).
Rolland et al., HIV-1 Group M Conserved Elements Vaccine, PLoS Pathog, 2007, 3(11): e157, 1551-1555.
Giri, et al., "DNA Vaccines Against Human Immunodeficiency Virus Type1 in the Past Decade", Clin, Microbiol, Rev. 17(2), 2004, 370-389.
Nat. Inst Aller, Inf. Des. (NAIAD), "Prime Boost", Vaccine Schedule for Prevention of HIV Infection, NCT00109629, 2005, 1-9.
CEvacPeptides.png references in Roland et al., 2007.

Figure 13 p24CEc
configuration p24CEc: CE8~9~3~4~5~6

CE8 CE9 CE3
P24CE1c QGQMVHQAISPRTLNAWVKVLAKEEKAFSPEVIPMFSALSEGATPQDLNAAKVGGHQAAMQMLKETINEEAAEWDRAAAE
P24CE2c QGQMVHQALSPRTLNAWVKVLAKEEKGFNPEVIPMFTALSEGATPQDLNAAKVGGHQAAMQMLKDTINEEAAEWDRAAAE

CE4 CE5 CE6
p24CE1c PRGSDIAGTTSTLQEQIGWAAAKRWIILGLNKIVRMYSPTSIAAKYVDRFYKTLRAEQA
p34CE2c PRGSDIAGTTSTLQEQIAWAAAKRWIILGLNKIVRMYSPVSIAAKYVDRFFKTLRAEQA p24CE1c
QGQMVHQAISPRTLNAWVKVLAKEEKAFSPEVIPMFSALSEGATPQDLNAAKVGGHQAAMQMLKETINEEAAEWDRAAAE
PRGSDIAGTTSTLQEQIGWAAAKRWIILGLNKIVRMYSPTSIAAKYVDRFYKTLRAEQA p24CE2c
QGQMVHQALSPRTLNAWVKVLAKEEKGFNPEVIPMFTALSEGATPQDLNAAKVGGHQAAMQMLKDTINEEAAEWDRAAAE
PRGSDIAGTTSTLQEQIAWAAAKRWIILGLNKIVRMYSPVSIAAKYVDRFFKTLRAEQA p24CEd
configuration p24CEd: CE9~3~4~5~6~8

CE9 CE3 CE4
p24CE1d EEKAFSPEVIPMFSALSEGATPQDLNAAKVGGHQAAMQMLKETINEEAAEWDRAAAEPRGSDIAGTTSTLQEQIGWAAA
P24CE2d EEKGFNPEVIPMFTALSEGATPQDLNAAKVGGHQAAMQMLKDTINEEAAEWDRAAAEPRGSDIAGTTSTLQEQIAWAAA

CE5 CE6 CE8
p24CE1d KRWIILGLNKIVRMYSPTSIAAKYVDRFYKTLRAEQAALQGQMVHQAISPRTLNAWVKV
p24CE2d KRWIILGLNKIVRMYSPVSIAAKYVDRFFKTLRAEQAALQGQMVHQALSPRTLNAWVKV p24CE1d
EEKAFSPEVIPMFSALSEGATPQDLNAAKVGGHQAAMQMLKETINEEAAEWDRAAAEPRGSDIAGTTSTLQEQIGWAAA
KRWIILGLNKIVRMYSPTSIAAKYVDRFYKTLRAEQAALQGQMVHQAISPRTLNAWVKV p24CE2d
EEKGFNPEVIPMFTALSEGATPQDLNAAKVGGHQAAMQMLKDTINEEAAEWDRAAAEPRGSDIAGTTSTLQEQIAWAAA
KRWIILGLNKIVRMYSPVSIAAKYVDRFFKTLRAEQAALQGQMVHQALSPRTLNAWVKV

Figure 14B:
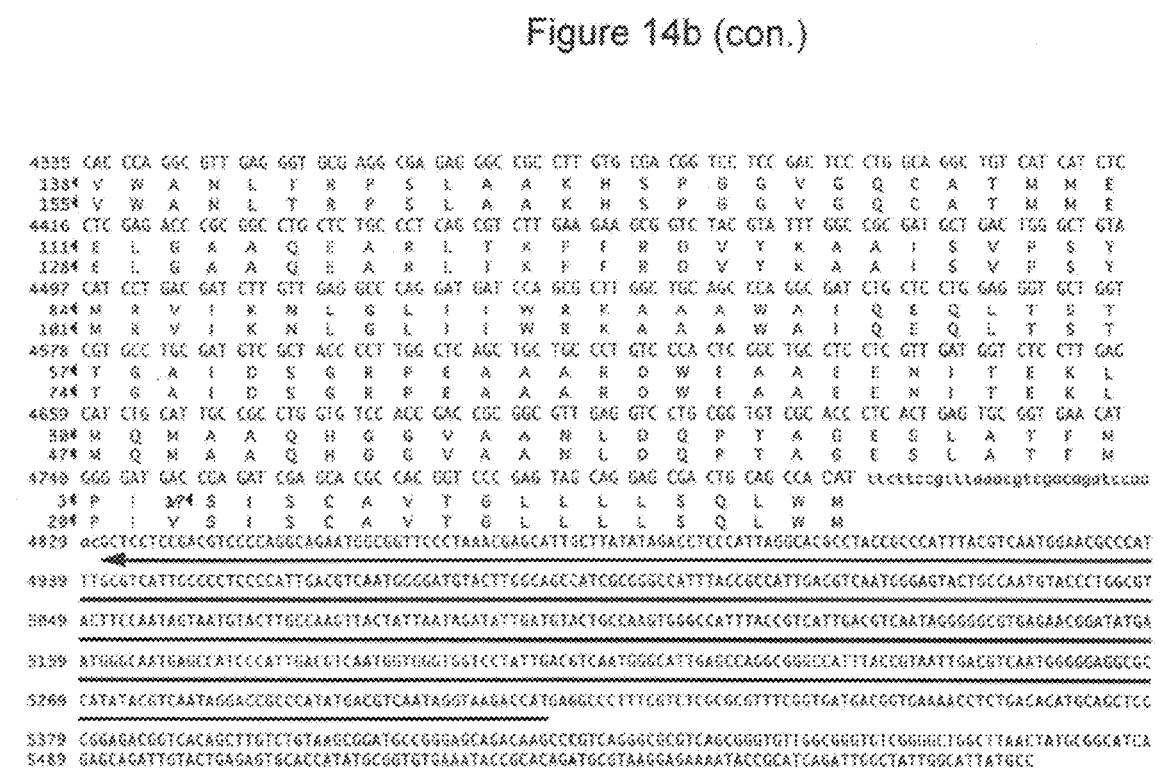

Figure 14b (con.)

```
4335 CAC CCA GGC GTT GAG GGT GCG AGG CGA GAG GGC CGC CTT GTG CGA CGG TCC TCC GAC TCC CTG GCA GGC TGT CAT CAT CTC
 138◄ V   W   A   N   L   T   R   P   S   L   A   A   K   H   S   P   G   G   V   G   Q   C   A   T   M   M   E
 155◄ V   W   A   N   L   T   R   P   S   L   A   A   K   H   S   P   G   G   V   G   Q   C   A   T   M   M   E
4416 CTC GAG ACC CGC GGC CTG CTC TGC CCT CAG CGT CTT GAA GAA GCG GTC TAC GTA TTT GGC CGC GAT GCT GAC TGG GCT GTA
 111◄ E   L   G   A   A   Q   E   A   R   L   T   K   F   F   R   D   V   Y   K   A   A   I   S   V   P   S   Y
 128◄ E   L   G   A   A   Q   E   A   R   L   T   K   F   F   R   D   V   Y   K   A   A   I   S   V   P   S   Y
4497 CAT CCT GAC GAT CTT GTT GAG GCC CAG GAT GAT CCA GCG CTT GGC TGC AGC CCA GGC GAT CTG CTC CTG GAG GGT GCT GGT
  84◄ M   R   V   I   K   N   L   G   L   I   I   W   R   K   A   A   A   W   A   I   Q   E   Q   L   T   S   T
 101◄ M   R   V   I   K   N   L   G   L   I   I   W   R   K   A   A   A   W   A   I   Q   E   Q   L   T   S   T
4578 CGT GCC TGC GAT GTC GCT ACC CCT TGG CTC AGC TGC TGC CCT GTC CCA CTC GGC TGC CTC CTC GTT GAT GGT CTC CTT GAG
  57◄ T   G   A   I   D   S   G   R   P   E   A   A   A   R   D   W   E   A   A   E   E   N   I   T   E   K   L
  74◄ T   G   A   I   D   S   G   R   P   E   A   A   A   R   D   W   E   A   A   E   E   N   I   T   E   K   L
4659 CAT CTG CAT TGC CGC CTG GTG TCC ACC GAC CGC GGC GTT GAG GTC CTG CGG TGT CGC ACC CTC ACT GAG TGC GGT GAA CAT
  30◄ M   Q   M   A   A   Q   H   G   G   V   A   A   N   L   D   Q   P   T   A   G   E   S   L   A   T   F   N
  47◄ M   Q   M   A   A   Q   H   G   G   V   A   A   N   L   D   Q   P   T   A   G   E   S   L   A   T   F   N
4740 GGG GAT GAC CGA GAT CGA GCA CGC CAC GGT CCC GAG TAG CAG GAG CGA CTG CAG CCA CAT ttcttccgtttaaacgtcggccagatccaa
   3◄ P   I  37◄ S   I   S   C   A   V   T   G   L   L   L   L   S   Q   L   W   M
  20◄ P   I   V   S   I   S   C   A   V   T   G   L   L   L   L   S   Q   L   W   M
4829 aCGCTCCTCCGACGTCCCCAGGCAGAATGGCGGTTCCCTAAACGAGCATTGCTTATATAGACCTCCCATTAGGCACGCCTACCGCCCATTTACGTCAATGGAACGCCCAT
4939 TTGCGTCATTGCCCCTCCCCATTGACGTCAATGGGGATGTACTTGGCAGCCATCGCGGGCCATTTACCGCCATTGACGTCAATGGGAGTACTGCCAATGTACCCTGGCGT
5049 ACTTCCAATAGTAATGTACTTGCCAAGTTACTATTAATAGATATTGATGTACTGCCAAGTGGGCCATTTACCGTCATTGACGTCAATAGGGGGCGTGAGAACGGATATGA
5159 ATGGGCAATGAGCCATCCCATTGACGTCAATGGTGGGTGGTCCTATTGACGTCAATGGGCATTGAGCCAGGCGGGCCATTTACCGTAATTGACGTCAATGGGGGAGGCGC
5269 CATATACGTCAATAGGACCGCCCATATGACGTCAATAGGTAAGACCATGAGGCCCTTTCGTCTCGCGCGTTTCGGTGATGACGGTGAAAACCTCTGACACATGCAGCTCC
5379 CGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTAACTATGCGGCATCA
5489 GAGCAGATTGTACTGAGAGTGCACCATATGCGGTGTGAAATACCGCACAGATGCGTAAGGAGAAAATACCGCATCAGATTGGCTATTGGCATTATGCC
```

Figure 15b (con.)
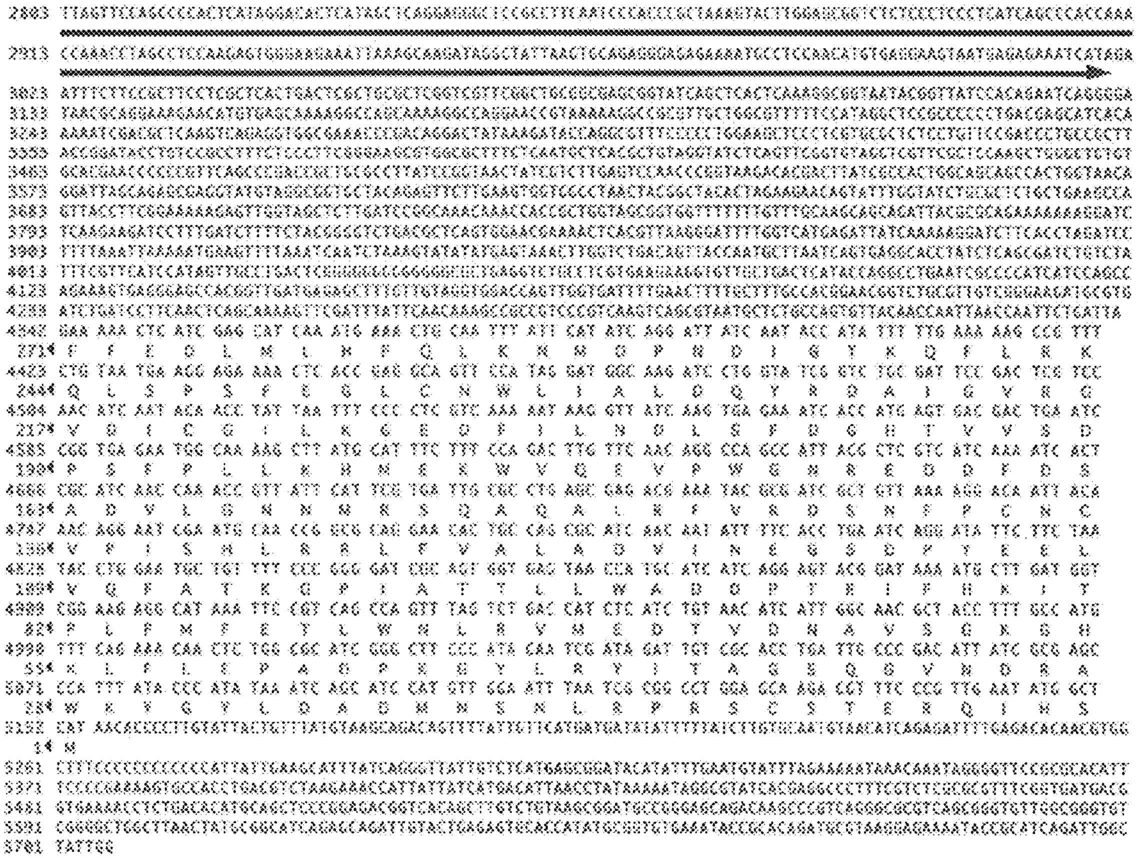

Figure 16b (con.)
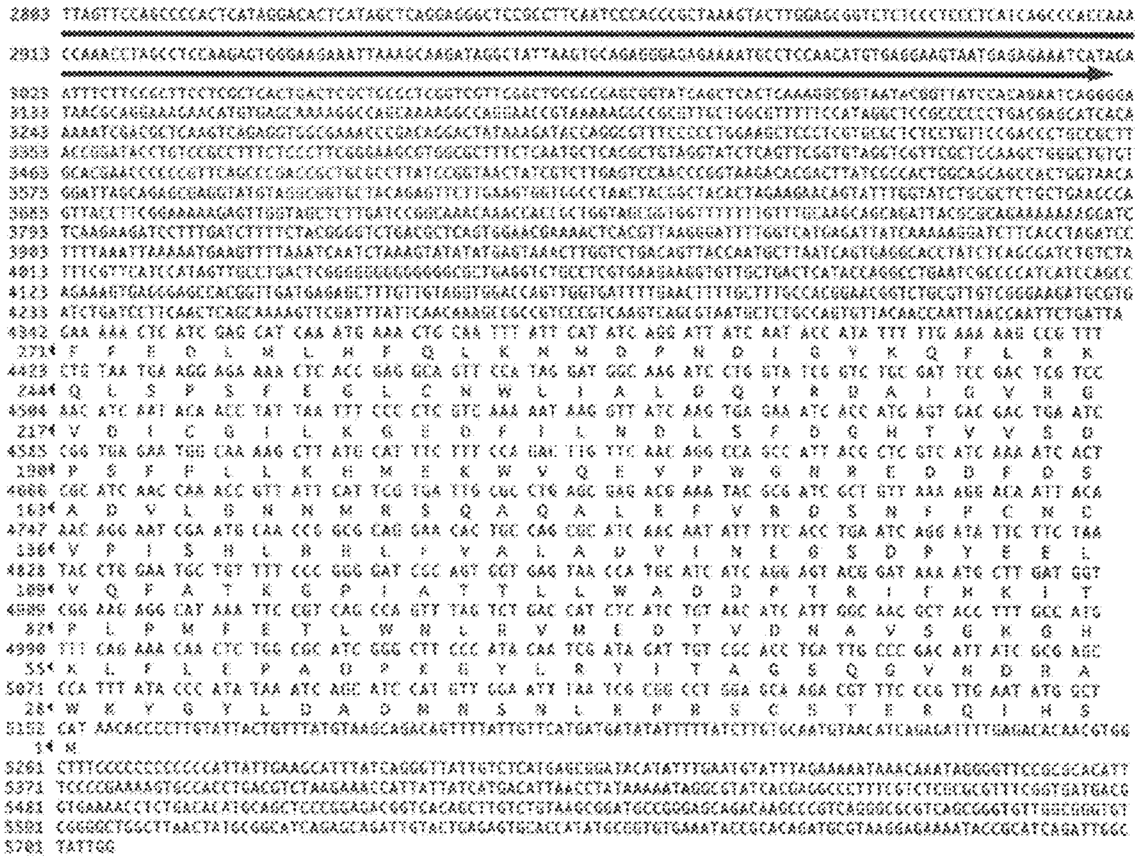

Figure 17B:
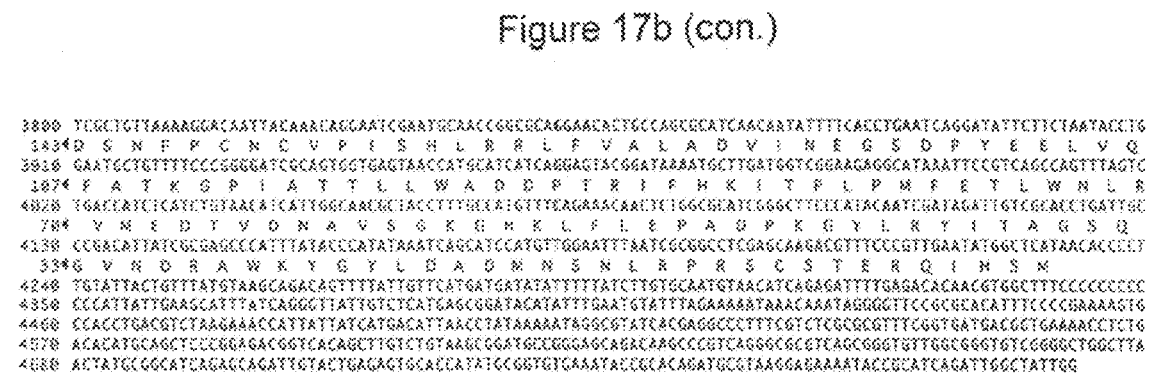

Figure 17b (con.)

```
3800 TCGCTGTTAAAAGGACAATTACAAACAGGAATCGAATGCAACCGGCGCAGGAACACTGCCAGCGCATCAACAATATTTTCACCTGAATCAGGATATTCTTCTAATACCTG
 143◀D  S  N  F  P  C  N  C  V  P  I  S  H  L  R  R  L  F  V  A  L  A  D  V  I  N  E  G  S  D  P  Y  E  E  L  V  Q
3910 GAATGCTGTTTTCCCGGGGATCGCAGTGGTGAGTAACCATGCATCATCAGGAGTACGGATAAAATGCTTGATGGTCGGAAGAGGCATAAATTCCGTCAGCCAGTTTAGTC
 107◀ F  A  T  K  G  P  I  A  T  T  L  L  W  A  D  D  P  T  R  I  F  H  K  I  T  P  L  P  M  F  E  T  L  W  N  L  R
4020 TGACCATCTCATCTGTAACATCATTGGCAACGCTACCTTTGCCATGTTTCAGAAACAACTCTGGCGCATCGGGCTTCCCATACAATCGATAGATTGTCGCACCTGATTGC
  70◀  V  N  E  D  T  V  O  N  A  V  S  G  K  G  M  K  L  F  L  E  P  A  D  P  K  G  Y  L  R  Y  I  T  A  G  S  Q
4130 CCGACATTATCGCGAGCCCATTTATACCCATATAAATCAGCATCCATGTTGGAATTTAATCGCGGCCTCGAGCAAGACGTTTCCCGTTGAATATGGCTCATAACACCCCT
  33◀G  V  N  D  R  A  W  K  Y  G  Y  L  D  A  D  N  N  S  N  L  R  P  R  S  C  S  T  E  R  Q  I  N  S  M
4240 TGTATTACTGTTTATGTAAGCAGACAGTTTTATTGTTCATGATGATATATTTTTATCTTGTGCAATGTAACATCAGAGATTTTGAGACACAACGTGGCTTTCCCCCCCCC
4350 CCCATTATTGAAGCATTTATCAGGGTTATTGTCTCATGAGCGGATACATATTTGAATGTATTTAGAAAAATAAACAAATAGGGGTTCCGCGCACATTTCCCCGAAAAGTG
4460 CCACCTGACGTCTAAGAAACCATTATTATCATGACATTAACCTATAAAAATAGGCGTATCACGAGGCCCTTTCGTCTCGCGCGTTTCGGTGATGACGGTGAAAACCTCTG
4570 ACACATGCAGCTCCCGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTA
4680 ACTATGCGGCATCAGAGCAGATTGTACTGAGAGTGCACCATATGCGGTGTGAAATACCGCACAGATGCGTAAGGAGAAAATACCGCATCAGATTGGCTATTGG
```

Figure 18B:
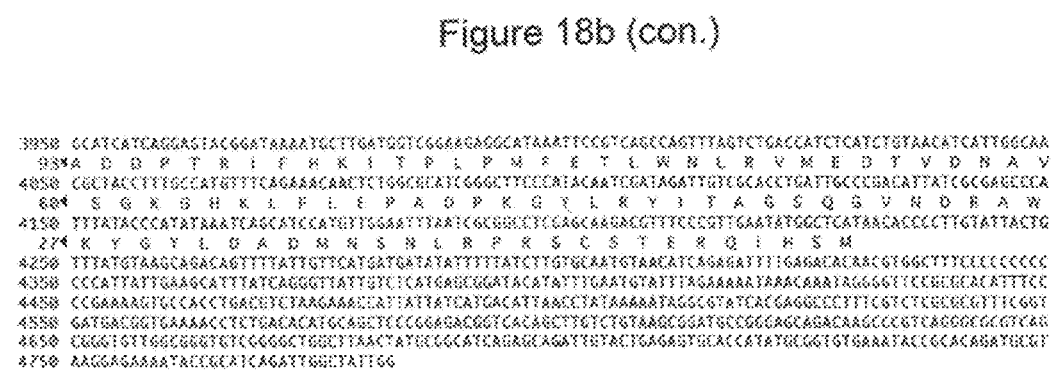

Figure 18b (con.)

```
3950 GCATCATCAGGAGTACGGATAAAATGCTTGATGGTCGGAAGAGGCATAAATTCCGTCAGCCAGTTTAGTCTGACCATCTCATCTGTAACATCATTGGCAA
  93◄A  D  D  P  T  R  I  F  H  K  I  T  P  L  P  M  F  E  T  L  W  N  L  R  V  M  E  D  T  V  D  N  A  V
4050 CGCTACCTTTGCCATGTTTCAGAAACAACTCTGGCGCATCGGGCTTCCCATACAATCGATAGATTGTCGCACCTGATTGCCCGACATTATCGCGAGCCCA
  60◄  S  G  K  G  H  K  L  F  L  E  P  A  D  P  K  G  Y  L  R  Y  I  T  A  G  S  Q  G  V  N  D  R  A  W
4150 TTTATACCCATATAAATCAGCATCCATGTTGGAATTTAATCGCGGCCTCGAGCAAGACGTTTCCCGTTGAATATGGCTCATAACACCCCTTGTATTACTG
  27◄ K  Y  G  Y  L  D  A  D  M  N  S  N  L  R  P  R  S  C  S  T  E  R  Q  I  H  S  M
4250 TTTATGTAAGCAGACAGTTTTATTGTTCATGATGATATATTTTTATCTTGTGCAATGTAACATCAGAGATTTTGAGACACAACGTGGCTTTCCCCCCCCC
4350 CCCATTATTGAAGCATTTATCAGGGTTATTGTCTCATGAGCGGATACATATTTGAATGTATTTAGAAAAATAAACAAATAGGGGTTCCGCGCACATTTCC
4450 CCGAAAAGTGCCACCTGACGTCTAAGAAACCATTATTATCATGACATTAACCTATAAAAATAGGCGTATCACGAGGCCCTTTCGTCTCGCGCGTTTCGGT
4550 GATGACGGTGAAAACCTCTGACACATGCAGCTCCCGGAGACGGTCACAGCTTGTCTGTAAGCGGATGCCGGGAGCAGACAAGCCCGTCAGGGCGCGTCAG
4650 CGGGTGTTGGCGGGTGTCGGGGCTGGCTTAACTATGCGGCATCAGAGCAGATTGTACTGAGAGTGCACCATATGCGGTGTGAAATACCGCACAGATGCGT
4750 AAGGAGAAAATACCGCATCAGATTGGCTATTGG
```

Testing of three Prime-Boost Vaccination Strategies

| Groups | 0 | 2 months | 4 months | prime | boost |
|---|---|---|---|---|---|
| Group 1 | SP-p24CE1 + SP-p24CE2 | SP-p24CE1 + SP-p24CE2 | p55gag | Conserved element | $p55^{gag}$ |
| Group 2 | p55gag | **p55gag** | **SP-p24CE1 + SP-p24CE2 +** | $p55^{gag}$ | Conserved element |
| Group 3 | SP-p24CE1 + SP-p24CE2 + p55gag | SP-p24CE1 + SP-p24CE2 + p55gag | SP-p24CE1 + SP-p24CE2 + p55gag | Conserved element + $p55^{gag}$ | Conserved element + $p55^{gag}$ |

SEQUENCE LISTING

<160> NUMBER OF SEQ ID NOS: 62

<210> SEQ ID NO 1
<211> LENGTH: 12
<212> TYPE: PRT
<213> ORGANISM: Artificial Sequence
<220> FEATURE:
<223> OTHER INFORMATION: synthetic HIV-1 p24 gag conserved element 1
(CE1) for p24CE1 (Core1) vaccine

<400> SEQUENCE: 1

Ile Ser Pro Arg Thr Leu Asn Ala Trp Val Lys Val
1 5 10

<210> SEQ ID NO 2
<211> LENGTH: 18
<212> TYPE: PRT
<213> ORGANISM: Artificial Sequence
<220> FEATURE:
<223> OTHER INFORMATION: synthetic HIV-1 p24 gag conserved element 2
(CE2) for p24CE1 (Core1) vaccine

<400> SEQUENCE: 2

Val Ile Pro Met Phe Ser Ala Leu Ser Glu Gly Ala Thr Pro Gln Asp
1 5 10 15

Leu Asn

<210> SEQ ID NO 3
<211> LENGTH: 24
<212> TYPE: PRT
<213> ORGANISM: Artificial Sequence
<220> FEATURE:
<223> OTHER INFORMATION: synthetic HIV-1 p24 gag conserved element 3
(CE3) for p24CE1 (Core1) vaccine

<400> SEQUENCE: 3

Val Gly Gly His Gln Ala Ala Met Gln Met Leu Lys Asp Thr Ile Asn
1 5 10 15

Glu Glu Ala Ala Glu Trp Asp Arg
20

<210> SEQ ID NO 4
<211> LENGTH: 19
<212> TYPE: PRT
<213> ORGANISM: Artificial Sequence
<220> FEATURE:
<223> OTHER INFORMATION: synthetic HIV-1 p24 gag conserved element 4
(CE4) for p24CE1 (Core1) vaccine

<400> SEQUENCE: 4

Pro Arg Gly Ser Asp Ile Ala Gly Thr Thr Ser Thr Leu Gln Glu Gln
1 5 10 15

Ile Gly Trp

<210> SEQ ID NO 5
<211> LENGTH: 20
<212> TYPE: PRT
<213> ORGANISM: Artificial Sequence
<220> FEATURE:
<223> OTHER INFORMATION: synthetic HIV-1 p24 gag conserved element 5 (CE5) for p24CE1 (Core1) vaccine

<400> SEQUENCE: 5

Lys Arg Trp Ile Ile Leu Gly Leu Asn Lys Ile Val Arg Met Tyr Ser
1 5 10 15

Pro Thr Ser Ile
20

<210> SEQ ID NO 6
<211> LENGTH: 14
<212> TYPE: PRT
<213> ORGANISM: Artificial Sequence
<220> FEATURE:
<223> OTHER INFORMATION: synthetic HIV-1 p24 gag conserved element 6 (CE6) for p24CE1 (Core1) vaccine

<400> SEQUENCE: 6

Tyr Val Asp Arg Phe Tyr Lys Thr Leu Arg Ala Glu Gln Ala
1 5 10

<210> SEQ ID NO 7
<211> LENGTH: 17
<212> TYPE: PRT
<213> ORGANISM: Artificial Sequence
<220> FEATURE:
<223> OTHER INFORMATION: synthetic HIV-1 p24 gag conserved element 7 (CE7) for p24CE1 (Core1) vaccine

<400> SEQUENCE: 7

Leu Glu Glu Met Met Thr Ala Cys Gln Gly Val Gly Gly Pro Gly His
1 5 10 15

Lys

<210> SEQ ID NO 8
<211> LENGTH: 12
<212> TYPE: PRT
<213> ORGANISM: Artificial Sequence
<220> FEATURE:
<223> OTHER INFORMATION: synthetic HIV-1 p24 gag conserved element 1 (CE1) for p24CE2 (Core2) vaccine

<400> SEQUENCE: 8

Leu Ser Pro Arg Thr Leu Asn Ala Trp Val Lys Val
1 5 10

<210> SEQ ID NO 9
<211> LENGTH: 18
<212> TYPE: PRT
<213> ORGANISM: Artificial Sequence
<220> FEATURE:
<223> OTHER INFORMATION: synthetic HIV-1 p24 gag conserved element 2 (CE2) for p24CE2 (Core2) vaccine

<400> SEQUENCE: 9

Val Ile Pro Met Phe Thr Ala Leu Ser Glu Gly Ala Thr Pro Gln Asp
1               5                   10                  15

Leu Asn

<210> SEQ ID NO 10
<211> LENGTH: 24
<212> TYPE: PRT
<213> ORGANISM: Artificial Sequence
<220> FEATURE:
<223> OTHER INFORMATION: synthetic HIV-1 p24 gag conserved element 3
      (CE3) for p24CE2 (Core2) vaccine

<400> SEQUENCE: 10

Val Gly Gly His Gln Ala Ala Met Gln Met Leu Lys Glu Thr Ile Asn
1               5                   10                  15

Glu Glu Ala Ala Glu Trp Asp Arg
            20

<210> SEQ ID NO 11
<211> LENGTH: 19
<212> TYPE: PRT
<213> ORGANISM: Artificial Sequence
<220> FEATURE:
<223> OTHER INFORMATION: synthetic HIV-1 p24 gag conserved element 4
      (CE4) for p24CE2 (Core2) vaccine

<400> SEQUENCE: 11

Pro Arg Gly Ser Asp Ile Ala Gly Thr Thr Ser Thr Leu Gln Glu Gln
1               5                   10                  15

Ile Ala Trp

<210> SEQ ID NO 12
<211> LENGTH: 20
<212> TYPE: PRT
<213> ORGANISM: Artificial Sequence
<220> FEATURE:
<223> OTHER INFORMATION: synthetic HIV-1 p24 gag conserved element 5
      (CE5) for p24CE2 (Core2) vaccine

<400> SEQUENCE: 12

Lys Arg Trp Ile Ile Leu Gly Leu Asn Lys Ile Val Arg Met Tyr Ser
1               5                   10                  15

Pro Val Ser Ile
            20

<210> SEQ ID NO 13
<211> LENGTH: 14
<212> TYPE: PRT
<213> ORGANISM: Artificial Sequence
<220> FEATURE:
<223> OTHER INFORMATION: synthetic HIV-1 p24 gag conserved element 6
      (CE6) for p24CE1 (Core 1) vaccine

<400> SEQUENCE: 13

Tyr Val Asp Arg Phe Phe Lys Thr Leu Arg Ala Glu Gln Ala
1               5                   10

<210> SEQ ID NO 14
<211> LENGTH: 17
<212> TYPE: PRT
<213> ORGANISM: Artificial Sequence
<220> FEATURE:

<223> OTHER INFORMATION: synthetic HIV-1 p24 gag conserved element 7
(CE7) for p24CE2 (Core2) vaccine

<400> SEQUENCE: 14

Leu Glu Glu Met Met Thr Ala Cys Gln Gly Val Gly Gly Pro Ser His
1 5 10 15

Lys

<210> SEQ ID NO 15
<211> LENGTH: 140
<212> TYPE: PRT
<213> ORGANISM: Artificial Sequence
<220> FEATURE:
<223> OTHER INFORMATION: synthetic HIV-1 p24 gag conserved elements 1-7
(CE1-7) collinearly arranged for p24CE1 (Core1) vaccine with short
linker sequences, first conserved element polypeptide,
configuration p24CE1 CE2-3-4-5-6-7-1

<400> SEQUENCE: 15

Val Ile Pro Met Phe Ser Ala Leu Ser Glu Gly Ala Thr Pro Gln Asp
1 5 10 15

Leu Asn Ala Ala Val Gly Gly His Gln Ala Ala Met Gln Met Leu Lys
20 25 30

Asp Thr Ile Asn Glu Glu Ala Ala Glu Trp Asp Arg Ala Ala Ala Glu
35 40 45

Pro Arg Gly Ser Asp Ile Ala Gly Thr Thr Ser Thr Leu Gln Glu Gln
50 55 60

Ile Gly Trp Ala Ala Ala Lys Arg Trp Ile Ile Leu Gly Leu Asn Lys
65 70 75 80

Ile Val Arg Met Tyr Ser Pro Thr Ser Ile Ala Ala Lys Tyr Val Asp
85 90 95

Arg Phe Tyr Lys Thr Leu Arg Ala Glu Gln Ala Ala Gly Leu Glu Glu
100 105 110

Met Met Thr Ala Cys Gln Gly Val Gly Gly Pro Gly His Lys Ala Ala
115 120 125

Ile Ser Pro Arg Thr Leu Asn Ala Trp Val Lys Val
130 135 140

<210> SEQ ID NO 16
<211> LENGTH: 140
<212> TYPE: PRT
<213> ORGANISM: Artificial Sequence
<220> FEATURE:
<223> OTHER INFORMATION: synthetic HIV-1 p24 gag conserved elements 8-14
(CE8-14) collinearly arranged for p24CE2 (Core2) vaccine with
short linker sequences, second conserved element polypeptide,
configuration p24CE2 CE9-10-11-12-13-14-8

<400> SEQUENCE: 16

Val Ile Pro Met Phe Thr Ala Leu Ser Glu Gly Ala Thr Pro Gln Asp
1 5 10 15

Leu Asn Ala Ala Val Gly Gly His Gln Ala Ala Met Gln Met Leu Lys
20 25 30

Glu Thr Ile Asn Glu Glu Ala Ala Glu Trp Asp Arg Ala Ala Ala Glu
35 40 45

Pro Arg Gly Ser Asp Ile Ala Gly Thr Thr Ser Thr Leu Gln Glu Gln
50 55 60

Ile Ala Trp Ala Ala Ala Lys Arg Trp Ile Ile Leu Gly Leu Asn Lys
65 70 75 80

```
Ile Val Arg Met Tyr Ser Pro Val Ser Ile Ala Ala Lys Tyr Val Asp
                85                  90                  95

Arg Phe Phe Lys Thr Leu Arg Ala Glu Gln Ala Ala Gly Leu Glu Glu
            100                 105                 110

Met Met Thr Ala Cys Gln Gly Val Gly Gly Pro Ser His Lys Ala Ala
        115                 120                 125

Leu Ser Pro Arg Thr Leu Asn Ala Trp Val Lys Val
    130                 135                 140


<210> SEQ ID NO 17
<211> LENGTH: 5586
<212> TYPE: DNA
<213> ORGANISM: Artificial Sequence
<220> FEATURE:
<223> OTHER INFORMATION: synthetic HIV-1 p24 gag conserved element
      p24CE1+p24CE2 (Core1 plus Core2) vaccine
      construct, p24CE1 encoded by plasmid 306H

<400> SEQUENCE: 17

cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

atggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacaagaaat gtggctccag    780

agcctgctac tcctggggac ggtggcctgc agcatctcgg tcatcccgat gttctcggcg    840

ctcagcgagg gagcgacgcc gcaggacctg aacgcggccg tcggaggtca ccaggcagcg    900

atgcagatgc tgaaggacac gatcaacgag gaggcggccg agtgggaccg ggcggcagcc    960

gagccacgcg gttccgacat cgcgggcacc acctcgacgc tccaggagca gatcgggtgg   1020

gccgcagcta agcgctggat catcctcggg ctgaacaaga tcgtccggat gtacagcccg   1080

acgtcgatcg ctgctaagta cgttgaccgg ttctacaaga ccctgagggc cgagcaggcg   1140

gccggactgg aggagatgat gaccgcgtgc caggggggtcg gtggaccagg gcacaaggcc   1200

gcgatctcgc cgcgcacgct gaacgcgtgg gtgaaggtct gataagaatt cgctagcggc   1260

gcgccagatc tgatatcgga tctgctgtgc cttctagttg ccagccatct gttgtttgcc   1320

cctcccccgt gccttccttg accctggaag gtgccactcc cactgtcctt tcctaataaa   1380

atgaggaaat tgcatcgcat tgtctgagta ggtgtcattc tattctgggg ggtggggtgg   1440

ggcaggacag caagggggag gattgggaag acaatagcag gcatgctggg gatgcggtgg   1500

gctctatggg tacccaggtg ctgaagaatt gacccggttc ctcctgggcc agaaagaagc   1560

aggcacatcc ccttctctgt gacacaccct gtccacgccc ctggttctta gttccagccc   1620
```

-continued

```
cactcatagg acactcatag ctcaggaggg ctccgccttc aatcccaccc gctaaagtac   1680
ttggagcggt ctctccctcc ctcatcagcc caccaaacca aacctagcct ccaagagtgg   1740
gaagaaatta aagcaagata ggctattaag tgcagaggga gagaaaatgc ctccaacatg   1800
tgaggaagta atgagagaaa tcatagaatt tcttccgctt cctcgctcac tgactcgctg   1860
cgctcggtcg ttcggctgcg gcgagcggta tcagctcact caaaggcggt aatacggtta   1920
tccacagaat caggggataa cgcaggaaag aacatgtgag caaaaggcca gcaaaaggcc   1980
aggaaccgta aaaaggccgc gttgctggcg tttttccata ggctccgccc ccctgacgag   2040
catcacaaaa atcgacgctc aagtcagagg tggcgaaacc cgacaggact ataaagatac   2100
caggcgtttc cccctggaag ctccctcgtg cgctctcctg ttccgaccct gccgcttacc   2160
ggatacctgt ccgcctttct cccttcggga agcgtggcgc tttctcatag ctcacgctgt   2220
aggtatctca gttcggtgta ggtcgttcgc tccaagctgg gctgtgtgca cgaacccccc   2280
gttcagcccg accgctgcgc cttatccggt aactatcgtc ttgagtccaa cccggtaaga   2340
cacgacttat cgccactggc agcagccact ggtaacagga ttagcagagc gaggtatgta   2400
ggcggtgcta cagagttctt gaagtggtgg cctaactacg gctacactag aagaacagta   2460
tttggtatct gcgctctgct gaagccagtt accttcggaa aaagagttgg tagctcttga   2520
tccggcaaac aaaccaccgc tggtagcggt ggtttttttg tttgcaagca gcagattacg   2580
cgcagaaaaa aaggatctca agaagatcct ttgatctttt ctacggggtc tgacgctcag   2640
tggaacgaaa actcacgtta agggattttg gtcatgagat tatcaaaaag gatcttcacc   2700
tagatccttt taaattaaaa atgaagtttt aaatcaatct aaagtatata tgagtaaact   2760
tggtctgaca gttaccaatg cttaatcagt gaggcaccta tctcagcgat ctgtctattt   2820
cgttcatcca tagttgcctg actcgggggg ggggggcgct gaggtctgcc tcgtgaagaa   2880
ggtgttgctg actcatacca ggcctgaatc gccccatcat ccagccagaa agtgagggag   2940
ccacggttga tgagagcttt gttgtaggtg gaccagttgg tgattttgaa cttttgcttt   3000
gccacggaac ggtctgcgtt gtcgggaaga tgcgtgatct gatccttcaa ctcagcaaaa   3060
gttcgattta ttcaacaaag ccgccgtccc gtcaagtcag cgtaatgctc tgccagtgtt   3120
acaaccaatt aaccaattct gattagaaaa actcatcgag catcaaatga aactgcaatt   3180
tattcatatc aggattatca ataccatatt tttgaaaaag ccgtttctgt aatgaaggag   3240
aaaactcacc gaggcagttc cataggatgg caagatcctg gtatcggtct gcgattccga   3300
ctcgtccaac atcaatacaa cctattaatt tcccctcgtc aaaaataagg ttatcaagtg   3360
agaaatcacc atgagtgacg actgaatccg gtgagaatgg caaaagctta tgcatttctt   3420
tccagacttg ttcaacaggc cagccattac gctcgtcatc aaaatcactc gcatcaacca   3480
aaccgttatt cattcgtgat tgcgcctgag cgagacgaaa tacgcgatcg ctgttaaaag   3540
gacaattaca aacaggaatc gaatgcaacc ggcgcaggaa cactgccagc gcatcaacaa   3600
tattttcacc tgaatcagga tattcttcta atacctggaa tgctgttttc ccggggatcg   3660
cagtggtgag taaccatgca tcatcaggag tacggataaa atgcttgatg gtcggaagag   3720
gcataaattc cgtcagccag tttagtctga ccatctcatc tgtaacatca ttggcaacgc   3780
tacctttgcc atgtttcaga aacaactctg gcgcatcggg cttcccatac aatcgataga   3840
ttgtcgcacc tgattgcccg acattatcgc gagcccattt atacccatat aaatcagcat   3900
ccatgttgga atttaatcgc ggcctcgagc aagacgtttc ccgttgaata tggctcataa   3960
cacccccttgt attactgttt atgtaagcag acagttttat tgttcatgat gatatatttt   4020
```

-continued

```
tatcttgtgc aatgtaacat cagagatttt gagacacaac gtggatcatc cagacatgat   4080

aagatacatt gatgagtttg gacaaaccac aactagaatg cagtgaaaaa aatgctttat   4140

ttgtgaaatt tgtgatgcta ttgctttatt tgtaaccatt ataagctgca ataaacaagt   4200

taacaacaac aattgcattc attttatgtt tcaggttcag ggggaggtgt gggaggtttt   4260

ttaaagcaag taaaacctct acaaatgtgg tatggctgat tatgatcgtc gaggatccgg   4320

cgttatcaga ccttcaccca ggcgttgagg gtgcgaggcg agagggccgc cttgtgcgac   4380

ggtcctccga ctccctggca ggctgtcatc atctcctcga gacccgcggc ctgctctgcc   4440

ctcagcgtct tgaagaagcg gtctacgtat ttggccgcga tgctgactgg gctgtacatc   4500

ctgacgatct tgttgaggcc caggatgatc cagcgcttgg ctgcagccca ggcgatctgc   4560

tcctggaggg tgctggtcgt gcctgcgatg tcgctacccc ttggctcagc tgctgccctg   4620

tcccactcgg ctgcctcctc gttgatggtc tccttgagca tctgcattgc cgcctggtgt   4680

ccaccgaccg cggcgttgag gtcctgcggt gtcgcaccct cactgagtgc ggtgaacatg   4740

gggatgaccg agatcgagca cgccacggtc ccgagtagca ggagcgactg cagccacatt   4800

tcttccgttt aaacgtcgac agatccaaac gctcctccga cgtccccagg cagaatggcg   4860

gttccctaaa cgagcattgc ttatatagac ctcccattag gcacgcctac cgcccattta   4920

cgtcaatgga acgcccattt gcgtcattgc cctccccat tgacgtcaat ggggatgtac   4980

ttggcagcca tcgcgggcca tttaccgcca ttgacgtcaa tgggagtact gccaatgtac   5040

cctggcgtac ttccaatagt aatgtacttg ccaagttact attaatagat attgatgtac   5100

tgccaagtgg gccatttacc gtcattgacg tcaatagggg gcgtgagaac ggatatgaat   5160

gggcaatgag ccatcccatt gacgtcaatg gtgggtggtc ctattgacgt caatgggcat   5220

tgagccaggc gggccattta ccgtaattga cgtcaatggg ggaggcgcca tatacgtcaa   5280

taggaccgcc catatgacgt caataggtaa gaccatgagg ccctttcgtc tcgcgcgttt   5340

cggtgatgac ggtgaaaacc tctgacacat gcagctcccg gagacggtca cagcttgtct   5400

gtaagcggat gccgggagca gacaagcccg tcagggcgcg tcagcgggtg ttggcgggtg   5460

tcggggctgg cttaactatg cggcatcaga gcagattgta ctgagagtgc accatatgcg   5520

gtgtgaaata ccgcacagat gcgtaaggag aaaataccgc atcagattgg ctattggcat   5580

tatgcc                                                              5586


<210> SEQ ID NO 18
<211> LENGTH: 157
<212> TYPE: PRT
<213> ORGANISM: Artificial Sequence
<220> FEATURE:
<223> OTHER INFORMATION: synthetic HIV-1 p24 gag conserved element
      p24CE1 (including GM-CSF signal peptide)

<400> SEQUENCE: 18

Met Trp Leu Gln Ser Leu Leu Leu Leu Gly Thr Val Ala Cys Ser Ile
1               5                   10                  15

Ser Val Ile Pro Met Phe Ser Ala Leu Ser Glu Gly Ala Thr Pro Gln
            20                  25                  30

Asp Leu Asn Ala Ala Val Gly Gly His Gln Ala Ala Met Gln Met Leu
        35                  40                  45

Lys Asp Thr Ile Asn Glu Glu Ala Ala Glu Trp Asp Arg Ala Ala Ala
    50                  55                  60
```

-continued

```
Glu Pro Arg Gly Ser Asp Ile Ala Gly Thr Thr Ser Thr Leu Gln Glu
65                  70                  75                  80

Gln Ile Gly Trp Ala Ala Ala Lys Arg Trp Ile Ile Leu Gly Leu Asn
                85                  90                  95

Lys Ile Val Arg Met Tyr Ser Pro Thr Ser Ile Ala Ala Lys Tyr Val
            100                 105                 110

Asp Arg Phe Tyr Lys Thr Leu Arg Ala Glu Gln Ala Ala Gly Leu Glu
        115                 120                 125

Glu Met Met Thr Ala Cys Gln Gly Val Gly Gly Pro Gly His Lys Ala
    130                 135                 140

Ala Ile Ser Pro Arg Thr Leu Asn Ala Trp Val Lys Val
145                 150                 155


<210> SEQ ID NO 19
<211> LENGTH: 157
<212> TYPE: PRT
<213> ORGANISM: Artificial Sequence
<220> FEATURE:
<223> OTHER INFORMATION: synthetic HIV-1 p24 gag conserved element
      p24CE2 (including GM-CSF signal peptide)

<400> SEQUENCE: 19

Met Trp Leu Gln Ser Leu Leu Leu Leu Gly Thr Val Ala Cys Ser Ile
1               5                   10                  15

Ser Val Ile Pro Met Phe Thr Ala Leu Ser Glu Gly Ala Thr Pro Gln
            20                  25                  30

Asp Leu Asn Ala Ala Val Gly Gly His Gln Ala Ala Met Gln Met Leu
        35                  40                  45

Lys Glu Thr Ile Asn Glu Glu Ala Ala Glu Trp Asp Arg Ala Ala Ala
    50                  55                  60

Glu Pro Arg Gly Ser Asp Ile Ala Gly Thr Thr Ser Thr Leu Gln Glu
65                  70                  75                  80

Gln Ile Ala Trp Ala Ala Ala Lys Arg Trp Ile Ile Leu Gly Leu Asn
                85                  90                  95

Lys Ile Val Arg Met Tyr Ser Pro Val Ser Ile Ala Ala Lys Tyr Val
            100                 105                 110

Asp Arg Phe Phe Lys Thr Leu Arg Ala Glu Gln Ala Ala Gly Leu Glu
        115                 120                 125

Glu Met Met Thr Ala Cys Gln Gly Val Gly Gly Pro Ser His Lys Ala
    130                 135                 140

Ala Leu Ser Pro Arg Thr Leu Asn Ala Trp Val Lys Val
145                 150                 155


<210> SEQ ID NO 20
<211> LENGTH: 5706
<212> TYPE: DNA
<213> ORGANISM: Artificial Sequence
<220> FEATURE:
<223> OTHER INFORMATION: synthetic lysosomal associated membrane protein
      1 (LAMP-1) fusion protein with p24CE2 (Core2) vaccine construct,
      LAMP-p24CE2 encoded by plasmid 202H

<400> SEQUENCE: 20

cctggccatt gcatacgttg tatccatatc ataatatgta catttatatt ggctcatgtc      60

caacattacc gccatgttga cattgattat tgactagtta ttaatagtaa tcaattacgg     120

ggtcattagt tcatagccca tatatggagt tccgcgttac ataacttacg gtaaatggcc     180

cgcctggctg accgcccaac gacccccgcc cattgacgtc aataatgacg tatgttccca     240
```

-continued

```
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gactagcatg gcgccccgca    780
gcgcccggcg acccctgctg ctgctactgc tgttgctgct gctcggcctc atgcattgtg    840
cgtcagcagc aatgtttatg gtgaaaaatg gcaacgggac cgcgtgcata atggccaact    900
tctctgctgc cttctcagtg aactacgaca ccaagagtgg ccctaagaac atgacccttg    960
acctgccatc agatgccaca gtggtgctca accgcagctc ctgtggaaaa gagaacactt   1020
ctgaccccag tctcgtgatt gcttttggaa gaggacatac actcactctc aatttcacga   1080
gaaatgcaac acgttacagc gttcagctca tgagttttgt ttataacttg tcagacacac   1140
accttttccc caatgcgagc tccaaagaaa tcaagactgt ggaatctata actgacatca   1200
gggcagatat agataaaaaa tacagatgtg ttagtggcac ccaggtccac atgaacaacg   1260
tgaccgtaac gctccatgat gccaccatcc aggcgtacct ttccaacagc agcttcagca   1320
ggggagagac acgctgtgaa caagacaggc cttccccaac cacagcgccc cctgcgccac   1380
ccagcccctc gccctcaccc gtgcccaaga gcccctctgt ggacaagtac aacgtgagcg   1440
gcaccaacgg gacctgcctg ctggccagca tggggctgca gctgaacctc acctatgaga   1500
ggaaggacaa cacgacggtg acaaggcttc tcaacatcaa ccccaacaag acctcggcca   1560
gcgggagctg cggcgcccac ctggtgactc tggagctgca cagcgagggc accaccgtcc   1620
tgctcttcca gttcgggatg aatgcaagtt ctagccggtt tttcctacaa ggaatccagt   1680
tgaatacaat tcttcctgac gccagagacc ctgcctttaa agctgccaac ggctccctgc   1740
gagcgctgca ggccacagtc ggcaattcct acaagtgcaa cgcggaggag cacgtccgtg   1800
tcacgaaggc gttttcagtc aatatattca aagtgtgggt ccaggctttc aaggtggaag   1860
gtggccagtt tggctctgtg gaggagtgtc tgctggacga gaacagcctc gaggatatcg   1920
tcatcccgat gttcacggcg ctcagcgagg gagcgacgcc gcaggacctg aacgcggccg   1980
tcggaggtca ccaggcagcg atgcagatgc tgaaggagac gatcaacgag gaggcggccg   2040
agtgggaccg ggcggcagcc gagccacgcg gttccgacat cgcgggcacc acctcgacgc   2100
tccaggagca gatcgcgtgg gccgcagcta agcgctggat catcctcggg ctgaacaaga   2160
tcgtccggat gtacagcccg gtctcgatcg ctgctaagta cgttgaccgg ttcttcaaga   2220
ccctgagggc cgagcaggcg gccggactgg aggagatgat gaccgcgtgc caggggggtcg   2280
gtggaccatc gcacaaggcc gcgctctcgc cgcgcacgct gaacgcgtgg gtgaaggtcg   2340
gatccgaatt cacgctgatc cccatcgctg tgggtggtgc cctggcgggg ctggtcctca   2400
tcgtcctcat cgcctacctc gtcggcagga agaggagtca cgcaggctac cagactatct   2460
agggtacctc taggatctgc tgtgccttct agttgccagc catctgttgt ttgcccctcc   2520
cccgtgcctt ccttgaccct ggaaggtgcc actcccactg tcctttccta ataaaatgag   2580
```

-continued

```
gaaattgcat cgcattgtct gagtaggtgt cattctattc tggggggtgg ggtggggcag   2640
gacagcaagg gggaggattg ggaagacaat agcaggcatg ctggggatgc ggtgggctct   2700
atgggtaccc aggtgctgaa gaattgaccc ggttcctcct gggccagaaa gaagcaggca   2760
catccccttc tctgtgacac accctgtcca cgcccctggt tcttagttcc agccccactc   2820
ataggacact catagctcag gagggctccg ccttcaatcc cacccgctaa agtacttgga   2880
gcggtctctc cctccctcat cagcccacca aaccaaacct agcctccaag agtgggaaga   2940
aattaaagca agataggcta ttaagtgcag agggagagaa aatgcctcca acatgtgagg   3000
aagtaatgag agaaatcata gaatttcttc cgcttcctcg ctcactgact cgctgcgctc   3060
ggtcgttcgg ctgcggcgag cggtatcagc tcactcaaag gcggtaatac ggttatccac   3120
agaatcaggg gataacgcag gaaagaacat gtgagcaaaa ggccagcaaa aggccaggaa   3180
ccgtaaaaag gccgcgttgc tggcgttttt ccataggctc cgcccccctg acgagcatca   3240
caaaaatcga cgctcaagtc agaggtggcg aaacccgaca ggactataaa gataccaggc   3300
gtttccccct ggaagctccc tcgtgcgctc tcctgttccg accctgccgc ttaccggata   3360
cctgtccgcc tttctccctt cgggaagcgt ggcgctttct caatgctcac gctgtaggta   3420
tctcagttcg gtgtaggtcg ttcgctccaa gctgggctgt gtgcacgaac cccccgttca   3480
gcccgaccgc tgcgccttat ccggtaacta tcgtcttgag tccaacccgg taagacacga   3540
cttatcgcca ctggcagcag ccactggtaa caggattagc agagcgaggt atgtaggcgg   3600
tgctacagag ttcttgaagt ggtggcctaa ctacggctac actagaagaa cagtatttgg   3660
tatctgcgct ctgctgaagc cagttacctt cggaaaaaga gttggtagct cttgatccgg   3720
caaacaaacc accgctggta gcggtggttt ttttgtttgc aagcagcaga ttacgcgcag   3780
aaaaaaagga tctcaagaag atcctttgat cttttctacg gggtctgacg ctcagtggaa   3840
cgaaaactca cgttaaggga ttttggtcat gagattatca aaaaggatct tcacctagat   3900
ccttttaaat taaaaatgaa gttttaaatc aatctaaagt atatatgagt aaacttggtc   3960
tgacagttac caatgcttaa tcagtgaggc acctatctca gcgatctgtc tatttcgttc   4020
atccatagtt gcctgactcg gggggggggg ggcgctgagg tctgcctcgt gaagaaggtg   4080
ttgctgactc ataccaggcc tgaatcgccc catcatccag ccagaaagtg agggagccac   4140
ggttgatgag agctttgttg taggtggacc agttggtgat tttgaacttt tgctttgcca   4200
cggaacggtc tgcgttgtcg ggaagatgcg tgatctgatc cttcaactca gcaaaagttc   4260
gatttattca acaaagccgc cgtcccgtca agtcagcgta atgctctgcc agtgttacaa   4320
ccaattaacc aattctgatt agaaaaactc atcgagcatc aaatgaaact gcaatttatt   4380
catatcagga ttatcaatac catatttttg aaaaagccgt ttctgtaatg aaggagaaaa   4440
ctcaccgagg cagttccata ggatggcaag atcctggtat cggtctgcga ttccgactcg   4500
tccaacatca atacaaccta ttaatttccc ctcgtcaaaa ataaggttat caagtgagaa   4560
atcaccatga gtgacgactg aatccggtga gaatggcaaa agcttatgca tttctttcca   4620
gacttgttca acaggccagc cattacgctc gtcatcaaaa tcactcgcat caaccaaacc   4680
gttattcatt cgtgattgcg cctgagcgag acgaaatacg cgatcgctgt taaaaggaca   4740
attacaaaca ggaatcgaat gcaaccggcg caggaacact gccagcgcat caacaatatt   4800
ttcacctgaa tcaggatatt cttctaatac ctggaatgct gttttcccgg ggatcgcagt   4860
ggtgagtaac catgcatcat caggagtacg gataaaatgc ttgatggtcg gaagaggcat   4920
aaattccgtc agccagttta gtctgaccat ctcatctgta acatcattgg caacgctacc   4980
```

-continued

```
tttgccatgt ttcagaaaca actctggcgc atcgggcttc ccatacaatc gatagattgt   5040

cgcacctgat tgcccgacat tatcgcgagc ccatttatac ccatataaat cagcatccat   5100

gttggaattt aatcgcggcc tggagcaaga cgtttcccgt tgaatatggc tcataacacc   5160

ccttgtatta ctgtttatgt aagcagacag ttttattgtt catgatgata tatttttatc   5220

ttgtgcaatg taacatcaga gattttgaga cacaacgtgg ctttcccccc ccccccatta   5280

ttgaagcatt tatcagggtt attgtctcat gagcggatac atatttgaat gtatttagaa   5340

aaataaacaa ataggggttc cgcgcacatt tccccgaaaa gtgccacctg acgtctaaga   5400

aaccattatt atcatgacat taacctataa aaataggcgt atcacgaggc cctttcgtct   5460

cgcgcgtttc ggtgatgacg gtgaaaacct ctgacacatg cagctcccgg agacggtcac   5520

agcttgtctg taagcggatg ccgggagcag acaagcccgt cagggcgcgt cagcgggtgt   5580

tggcgggtgt cggggctggc ttaactatgc ggcatcagag cagattgtac tgagagtgca   5640

ccatatgcgg tgtgaaatac cgcacagatg cgtaaggaga aaataccgca tcagattggc   5700

tattgg                                                              5706
```

```
<210> SEQ ID NO 21
<211> LENGTH: 564
<212> TYPE: PRT
<213> ORGANISM: Artificial Sequence
<220> FEATURE:
<223> OTHER INFORMATION: synthetic lysosomal associated membrane protein
      1 (LAMP-1) fusion protein with p24CE2 (Core2) vaccine construct,
      LAMP-p24CE2 encoded by plasmid 202H

<400> SEQUENCE: 21

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205
```

```
Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
    370                 375                 380

Val Ile Pro Met Phe Thr Ala Leu Ser Glu Gly Ala Thr Pro Gln Asp
385                 390                 395                 400

Leu Asn Ala Ala Val Gly Gly His Gln Ala Ala Met Gln Met Leu Lys
                405                 410                 415

Glu Thr Ile Asn Glu Glu Ala Ala Glu Trp Asp Arg Ala Ala Ala Glu
            420                 425                 430

Pro Arg Gly Ser Asp Ile Ala Gly Thr Thr Ser Thr Leu Gln Glu Gln
        435                 440                 445

Ile Ala Trp Ala Ala Ala Lys Arg Trp Ile Ile Leu Gly Leu Asn Lys
    450                 455                 460

Ile Val Arg Met Tyr Ser Pro Val Ser Ile Ala Ala Lys Tyr Val Asp
465                 470                 475                 480

Arg Phe Phe Lys Thr Leu Arg Ala Glu Gln Ala Ala Gly Leu Glu Glu
                485                 490                 495

Met Met Thr Ala Cys Gln Gly Val Gly Gly Pro Ser His Lys Ala Ala
            500                 505                 510

Leu Ser Pro Arg Thr Leu Asn Ala Trp Val Lys Val Gly Ser Glu Phe
        515                 520                 525

Thr Leu Ile Pro Ile Ala Val Gly Gly Ala Leu Ala Gly Leu Val Leu
    530                 535                 540

Ile Val Leu Ile Ala Tyr Leu Val Gly Arg Lys Arg Ser His Ala Gly
545                 550                 555                 560

Tyr Gln Thr Ile


<210> SEQ ID NO 22
<211> LENGTH: 5706
<212> TYPE: DNA
<213> ORGANISM: Artificial Sequence
<220> FEATURE:
<223> OTHER INFORMATION: synthetic lysosomal associated membrane protein
      1 (LAMP-1) fusion protein with p24CE1 (Core1) vaccine construct,
      LAMP-p24CE1 encoded by plasmid 191H
```

<400> SEQUENCE: 22

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gactagcatg gcgccccgca    780
gcgcccggcg accccctgctg ctgctactgc tgttgctgct gctcggcctc atgcattgtg    840
cgtcagcagc aatgtttatg gtgaaaaatg gcaacgggac cgcgtgcata atggccaact    900
tctctgctgc cttctcagtg aactacgaca ccaagagtgg ccctaagaac atgacccttg    960
acctgccatc agatgccaca gtggtgctca accgcagctc ctgtggaaaa gagaacactt   1020
ctgaccccag tctcgtgatt gcttttggaa gaggacatac actcactctc aatttcacga   1080
gaaatgcaac acgttacagc gttcagctca tgagttttgt ttataacttg tcagacacac   1140
accttttccc caatgcgagc tccaaagaaa tcaagactgt ggaatctata actgacatca   1200
gggcagatat agataaaaaa tacagatgtg ttagtggcac ccaggtccac atgaacaacg   1260
tgaccgtaac gctccatgat gccaccatcc aggcgtacct ttccaacagc agcttcagca   1320
ggggagagac acgctgtgaa caagacaggc cttccccaac cacagcgccc cctgcgccac   1380
ccagcccctc gccctcaccc gtgcccaaga gcccctctgt ggacaagtac aacgtgagcg   1440
gcaccaacgg gacctgcctg ctggccagca tggggctgca gctgaacctc acctatgaga   1500
ggaaggacaa cacgacggtg acaaggcttc tcaacatcaa ccccaacaag acctcggcca   1560
gcgggagctg cggcgcccac ctggtgactc tggagctgca cagcgagggc accaccgtcc   1620
tgctcttcca gttcgggatg aatgcaagtt ctagccggtt tttcctacaa ggaatccagt   1680
tgaatacaat tcttcctgac gccagagacc ctgcctttaa agctgccaac ggctccctgc   1740
gagcgctgca ggccacagtc ggcaattcct acaagtgcaa cgcggaggag cacgtccgtg   1800
tcacgaaggc gttttcagtc aatatattca aagtgtgggt ccaggctttc aaggtggaag   1860
gtggccagtt tggctctgtg gaggagtgtc tgctggacga gaacagcctc gaggatatcg   1920
tcatcccgat gttctcggcg ctcagcgagg gagcgacgcc gcaggacctg aacgcggccg   1980
tcggaggtca ccaggcagcg atgcagatgc tgaaggacac gatcaacgag gaggcggccg   2040
agtgggaccg ggcggcagcc gagccacgcg gttccgacat cgcgggcacc acctcgacgc   2100
tccaggagca gatcgggtgg gccgcagcta agcgctggat catcctcggg ctgaacaaga   2160
tcgtccggat gtacagcccg acgtcgatcg ctgctaagta cgttgaccgg ttctacaaga   2220
ccctgagggc cgagcaggcg gccggactgg aggagatgat gaccgcgtgc caggggggtcg   2280
gtggaccagg gcacaaggcc gcgatctcgc cgcgcacgct gaacgcgtgg gtgaaggtcg   2340
```

-continued

```
gatccgaatt cacgctgatc cccatcgctg tgggtggtgc cctggcgggg ctggtcctca   2400
tcgtcctcat cgcctacctc gtcggcagga agaggagtca cgcaggctac cagactatct   2460
agggtacctc taggatctgc tgtgccttct agttgccagc catctgttgt ttgcccctcc   2520
cccgtgcctt ccttgaccct ggaaggtgcc actcccactg tcctttccta ataaaatgag   2580
gaaattgcat cgcattgtct gagtaggtgt cattctattc tggggggtgg ggtggggcag   2640
gacagcaagg gggaggattg ggaagacaat agcaggcatg ctggggatgc ggtgggctct   2700
atgggtaccc aggtgctgaa gaattgaccc ggttcctcct gggccagaaa gaagcaggca   2760
catccccttc tctgtgacac accctgtcca cgcccctggt tcttagttcc agccccactc   2820
ataggacact catagctcag gagggctccg ccttcaatcc cacccgctaa agtacttgga   2880
gcggtctctc cctccctcat cagcccacca aaccaaacct agcctccaag agtgggaaga   2940
aattaaagca agataggcta ttaagtgcag agggagagaa aatgcctcca acatgtgagg   3000
aagtaatgag agaaatcata gaatttcttc cgcttcctcg ctcactgact cgctgcgctc   3060
ggtcgttcgg ctgcggcgag cggtatcagc tcactcaaag gcggtaatac ggttatccac   3120
agaatcaggg gataacgcag gaaagaacat gtgagcaaaa ggccagcaaa aggccaggaa   3180
ccgtaaaaag gccgcgttgc tggcgttttt ccataggctc cgcccccctg acgagcatca   3240
caaaaatcga cgctcaagtc agaggtggcg aaacccgaca ggactataaa gataccaggc   3300
gtttccccct ggaagctccc tcgtgcgctc tcctgttccg accctgccgc ttaccggata   3360
cctgtccgcc tttctccctt cgggaagcgt ggcgctttct caatgctcac gctgtaggta   3420
tctcagttcg gtgtaggtcg ttcgctccaa gctgggctgt gtgcacgaac cccccgttca   3480
gcccgaccgc tgcgccttat ccggtaacta tcgtcttgag tccaacccgg taagacacga   3540
cttatcgcca ctggcagcag ccactggtaa caggattagc agagcgaggt atgtaggcgg   3600
tgctacagag ttcttgaagt ggtggcctaa ctacggctac actagaagaa cagtatttgg   3660
tatctgcgct ctgctgaagc cagttacctt cggaaaaaga gttggtagct cttgatccgg   3720
caaacaaacc accgctggta gcggtggttt ttttgtttgc aagcagcaga ttacgcgcag   3780
aaaaaaagga tctcaagaag atcctttgat cttttctacg gggtctgacg ctcagtggaa   3840
cgaaaactca cgttaaggga ttttggtcat gagattatca aaaaggatct tcacctagat   3900
ccttttaaat taaaaatgaa gttttaaatc aatctaaagt atatatgagt aaacttggtc   3960
tgacagttac caatgcttaa tcagtgaggc acctatctca gcgatctgtc tatttcgttc   4020
atccatagtt gcctgactcg gggggggggg ggcgctgagg tctgcctcgt gaagaaggtg   4080
ttgctgactc ataccaggcc tgaatcgccc catcatccag ccagaaagtg agggagccac   4140
ggttgatgag agctttgttg taggtggacc agttggtgat tttgaacttt tgctttgcca   4200
cggaacggtc tgcgttgtcg ggaagatgcg tgatctgatc cttcaactca gcaaaagttc   4260
gatttattca acaaagccgc cgtcccgtca agtcagcgta atgctctgcc agtgttacaa   4320
ccaattaacc aattctgatt agaaaaactc atcgagcatc aaatgaaact gcaatttatt   4380
catatcagga ttatcaatac catatttttg aaaaagccgt ttctgtaatg aaggagaaaa   4440
ctcaccgagg cagttccata ggatggcaag atcctggtat cggtctgcga ttccgactcg   4500
tccaacatca atacaaccta ttaatttccc ctcgtcaaaa ataaggttat caagtgagaa   4560
atcaccatga gtgacgactg aatccggtga gaatggcaaa agcttatgca tttctttcca   4620
gacttgttca acaggccagc cattacgctc gtcatcaaaa tcactcgcat caaccaaacc   4680
```

-continued

```
gttattcatt cgtgattgcg cctgagcgag acgaaatacg cgatcgctgt taaaaggaca   4740

attacaaaca ggaatcgaat gcaaccggcg caggaacact gccagcgcat caacaatatt   4800

ttcacctgaa tcaggatatt cttctaatac ctggaatgct gttttcccgg ggatcgcagt   4860

ggtgagtaac catgcatcat caggagtacg gataaaatgc ttgatggtcg gaagaggcat   4920

aaattccgtc agccagttta gtctgaccat ctcatctgta acatcattgg caacgctacc   4980

tttgccatgt ttcagaaaca actctggcgc atcgggcttc ccatacaatc gatagattgt   5040

cgcacctgat tgcccgacat tatcgcgagc ccatttatac ccatataaat cagcatccat   5100

gttggaattt aatcgcggcc tggagcaaga cgtttcccgt tgaatatggc tcataacacc   5160

ccttgtatta ctgtttatgt aagcagacag ttttattgtt catgatgata tatttttatc   5220

ttgtgcaatg taacatcaga gattttgaga cacaacgtgg ctttcccccc ccccccatta   5280

ttgaagcatt tatcagggtt attgtctcat gagcggatac atatttgaat gtatttagaa   5340

aaataaacaa ataggggttc cgcgcacatt tccccgaaaa gtgccacctg acgtctaaga   5400

aaccattatt atcatgacat taacctataa aaataggcgt atcacgaggc cctttcgtct   5460

cgcgcgtttc ggtgatgacg gtgaaaacct ctgacacatg cagctcccgg agacggtcac   5520

agcttgtctg taagcggatg ccgggagcag acaagcccgt cagggcgcgt cagcgggtgt   5580

tggcgggtgt cggggctggc ttaactatgc ggcatcagag cagattgtac tgagagtgca   5640

ccatatgcgg tgtgaaatac cgcacagatg cgtaaggaga aaataccgca tcagattggc   5700

tattgg                                                              5706
```

<210> SEQ ID NO 23
<211> LENGTH: 564
<212> TYPE: PRT
<213> ORGANISM: Artificial Sequence
<220> FEATURE:
<223> OTHER INFORMATION: synthetic lysosomal associated membrane protein 1 (LAMP-1) fusion protein with p24CE1 (Core1) vaccine construct, LAMP-p24CE1 encoded by plasmid 191H

<400> SEQUENCE: 23

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160
```

-continued

```
His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
    370                 375                 380

Val Ile Pro Met Phe Ser Ala Leu Ser Glu Gly Ala Thr Pro Gln Asp
385                 390                 395                 400

Leu Asn Ala Ala Val Gly Gly His Gln Ala Ala Met Gln Met Leu Lys
                405                 410                 415

Asp Thr Ile Asn Glu Glu Ala Ala Glu Trp Asp Arg Ala Ala Ala Glu
            420                 425                 430

Pro Arg Gly Ser Asp Ile Ala Gly Thr Thr Ser Thr Leu Gln Glu Gln
        435                 440                 445

Ile Gly Trp Ala Ala Ala Lys Arg Trp Ile Ile Leu Gly Leu Asn Lys
    450                 455                 460

Ile Val Arg Met Tyr Ser Pro Thr Ser Ile Ala Ala Lys Tyr Val Asp
465                 470                 475                 480

Arg Phe Tyr Lys Thr Leu Arg Ala Glu Gln Ala Ala Gly Leu Glu Glu
                485                 490                 495

Met Met Thr Ala Cys Gln Gly Val Gly Gly Pro Gly His Lys Ala Ala
            500                 505                 510

Ile Ser Pro Arg Thr Leu Asn Ala Trp Val Lys Val Gly Ser Glu Phe
        515                 520                 525

Thr Leu Ile Pro Ile Ala Val Gly Gly Ala Leu Ala Gly Leu Val Leu
    530                 535                 540

Ile Val Leu Ile Ala Tyr Leu Val Gly Arg Lys Arg Ser His Ala Gly
545                 550                 555                 560

Tyr Gln Thr Ile
```

<210> SEQ ID NO 24
<211> LENGTH: 4506
<212> TYPE: DNA
<213> ORGANISM: Artificial Sequence
<220> FEATURE:
<223> OTHER INFORMATION: synthetic GM-CSF signal peptide (SP) fusion
protein with p24CE2 (Core2) vaccine construct,
SP-p24CE2 encoded by plasmid 235H

<400> SEQUENCE: 24
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420
ggcagtacat ctacgtatta gtcatcgcta ttaccatggt gatgcggttt tggcagtaca 480
tcaatgggcg tggatagcgg tttgactcac ggggatttcc aagtctccac cccattgacg 540
tcaatgggag tttgttttgg caccaaaatc aacgggactt tccaaaatgt cgtaacaact 600
ccgccccatt gacgcaaatg ggcggtaggc gtgtacggtg ggaggtctat ataagcagag 660
ctcgtttagt gaaccgtcag atcgcctgga gacgccatcc acgctgtttt gacctccata 720
gaagacaccg ggaccgatcc agcctccgcg ggcgcgcgtc gacaagaaat gtggctccag 780
agcctgctac tcctggggac ggtggcctgc agcatctcgg tcatcccgat gttcacggcg 840
ctcagcgagg gagcgacgcc gcaggacctg aacgcggccg tcggaggtca ccaggcagcg 900
atgcagatgc tgaaggagac gatcaacgag gaggcggccg agtgggaccg ggcggcagcc 960
gagccacgcg gttccgacat cgcgggcacc acctcgacgc tccaggagca gatcgcgtgg 1020
gccgcagcta agcgctggat catcctcggg ctgaacaaga tcgtccggat gtacagcccg 1080
gtctcgatcg ctgctaagta cgttgaccgg ttcttcaaga ccctgagggc cgagcaggcg 1140
gccggactgg aggagatgat gaccgcgtgc caggggggtcg gtggaccatc gcacaaggcc 1200
gcgctctcgc cgcgcacgct gaacgcgtgg gtgaaggtct gataagaatt cgcggatatc 1260
ggttaacgga tccagatctg ctgtgccttc tagttgccag ccatctgttg tttgcccctc 1320
ccccgtgcct tccttgaccc tggaaggtgc cactcccact gtcctttcct aataaaatga 1380
ggaaattgca tcgcattgtc tgagtaggtg tcattctatt ctggggggtg gggtggggca 1440
ggacagcaag ggggaggatt gggaagacaa tagcaggcat gctggggatg cggtgggctc 1500
tatgggtacc caggtgctga agaattgacc cggttcctcc tgggccagaa agaagcaggc 1560
acatcccctt ctctgtgaca caccctgtcc acgcccctgg ttcttagttc cagccccact 1620
cataggacac tcatagctca ggagggctcc gccttcaatc ccacccgcta aagtacttgg 1680
agcggtctct ccctccctca tcagcccacc aaaccaaacc tagcctccaa gagtgggaag 1740
aaattaaagc aagataggct attaagtgca gagggagaga aaatgcctcc aacatgtgag 1800
gaagtaatga gagaaatcat agaatttctt ccgcttcctc gctcactgac tcgctgcgct 1860
cggtcgttcg gctgcggcga gcggtatcag ctcactcaaa ggcggtaata cggttatcca 1920
cagaatcagg ggataacgca ggaaagaaca tgtgagcaaa aggccagcaa aaggccagga 1980
accgtaaaaa ggccgcgttg ctggcgtttt tccataggct ccgcccccct gacgagcatc 2040

-continued acaaaaatcg acgctcaagt cagaggtggc gaaacccgac aggactataa agataccagg 2100
cgtttccccc tggaagctcc ctcgtgcgct ctcctgttcc gaccctgccg cttaccggat 2160
acctgtccgc ctttctccct tcgggaagcg tggcgctttc tcatagctca cgctgtaggt 2220
atctcagttc ggtgtaggtc gttcgctcca agctgggctg tgtgcacgaa ccccccgttc 2280
agcccgaccg ctgcgcctta tccggtaact atcgtcttga gtccaacccg gtaagacacg 2340
acttatcgcc actggcagca gccactggta acaggattag cagagcgagg tatgtaggcg 2400
gtgctacaga gttcttgaag tggtggccta actacggcta cactagaaga acagtatttg 2460
gtatctgcgc tctgctgaag ccagttacct tcggaaaaag agttggtagc tcttgatccg 2520
gcaaacaaac caccgctggt agcggtggtt tttttgtttg caagcagcag attacgcgca 2580
gaaaaaaagg atctcaagaa gatcctttga tcttttctac ggggtctgac gctcagtgga 2640
acgaaaactc acgttaaggg attttggtca tgagattatc aaaaaggatc ttcacctaga 2700
tccttttaaa ttaaaaatga agttttaaat caatctaaag tatatatgag taaacttggt 2760
ctgacagtta ccaatgctta atcagtgagg cacctatctc agcgatctgt ctatttcgtt 2820
catccatagt tgcctgactc gggggggggg ggcgctgagg tctgcctcgt gaagaaggtg 2880
ttgctgactc ataccaggcc tgaatcgccc catcatccag ccagaaagtg agggagccac 2940
ggttgatgag agctttgttg taggtggacc agttggtgat tttgaacttt tgctttgcca 3000
cggaacggtc tgcgttgtcg ggaagatgcg tgatctgatc cttcaactca gcaaaagttc 3060
gatttattca acaaagccgc cgtcccgtca agtcagcgta atgctctgcc agtgttacaa 3120
ccaattaacc aattctgatt agaaaaactc atcgagcatc aaatgaaact gcaatttatt 3180
catatcagga ttatcaatac catatttttg aaaaagccgt ttctgtaatg aaggagaaaa 3240
ctcaccgagg cagttccata ggatggcaag atcctggtat cggtctgcga ttccgactcg 3300
tccaacatca atacaaccta ttaatttccc ctcgtcaaaa ataaggttat caagtgagaa 3360
atcaccatga gtgacgactg aatccggtga gaatggcaaa agcttatgca tttctttcca 3420
gacttgttca acaggccagc cattacgctc gtcatcaaaa tcactcgcat caaccaaacc 3480
gttattcatt cgtgattgcg cctgagcgag acgaaatacg cgatcgctgt taaaaggaca 3540
attacaaaca ggaatcgaat gcaaccggcg caggaacact gccagcgcat caacaatatt 3600
ttcacctgaa tcaggatatt cttctaatac ctggaatgct gttttcccgg ggatcgcagt 3660
ggtgagtaac catgcatcat caggagtacg gataaaatgc ttgatggtcg gaagaggcat 3720
aaattccgtc agccagttta gtctgaccat ctcatctgta acatcattgg caacgctacc 3780
tttgccatgt ttcagaaaca actctggcgc atcgggcttc ccatacaatc gatagattgt 3840
cgcacctgat tgcccgacat tatcgcgagc ccatttatac ccatataaat cagcatccat 3900
gttggaattt aatcgcggcc tcgagcaaga cgtttcccgt tgaatatggc tcataacacc 3960
ccttgtatta ctgtttatgt aagcagacag ttttattgtt catgatgata tatttttatc 4020
ttgtgcaatg taacatcaga gattttgaga cacaacgtgg ctttcccccc ccccccatta 4080
ttgaagcatt tatcagggtt attgtctcat gagcggatac atatttgaat gtatttagaa 4140
aaataaacaa ataggggttc cgcgcacatt tccccgaaaa gtgccacctg acgtctaaga 4200
aaccattatt atcatgacat taacctataa aaataggcgt atcacgaggc cctttcgtct 4260
cgcgcgtttc ggtgatgacg gtgaaaacct ctgacacatg cagctcccgg agacggtcac 4320
agcttgtctg taagcggatg ccgggagcag acaagcccgt cagggcgcgt cagcgggtgt 4380
tggcgggtgt cggggctggc ttaactatgc ggcatcagag cagattgtac tgagagtgca 4440
ccatatgcgg tgtgaaatac cgcacagatg cgtaaggaga aaataccgca tcagattggc 4500
tattgg 4506

<210> SEQ ID NO 25
<211> LENGTH: 157
<212> TYPE: PRT
<213> ORGANISM: Artificial Sequence
<220> FEATURE:
<223> OTHER INFORMATION: synthetic GM-CSF signal peptide (SP) fusion protein with p24CE2 (Core2) vaccine construct, SP-p24CE2 encoded by plasmid 235H

<400> SEQUENCE: 25

Met Trp Leu Gln Ser Leu Leu Leu Leu Gly Thr Val Ala Cys Ser Ile
1 5 10 15

Ser Val Ile Pro Met Phe Thr Ala Leu Ser Glu Gly Ala Thr Pro Gln
20 25 30

Asp Leu Asn Ala Ala Val Gly Gly His Gln Ala Ala Met Gln Met Leu
35 40 45

Lys Glu Thr Ile Asn Glu Glu Ala Ala Glu Trp Asp Arg Ala Ala Ala
50 55 60

Glu Pro Arg Gly Ser Asp Ile Ala Gly Thr Thr Ser Thr Leu Gln Glu
65 70 75 80

Gln Ile Ala Trp Ala Ala Ala Lys Arg Trp Ile Ile Leu Gly Leu Asn
85 90 95

Lys Ile Val Arg Met Tyr Ser Pro Val Ser Ile Ala Ala Lys Tyr Val
100 105 110

Asp Arg Phe Phe Lys Thr Leu Arg Ala Glu Gln Ala Ala Gly Leu Glu
115 120 125

Glu Met Met Thr Ala Cys Gln Gly Val Gly Gly Pro Ser His Lys Ala
130 135 140

Ala Leu Ser Pro Arg Thr Leu Asn Ala Trp Val Lys Val
145 150 155

<210> SEQ ID NO 26
<211> LENGTH: 4782
<212> TYPE: DNA
<213> ORGANISM: Artificial Sequence
<220> FEATURE:
<223> OTHER INFORMATION: synthetic monocyte chemoattractant protein 3 (MCP-3) fusion protein with p24CE1 (Core1) vaccine construct, MCP3-p24CE1 encoded by plasmid 230H

<400> SEQUENCE: 26
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420
ggcagtacat ctacgtatta gtcatcgcta ttaccatggt gatgcggttt tggcagtaca 480
tcaatgggcg tggatagcgg tttgactcac ggggatttcc aagtctccac cccattgacg 540
tcaatgggag tttgttttgg caccaaaatc aacgggactt tccaaaatgt cgtaacaact 600

```
ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacaagaaat gtggaagccg    780

atgccctcgc caagcaacat gaaggcgtcc gccgcgctcc tgtgcctgct cctcacggcc    840

gcggctttca gcccccaggg gctcgcgcag ccggtcggga tcaacacgag cacgacctgc    900

tgctaccggt tcatcaacaa gaagatcccg aagcagcgtc tggagagcta ccgccggacc    960

acgtcgagcc actgcccgcg ggaggcggtc atcttcaaga cgaagctgga caaggagatc   1020

tgcgccgacc cgacgcagaa gtgggttcag gacttcatga agcacctgga caagaagacg   1080

cagacgccga agctggtcat cccgatgttc tcggcgctca gcgagggagc gacgccgcag   1140

gacctgaacg cggccgtcgg aggtcaccag gcagcgatgc agatgctgaa ggacacgatc   1200

aacgaggagg cggccgagtg ggaccgggcg gcagccgagc cacgcggttc cgacatcgcg   1260

ggcaccacct cgacgctcca ggagcagatc gggtgggccg cagctaagcg ctggatcatc   1320

ctcgggctga acaagatcgt ccggatgtac agcccgacgt cgatcgctgc taagtacgtt   1380

gaccggttct acaagaccct gagggccgag caggcggccg gactggagga gatgatgacc   1440

gcgtgccagg gggtcggtgg accagggcac aaggccgcga tctcgccgcg cacgctgaac   1500

gcgtgggtga aggtctgata agaattcgcg gatatcggtt aacggatcca gatctgctgt   1560

gccttctagt tgccagccat ctgttgtttg cccctccccc gtgccttcct tgaccctgga   1620

aggtgccact cccactgtcc tttcctaata aaatgaggaa attgcatcgc attgtctgag   1680

taggtgtcat tctattctgg ggggtggggt ggggcaggac agcaaggggg aggattggga   1740

agacaatagc aggcatgctg gggatgcggt gggctctatg ggtacccagg tgctgaagaa   1800

ttgacccggt tcctcctggg ccagaaagaa gcaggcacat ccccttctct gtgacacacc   1860

ctgtccacgc ccctggttct tagttccagc cccactcata ggacactcat agctcaggag   1920

ggctccgcct tcaatcccac ccgctaaagt acttggagcg gtctctccct ccctcatcag   1980

cccaccaaac caaacctagc ctccaagagt gggaagaaat taaagcaaga taggctatta   2040

agtgcagagg gagagaaaat gcctccaaca tgtgaggaag taatgagaga aatcatagaa   2100

tttcttccgc ttcctcgctc actgactcgc tgcgctcggt cgttcggctg cggcgagcgg   2160

tatcagctca ctcaaaggcg gtaatacggt tatccacaga atcaggggat aacgcaggaa   2220

agaacatgtg agcaaaaggc cagcaaaagg ccaggaaccg taaaaaggcc gcgttgctgg   2280

cgtttttcca taggctccgc ccccctgacg agcatcacaa aaatcgacgc tcaagtcaga   2340

ggtggcgaaa cccgacagga ctataaagat accaggcgtt tccccctgga agctccctcg   2400

tgcgctctcc tgttccgacc ctgccgctta ccggatacct gtccgccttt ctcccttcgg   2460

gaagcgtggc gctttctcat agctcacgct gtaggtatct cagttcggtg taggtcgttc   2520

gctccaagct gggctgtgtg cacgaacccc ccgttcagcc cgaccgctgc gccttatccg   2580

gtaactatcg tcttgagtcc aacccggtaa gacacgactt atcgccactg gcagcagcca   2640

ctggtaacag gattagcaga gcgaggtatg taggcggtgc tacagagttc ttgaagtggt   2700

ggcctaacta cggctacact agaagaacag tatttggtat ctgcgctctg ctgaagccag   2760

ttaccttcgg aaaaagagtt ggtagctctt gatccggcaa acaaaccacc gctggtagcg   2820

gtggtttttt tgtttgcaag cagcagatta cgcgcagaaa aaaaggatct caagaagatc   2880

ctttgatctt ttctacgggg tctgacgctc agtggaacga aaactcacgt taagggattt   2940

tggtcatgag attatcaaaa aggatcttca cctagatcct tttaaattaa aaatgaagtt   3000
```

```
ttaaatcaat ctaaagtata tatgagtaaa cttggtctga cagttaccaa tgcttaatca   3060
gtgaggcacc tatctcagcg atctgtctat ttcgttcatc catagttgcc tgactcgggg   3120
ggggggggcg ctgaggtctg cctcgtgaag aaggtgttgc tgactcatac caggcctgaa   3180
tcgccccatc atccagccag aaagtgaggg agccacggtt gatgagagct ttgttgtagg   3240
tggaccagtt ggtgattttg aacttttgct ttgccacgga acggtctgcg ttgtcgggaa   3300
gatgcgtgat ctgatccttc aactcagcaa aagttcgatt tattcaacaa agccgccgtc   3360
ccgtcaagtc agcgtaatgc tctgccagtg ttacaaccaa ttaaccaatt ctgattagaa   3420
aaactcatcg agcatcaaat gaaactgcaa tttattcata tcaggattat caataccata   3480
tttttgaaaa agccgtttct gtaatgaagg agaaaactca ccgaggcagt tccataggat   3540
ggcaagatcc tggtatcggt ctgcgattcc gactcgtcca acatcaatac aacctattaa   3600
tttcccctcg tcaaaaataa ggttatcaag tgagaaatca ccatgagtga cgactgaatc   3660
cggtgagaat ggcaaaagct tatgcatttc tttccagact tgttcaacag gccagccatt   3720
acgctcgtca tcaaaatcac tcgcatcaac caaaccgtta ttcattcgtg attgcgcctg   3780
agcgagacga aatacgcgat cgctgttaaa aggacaatta caaacaggaa tcgaatgcaa   3840
ccggcgcagg aacactgcca gcgcatcaac aatattttca cctgaatcag gatattcttc   3900
taatacctgg aatgctgttt tcccggggat cgcagtggtg agtaaccatg catcatcagg   3960
agtacggata aaatgcttga tggtcggaag aggcataaat tccgtcagcc agtttagtct   4020
gaccatctca tctgtaacat cattggcaac gctacctttg ccatgtttca gaaacaactc   4080
tggcgcatcg ggcttcccat acaatcgata gattgtcgca cctgattgcc cgacattatc   4140
gcgagcccat ttatacccat ataaatcagc atccatgttg gaatttaatc gcggcctcga   4200
gcaagacgtt tcccgttgaa tatggctcat aacacccctt gtattactgt ttatgtaagc   4260
agacagtttt attgttcatg atgatatatt tttatcttgt gcaatgtaac atcagagatt   4320
ttgagacaca acgtggcttt cccccccccc ccattattga agcatttatc agggttattg   4380
tctcatgagc ggatacatat ttgaatgtat ttagaaaaat aaacaaatag gggttccgcg   4440
cacatttccc cgaaaagtgc cacctgacgt ctaagaaacc attattatca tgacattaac   4500
ctataaaaat aggcgtatca cgaggccctt tcgtctcgcg cgtttcggtg atgacggtga   4560
aaacctctga cacatgcagc tcccggagac ggtcacagct tgtctgtaag cggatgccgg   4620
gagcagacaa gcccgtcagg gcgcgtcagc gggtgttggc gggtgtcggg gctggcttaa   4680
ctatgcggca tcagagcaga ttgtactgag agtgcaccat atgcggtgtg aaataccgca   4740
cagatgcgta aggagaaaat accgcatcag attggctatt gg                      4782
```

<210> SEQ ID NO 27
<211> LENGTH: 249
<212> TYPE: PRT
<213> ORGANISM: Artificial Sequence
<220> FEATURE:
<223> OTHER INFORMATION: synthetic monocyte chemoattractant protein 3 (MCP-3) fusion protein with p24CE1 (Core1) vaccine construct, MCP3-p24CE1 encoded by plasmid 230H

<400> SEQUENCE: 27

```
Met Trp Lys Pro Met Pro Ser Pro Ser Asn Met Lys Ala Ser Ala Ala
1               5                   10                  15

Leu Leu Cys Leu Leu Leu Thr Ala Ala Ala Phe Ser Pro Gln Gly Leu
            20                  25                  30
```

-continued

```
Ala Gln Pro Val Gly Ile Asn Thr Ser Thr Thr Cys Cys Tyr Arg Phe
        35                  40                  45

Ile Asn Lys Lys Ile Pro Lys Gln Arg Leu Glu Ser Tyr Arg Arg Thr
    50                  55                  60

Thr Ser Ser His Cys Pro Arg Glu Ala Val Ile Phe Lys Thr Lys Leu
65                  70                  75                  80

Asp Lys Glu Ile Cys Ala Asp Pro Thr Gln Lys Trp Val Gln Asp Phe
                85                  90                  95

Met Lys His Leu Asp Lys Lys Thr Gln Thr Pro Lys Leu Val Ile Pro
            100                 105                 110

Met Phe Ser Ala Leu Ser Glu Gly Ala Thr Pro Gln Asp Leu Asn Ala
        115                 120                 125

Ala Val Gly Gly His Gln Ala Ala Met Gln Met Leu Lys Asp Thr Ile
    130                 135                 140

Asn Glu Glu Ala Ala Glu Trp Asp Arg Ala Ala Ala Glu Pro Arg Gly
145                 150                 155                 160

Ser Asp Ile Ala Gly Thr Thr Ser Thr Leu Gln Glu Gln Ile Gly Trp
                165                 170                 175

Ala Ala Ala Lys Arg Trp Ile Ile Leu Gly Leu Asn Lys Ile Val Arg
            180                 185                 190

Met Tyr Ser Pro Thr Ser Ile Ala Ala Lys Tyr Val Asp Arg Phe Tyr
        195                 200                 205

Lys Thr Leu Arg Ala Glu Gln Ala Ala Gly Leu Glu Glu Met Met Thr
    210                 215                 220

Ala Cys Gln Gly Val Gly Gly Pro Gly His Lys Ala Ala Ile Ser Pro
225                 230                 235                 240

Arg Thr Leu Asn Ala Trp Val Lys Val
                245
```

<210> SEQ ID NO 28
<211> LENGTH: 4782
<212> TYPE: DNA
<213> ORGANISM: Artificial Sequence
<220> FEATURE:
<223> OTHER INFORMATION: synthetic monocyte chemoattractant protein 3 (MCP-3) fusion protein with p24CE2 (Core2) vaccine construct, MCP3-p24CE2 encoded by plasmid 231H

<400> SEQUENCE: 28

```
cctggccatt gcatacgttg tatccatatc ataatatgta catttatatt ggctcatgtc      60

caacattacc gccatgttga cattgattat tgactagtta ttaatagtaa tcaattacgg     120

ggtcattagt tcatagccca tatatggagt tccgcgttac ataacttacg gtaaatggcc     180

cgcctggctg accgcccaac gacccccgcc cattgacgtc aataatgacg tatgttccca     240

tagtaacgcc aatagggact ttccattgac gtcaatgggt ggagtattta cggtaaactg     300

cccacttggc agtacatcaa gtgtatcata tgccaagtac gccccctatt gacgtcaatg     360

atggtaaatg gcccgcctgg cattatgccc agtacatgac cttatgggac tttcctactt     420

ggcagtacat ctacgtatta gtcatcgcta ttaccatggt gatgcggttt tggcagtaca     480

tcaatgggcg tggatagcgg tttgactcac ggggatttcc aagtctccac cccattgacg     540

tcaatgggag tttgttttgg caccaaaatc aacgggactt tccaaaatgt cgtaacaact     600

ccgccccatt gacgcaaatg ggcggtaggc gtgtacggtg ggaggtctat ataagcagag     660

ctcgtttagt gaaccgtcag atcgcctgga gacgccatcc acgctgtttt gacctccata     720

gaagacaccg ggaccgatcc agcctccgcg ggcgcgcgtc gacaagaaat gtggaagccg     780
```

-continued

```
atgccctcgc caagcaacat gaaggcgtcc gccgcgctcc tgtgcctgct cctcacggcc    840
gcggctttca gcccccaggg gctcgcgcag ccggtcggga tcaacacgag cacgacctgc    900
tgctaccggt tcatcaacaa gaagatcccg aagcagcgtc tggagagcta ccgccggacc    960
acgtcgagcc actgcccgcg ggaggcggtc atcttcaaga cgaagctgga caaggagatc   1020
tgcgccgacc cgacgcagaa gtgggttcag gacttcatga agcacctgga caagaagacg   1080
cagacgccga agctggtcat cccgatgttc acggcgctca gcgagggagc gacgccgcag   1140
gacctgaacg cggccgtcgg aggtcaccag gcagcgatgc agatgctgaa ggagacgatc   1200
aacgaggagg cggccgagtg ggaccgggcg gcagccgagc cacgcggttc cgacatcgcg   1260
ggcaccacct cgacgctcca ggagcagatc gcgtgggccg cagctaagcg ctggatcatc   1320
ctcgggctga acaagatcgt ccggatgtac agcccggtct cgatcgctgc taagtacgtt   1380
gaccggttct tcaagaccct gagggccgag caggcggccg gactggagga gatgatgacc   1440
gcgtgccagg gggtcggtgg accatcgcac aaggccgcgc tctcgccgcg cacgctgaac   1500
gcgtgggtga aggtctgata agaattcgcg gatatcggtt aacggatcca gatctgctgt   1560
gccttctagt tgccagccat ctgttgtttg cccctccccc gtgccttcct tgaccctgga   1620
aggtgccact cccactgtcc tttcctaata aaatgaggaa attgcatcgc attgtctgag   1680
taggtgtcat tctattctgg ggggtggggt ggggcaggac agcaaggggg aggattggga   1740
agacaatagc aggcatgctg gggatgcggt gggctctatg ggtacccagg tgctgaagaa   1800
ttgacccggt tcctcctggg ccagaaagaa gcaggcacat ccccttctct gtgacacacc   1860
ctgtccacgc ccctggttct tagttccagc cccactcata ggacactcat agctcaggag   1920
ggctccgcct tcaatcccac ccgctaaagt acttggagcg gtctctccct ccctcatcag   1980
cccaccaaac caaacctagc ctccaagagt gggaagaaat taaagcaaga taggctatta   2040
agtgcagagg gagagaaaat gcctccaaca tgtgaggaag taatgagaga aatcatagaa   2100
tttcttccgc ttcctcgctc actgactcgc tgcgctcggt cgttcggctg cggcgagcgg   2160
tatcagctca ctcaaaggcg gtaatacggt tatccacaga atcaggggat aacgcaggaa   2220
agaacatgtg agcaaaaggc cagcaaaagg ccaggaaccg taaaaaggcc gcgttgctgg   2280
cgtttttcca taggctccgc ccccctgacg agcatcacaa aaatcgacgc tcaagtcaga   2340
ggtggcgaaa cccgacagga ctataaagat accaggcgtt tccccctgga agctccctcg   2400
tgcgctctcc tgttccgacc ctgccgctta ccggatacct gtccgccttt ctcccttcgg   2460
gaagcgtggc gctttctcat agctcacgct gtaggtatct cagttcggtg taggtcgttc   2520
gctccaagct gggctgtgtg cacgaacccc ccgttcagcc cgaccgctgc gccttatccg   2580
gtaactatcg tcttgagtcc aacccggtaa gacacgactt atcgccactg gcagcagcca   2640
ctggtaacag gattagcaga gcgaggtatg taggcggtgc tacagagttc ttgaagtggt   2700
ggcctaacta cggctacact agaagaacag tatttggtat ctgcgctctg ctgaagccag   2760
ttaccttcgg aaaaagagtt ggtagctctt gatccggcaa acaaaccacc gctggtagcg   2820
gtggtttttt tgtttgcaag cagcagatta cgcgcagaaa aaaaggatct caagaagatc   2880
ctttgatctt ttctacgggg tctgacgctc agtggaacga aaactcacgt taagggattt   2940
tggtcatgag attatcaaaa aggatcttca cctagatcct tttaaattaa aaatgaagtt   3000
ttaaatcaat ctaaagtata tatgagtaaa cttggtctga cagttaccaa tgcttaatca   3060
gtgaggcacc tatctcagcg atctgtctat ttcgttcatc catagttgcc tgactcgggg   3120
```

-continued

```
ggggggggcg ctgaggtctg cctcgtgaag aaggtgttgc tgactcatac caggcctgaa   3180

tcgccccatc atccagccag aaagtgaggg agccacggtt gatgagagct ttgttgtagg   3240

tggaccagtt ggtgattttg aacttttgct ttgccacgga acggtctgcg ttgtcgggaa   3300

gatgcgtgat ctgatccttc aactcagcaa aagttcgatt tattcaacaa agccgccgtc   3360

ccgtcaagtc agcgtaatgc tctgccagtg ttacaaccaa ttaaccaatt ctgattagaa   3420

aaactcatcg agcatcaaat gaaactgcaa tttattcata tcaggattat caataccata   3480

tttttgaaaa agccgtttct gtaatgaagg agaaaactca ccgaggcagt tccataggat   3540

ggcaagatcc tggtatcggt ctgcgattcc gactcgtcca acatcaatac aacctattaa   3600

tttcccctcg tcaaaaataa ggttatcaag tgagaaatca ccatgagtga cgactgaatc   3660

cggtgagaat ggcaaaagct tatgcatttc tttccagact tgttcaacag gccagccatt   3720

acgctcgtca tcaaaatcac tcgcatcaac caaaccgtta ttcattcgtg attgcgcctg   3780

agcgagacga aatacgcgat cgctgttaaa aggacaatta caaacaggaa tcgaatgcaa   3840

ccggcgcagg aacactgcca gcgcatcaac aatattttca cctgaatcag gatattcttc   3900

taatacctgg aatgctgttt tcccggggat cgcagtggtg agtaaccatg catcatcagg   3960

agtacggata aaatgcttga tggtcggaag aggcataaat tccgtcagcc agtttagtct   4020

gaccatctca tctgtaacat cattggcaac gctacctttg ccatgtttca gaaacaactc   4080

tggcgcatcg ggcttcccat acaatcgata gattgtcgca cctgattgcc cgacattatc   4140

gcgagcccat ttatacccat ataaatcagc atccatgttg gaatttaatc gcggcctcga   4200

gcaagacgtt tcccgttgaa tatggctcat aacacccctt gtattactgt ttatgtaagc   4260

agacagtttt attgttcatg atgatatatt tttatcttgt gcaatgtaac atcagagatt   4320

ttgagacaca acgtggcttt cccccccccc ccattattga agcatttatc agggttattg   4380

tctcatgagc ggatacatat ttgaatgtat ttagaaaaat aaacaaatag gggttccgcg   4440

cacatttccc cgaaaagtgc cacctgacgt ctaagaaacc attattatca tgacattaac   4500

ctataaaaat aggcgtatca cgaggccctt tcgtctcgcg cgtttcggtg atgacggtga   4560

aaacctctga cacatgcagc tcccggagac ggtcacagct tgtctgtaag cggatgccgg   4620

gagcagacaa gcccgtcagg gcgcgtcagc gggtgttggc gggtgtcggg gctggcttaa   4680

ctatgcggca tcagagcaga ttgtactgag agtgcaccat atgcggtgtg aaataccgca   4740

cagatgcgta aggagaaaat accgcatcag attggctatt gg                      4782
```

<210> SEQ ID NO 29
<211> LENGTH: 249
<212> TYPE: PRT
<213> ORGANISM: Artificial Sequence
<220> FEATURE:
<223> OTHER INFORMATION: synthetic monocyte chemoattractant protein 3 (MCP-3) fusion protein with p24CE2 (Core2) vaccine construct, MCP3-p24CE2 encoded by plasmid 231H

<400> SEQUENCE: 29

```
Met Trp Lys Pro Met Pro Ser Pro Ser Asn Met Lys Ala Ser Ala Ala
1               5                   10                  15

Leu Leu Cys Leu Leu Leu Thr Ala Ala Ala Phe Ser Pro Gln Gly Leu
            20                  25                  30

Ala Gln Pro Val Gly Ile Asn Thr Ser Thr Thr Cys Cys Tyr Arg Phe
        35                  40                  45

Ile Asn Lys Lys Ile Pro Lys Gln Arg Leu Glu Ser Tyr Arg Arg Thr
    50                  55                  60
```

```
Thr Ser Ser His Cys Pro Arg Glu Ala Val Ile Phe Lys Thr Lys Leu
65                  70                  75                  80

Asp Lys Glu Ile Cys Ala Asp Pro Thr Gln Lys Trp Val Gln Asp Phe
                85                  90                  95

Met Lys His Leu Asp Lys Lys Thr Gln Thr Pro Lys Leu Val Ile Pro
            100                 105                 110

Met Phe Thr Ala Leu Ser Glu Gly Ala Thr Pro Gln Asp Leu Asn Ala
        115                 120                 125

Ala Val Gly Gly His Gln Ala Ala Met Gln Met Leu Lys Glu Thr Ile
    130                 135                 140

Asn Glu Glu Ala Ala Glu Trp Asp Arg Ala Ala Ala Glu Pro Arg Gly
145                 150                 155                 160

Ser Asp Ile Ala Gly Thr Thr Ser Thr Leu Gln Glu Gln Ile Ala Trp
                165                 170                 175

Ala Ala Ala Lys Arg Trp Ile Ile Leu Gly Leu Asn Lys Ile Val Arg
            180                 185                 190

Met Tyr Ser Pro Val Ser Ile Ala Ala Lys Tyr Val Asp Arg Phe Phe
        195                 200                 205

Lys Thr Leu Arg Ala Glu Gln Ala Ala Gly Leu Glu Glu Met Met Thr
    210                 215                 220

Ala Cys Gln Gly Val Gly Gly Pro Ser His Lys Ala Ala Leu Ser Pro
225                 230                 235                 240

Arg Thr Leu Asn Ala Trp Val Lys Val
                245
```

<210> SEQ ID NO 30
<211> LENGTH: 501
<212> TYPE: DNA
<213> ORGANISM: Artificial Sequence
<220> FEATURE:
<223> OTHER INFORMATION: synthetic GM-CSF signal peptide (SP) fusion protein with p24CE1c alternative conserved element vaccine construct, SP-p24CE1c configuration CE 8-9-3-4-5-6

<400> SEQUENCE: 30

```
atgtggctcc agagcctgct actcctgggg acggtggcct gcagcatctc gcaggggcag      60

atggtccacc aggcgatctc gccgcgcacg ctgaacgcgt gggtgaaggt cctggcgaag     120

gaggagaagg cgttcagccc ggaggtcatc ccgatgttct cggcgctcag cgagggagcg     180

acgccgcagg acctgaacgc ggccaaggtc ggaggtcacc aggcagcgat gcagatgctg     240

aaggagacga tcaacgagga ggcggccgag tgggaccggg cggcagccga gccacgcggt     300

tccgacatcg cgggcaccac ctcgacgctc caggagcaga tcgggtgggc cgcagctaag     360

cgctggatca tcctcgggct gaacaagatc gtccggatgt acagcccgac gtcgatcgct     420

gctaaatacg ttgaccggtt ctacaagacc ctgagggccg agcaggcgga ttacaaggac     480

gatgacgaca agctgtgata a                                               501
```

<210> SEQ ID NO 31
<211> LENGTH: 165
<212> TYPE: PRT
<213> ORGANISM: Artificial Sequence
<220> FEATURE:
<223> OTHER INFORMATION: synthetic GM-CSF signal peptide (SP) fusion protein with p24CE1c alternative conserved element vaccine construct, SP-p24CE1c configuration CE 8-9-3-4-5-6

<400> SEQUENCE: 31

```
Met Trp Leu Gln Ser Leu Leu Leu Leu Gly Thr Val Ala Cys Ser Ile
1               5                   10                  15

Ser Gln Gly Gln Met Val His Gln Ala Ile Ser Pro Arg Thr Leu Asn
            20                  25                  30

Ala Trp Val Lys Val Leu Ala Lys Glu Glu Lys Ala Phe Ser Pro Glu
        35                  40                  45

Val Ile Pro Met Phe Ser Ala Leu Ser Glu Gly Ala Thr Pro Gln Asp
    50                  55                  60

Leu Asn Ala Ala Lys Val Gly Gly His Gln Ala Ala Met Gln Met Leu
65                  70                  75                  80

Lys Glu Thr Ile Asn Glu Glu Ala Ala Glu Trp Asp Arg Ala Ala Ala
                85                  90                  95

Glu Pro Arg Gly Ser Asp Ile Ala Gly Thr Thr Ser Thr Leu Gln Glu
            100                 105                 110

Gln Ile Gly Trp Ala Ala Ala Lys Arg Trp Ile Ile Leu Gly Leu Asn
        115                 120                 125

Lys Ile Val Arg Met Tyr Ser Pro Thr Ser Ile Ala Ala Lys Tyr Val
    130                 135                 140

Asp Arg Phe Tyr Lys Thr Leu Arg Ala Glu Gln Ala Asp Tyr Lys Asp
145                 150                 155                 160

Asp Asp Asp Lys Leu
                165
```

<210> SEQ ID NO 32
<211> LENGTH: 20
<212> TYPE: PRT
<213> ORGANISM: Artificial Sequence
<220> FEATURE:
<223> OTHER INFORMATION: synthetic HIV-1 p24 gag conserved element 8 (CE8) for p24CE1c alternative conserved element vaccine

<400> SEQUENCE: 32

```
Gln Gly Gln Met Val His Gln Ala Ile Ser Pro Arg Thr Leu Asn Ala
1               5                   10                  15

Trp Val Lys Val
            20
```

<210> SEQ ID NO 33
<211> LENGTH: 26
<212> TYPE: PRT
<213> ORGANISM: Artificial Sequence
<220> FEATURE:
<223> OTHER INFORMATION: synthetic HIV-1 p24 gag conserved element 9 (CE9) for p24CE1c alternative conserved element vaccine

<400> SEQUENCE: 33

```
Glu Glu Lys Ala Phe Ser Pro Glu Val Ile Pro Met Phe Ser Ala Leu
1               5                   10                  15

Ser Glu Gly Ala Thr Pro Gln Asp Leu Asn
            20                  25
```

<210> SEQ ID NO 34
<211> LENGTH: 474
<212> TYPE: DNA
<213> ORGANISM: Artificial Sequence
<220> FEATURE:
<223> OTHER INFORMATION: synthetic GM-CSF signal peptide (SP) fusion protein with p24CE2c alternative conserved element vaccine construct, SP-p24CE2c configuration CE 8-9-3-4-5-6

<400> SEQUENCE: 34
atgtggctcc agagcctgct actcctgggg acggtggcct gcagcatctc gcaggggcag 60
atggtccacc aggcgctgtc gccgcgcacg ctgaacgcgt gggtgaaggt cctggcgaag 120
gaggagaagg ggttcaaccc ggaggtcatc ccgatgttca cggcgctcag cgagggagcg 180
acgccgcagg acctgaacgc ggccaaggtc ggaggtcacc aggcagcgat gcagatgctg 240
aaggacacga tcaacgagga ggcggccgag tgggaccggg cggcagccga gccacgcggt 300
tccgacatcg cgggcaccac ctcgacgctc caggagcaga tcgcgtgggc cgcagctaag 360
cgctggatca tcctcgggct gaacaagatc gtccggatgt acagcccggt ctcgatcgct 420
gctaaatacg ttgaccggtt cttcaagacc ctgagggccg agcaggcgtg ataa 474

<210> SEQ ID NO 35
<211> LENGTH: 156
<212> TYPE: PRT
<213> ORGANISM: Artificial Sequence
<220> FEATURE:
<223> OTHER INFORMATION: synthetic GM-CSF signal peptide (SP) fusion protein with p24CE2c alternative conserved element vaccine construct, SP-p24CE2c configuration CE 8-9-3-4-5-6

<400> SEQUENCE: 35

```
Met Trp Leu Gln Ser Leu Leu Leu Leu Gly Thr Val Ala Cys Ser Ile
1               5                   10                  15

Ser Gln Gly Gln Met Val His Gln Ala Leu Ser Pro Arg Thr Leu Asn
            20                  25                  30

Ala Trp Val Lys Val Leu Ala Lys Glu Glu Lys Gly Phe Asn Pro Glu
        35                  40                  45

Val Ile Pro Met Phe Thr Ala Leu Ser Glu Gly Ala Thr Pro Gln Asp
    50                  55                  60

Leu Asn Ala Ala Lys Val Gly Gly His Gln Ala Ala Met Gln Met Leu
65                  70                  75                  80

Lys Asp Thr Ile Asn Glu Glu Ala Ala Glu Trp Asp Arg Ala Ala Ala
                85                  90                  95

Glu Pro Arg Gly Ser Asp Ile Ala Gly Thr Thr Ser Thr Leu Gln Glu
            100                 105                 110

Gln Ile Ala Trp Ala Ala Ala Lys Arg Trp Ile Ile Leu Gly Leu Asn
        115                 120                 125

Lys Ile Val Arg Met Tyr Ser Pro Val Ser Ile Ala Ala Lys Tyr Val
    130                 135                 140

Asp Arg Phe Phe Lys Thr Leu Arg Ala Glu Gln Ala
145                 150                 155
```

<210> SEQ ID NO 36
<211> LENGTH: 471
<212> TYPE: DNA
<213> ORGANISM: Artificial Sequence
<220> FEATURE:
<223> OTHER INFORMATION: synthetic GM-CSF signal peptide (SP) fusion protein with p24CE2d alternative conserved element vaccine construct, SP-p24CE2d configuration CE 9-3-4-5-6-8

<400> SEQUENCE: 36
atgtggctcc agagcctgct actcctgggg acggtggcct gcagcatctc ggaggagaag 60
gggttcaacc cggaggtcat cccgatgttc acggcgctca gcgagggagc gacgccgcag 120
gacctgaacg cggccaaggt cggaggtcac caggcagcga tgcagatgct gaaggacacg 180

-continued

```
atcaacgagg aggcggccga gtgggaccgg gcggcagccg agccacgcgg ttccgacatc    240

gcgggcacca cctcgacgct ccaggagcag atcgcgtggg ccgcagctaa gcgctggatc    300

atcctcgggc tgaacaagat cgtccggatg tacagcccgg tctcgatcgc tgctaaatac    360

gttgaccggt tcttcaagac cctgagggcc gagcaggcgg cgctgcaggg gcagatggtc    420

caccaggcgc tgtcgccgcg cacgctgaac gcgtgggtga aggtctgata a             471
```

<210> SEQ ID NO 37
<211> LENGTH: 155
<212> TYPE: PRT
<213> ORGANISM: Artificial Sequence
<220> FEATURE:
<223> OTHER INFORMATION: synthetic GM-CSF signal peptide (SP) fusion protein with p24CE2d alternative conserved element vaccine construct, SP-p24CE2d configuration CE 9-3-4-5-6-8

<400> SEQUENCE: 37

```
Met Trp Leu Gln Ser Leu Leu Leu Leu Gly Thr Val Ala Cys Ser Ile
1               5                   10                  15

Ser Glu Glu Lys Gly Phe Asn Pro Glu Val Ile Pro Met Phe Thr Ala
            20                  25                  30

Leu Ser Glu Gly Ala Thr Pro Gln Asp Leu Asn Ala Ala Lys Val Gly
        35                  40                  45

Gly His Gln Ala Ala Met Gln Met Leu Lys Asp Thr Ile Asn Glu Glu
    50                  55                  60

Ala Ala Glu Trp Asp Arg Ala Ala Ala Glu Pro Arg Gly Ser Asp Ile
65                  70                  75                  80

Ala Gly Thr Thr Ser Thr Leu Gln Glu Gln Ile Ala Trp Ala Ala Ala
                85                  90                  95

Lys Arg Trp Ile Ile Leu Gly Leu Asn Lys Ile Val Arg Met Tyr Ser
            100                 105                 110

Pro Val Ser Ile Ala Ala Lys Tyr Val Asp Arg Phe Phe Lys Thr Leu
        115                 120                 125

Arg Ala Glu Gln Ala Ala Leu Gln Gly Gln Met Val His Gln Ala Leu
    130                 135                 140

Ser Pro Arg Thr Leu Asn Ala Trp Val Lys Val
145                 150                 155
```

<210> SEQ ID NO 38
<211> LENGTH: 471
<212> TYPE: DNA
<213> ORGANISM: Artificial Sequence
<220> FEATURE:
<223> OTHER INFORMATION: synthetic GM-CSF signal peptide (SP) fusion protein with p24CE1d alternative conserved element vaccine construct, SP-p24CE2d configuration CE 9-3-4-5-6-8

<400> SEQUENCE: 38

```
atgtggctcc agagcctgct actcctgggg acggtggcct gcagcatctc ggaggagaag     60

gcgttcagcc cggaggtcat cccgatgttc tcggcgctca gcgagggagc gacgccgcag    120

gacctgaacg cggccaaggt cggaggtcac caggcagcga tgcagatgct gaaggagacg    180

atcaacgagg aggcggccga gtgggaccgg gcggcagccg agccacgcgg ttccgacatc    240

gcgggcacca cctcgacgct ccaggagcag atcgggtggg ccgcagctaa gcgctggatc    300

atcctcgggc tgaacaagat cgtccggatg tacagcccga cgtcgatcgc tgctaaatac    360

gttgaccggt tctacaagac cctgagggcc gagcaggcgg cgctgcaggg gcagatggtc    420

caccaggcga tctcgccgcg cacgctgaac gcgtgggtga aggtctgata a             471
```

<210> SEQ ID NO 39
<211> LENGTH: 155
<212> TYPE: PRT
<213> ORGANISM: Artificial Sequence
<220> FEATURE:
<223> OTHER INFORMATION: synthetic GM-CSF signal peptide (SP) fusion protein with p24CE1d alternative conserved element vaccine construct, SP-p24CE2d configuration CE 9-3-4-5-6-8

<400> SEQUENCE: 39

Met Trp Leu Gln Ser Leu Leu Leu Leu Gly Thr Val Ala Cys Ser Ile
1 5 10 15

Ser Glu Glu Lys Ala Phe Ser Pro Glu Val Ile Pro Met Phe Ser Ala
20 25 30

Leu Ser Glu Gly Ala Thr Pro Gln Asp Leu Asn Ala Ala Lys Val Gly
35 40 45

Gly His Gln Ala Ala Met Gln Met Leu Lys Glu Thr Ile Asn Glu Glu
50 55 60

Ala Ala Glu Trp Asp Arg Ala Ala Ala Glu Pro Arg Gly Ser Asp Ile
65 70 75 80

Ala Gly Thr Thr Ser Thr Leu Gln Glu Gln Ile Gly Trp Ala Ala Ala
85 90 95

Lys Arg Trp Ile Ile Leu Gly Leu Asn Lys Ile Val Arg Met Tyr Ser
100 105 110

Pro Thr Ser Ile Ala Ala Lys Tyr Val Asp Arg Phe Tyr Lys Thr Leu
115 120 125

Arg Ala Glu Gln Ala Ala Leu Gln Gly Gln Met Val His Gln Ala Ile
130 135 140

Ser Pro Arg Thr Leu Asn Ala Trp Val Lys Val
145 150 155

<210> SEQ ID NO 40
<211> LENGTH: 20
<212> TYPE: PRT
<213> ORGANISM: Artificial Sequence
<220> FEATURE:
<223> OTHER INFORMATION: synthetic HIV-1 p24 gag conserved element 8 (CE8) variant for CE2 constructs in conserved element vaccine

<400> SEQUENCE: 40

Gln Gly Gln Met Val His Gln Ala Leu Ser Pro Arg Thr Leu Asn Ala
1 5 10 15

Trp Val Lys Val
20

<210> SEQ ID NO 41
<211> LENGTH: 26
<212> TYPE: PRT
<213> ORGANISM: Artificial Sequence
<220> FEATURE:
<223> OTHER INFORMATION: synthetic HIV-1 p24 gag conserved element 9 (CE9) variant for CE2 constructs in conserved element vaccine

<400> SEQUENCE: 41

Glu Glu Lys Gly Phe Asn Pro Glu Val Ile Pro Met Phe Thr Ala Leu
1 5 10 15

Ser Glu Gly Ala Thr Pro Gln Asp Leu Asn
20 25

<210> SEQ ID NO 42
<211> LENGTH: 4
<212> TYPE: PRT
<213> ORGANISM: Artificial Sequence
<220> FEATURE:
<223> OTHER INFORMATION: synthetic short alanine linker

<400> SEQUENCE: 42

Ala Ala Ala Glu
1

<210> SEQ ID NO 43
<211> LENGTH: 4
<212> TYPE: PRT
<213> ORGANISM: Artificial Sequence
<220> FEATURE:
<223> OTHER INFORMATION: synthetic short alanine linker

<400> SEQUENCE: 43

Ala Ala Ala Ala
1

<210> SEQ ID NO 44
<211> LENGTH: 5
<212> TYPE: PRT
<213> ORGANISM: Artificial Sequence
<220> FEATURE:
<223> OTHER INFORMATION: synthetic short alanine linker

<400> SEQUENCE: 44

Ala Ala Ala Ala Leu
1 5

<210> SEQ ID NO 45
<211> LENGTH: 9
<212> TYPE: PRT
<213> ORGANISM: Artificial Sequence
<220> FEATURE:
<223> OTHER INFORMATION: synthetic p55 gag T cell response immunodominant epitope

<400> SEQUENCE: 45

Ala Met Gln Met Leu Lys Glu Thr Ile
1 5

<210> SEQ ID NO 46
<211> LENGTH: 139
<212> TYPE: PRT
<213> ORGANISM: Artificial Sequence
<220> FEATURE:
<223> OTHER INFORMATION: synthetic p24CE1c alternative conserved element vaccine construct, configuration CE 8-9-3-4-5-6

<400> SEQUENCE: 46

Gln Gly Gln Met Val His Gln Ala Ile Ser Pro Arg Thr Leu Asn Ala
1 5 10 15

Trp Val Lys Val Leu Ala Lys Glu Glu Lys Ala Phe Ser Pro Glu Val
20 25 30

Ile Pro Met Phe Ser Ala Leu Ser Glu Gly Ala Thr Pro Gln Asp Leu
35 40 45

Asn Ala Ala Lys Val Gly Gly His Gln Ala Ala Met Gln Met Leu Lys
50 55 60

Glu Thr Ile Asn Glu Glu Ala Ala Glu Trp Asp Arg Ala Ala Ala Glu
65 70 75 80

```
Pro Arg Gly Ser Asp Ile Ala Gly Thr Thr Ser Thr Leu Gln Glu Gln
                85                  90                  95

Ile Gly Trp Ala Ala Ala Lys Arg Trp Ile Ile Leu Gly Leu Asn Lys
            100                 105                 110

Ile Val Arg Met Tyr Ser Pro Thr Ser Ile Ala Ala Lys Tyr Val Asp
        115                 120                 125

Arg Phe Tyr Lys Thr Leu Arg Ala Glu Gln Ala
    130                 135


<210> SEQ ID NO 47
<211> LENGTH: 139
<212> TYPE: PRT
<213> ORGANISM: Artificial Sequence
<220> FEATURE:
<223> OTHER INFORMATION: synthetic p24CE2c alternative conserved element
      vaccine construct, configuration CE 8-9-3-4-5-6

<400> SEQUENCE: 47

Gln Gly Gln Met Val His Gln Ala Leu Ser Pro Arg Thr Leu Asn Ala
1               5                   10                  15

Trp Val Lys Val Leu Ala Lys Glu Glu Lys Gly Phe Asn Pro Glu Val
            20                  25                  30

Ile Pro Met Phe Thr Ala Leu Ser Glu Gly Ala Thr Pro Gln Asp Leu
        35                  40                  45

Asn Ala Ala Lys Val Gly Gly His Gln Ala Ala Met Gln Met Leu Lys
    50                  55                  60

Asp Thr Ile Asn Glu Glu Ala Ala Glu Trp Asp Arg Ala Ala Ala Glu
65                  70                  75                  80

Pro Arg Gly Ser Asp Ile Ala Gly Thr Thr Ser Thr Leu Gln Glu Gln
                85                  90                  95

Ile Ala Trp Ala Ala Ala Lys Arg Trp Ile Ile Leu Gly Leu Asn Lys
            100                 105                 110

Ile Val Arg Met Tyr Ser Pro Val Ser Ile Ala Ala Lys Tyr Val Asp
        115                 120                 125

Arg Phe Phe Lys Thr Leu Arg Ala Glu Gln Ala
    130                 135


<210> SEQ ID NO 48
<211> LENGTH: 138
<212> TYPE: PRT
<213> ORGANISM: Artificial Sequence
<220> FEATURE:
<223> OTHER INFORMATION: synthetic p24CE1d alternative conserved element
      vaccine construct, configuration CE 9-3-4-5-6-8

<400> SEQUENCE: 48

Glu Glu Lys Ala Phe Ser Pro Glu Val Ile Pro Met Phe Ser Ala Leu
1               5                   10                  15

Ser Glu Gly Ala Thr Pro Gln Asp Leu Asn Ala Ala Lys Val Gly Gly
            20                  25                  30

His Gln Ala Ala Met Gln Met Leu Lys Glu Thr Ile Asn Glu Glu Ala
        35                  40                  45

Ala Glu Trp Asp Arg Ala Ala Ala Glu Pro Arg Gly Ser Asp Ile Ala
    50                  55                  60

Gly Thr Thr Ser Thr Leu Gln Glu Gln Ile Gly Trp Ala Ala Ala Lys
65                  70                  75                  80

Arg Trp Ile Ile Leu Gly Leu Asn Lys Ile Val Arg Met Tyr Ser Pro
                85                  90                  95
```

Thr Ser Ile Ala Ala Lys Tyr Val Asp Arg Phe Tyr Lys Thr Leu Arg
100 105 110

Ala Glu Gln Ala Ala Leu Gln Gly Gln Met Val His Gln Ala Ile Ser
115 120 125

Pro Arg Thr Leu Asn Ala Trp Val Lys Val
130 135

<210> SEQ ID NO 49
<211> LENGTH: 138
<212> TYPE: PRT
<213> ORGANISM: Artificial Sequence
<220> FEATURE:
<223> OTHER INFORMATION: synthetic p24CE2d alternative conserved element vaccine construct, configuration CE 9-3-4-5-6-8

<400> SEQUENCE: 49

Glu Glu Lys Gly Phe Asn Pro Glu Val Ile Pro Met Phe Thr Ala Leu
1 5 10 15

Ser Glu Gly Ala Thr Pro Gln Asp Leu Asn Ala Ala Lys Val Gly Gly
20 25 30

His Gln Ala Ala Met Gln Met Leu Lys Asp Thr Ile Asn Glu Glu Ala
35 40 45

Ala Glu Trp Asp Arg Ala Ala Ala Glu Pro Arg Gly Ser Asp Ile Ala
50 55 60

Gly Thr Thr Ser Thr Leu Gln Glu Gln Ile Ala Trp Ala Ala Ala Lys
65 70 75 80

Arg Trp Ile Ile Leu Gly Leu Asn Lys Ile Val Arg Met Tyr Ser Pro
85 90 95

Val Ser Ile Ala Ala Lys Tyr Val Asp Arg Phe Phe Lys Thr Leu Arg
100 105 110

Ala Glu Gln Ala Ala Leu Gln Gly Gln Met Val His Gln Ala Leu Ser
115 120 125

Pro Arg Thr Leu Asn Ala Trp Val Lys Val
130 135

<210> SEQ ID NO 50
<211> LENGTH: 231
<212> TYPE: PRT
<213> ORGANISM: Artificial Sequence
<220> FEATURE:
<223> OTHER INFORMATION: synthetic HXB2 p24 gag/clade B

<400> SEQUENCE: 50

Pro Ile Val Gln Asn Ile Gln Gly Gln Met Val His Gln Ala Ile Ser
1 5 10 15

Pro Arg Thr Leu Asn Ala Trp Val Lys Val Val Glu Glu Lys Ala Phe
20 25 30

Ser Pro Glu Val Ile Pro Met Phe Ser Ala Leu Ser Glu Gly Ala Thr
35 40 45

Pro Gln Asp Leu Asn Thr Met Leu Asn Thr Val Gly Gly His Gln Ala
50 55 60

Ala Met Gln Met Leu Lys Glu Thr Ile Asn Glu Glu Ala Ala Glu Trp
65 70 75 80

Asp Arg Val His Pro Val His Ala Gly Pro Ile Ala Pro Gly Gln Met
85 90 95

Arg Glu Pro Arg Gly Ser Asp Ile Ala Gly Thr Thr Ser Thr Leu Gln
100 105 110

Glu Gln Ile Gly Trp Met Thr Asn Asn Pro Pro Ile Pro Val Gly Glu
115 120 125

Ile Tyr Lys Arg Trp Ile Ile Leu Gly Leu Asn Lys Ile Val Arg Met
130 135 140

Tyr Ser Pro Thr Ser Ile Leu Asp Ile Arg Gln Gly Pro Lys Glu Pro
145 150 155 160

Phe Arg Asp Tyr Val Asp Arg Phe Tyr Lys Thr Leu Arg Ala Glu Gln
165 170 175

Ala Ser Gln Glu Val Lys Asn Trp Met Thr Glu Thr Leu Leu Val Gln
180 185 190

Asn Ala Asn Pro Asp Cys Lys Thr Ile Leu Lys Ala Leu Gly Pro Ala
195 200 205

Ala Thr Leu Glu Glu Met Met Thr Ala Cys Gln Gly Val Gly Gly Pro
210 215 220

Gly His Lys Ala Arg Val Leu
225 230

<210> SEQ ID NO 51
<211> LENGTH: 231
<212> TYPE: PRT
<213> ORGANISM: Artificial Sequence
<220> FEATURE:
<223> OTHER INFORMATION: synthetic clade B consensus sequence

<400> SEQUENCE: 51

Pro Ile Val Gln Asn Ala Gln Gly Gln Met Val His Gln Ser Leu Ser
1 5 10 15

Pro Arg Thr Leu Asn Ala Trp Val Lys Val Ile Glu Glu Lys Ala Phe
20 25 30

Ser Pro Glu Val Ile Pro Met Phe Ser Ala Leu Ser Glu Gly Ala Thr
35 40 45

Pro Gln Asp Leu Asn Met Met Leu Asn Ile Val Gly Gly His Gln Ala
50 55 60

Ala Met Gln Met Leu Lys Asp Thr Ile Asn Glu Glu Ala Ala Glu Trp
65 70 75 80

Asp Arg Leu His Pro Val His Ala Gly Pro Ile Pro Pro Gly Gln Met
85 90 95

Arg Glu Pro Arg Gly Ser Asp Ile Ala Gly Thr Thr Ser Thr Pro Gln
100 105 110

Glu Gln Ile Gly Trp Met Thr Ser Asn Pro Pro Ile Pro Val Gly Asp
115 120 125

Ile Tyr Lys Arg Trp Ile Ile Leu Gly Leu Asn Lys Ile Val Arg Met
130 135 140

Tyr Ser Pro Val Ser Ile Leu Asp Ile Lys Gln Gly Pro Lys Glu Pro
145 150 155 160

Phe Arg Asp Tyr Val Asp Arg Phe Phe Lys Thr Leu Arg Ala Glu Gln
165 170 175

Ala Thr Gln Asp Val Lys Asn Trp Met Thr Glu Thr Leu Leu Val Gln
180 185 190

Asn Ala Asn Pro Asp Cys Lys Ser Ile Leu Arg Ala Leu Gly Ala Gly
195 200 205

Ala Thr Leu Glu Glu Met Met Thr Ala Cys Gln Gly Val Gly Gly Pro
210 215 220

Gly His Lys Ala Arg Val Leu
225 230

<210> SEQ ID NO 52
<211> LENGTH: 231
<212> TYPE: PRT
<213> ORGANISM: Artificial Sequence
<220> FEATURE:
<223> OTHER INFORMATION: synthetic clade A consensus sequence

<400> SEQUENCE: 52

Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 53
<211> LENGTH: 231
<212> TYPE: PRT
<213> ORGANISM: Artificial Sequence
<220> FEATURE:
<223> OTHER INFORMATION: synthetic clade C consensus sequence

<400> SEQUENCE: 53

Pro Ile Val Gln Asn Leu Gln Gly Gln Met Val His Gln Ala Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Thr Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Ala Pro Gly Gln Met
85 90 95

Arg Glu Pro Arg Gly Ser Asp Ile Ala Gly Thr Thr Ser Thr Leu Gln
100 105 110

Glu Gln Ile Ala Trp Met Thr Ser Asn Pro Pro Val Pro Val Gly Asp
115 120 125

Ile Tyr Lys Arg Trp Ile Ile Leu Gly Leu Asn Lys Ile Val Arg Met
130 135 140

Tyr Ser Pro Val Ser Ile Leu Asp Ile Lys Gln Gly Pro Lys Glu Pro
145 150 155 160

Phe Arg Asp Tyr Val Asp Arg Phe Phe Lys Thr Leu Arg Ala Glu Gln
165 170 175

Ala Thr Gln Asp Val Lys Asn Trp Met Thr Asp Thr Leu Leu Val Gln
180 185 190

Asn Ala Asn Pro Asp Cys Lys Thr Ile Leu Arg Ala Leu Gly Pro Gly
195 200 205

Ala Ser Leu Glu Glu Met Met Thr Ala Cys Gln Gly Val Gly Gly Pro
210 215 220

Ser His Lys Ala Arg Val Leu
225 230

<210> SEQ ID NO 54
<211> LENGTH: 231
<212> TYPE: PRT
<213> ORGANISM: Artificial Sequence
<220> FEATURE:
<223> OTHER INFORMATION: synthetic Group M consensus sequence

<400> SEQUENCE: 54

Pro Ile Val Gln Asn Leu Gln Gly Gln Met Val His Gln Ala Ile Ser
1 5 10 15

Pro Arg Thr Leu Asn Ala Trp Val Lys Val Ile Glu Glu Lys Ala Phe
20 25 30

Ser Pro Glu Val Ile Pro Met Phe Ser Ala Leu Ser Glu Gly Ala Thr
35 40 45

Pro Gln Asp Leu Asn Thr Met Leu Asn Thr Val Gly Gly His Gln Ala
50 55 60

Ala Met Gln Met Leu Lys Asp Thr Ile Asn Glu Glu Ala Ala Glu Trp
65 70 75 80

Asp Arg Leu His Pro Val His Ala Gly Pro Ile Pro Pro Gly Gln Met
85 90 95

Arg Glu Pro Arg Gly Ser Asp Ile Ala Gly Thr Thr Ser Thr Leu Gln
100 105 110

Glu Gln Ile Ala Trp Met Thr Ser Asn Pro Pro Ile Pro Val Gly Glu
115 120 125

Ile Tyr Lys Arg Trp Ile Ile Leu Gly Leu Asn Lys Ile Val Arg Met
130 135 140

Tyr Ser Pro Val Ser Ile Leu Asp Ile Arg Gln Gly Pro Lys Glu Pro
145 150 155 160

Phe Arg Asp Tyr Val Asp Arg Phe Phe Lys Thr Leu Arg Ala Glu Gln
165 170 175

Ala Thr Gln Asp Val Lys Asn Trp Met Thr Asp Thr Leu Leu Val Gln
180 185 190

Asn Ala Asn Pro Asp Cys Lys Thr Ile Leu Lys Ala Leu Gly Pro Gly
195 200 205

```
Ala Thr Leu Glu Glu Met Met Thr Ala Cys Gln Gly Val Gly Gly Pro
    210                 215                 220

Gly His Lys Ala Arg Val Leu
225                 230


<210> SEQ ID NO 55
<211> LENGTH: 231
<212> TYPE: PRT
<213> ORGANISM: Artificial Sequence
<220> FEATURE:
<223> OTHER INFORMATION: synthetic Group M Center-of-Tree (COT-M)
      sequence

<400> SEQUENCE: 55

Pro Ile Val Gln Asn Leu Gln Gly Gln Met Val His Gln Ala Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Ser Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Asp Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu
225                 230


<210> SEQ ID NO 56
<211> LENGTH: 17
<212> TYPE: PRT
<213> ORGANISM: Artificial Sequence
<220> FEATURE:
<223> OTHER INFORMATION: synthetic plasmid 306H peptide

<400> SEQUENCE: 56

Met Trp Leu Gln Ser Leu Leu Leu Leu Gly Thr Val Ala Cys Ser Ile
1               5                   10                  15

Ser
```

<210> SEQ ID NO 57
<211> LENGTH: 140
<212> TYPE: PRT
<213> ORGANISM: Artificial Sequence
<220> FEATURE:
<223> OTHER INFORMATION: synthetic plasmid 306H peptide, p24CE1

<400> SEQUENCE: 57

```
Val Ile Pro Met Phe Ser Ala Leu Ser Glu Gly Ala Thr Pro Gln Asp
1               5                   10                  15

Leu Asn Ala Ala Val Gly Gly His Gln Ala Ala Met Gln Met Leu Lys
            20                  25                  30

Asp Thr Ile Asn Glu Glu Ala Ala Glu Trp Asp Arg Ala Ala Ala Glu
        35                  40                  45

Pro Arg Gly Ser Asp Ile Ala Gly Thr Thr Ser Thr Leu Gln Glu Gln
    50                  55                  60

Ile Gly Trp Ala Ala Ala Lys Arg Trp Ile Ile Leu Gly Leu Asn Lys
65                  70                  75                  80

Ile Val Arg Met Tyr Ser Pro Thr Ser Ile Ala Ala Lys Tyr Val Asp
                85                  90                  95

Arg Phe Tyr Lys Thr Leu Arg Ala Glu Gln Ala Ala Gly Leu Glu Glu
            100                 105                 110

Met Met Thr Ala Cys Gln Gly Val Gly Gly Pro Gly His Lys Ala Ala
        115                 120                 125

Ile Ser Pro Arg Thr Leu Asn Ala Trp Val Lys Val
    130                 135                 140
```

<210> SEQ ID NO 58
<211> LENGTH: 271
<212> TYPE: PRT
<213> ORGANISM: Artificial Sequence
<220> FEATURE:
<223> OTHER INFORMATION: synthetic plasmid 306H, 202H, 191H, 230H, 231H and 235H peptide

<400> SEQUENCE: 58

```
Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175
```

-continued

```
Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270


<210> SEQ ID NO 59
<211> LENGTH: 140
<212> TYPE: PRT
<213> ORGANISM: Artificial Sequence
<220> FEATURE:
<223> OTHER INFORMATION: synthetic plasmid 202H peptide, p24CE2

<400> SEQUENCE: 59

Val Ile Pro Met Phe Thr Ala Leu Ser Glu Gly Ala Thr Pro Gln Asp
1               5                   10                  15

Leu Asn Ala Ala Val Gly Gly His Gln Ala Ala Met Gln Met Leu Lys
            20                  25                  30

Glu Thr Ile Asn Glu Glu Ala Ala Glu Trp Asp Arg Ala Ala Ala Glu
        35                  40                  45

Pro Arg Gly Ser Asp Ile Ala Gly Thr Thr Ser Thr Leu Gln Glu Gln
    50                  55                  60

Ile Ala Trp Ala Ala Ala Lys Arg Trp Ile Ile Leu Gly Leu Asn Lys
65                  70                  75                  80

Ile Val Arg Met Tyr Ser Pro Val Ser Ile Ala Ala Lys Tyr Val Asp
                85                  90                  95

Arg Phe Phe Lys Thr Leu Arg Ala Glu Gln Ala Ala Gly Leu Glu Glu
            100                 105                 110

Met Met Thr Ala Cys Gln Gly Val Gly Gly Pro Ser His Lys Ala Ala
        115                 120                 125

Leu Ser Pro Arg Thr Leu Asn Ala Trp Val Lys Val
    130                 135                 140


<210> SEQ ID NO 60
<211> LENGTH: 36
<212> TYPE: PRT
<213> ORGANISM: Artificial Sequence
<220> FEATURE:
<223> OTHER INFORMATION: synthetic plasmid 202H and 191H peptide

<400> SEQUENCE: 60

Thr Leu Ile Pro Ile Ala Val Gly Gly Ala Leu Ala Gly Leu Val Leu
1               5                   10                  15

Ile Val Leu Ile Ala Tyr Leu Val Gly Arg Lys Arg Ser His Ala Gly
            20                  25                  30

Tyr Gln Thr Ile
        35


<210> SEQ ID NO 61
<211> LENGTH: 380
<212> TYPE: PRT
```

-continued

<213> ORGANISM: Artificial Sequence
<220> FEATURE:
<223> OTHER INFORMATION: synthetic plasmid 191H peptide

<400> SEQUENCE: 61

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser
    370                 375                 380
```

-continued

```
<210> SEQ ID NO 62
<211> LENGTH: 109
<212> TYPE: PRT
<213> ORGANISM: Artificial Sequence
<220> FEATURE:
<223> OTHER INFORMATION: synthetic plasmid 230H and 231H peptide

<400> SEQUENCE: 62

Met Trp Lys Pro Met Pro Ser Pro Ser Asn Met Lys Ala Ser Ala Ala
1               5                   10                  15

Leu Leu Cys Leu Leu Leu Thr Ala Ala Ala Phe Ser Pro Gln Gly Leu
            20                  25                  30

Ala Gln Pro Val Gly Ile Asn Thr Ser Thr Thr Cys Cys Tyr Arg Phe
        35                  40                  45

Ile Asn Lys Lys Ile Pro Lys Gln Arg Leu Glu Ser Tyr Arg Arg Thr
    50                  55                  60

Thr Ser Ser His Cys Pro Arg Glu Ala Val Ile Phe Lys Thr Lys Leu
65                  70                  75                  80

Asp Lys Glu Ile Cys Ala Asp Pro Thr Gln Lys Trp Val Gln Asp Phe
                85                  90                  95

Met Lys His Leu Asp Lys Lys Thr Gln Thr Pro Lys Leu
            100                 105
```

ALTERING THE IMMUNDOMINANCE HIERARCHY USING A DNA VACCINE EXPRESSING CONSERVED REGIONS

CROSS-REFERENCE TO RELATED APPLICATIONS

This application is a division of U.S. application Ser. No. 15/235,430, filed on Aug. 12, 2016, which is a continuation of U.S. application Ser. No. 14/382,281, filed Aug. 29, 2014, now issued as U.S. Pat. No. 9,415,099, which is a National Stage of International Application No. PCT/US2013/028932, filed Mar. 4, 2013, and which claims the benefit of U.S. Provisional Application No. 61/606,265, filed Mar. 2, 2012. Each of the forementioned applications is herein incorporated by reference for all purposes.

REFERENCE TO SEQUENCE LISTING SUBMITTED AS AN ASCII TXT FILE

This application includes a Sequence Listing as a text file named "077867_1152987_606300US_SEQLIST.txt" created Aug. 17, 2019 and containing 104,804 bytes. The material contained in this text file is incorporated by reference in its entirety for all purposes.

BACKGROUND OF THE INVENTION

HIV-1 strains are highly variable and this diversity provides a major challenge for vaccine design. A candidate vaccine should provide protection against most clades of HIV. To address this problem, approaches to maximizing immunological strength and breadth are being explored, including strategies that use consensus, center-of-tree or ancestral sequences, multiple strains or mosaic immunogens, immunogens consisting of known epitopes from the database, and chimeric molecules expressing a selection of the most conserved epitopes from different clades of HIV [1-17, 56, 96].

In addition to sequence diversity, the presence of potential immunodominant epitopes provides another hurdle in the development of effective HIV vaccines. Accumulating evidence indicates that immunodominant epitopes exist, and that they may constitute an impediment for the production of effective universal HIV vaccines [18-31], as subdominant epitopes within HIV proteins have generally been associated with virologic control [19,22]. The use of any gene encompassing a complete protein as immunogen contains variable as well as conserved regions. Since variable sequences can mutate to escape immune responses while retaining function, and can contain immunodominant T cell epitopes, we argue that variable segments should be excluded from the design [32]. Our vaccine approach thus focuses on the induction of immune responses to nearly invariable proteome segments, many of which should be essential for the function of the virus, and the prevention of responses against variable segments and potentially immunodominant "decoy" epitopes [32-34].

The conserved element approach is supported by the following observations: (i) Viral proteins recover ancestral amino acid (AA) states when transmitted to a new host [35], and in the absence of the specific immune responses found in the previous host, they can recover a more fit state [36-38]; (ii) changes in conserved AA of viral proteins can destroy or significantly weaken HIV, indicating a critical role in virus biology [39-42]; (iii) CTL responses against specific viral proteins (e.g., Gag) are associated with relative control of viremia [43-50], and in the case of controllers and long-term non-progressors, high avidity CTLs targeting conserved regions have been identified [34,51]; (iv) immunodominance of some epitopes can obscure or prevent reactivity against other, potentially protective epitopes [52]; (v) some AA segments in viral proteins are conserved throughout a given HIV-1 subtype, the entire group M, and, in some instances, in HIV-2 and SIV [32,53]. Together, these considerations predicted that an HIV vaccine that does not contain variable epitopes, and thus lacks potentially immunodominant decoy epitopes, but instead consists of strictly conserved proteome elements is better fit to induce immune responses able to prevent virus acquisition or virus propagation [32,53]. The conserved elements used in our work differ from those used by others [11,12,16,17,54-56] that were selected using different criteria, as we have focused on both conservation and associations of particular sequences with immune control.

Previous work has been performed using Gag as a prototype vaccine, because Gag-specific T cell responses were found to correlate with control of viremia in clade B and C infected individuals [43,48-50]. Seven highly conserved elements (CE) were identified in HIV-1 $p24^{gag}$ [32,34] (see also FIG. 1A). Indeed, a cross-sectional ex vivo study showed broad recognition of several CE in the context of wide HLA diversity and identified T cell responses of high functional avidity and broad variant reactivity [34], predominantly in controller individuals, suggesting an association between these T-cell responses and HIV control.

The present invention address the need for an improved protocol for inducing an immune response by providing a strategy based on employing DNA constructs encoding conserve elements in conjunction with constructs encoding the substantially full-length protein from which the conserved element vaccine is derived.

BRIEF SUMMARY OF THE INVENTION

The immunogenic regimens of the present invention focus on immune responses to proteome segments important to the function of a protein, e.g., a viral protein such as a lentiviral gag protein, and preclude responses against segments that absorb much of the host immune response, but which can mutate to escape immune responses while retaining function (often referred to in the art as "immunodominant decoys") (32). A conserved element vaccine (CEvac) administered in accordance with the invention has properties of a universal vaccine against a virus, such as a lentivirus, e.g., HIV, and is able to induce immune responses to most or all circulating strains. In one embodiment, the invention provides a method of generating an immune response where the method comprises administering a $p24^{gag}$ DNA vaccine that expresses conserved elements, e.g., from 3 to 7 conserved elements (CE), of HIV-1 $p24^{gag}$ and excludes potential immunodominant or variable regions acting as potential decoy epitopes (32); followed by administration of a DNA vaccine encoding a full-length gag, e.g., $p55^{gag}$.

In some embodiments, the invention provides a method of inducing broad immune response including those direct to the highly conserved elements, the method comprising vaccinating with CEvac DNA and gag DNA either sequentially or by co-immunization where responses are not produced upon vaccination with full-length p55gag immunogen. This vaccination approach overcomes the problem of diversity by generating cross-clade gag-specific immune responses and broadens the p55gag induced T cell and humoral immunity. In some embodiments, the vaccines are delivered as DNA vaccines, e.g., plasmid DNA vaccines. In some embodiments, the vaccines are delivered as adenovirus vaccines or vaccinia virus vaccine, or using another virus vector-based vaccination strategy.

In some embodiments, the invention provides vaccine compositions comprising a nucleic acid encoding six or seven highly conserved elements from p24gag. In some embodiments, the elements encoded by the nucleic acid are arranged collinearly. In some embodiments, the seven elements are separated by alanine linkers for efficient proteolytic cleavage. In some embodiments, DNA vectors are engineered to express the Core proteins (conserved element polypeptides comprising multiple conserved elements) only, to express secreted Core proteins having the N-terminal GM-CSF signal peptide (SPCore) or to express as a core fusion to the monocyte chemoattractant protein 3 (MCP3) chemokine to stabilize the protein expression and enhance secretion of the proteins, or to the lysosomal associated membrane protein 1 (LAMP-1) to direct the proteins to the lysosomal compartment including access to the MHC class II pathway.

In some embodiments, a method of the invention comprises administering a nucleic acid encoding a conserved element from a protein, e.g., a viral protein such as Gag, and a nucleic acid encoding a naturally occurring variant of the conserved element, where the variant differs from the conserved element by 1 amino acid, e.g., where the conserved element is 8 amino acids in length; or has at least 80%, typically at least 90% or greater sequence identity to the conserved element. In some embodiments, the variant may differ from the conserved element by 1, 2, or 3 amino acids. The nucleic acids encoding the conserved element and variant conserved element may be present on the same vector or encoded by different vectors. In some embodiments, the conserved element is from HIV gag. In some embodiments where a nucleic acid encoding a conserved element and a nucleic acid encoding at least one variant conserved element are administered, the conserved element and variant conserved element sequences together account for at least 80%, or at least 90%, typically at least 91%, 92%, 93%, 94%, 95%, 96%, 97%, 98%, or 99% of naturally occurring variants of the protein. In some embodiments, conserved elements immunogens are constructed based on "regional focus", which will account for >80% of clade C HIV-1 or clade B HIV-1. Such an approach, for example, provides more specific vaccines.

The invention thus provides a methods of generating a broad immune response, the method comprising administering a nucleic acid encoding at least three conserved elements, typically at least 4, 5, or 6, or more conserved elements, from a protein of interest, to an individual and administering a nucleic acid encoding the full-length protein to the individual. In some embodiments the conserved element is from a highly diverse viral proteins, e.g., an HIV protein such as HIV gag or env.

In one aspect, the invention provides a method of inducing an immune response in a subject, the method comprising administering a first Gag conserved element nucleic acid that encodes a first Gag conserved element polypeptide ("CE1 polypeptide") that comprises six conserved elements from Gag to the subject, wherein the conserved elements are from different regions of Gag, and further, wherein each conserved element is at least 12 amino acids in length, but less than 30 amino acids in length and the conserved elements are not contiguous; and administering a nucleic acid encoding a full-length Gag protein. In some embodiments, the conserved elements are from HIV-1 p24gag. In some embodiments, the first conserved element polypeptide comprises at least one conserved element that has an amino acid sequence set forth in SEQ ID NOS:1-7, 32, or 33. In some embodiments, the first conserved element polypeptide comprises at least two, three, four five, or six conserved elements that have an amino acid sequence set forth in SEQ ID NOS:1-7, 32, or 33. In one embodiment, the first conserved element polypeptide comprises conserved elements that each have a sequence set forth in SEQ ID NOS: 1-7; or the first conserved element polypeptide comprises conserved elements that each have a sequence set forth in SEQ ID NOS:3-6, 32, and 33.

In some embodiments, the methods of the invention further comprise administering a second Gag conserved element nucleic acid that encodes a second Gag conserved element polypeptide ("CE2 polypeptide") that comprises at least one variant of a conserved element contained in the first Gag conserved element polypeptide, wherein the variant in the 2nd polypeptide differs from the variant in the first polypeptide by 1, 2, or 3 amino acids. Typically, the variant conserved element differs from the conserved element by only 1 amino acid. In some embodiment, the conserved element and variant conserved element each have a sequence set forth in FIG. 1; or FIG. 13. In one embodiment, the first conserved element polypeptide comprises the sequence of SEQ ID NO: 15 and the second Gag conserved element polypeptide comprises the sequence of SEQ ID NO: 16. In some embodiments the first conserved element polypeptide comprises the sequence of p24CE1c and the second conserved element comprises the sequence of p24CE2c as shown in FIG. 13. In some embodiments the first conserved element polypeptide comprises the sequence of p24CE1d and the second conserved element comprises the sequence of p24CE2d as shown in FIG. 13. The first and second Gag conserved element nucleic acids can be administered sequentially or concurrently. In some embodiments, one or more of the conserved element polypeptides comprise a signal peptide, such as GM-CSF or MCP-3. In some embodiments, one or more of the conserved element polypeptides comprise a sequence that targets the protein for degradation, e.g., a LAMP sequence. In some embodiments, the first and second nucleic acid Gag conserved element polypeptides are encoded by the same vector. In some embodiments, the first and second nucleic acid Gag conserved element polypeptides are encoded by different vectors. The nucleic acids encoding the first and second conserved element polypeptides may be administered multiple times. In some embodiments, the nucleic acid encoding the full-length Gag protein is administered after a nucleic acid encoding a conserved element polypeptide, e.g., at least 2 weeks or 4 weeks, or longer after a nucleic acid encoding a conserved element polypeptide.

In a further aspect, the invention provides a method of inducing an immune response to an HIV gag protein, the method comprising (a) administering:

(i) a nucleic acid encoding a polypeptide comprising SEQ ID NO: 15 and a nucleic acid encoding a polypeptide comprising SEQ ID NO: 16 to a subject; or (ii) a nucleic acid encoding a polypeptide comprising p24CE1c as shown in FIG. 13 and a nucleic acid encoding a polypeptide comprising p24CE2c as shown in FIG. 13 to the subject; or (iii) a nucleic acid encoding a polypeptide comprising p24CE1d as shown in FIG. 13 and a nucleic acid encoding a polypeptide comprising p24CE2d as shown in FIG. 13 to the subject; and (b) administering a nucleic acid encoding $p55^{gag}$.

In some embodiments, the nucleic acid pairs set forth in (i), (ii), or (iii) of step (a) are encoded by the same vector. In some embodiments, the polypeptides are fused to a GM-CSF signal peptide. In some embodiments, the nucleic acid encoding p55 gag is administered at least two weeks after step (a).

In a further aspect, the invention provides a method of inducing an immune response to an HIV gag protein, the method comprising administering at least one nucleic acid encoding a conserved element polypeptide comprising a sequence set forth in SEQ ID NO: 18, SEQ ID NO: 19, SEQ ID NO:21, SE ID NO:23, SEQ ID NO:25, SEQ ID NO:27, SEQ ID NO:29, SEQ ID NO:31, SEQ ID NO:35, SEQ ID NO:37, or SEQ ID NO:39 to the patient; and administering a nucleic acid encoding a full-length gag protein. In some embodiments, the full-length gag protein is administered at least 2 weeks after administering the nucleic acid encoding the conserved element polypeptide.

In a further aspect, the invention provides a method of inducing an immune response to a protein of interest, the method comprising administering a nucleic acid encoding a conserved element polypeptide, wherein the conserved elements are from the protein of interest and the polypeptide comprises at least three conserved elements, each of less than 30 amino acids in length where the conserved elements are joined by linkers; followed by administering a nucleic acid encoding the full-length protein, wherein the nucleic acid encoding the full-length protein is administered at least two weeks after the nucleic acid encoding the conserved element polypeptide.

In some embodiments the nucleic acid constructs encoding the conserved element polypeptides and full-length Gag polypeptide are administered intramuscularly by in vivo electroporation.

The graphs show absorbance (optical density, OD) and pooled plasma samples dilutions from mice vaccinated with the different p24CE1 plasmids (top panel), p24CE2 plasmids (middle panel), or $p55^{gag}$ DNA (bottom panel). (B) Humoral responses induced upon SP-p24CE or $p55^{gag}$ DNA vaccination in mice were analyzed by Western immunoblot assays. The membranes contain $p24^{gag}$ protein collected from supernatants of HEK293 cells transfected with 5 μg of the infectious molecular clone pNL4-3 (lane 1) or the p24CE proteins collected from the cell-associated fractions of cells transfected with SP-p24CE1 and SP-p24CE2 plasmids (lanes 2 and 3, respectively). The membranes were probed with plasma (1:5000 dilution) from mice vaccinated with a mixture of SP-p24CE1&2 DNAs (top panel) or $p55^{gag}$ DNA (bottom panel) followed by anti-mouse IgG-HRP labeled antibody and visualized by ECL. (C) Detection of humoral responses to full-length $p55^{gag}$ in mice vaccinated with p24CE or $p55^{gag}$ DNA by Western immunoblot assay. The $p55^{gag}$ proteins were obtained from HEK293 cells transfected with 0.5 μg of RNA/codon optimized plasmids expressing unprocessed $p55^{gag}$ from clades A, B and C or COT-M, respectively. The proteins were resolved on 10% NuPAGE Bis-Tris gels, and the membranes were probed with plasma (dilution 1:200) from mice immunized with DNAs expressing the secreted p24CE proteins SP-p24CE1 (top panel), SP-p24CE2 (middle panel) and $p55^{gag}$ (bottom panel).

Figure 7:
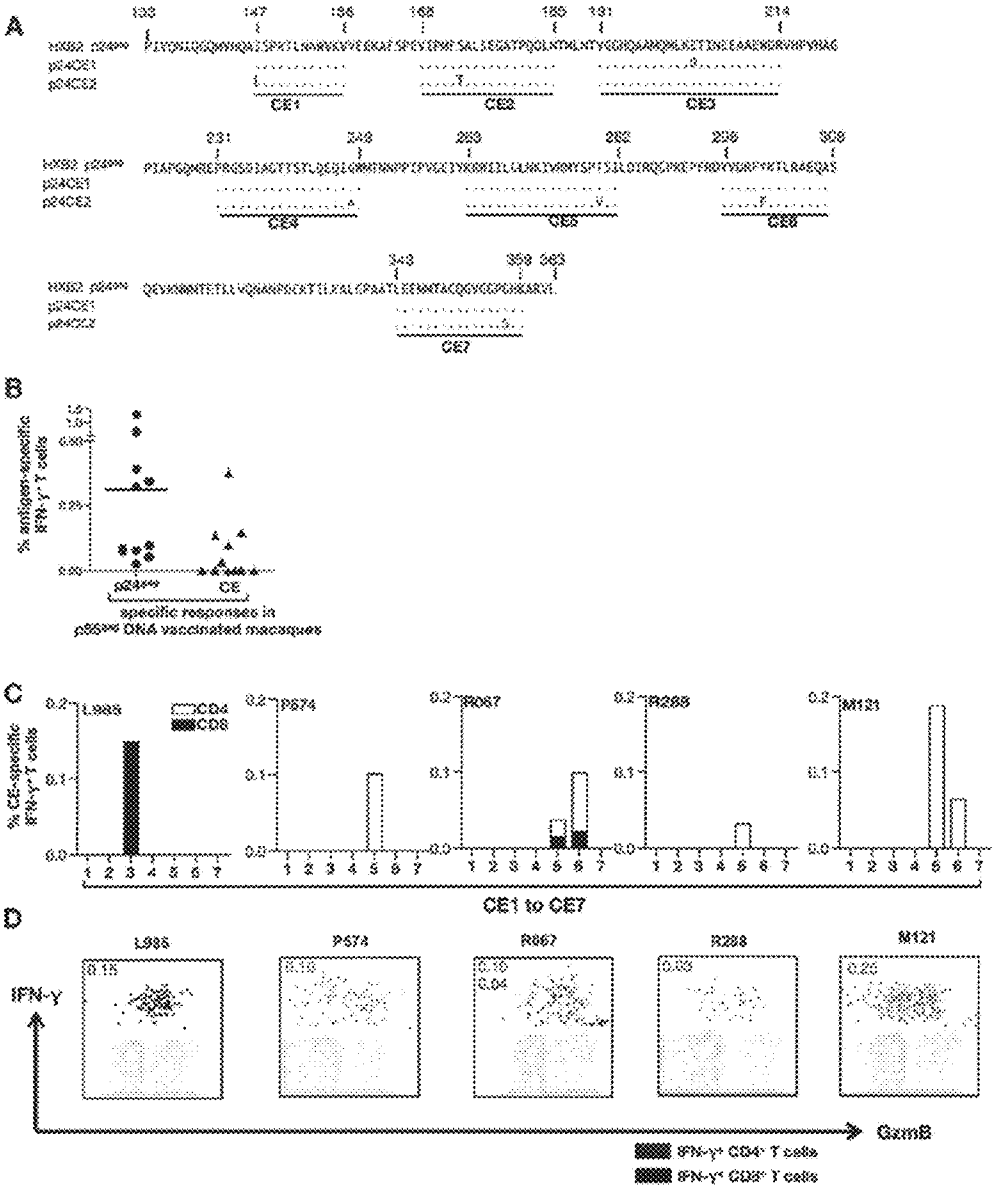

FIG. 7, A-D: $p55^{gag}$ DNA vaccination of macaques induces poor CE-specific cellular immune responses. (A) Alignment of the amino acid (AA) sequence of the 7 CE represented in the p24CE1 and p24CE2 proteins with HXB2 $p24^{gag}$ protein (SEQ ID NO:50). The toggled AA in each CE is shown. The numbering of the AA in HXB2 $p24^{gag}$ protein is according to the HIV data base at the www site hiv.lanl.gov/. (B) Both $p24^{gag}$-specific and CE-specific T cell responses were measured at 2 weeks after the last vaccination from 11 macaques, which were immunized with plasmid DNA encoding HIV Gag. (C) Mapping of the individual CE-specific responses in 5 (of 11) macaques that had responses to CE (panel B). The frequency of IFN-$\gamma^+$ T cells specific for each of the 7 CE is shown. Open bars: $CD4^+$ T cells; filled bars: $CD8^+$ T cells. (D). Dot plots showing the IFN-$\gamma^+$ and granzyme B (GzmB) production of the CE-specific $CD4^+$ (red) and $CD8^+$ (black) T cells from the 5 macaques shown in panel C.

Figure 8:
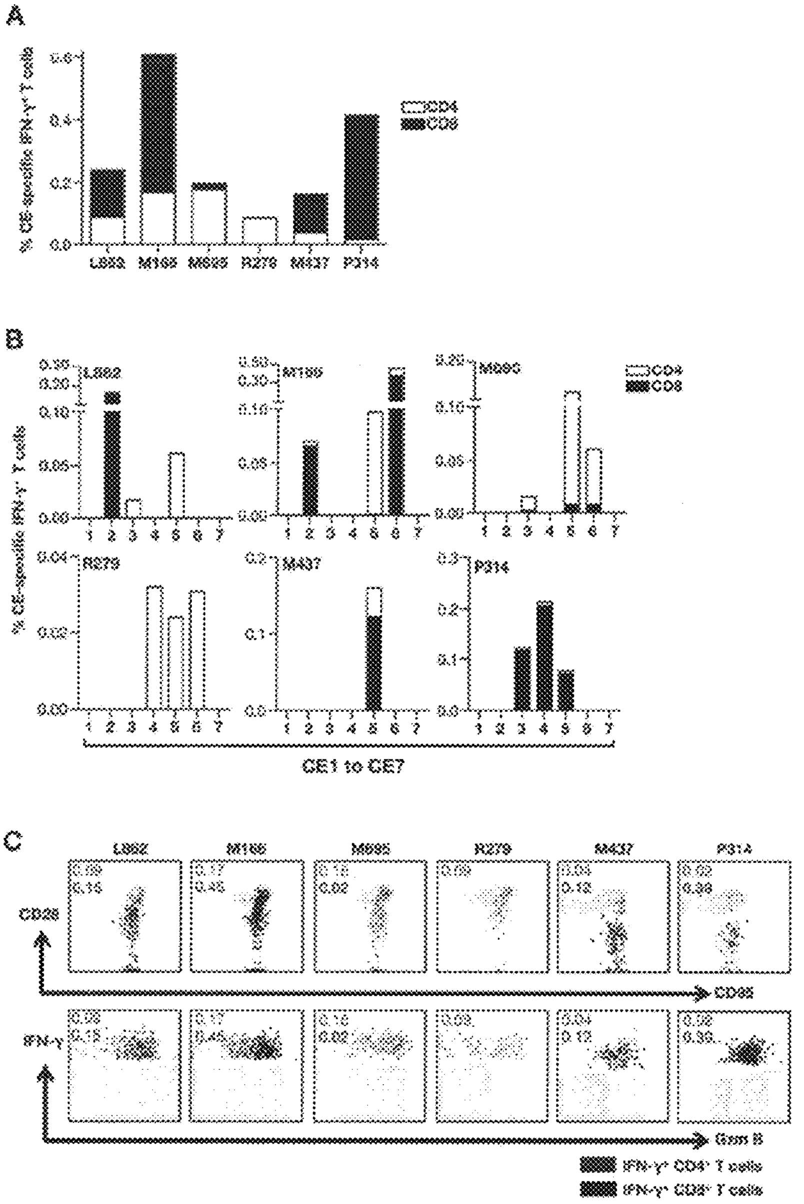

FIG. 8, A-C: CE-specific cellular immune responses upon vaccination of macaques with p24CE DNAs. (A) Macaques were vaccinated with p24CE DNA and the frequency of CE-specific T cells was measured 2 weeks after the $2^{nd}$ vaccination (EP2wk2). IFN-$\gamma^+CD4^+$ (open bars) and $CD8^+$ (filled bars) T cells are shown. (B) Mapping of individual CE-specific responses in the 6 immunized macaques from panel A. The frequency of IFN-$\gamma^+CD4^+$ (open bars) and $CD8^+$ (filled bars) T cells specific for each CE is shown. (C) Phenotypic characterization of the CE-specific $CD4^+$ (red) and $CD8^+$ (black) T cells with CD28+$CD95^+$ (central memory) or CD28-$CD95^+$ (effector memory phenotype) is shown in the top panel; IFN-$\gamma^+$ and granzyme B expression is shown in the bottom panel.

Figure 9:
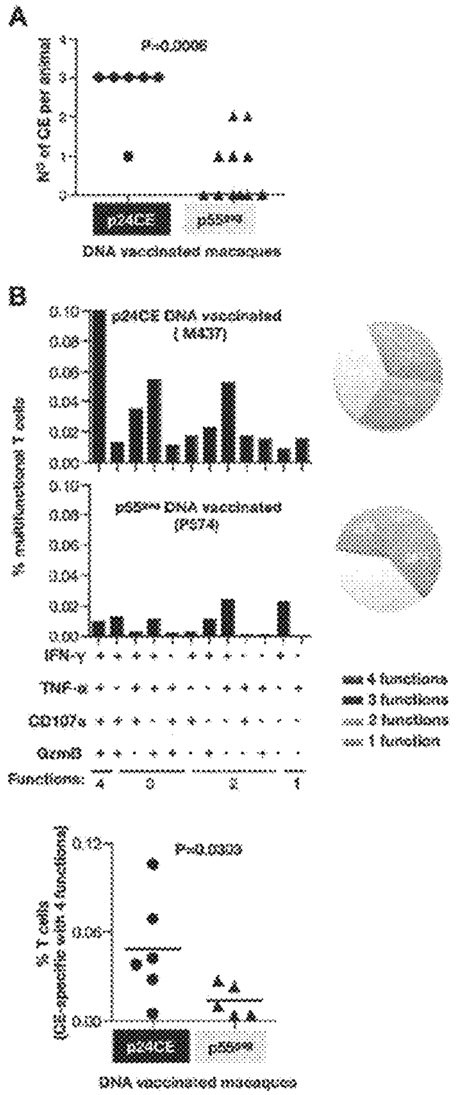

FIGS. 9, A and B: Induction of broad and polyfunctional T cell responses in p24CE vaccinated macaques. (A) The number of CE recognized per animal in macaques vaccinated with p24CE DNA and $p55^{gag}$ DNA are shown. (B) Frequency of CE-specific polyfunctional T cells was evaluated by their ability to produce IFN-γ, TNF-α, CD107a and granzyme B (GzmB). The data from one representative macaque from each group is shown: M437 (top panel) vaccinated with p24CE DNA; P574 (middle panel) vaccinated with $p55^{gag}$ DNA. The pie charts (right) show the proportion of polyfunctional responses in these macaques. Frequency of IFN-$\gamma^+$, TNF-$\alpha^+$, $CD107a^+$ and $GzmB^+$ polyfunctional CE-specific T cells (4 functions) as % of total T cells in macaques vaccinated with p24CE DNA and $p55^{gag}$ DNA, respectively, are shown (bottom panel). Median values are indicated.

Figure 10:
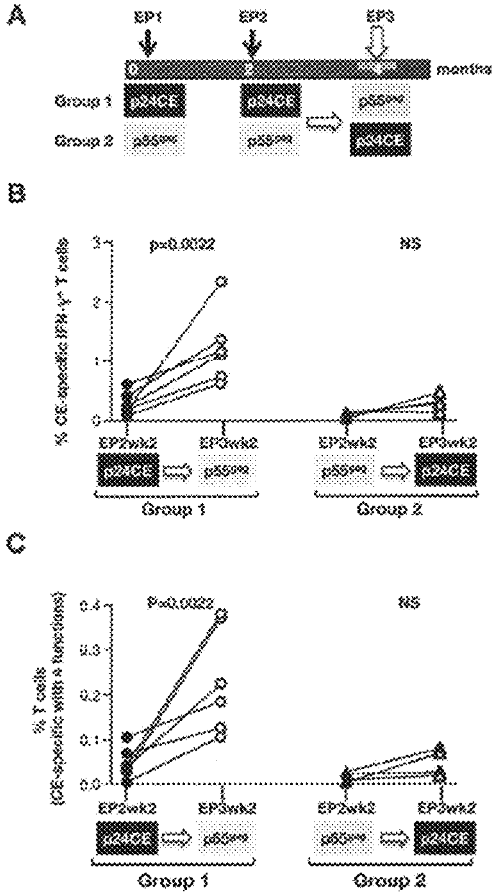

FIG. 10, A-C: Boosting of p24CE DNA primed macaques with $p55^{gag}$ DNA increases CE-specific cellular responses. (A) Vaccination schedule of group 1 with p24CE plasmid DNAs (EP1, EP2) followed by the heterologous $p55^{gag}$ DNA boost (EP3) and group 2 with $p55^{gag}$ DNA (EP1, EP2) followed by the heterologous p24CE DNA boost (EP3). (B) Frequency of the CE-specific IFN-$\gamma^+$ T cells in both groups before (EP2wk2) and after the heterologous boost (EP3wk2). (C) Frequency of IFN-$\gamma^+$ TNF-$\alpha^+$ $CD107a^+$ $GzmB^+$ polyfunctional CE-specific T cells (4-function) in groups 1 and 2 before and after the heterologous boost.

Figure 11:
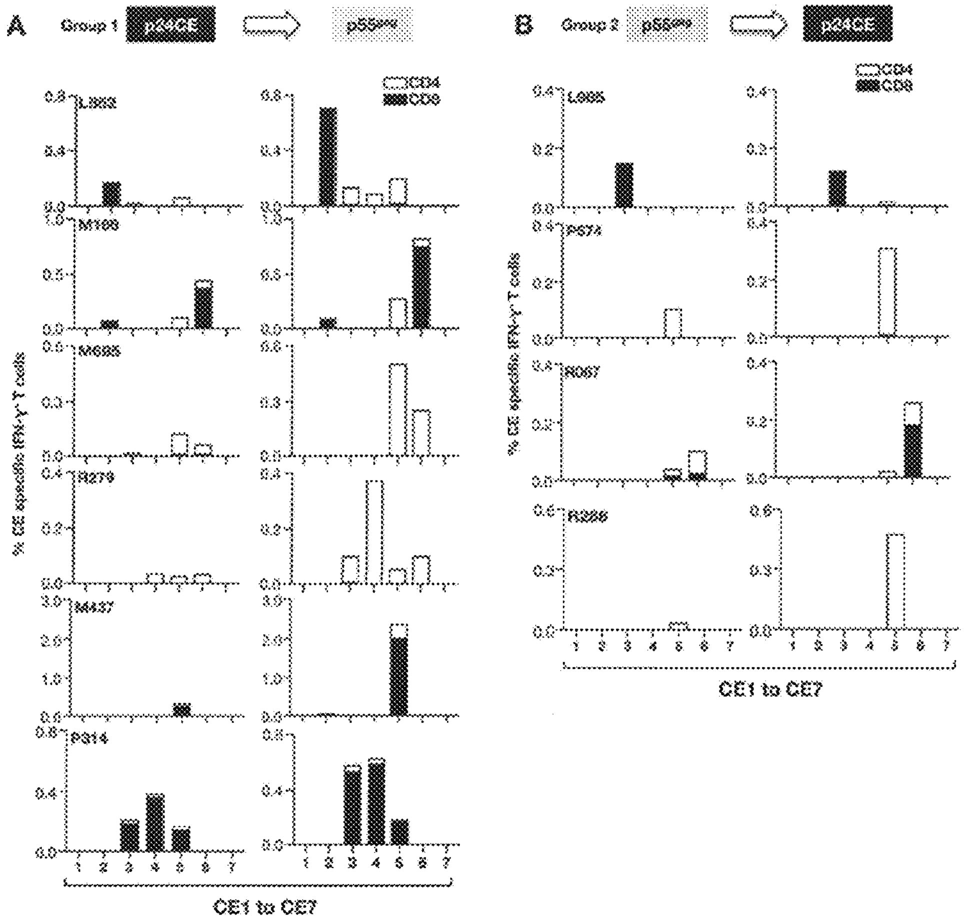

FIGS. 11, A and B: Mapping of CE-specific T cell responses before and after heterologous boost. The CE-specific responses were mapped as described for section B of FIG. 2. The plots show comparisons of the responses upon p24CE DNA vaccination followed by $p55^{gag}$ DNA boost (group 1, A) and upon $p55^{gag}$ DNA vaccination followed by p24CE boost (group 2, B). The percentage of IFN-$\gamma^+CD4^+$ (open bars) and $CD8^+$ (filled bars) T cells specific for each CE is shown.

Figure 12:
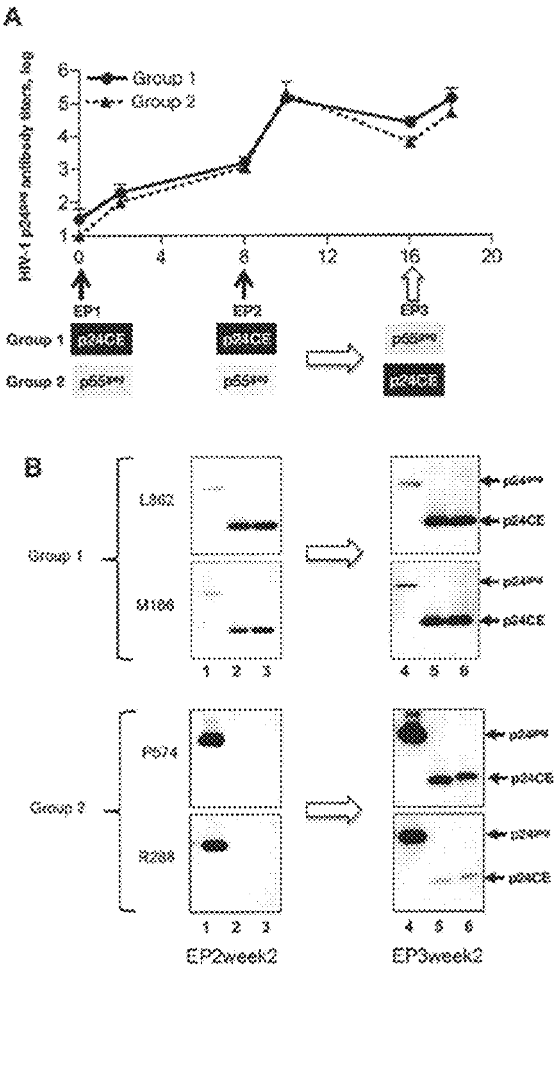
Figure 14A:
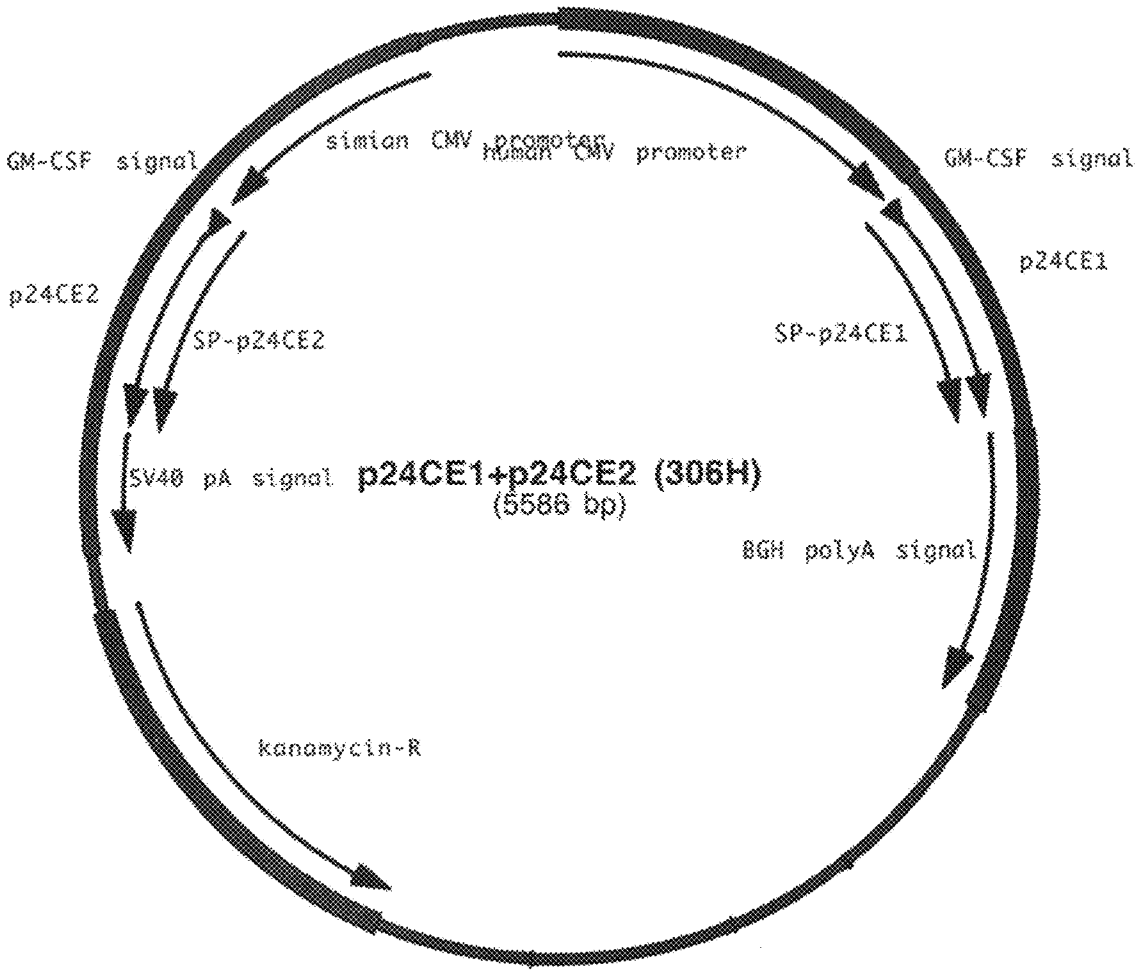
Figure 14B:
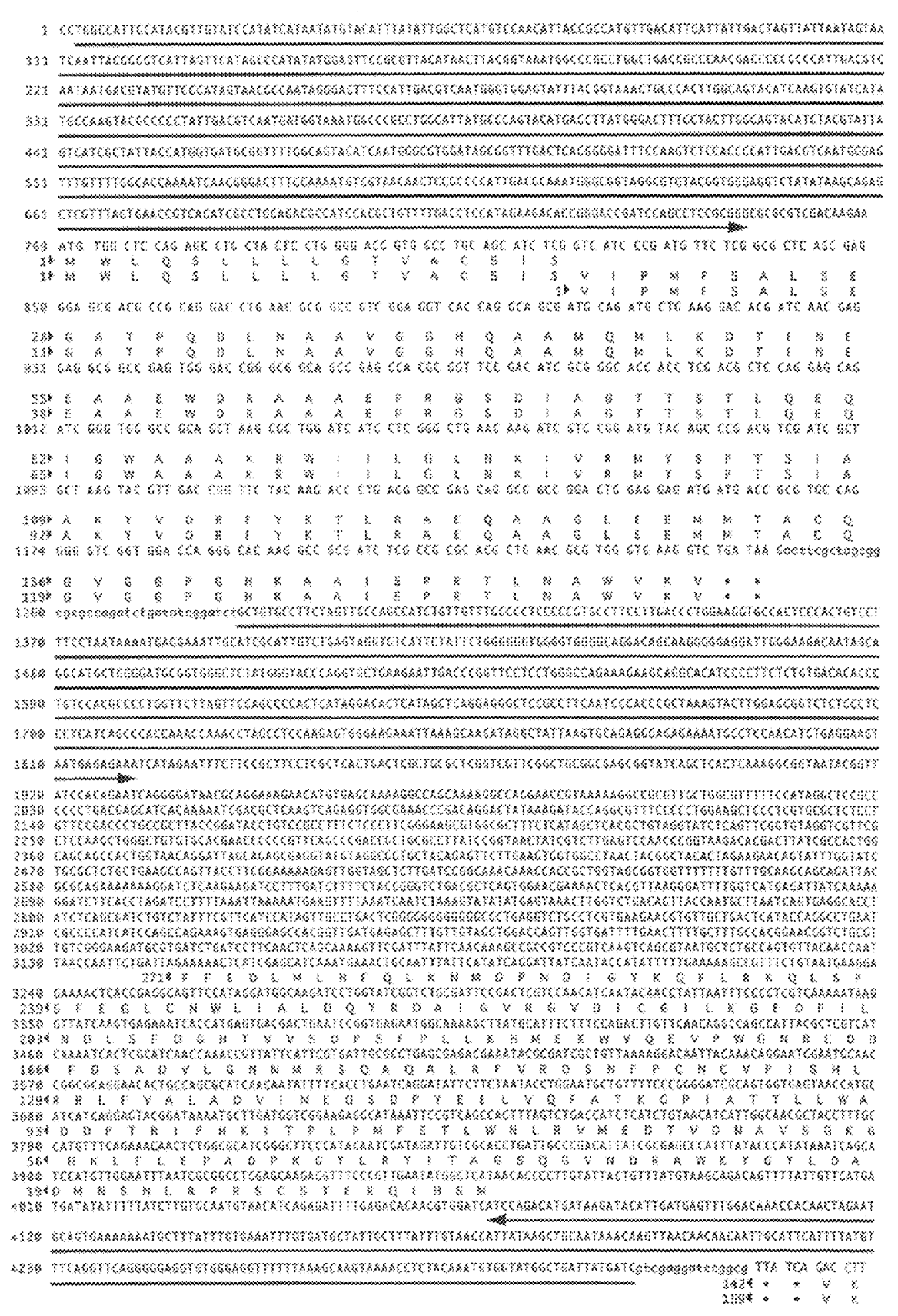
Figure 15A:
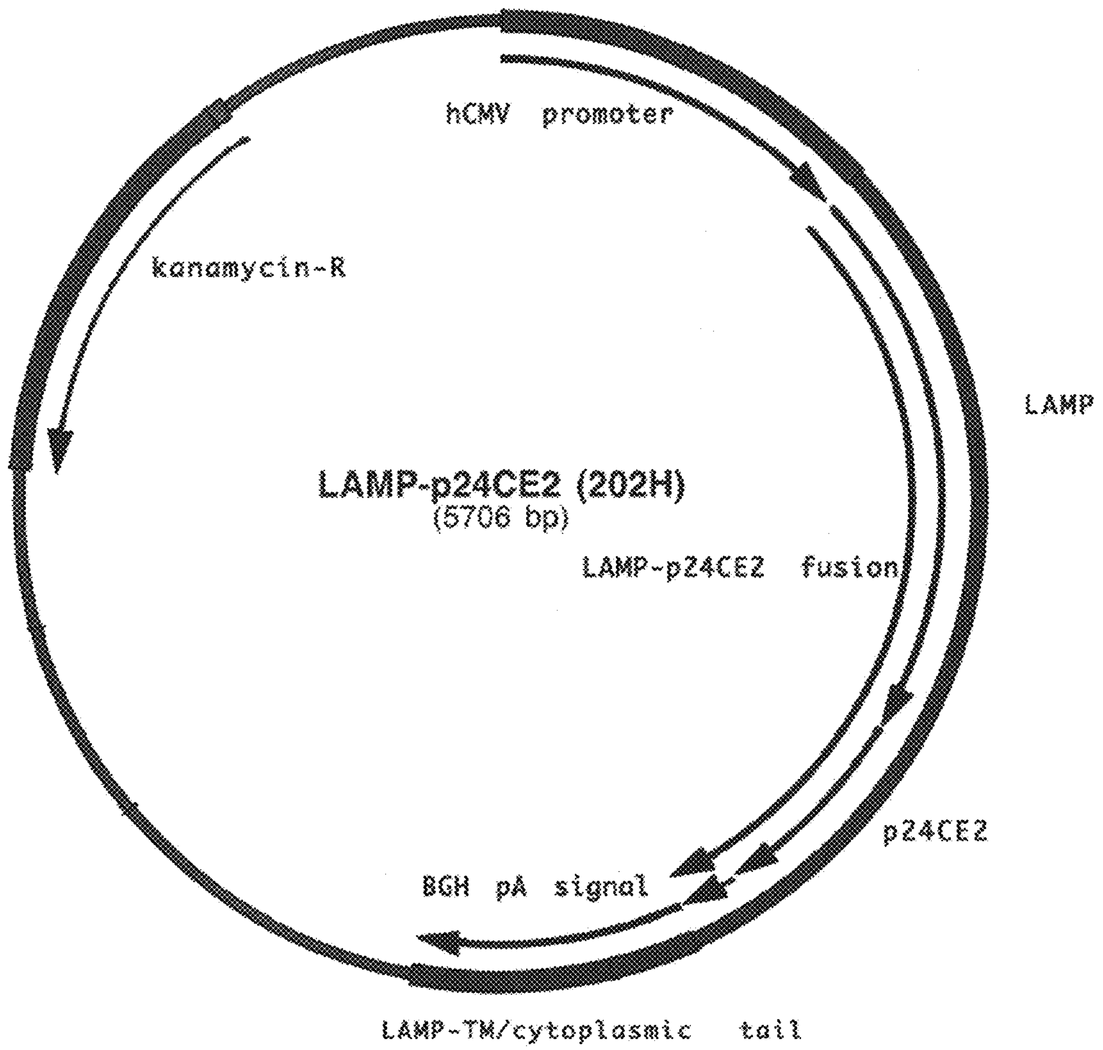
Figure 15B:
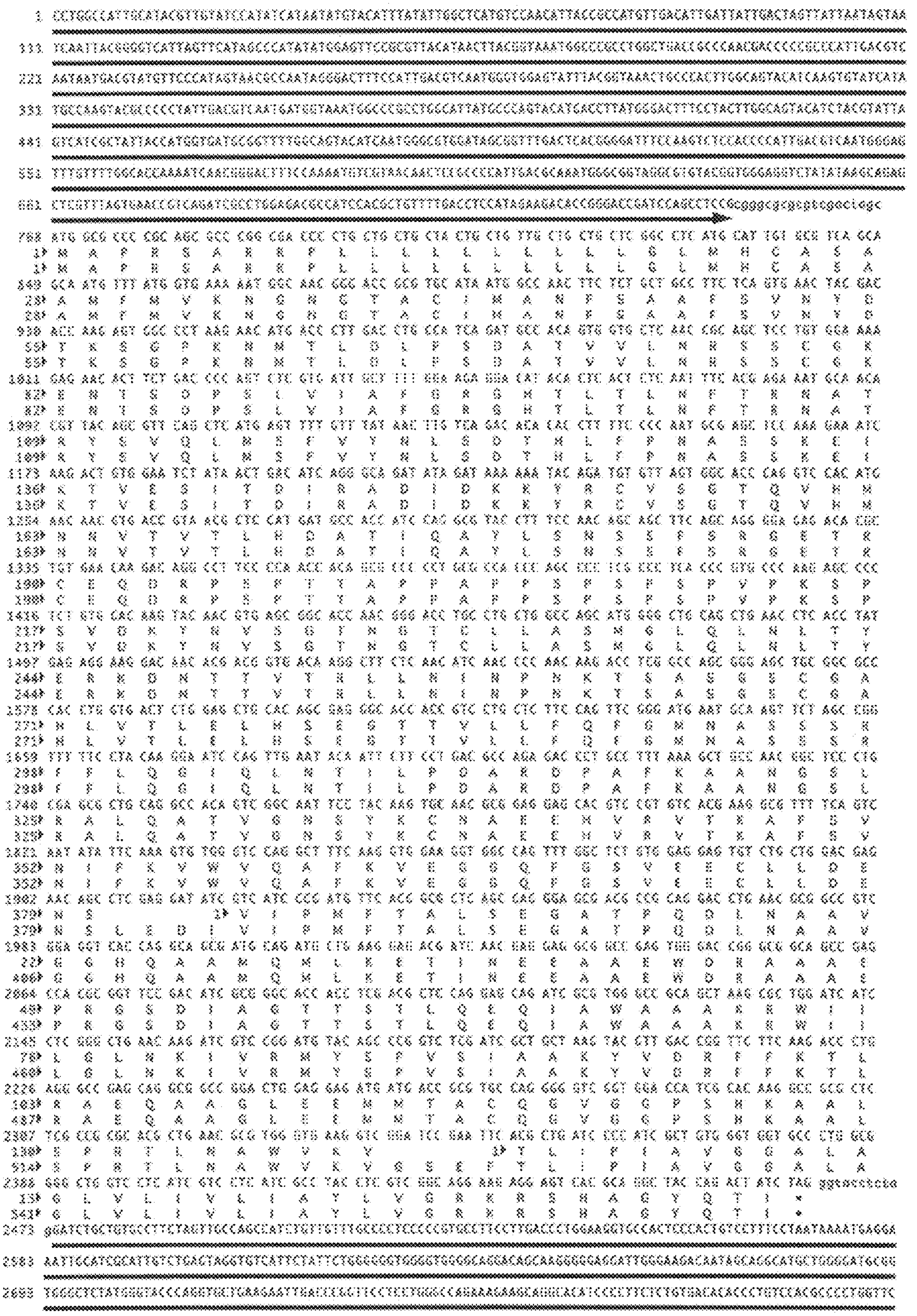
Figure 16:
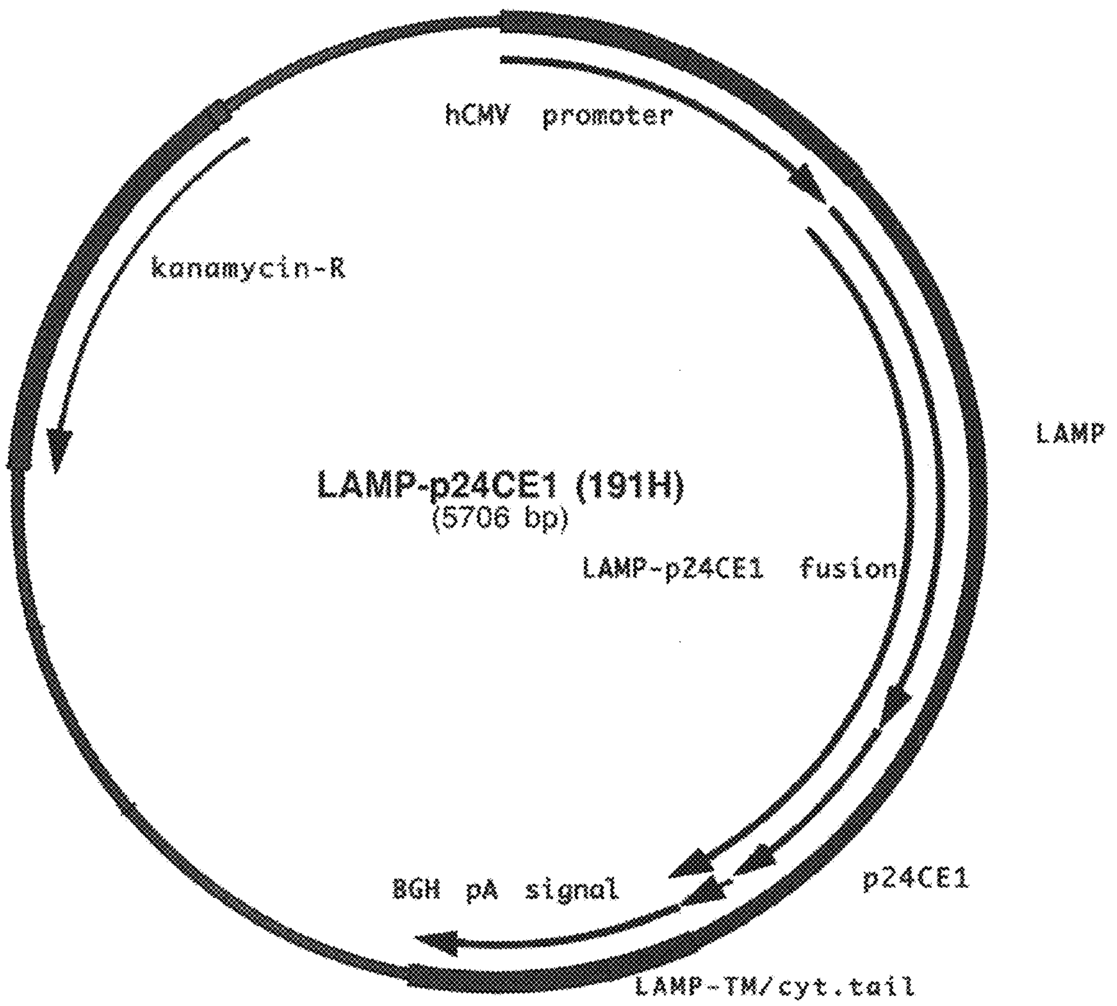
Figure 16B:
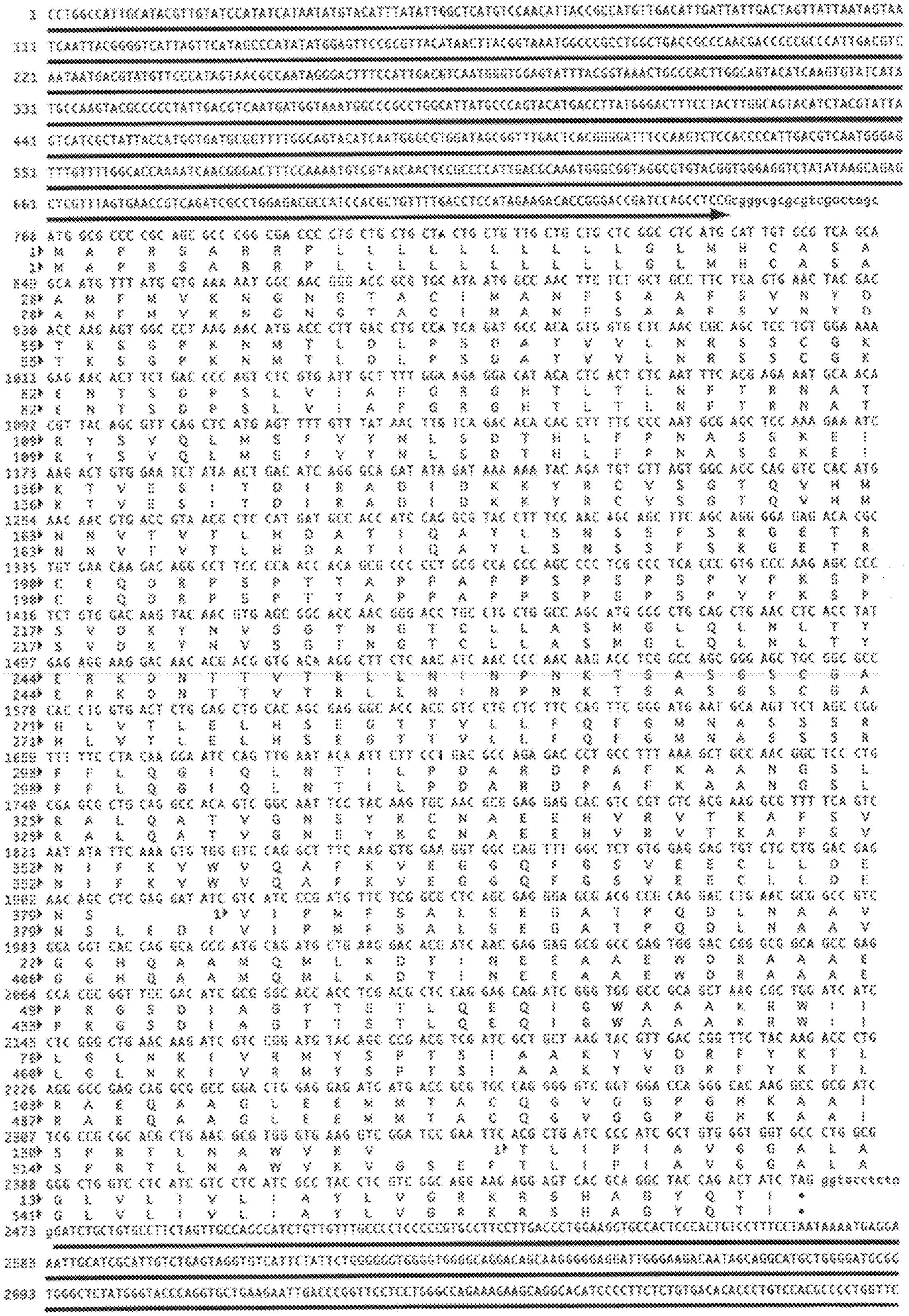
Figure 17A:
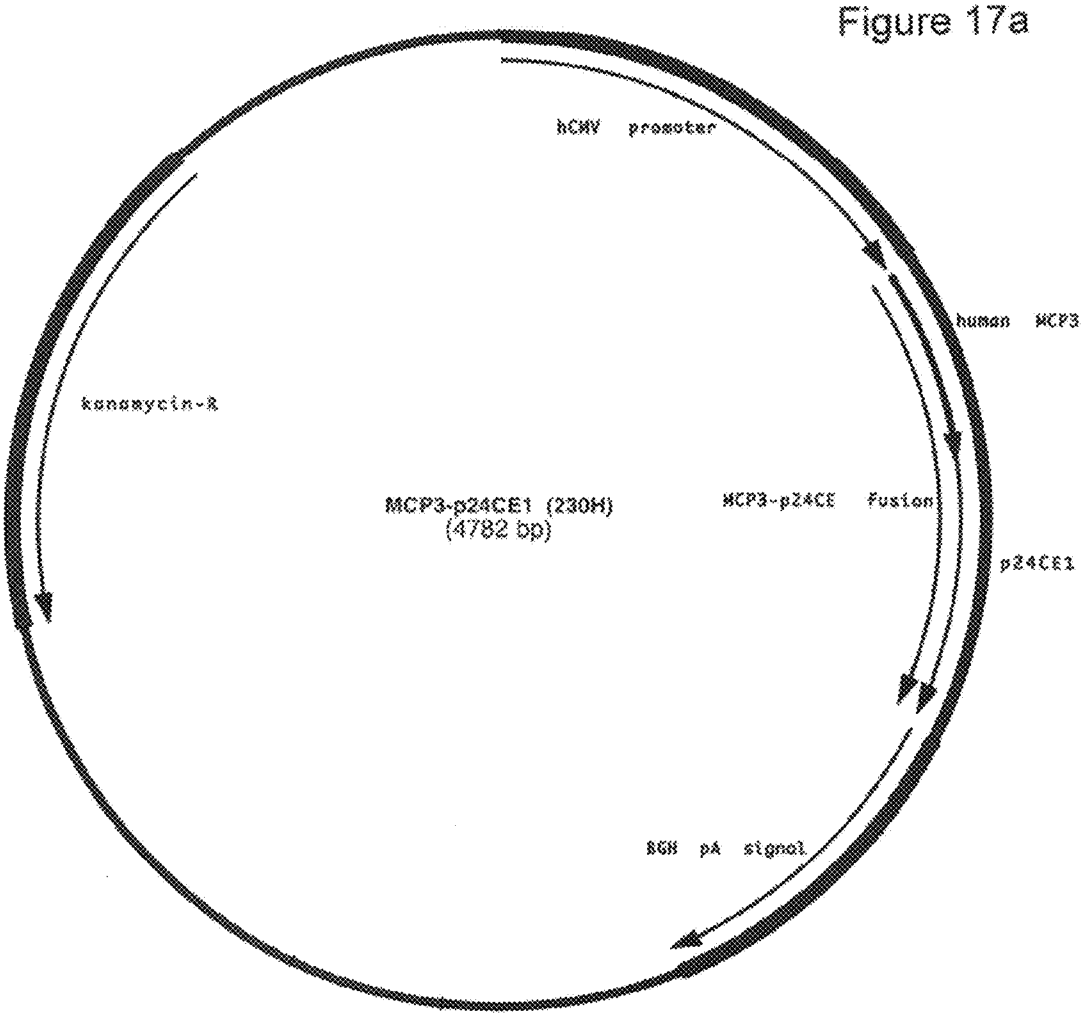
Figure 17B:
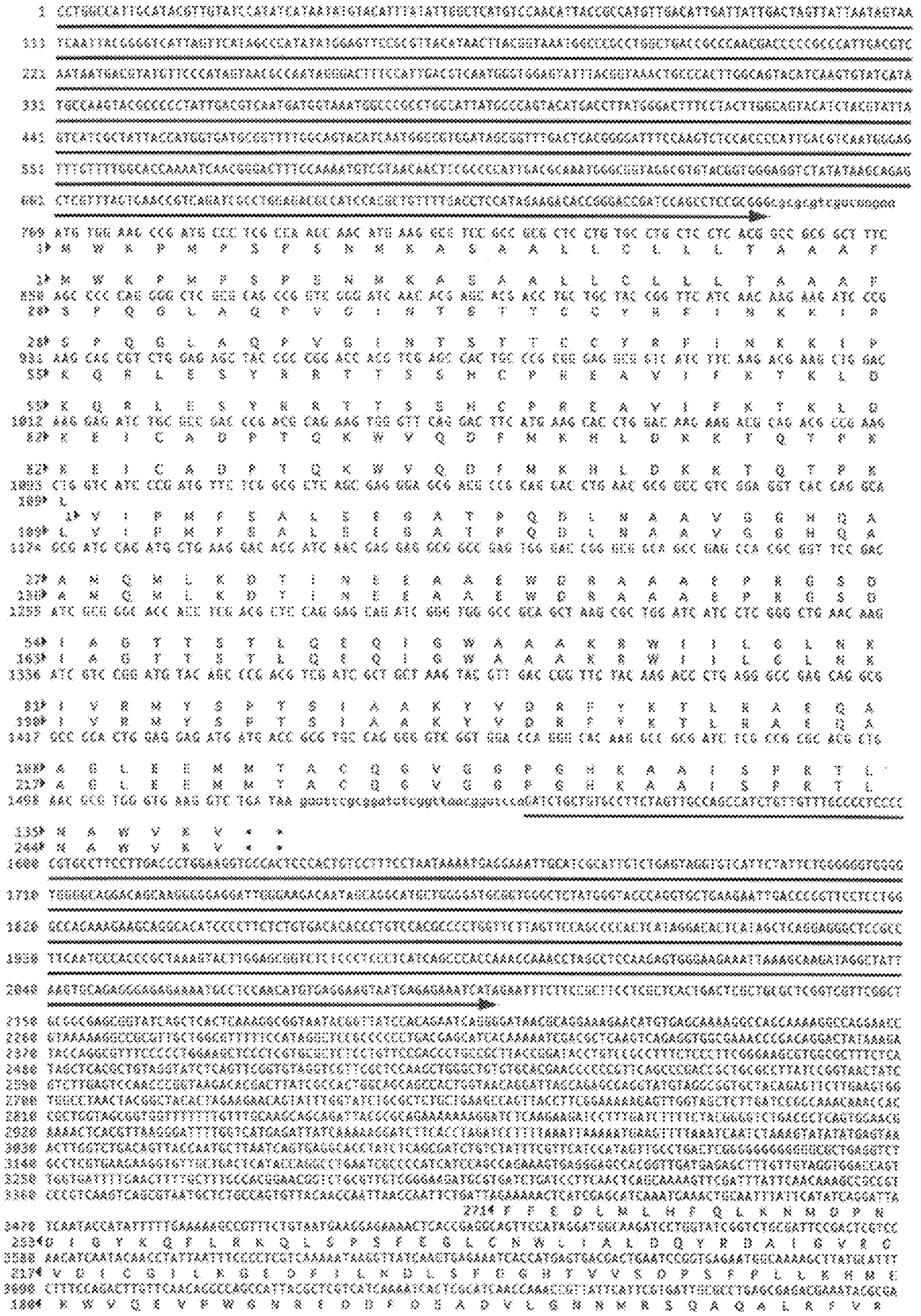
Figure 18A:
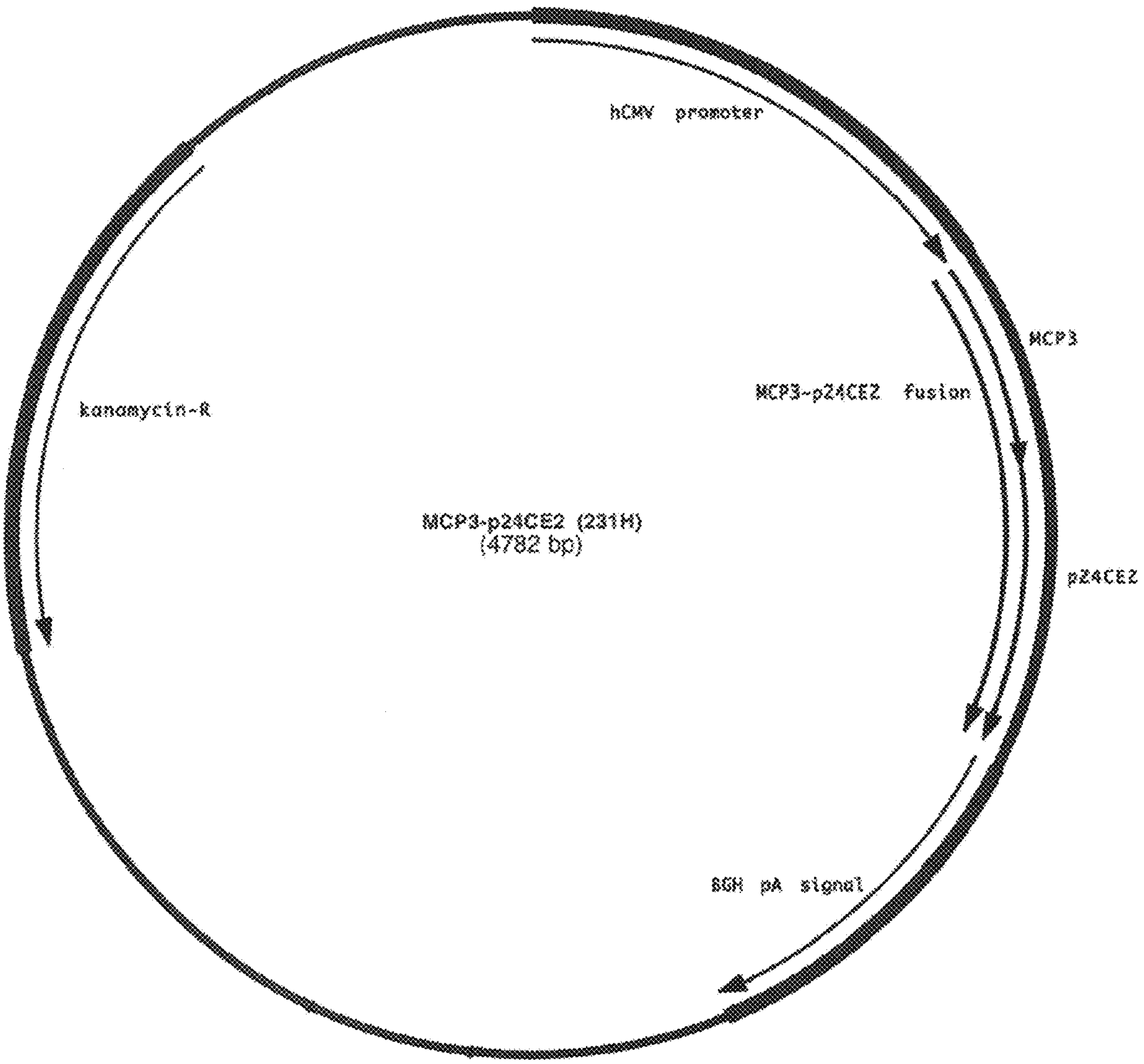
Figure 18B:
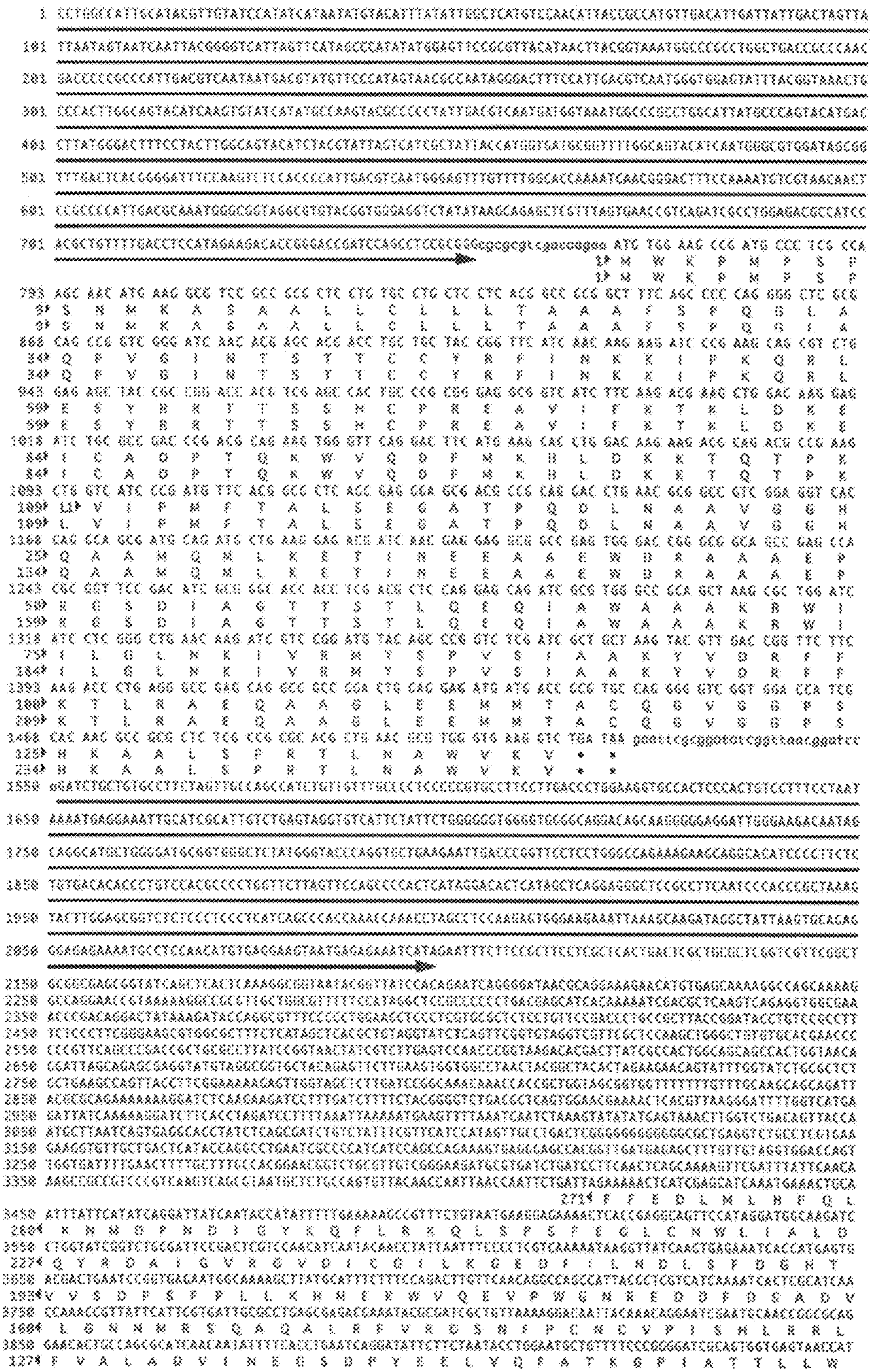
Figure 19:
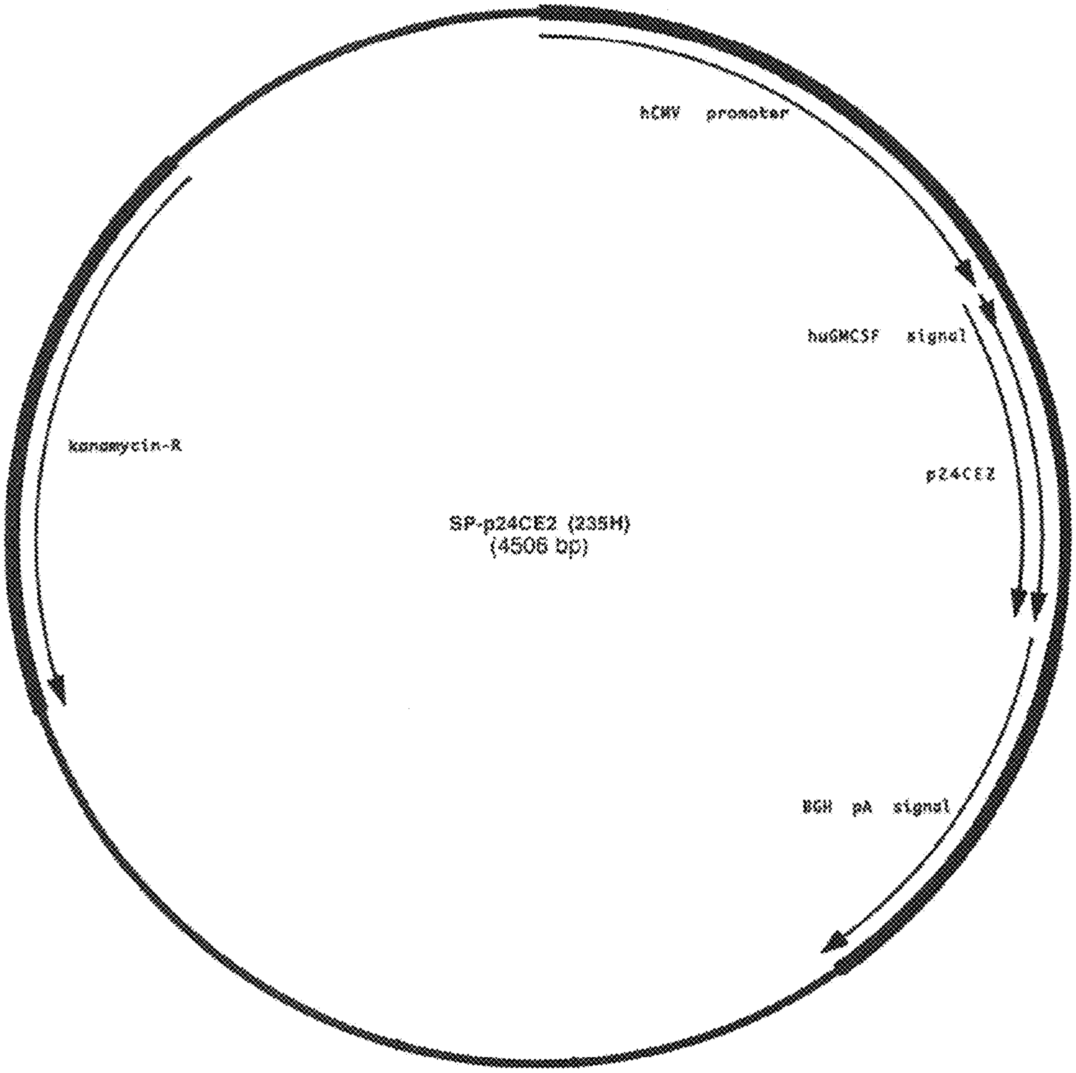
Figure 19B:
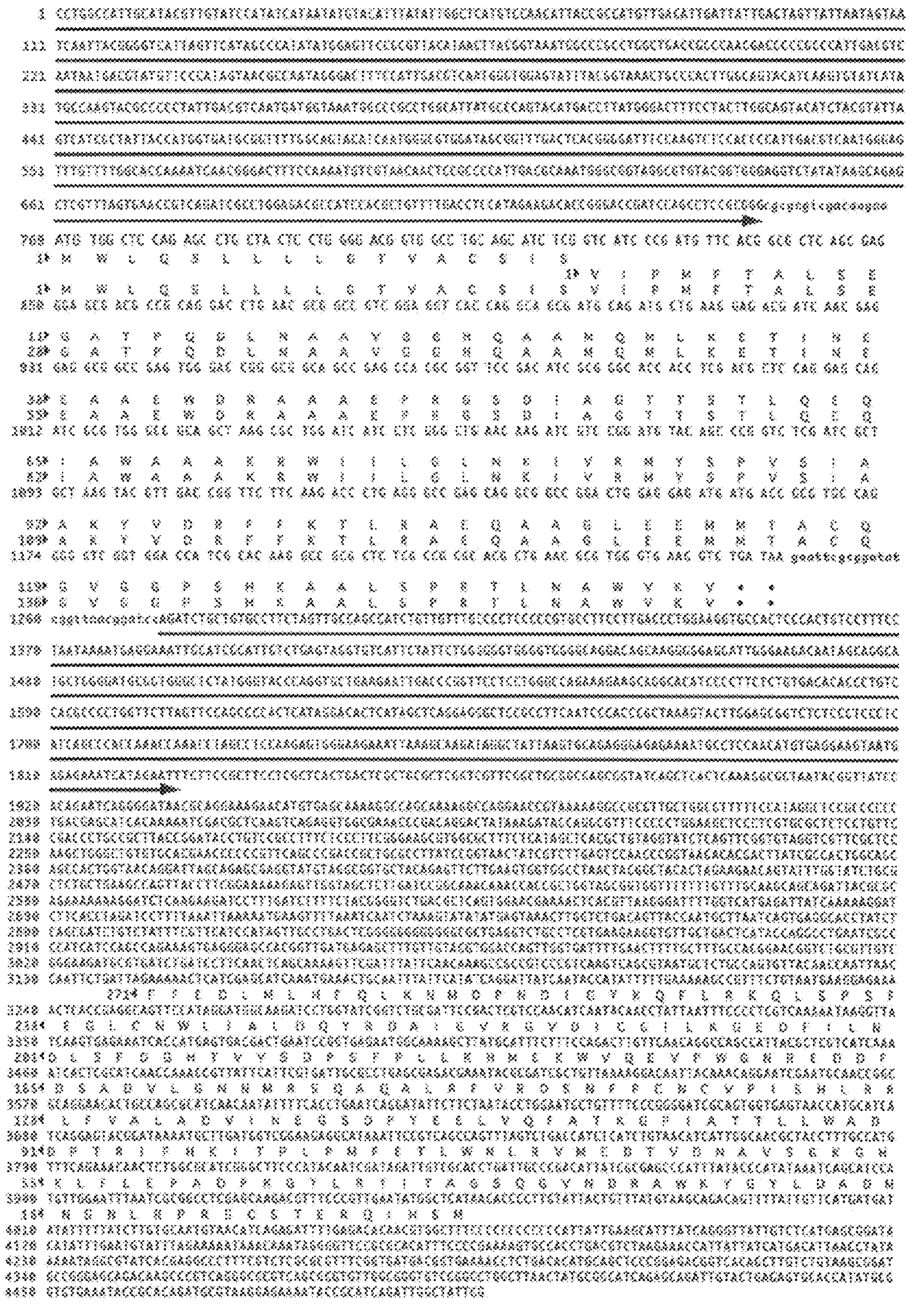

FIGS. 12, A and B: Humoral immune responses upon p24CE DNA vaccination are boosted by $p55^{gag}$ DNA vaccination. (A) Reciprocal $p24^{gag}$ binding antibody endpoint titers (log) measured in plasma by ELISA at the indicated time points for macaques in group 1 and group 2 before and after the heterologous boosts. (B) Western immunoblot analysis was used to test the reactivity of the vaccine-induced antibodies from macaques in group 1 and 2 to $p24^{gag}$ and the p24CE proteins. The membranes contain either $p24^{gag}$ protein (lanes 1 and 4), p24CE1 (lanes 2 and 5) or p24CE2 (lanes 3 and 6) and were probed with plasma from macaques from group 1 (dilution 1:2000) and group 2 (dilution 1:500) collected before (EP2wk2; lanes 1-3) and after (EP3wk2, lanes 4-6) the heterologous boost.

FIG. 13: Sequences and configurations of p24CEc polypeptides (SEQ ID NOS:46 and 47) and p24CEd polypeptides (SEQ ID NOS:48 and 49).

FIG. **14*a*-14*b*: Plasmid map (14*a*) and sequence (14*b***) (SEQ ID NOS:17, 56, 18, 57, 58, 19, 56, and 58) of plasmid 306H that encodes p24 CE1+p24 CE2.

FIG. **15*a*-15*b*: Plasmid map (15*a*) and sequence (15*b***) (SEQ ID NOS:20, 59, 21, 60, 61, and 58) of plasmid 202H that encodes LAMP-p24CE2.

FIG. **16*a*-16*b*: Plasmid map (16*a*) and sequence (16*b***) (SEQ ID NOS:22, 61, 23, 57, 60, and 58) of plasmid 191H that encodes LAMP-p24CE1.

FIG. **17*a*-17*b*: Plasmid map (17*a*) and sequence (17*b***) (SEQ ID NOS:26, 62, 27, 59, and 58) of plasmid 230H that encodes MCP3-p24CE1.

FIG. **18*a*-18*b*: Plasmid map (18*a*) and sequence (18*b***) (SEQ ID NOS:28, 62, 29, 59, and 58) of plasmid 231H that encodes MCP3-p24CE2.

FIG. **19*a*-19*b*: Plasmid map (19*a*) and sequence (19*b***) (SEQ ID NOS:24, 56, 58, 25, and 58) of plasmid 235H that encodes SP-p24CE2.

Figure 20:
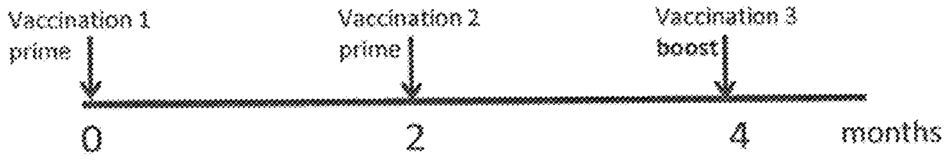

FIG. 20: Illustrative regimens for administering conserved element Gag vaccines and full-length $p55^{gag}$ vaccine.

Figure 21:
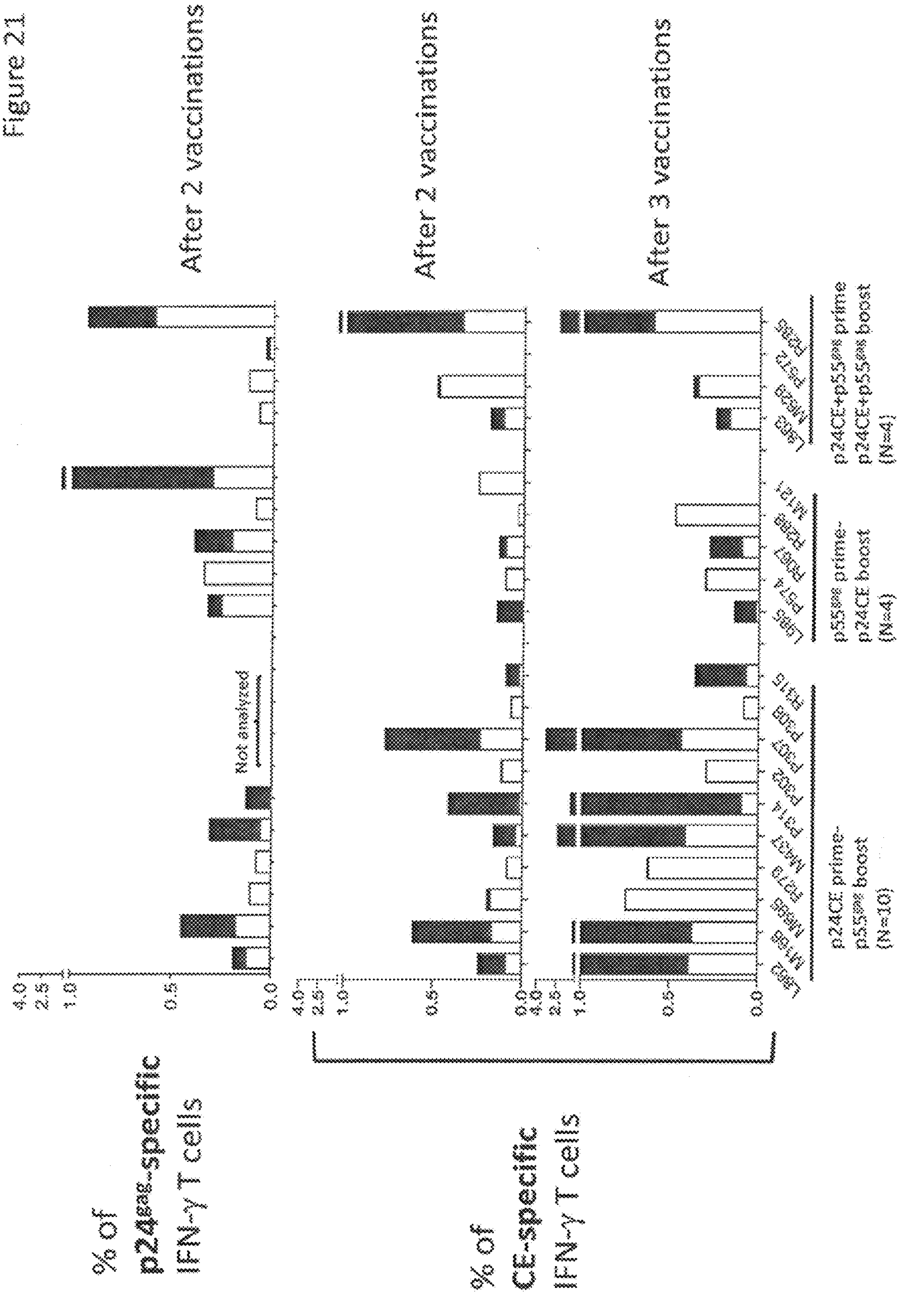

FIG. 21: Illustrative data showing cellular immune responses before and after the boost. Cellular immune responses were measured with peptides (15-mer overlapping by 11 amino acids) spanning the complete $p24^{gag}$.

Figure 22:
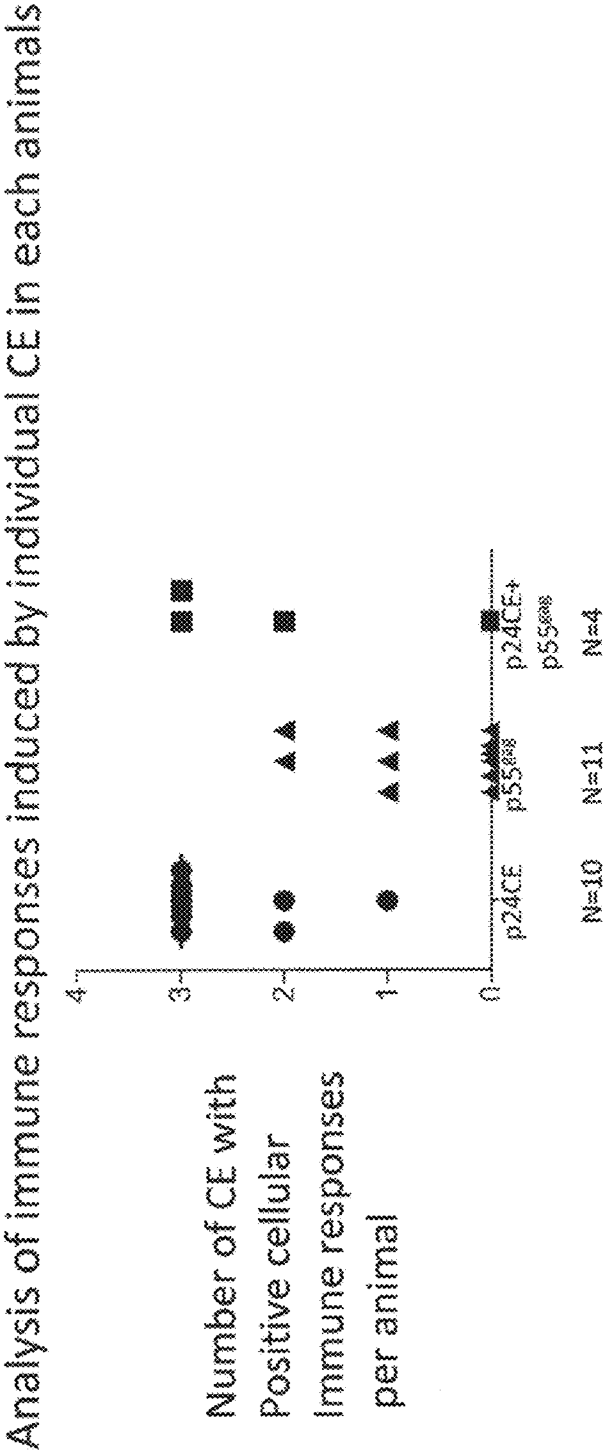

FIG. 22: Analysis of the responses to individual CE. The responses to each CE were mapped in all the animals using CE-specific peptides (mixture of 10-mer peptide overlapping by 9 amino acids and 15-mer overlapping by 11 amino acids) for each CE. The number of CE that showed positive responses per animal are shown.

Figure 23:
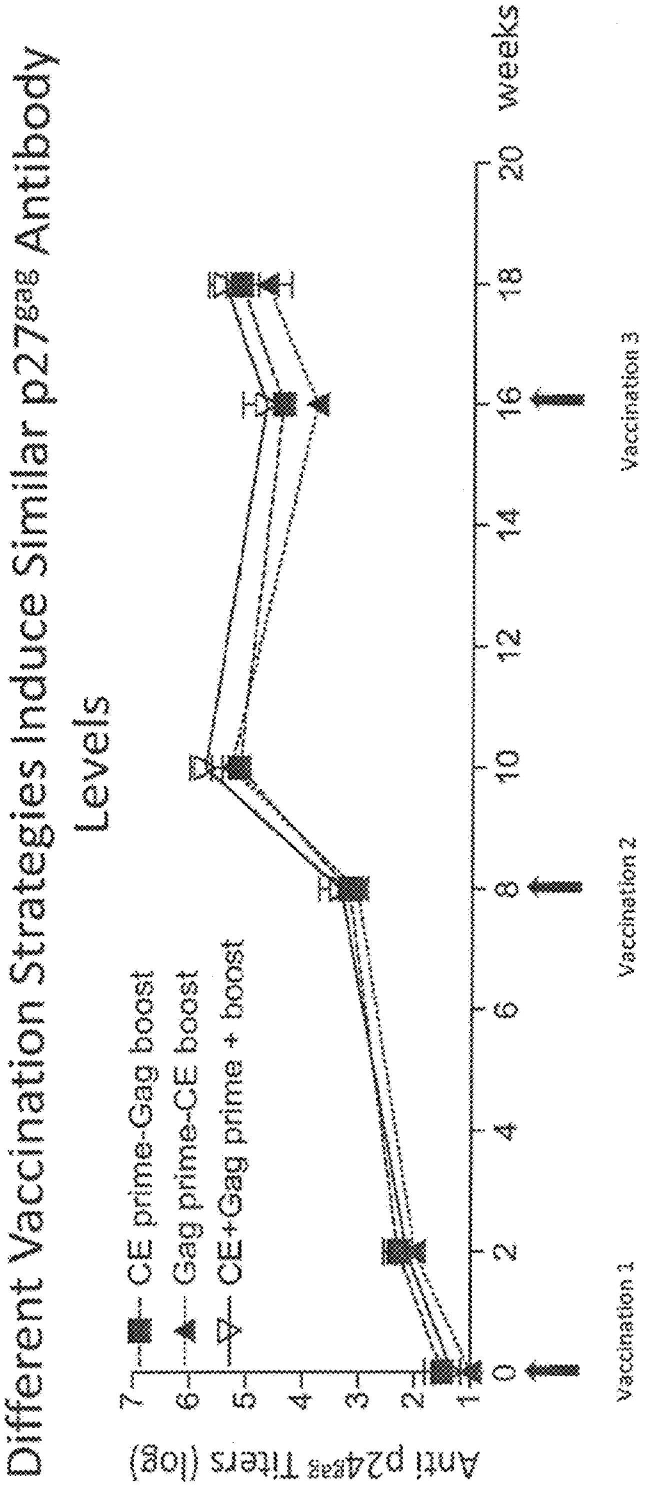

FIG. 23: Different vaccine strategies induced similar levels of $p27^{gag}$ antibody responses. Binding antibody titers were measured in the plasma by ELISA.

DETAILED DESCRIPTION OF THE INVENTION

Definitions

A "conserved element" as used herein refers to a protein sequence that is conserved across a protein that has high sequence diversity in nature, e.g., a viral protein such as an gag. The conserved element need not have 100% sequence identity across the diversity of naturally occurring sequence of the protein, but the sequence variability in the naturally occurring sequences is low, e.g., less than 20%. In some embodiments, the sequence variability is less than 10%. A conserved element is usually eight amino acids, or greater, e.g., 9, 10, 11, 12, 13, 14, 15, 16, 17, 18, 19, or 20 amino acids in length. Typically a conserved element is less than 50 amino acids in length and often is less than 40 or less than 30 amino acids. In some embodiments, a conserved element is less than 25 amino acids in length.

A "nucleic acid vaccine" as used herein includes both naked DNA vaccines, e.g., plasmid vaccine, and viral vector-based nucleic acids vaccines that are comprised by a viral vector and/or delivered as viral particles.

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term "nucleic acid" is used interchangeably with gene, cDNA, oligonucleotide, and polynucleotide. A "nucleic acid" encompasses RNA as well as DNA.

The terms "identical" or percent "identity," in the context of two or more nucleic acids or polypeptide sequences, refer to two or more sequences or subsequences that are the same or have a specified percentage of amino acid residues or nucleotides that are the same (e.g., about 80%, 85%, 90%, 91%, 92%, 93%, 94%, 95%, 96%, 97%, 98%, 99%, or higher identity over a specified region (a polypeptide sequence comprising conserved elements), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The terms "enhanced immune response" or "increased immune response" as used herein refers to an immune response to the conserved element nucleic acid and full-length, or substantially full length protein that are administered, where the immune response is increased in comparison to when only the conserved element vaccine or full-length protein is administered. An "enhanced immune response" may include increases in the level of immune cell activation and/or an increase in the duration of the response and/or immunological memory as well as an improvement in the kinetics of the immune response. The increase can be demonstrated by either a numerical increase, e.g., an increased in levels of antibody in a particular time frame, as assessed in an assay to measure the response assay or by prolonged longevity of the response.

The terms "treating" and "treatment" refer to delaying the onset of, retarding or reversing the progress of, or alleviating or preventing either the disease or condition to which the term applies, or one or more symptoms of such disease or condition.

An "antigen" refers to a molecule, typically a protein molecule in the current invention, containing one or more epitopes (either linear, conformational or both) that will stimulate a host's immune system to make a humoral and/or cellular antigen-specific response. The term is used interchangeably with the term "immunogen." Normally, an epitope will comprise between about 7 and 15 amino acids, such as, 9, 10, 12 or 15 amino acids. The term "antigen" includes both subunit antigens, (i.e., antigens which are separate and discrete from a whole organism with which the antigen is associated in nature), as well as inactivated organisms, such as viruses.

Introduction

The invention is based in part, on the discovery that administration of one or more nucleic acids encoding a polypeptide comprising conserved elements from a protein to a subject in conjunction with administration of a nucleic acid encoding the full-length protein, or substantially full-length protein, enhances the immune response to the conserved element sequences. The protein can be any protein, but is typically a viral protein that exhibits sequence diversity in naturally occurring variants. In some embodiments, the viral protein is a retrovirus protein, such as a lentiviral protein. In some embodiments, the viral protein is a retroviral Gag or Env protein.

In some embodiments, administration of the nucleic acid encoding the full-length protein, or substantially full-length protein, follows administration of a conserved element nucleic acid construct. Thus, the invention further provides methods of inducing an immune response comprising sequential administration of at least one conserved element nucleic acid construct followed by administration of a nucleic acid construct comprising substantially a full length protein from which the conserved elements are derived.

Conserved Element Nucleic Acid Constructs

Conserved elements of a protein sequence can be determined using known methods. For examples U.S. Patent Application Publication No. 20110269937, which is incorporated by reference, describes methods of evaluating protein sequences that exhibit natural variability to identify regions that are conserved using computational methods.

A conserved element nucleic acid construct is typically generated by linking nucleic acid sequences that encode multiple conserved elements that target conserved sequence that are present within all or a high percentage, e.g., at least 80%, at least 90%, or at least 95%, or greater, of the naturally occurring variants of the protein in a population. In typical embodiments, a conserved element is from a region of a protein that when mutated, has deleterious effects on the function of the protein. In typical embodiments, a conserved element does not comprise an amino acid sequence that does not occur in a naturally occurring variant, i.e., the conserved element does not contain amino acid substitutions that would result in a sequence that has not been identified in a naturally occurring variant.

In some embodiments a immunogenic compositions employed in the invention relates to a viral protein, e.g., a retrovirus protein such as Gag. Conserved elements of Gag have been identified (see, e.g., U.S. Patent Application Publication No. 20110269937; Rolland et al., *PLoS Pathog* 3: e157, 2007; Mothe et al., *PLoS One* 7: e29717, 2012).

Figure 1:
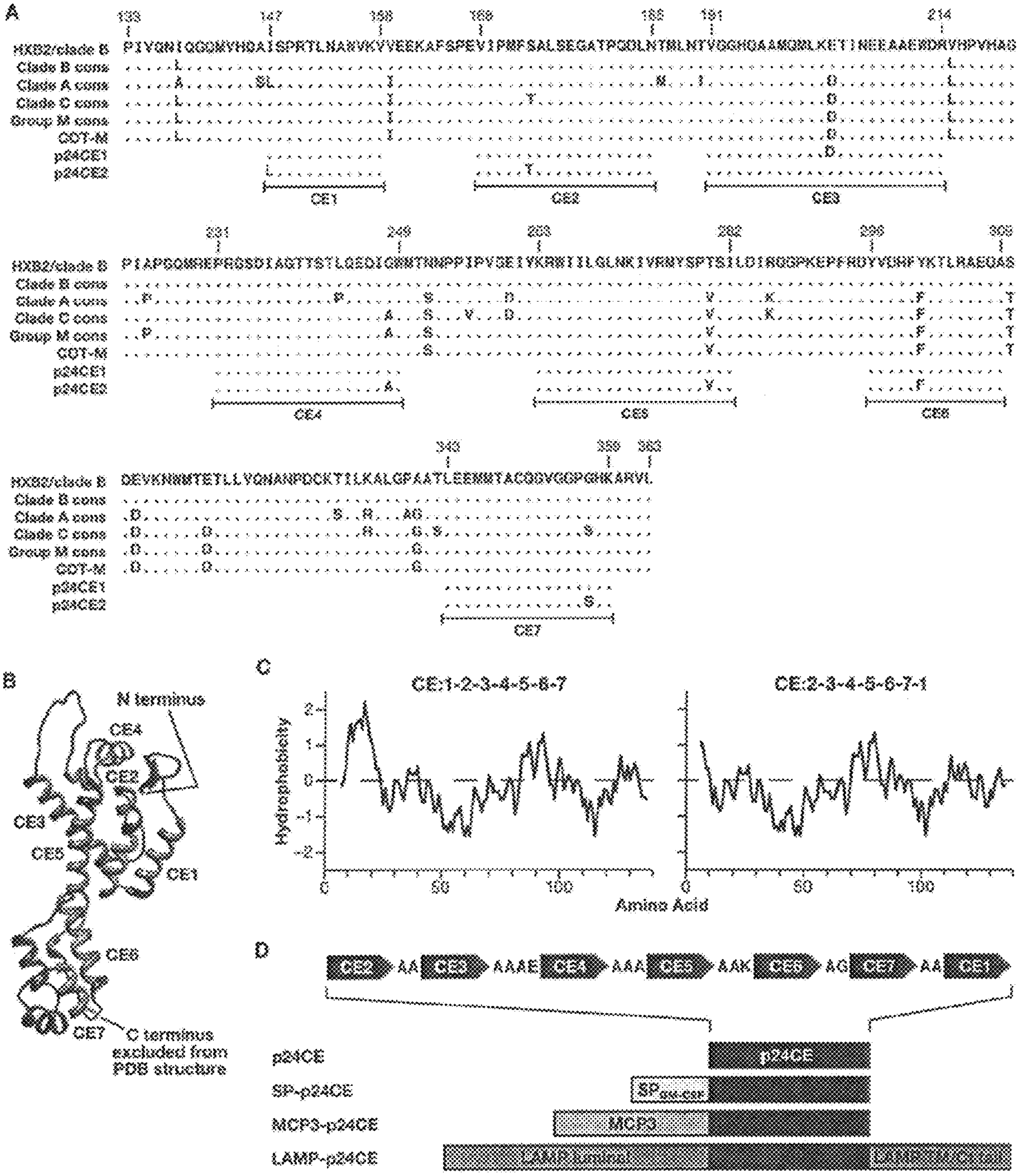
FIG. 1, A-D: Design of the p24CE DNA vaccine. (A) Alignment of the HXB2 $p24^{gag}$ protein sequence (SEQ ID NO:50) with the consensus clade A (SEQ ID NO:51), clade B (SEQ ID NO:52) and clade C (SEQ ID NO:53); the Group M consensus (SEQ ID NO:54), the Group M Center-of-Tree (COT-M) (SEQ ID NO:55); and the 7 CE included in p24CE1 and p24CE2. The 'toggle' amino acid differences between the CE1 and CE2 sequences are indicated. (B) Localization of CE within the hexameric $p24^{gag}$ structure. The $p24^{gag}$ structure is modified from Pomillos et al. [97] and shows the location of CE1-CE7 (red), the toggle AA (blue) and the AA not included in the CE (black). The crystal structure of the hexamer was obtained from the www http address ebi.ac.uk/pdbsum (C) Kyte-Dolittle hydrophobicity plots for two different collinear arrangements of the CEs. (D) The p24CE (p24CE1 and p24CE2) proteins are composed of 7 CE arranged collinearly and linked via amino acid linkers (AAAE=SEQ ID NO:42). The secreted SP-p24CE contains the GM-CSF signal peptide. MCP3-p24CE is a fusion protein with the Monocyte chemoattractant protein 3 (MCP-3) chemokine. LAMP-p24CE is a fusion with the lysosomal associated membrane protein 1 (LAMP-1).

In some embodiments, the nucleic acid construct encoding the conserved element polypeptide encodes a polypeptide that comprises at least one, two, three, four, five, six, or seven conserved elements set forth in FIG. 1. In some embodiments, the nucleic acid construct encodes a polypeptide that comprises at least 8, typically, at least 9, 10, 11, 12, 14, 15, 16, 17, 18, 19, 20, or more consecutive amino acids from the conserved elements set forth in FIG. 1; or in SEQ ID NOS:1-14, 32, 33, 40 and 41.

In typical embodiments, more than one nucleic acid construct encoding the conserved elements is used where one construct encodes a first set of conserved elements and the second construct encodes a second set of conserved elements where one or more elements, often each of the conserved elements, of the second set of conserved elements differs from the first set by 3 or fewer amino acids. The residues where the sequences differ, however, are at sites of naturally occurring variation, so that each of the conserved elements in the first and second sets corresponds to a naturally occurring protein sequence. In some embodiments, each element of the second set is at least 80% or at least 90% identical to the corresponding element in the first set of conserved sequences. The nucleic acid construct encoding the first set of conserved elements and the nucleic acid construct encoding the second set of conserved elements may be present in the same vector or different vectors.

Each conserved element useful for an immunogenic nucleic acid administered in accordance with the methods of the invention is typically fewer 30 amino acids in length. In some embodiments, the conserved element is less than 25, 24, 23, 22, 21, 20, or 15 amino acids in length. In some embodiments, the conserved element is 8, 9, 10, 11, 12, 13, 14, 15, 16, 17, 18, 19, 20, 21, 22, 23, 24, or 25 amino acids in length.

In the present invention, the conserved elements contained within the conserved elements are not contiguous in the native protein sequence. The individual conserved elements are typically joined to one another in the nucleic acid construct by a peptide linker, such as an alanine linker. Linker sequences are well known in the art. Typical peptide linker sequences contain Gly, Ser, Ala and Thr residues. Useful linkers include glycine-serine polymers; glycine-alanine polymers; alanine-serine polymers. In some embodiments, the linker is AA, AAAE (SEQ ID NO:42), AAAA (SEQ ID NO:43), AAK, AG, AA, LAK, AAK, AAAAL (SEQ ID NO:44), and the like.

The conserved elements may be present in any order in the construct, they need not occur in the order of the naturally occurring sequence. For example, a conserved element that occurs toward the N-terminus of a protein may be encoded at region of the construct encoding the C-terminal end.

In some embodiments, a nucleic acid encoding a conserved element polypeptide for use in the invention encodes a polypeptide that comprises the conserved elements set forth in SEQ ID NOS: 1-7. In some embodiments, such a nucleic acid construct encodes a polypeptide comprising the amino acid sequence of SEQ ID NO:15 ("Core1"). In some embodiments, a nucleic acid encoding a conserved element encodes a polypeptide comprising the conserved elements set forth in SEQ ID NOS:8-14. In some embodiments, such a nucleic acid construct encodes a polypeptide that comprises the amino acid sequence of SEQ ID NO: 16 ("Core2"). In some embodiments, a nucleic acid construct encoding a polypeptide comprising SEQ ID NO: 15 is administered with a nucleic acid construct encoding a polypeptide comprising SEQ ID NO: 16.

In some embodiments, a nucleic acid encoding a conserved element encodes a conserved elements set forth in SEQ ID NOS:3, 4, 5, 6, 32, 33, 40 or 41, or a variant thereof that differs by 1 amino acid. In some embodiments, a variant of SEQ ID NO:33 may differ at 1, 2, or 3 amino acids. In some embodiments, the conserved element polypeptide comprises a sequence set forth in FIG. 13.

In the present invention, a conserved element nucleic acid construct is administered in conjunction with the full-length protein, or substantially full-length protein, from which the conserved elements are obtained. In the context of the present invention, "substantially full-length" refers to the region of the protein that includes all of the conserved elements, i.e., a sufficient length of the naturally occurring protein is provided that includes all of the conserved elements that are used in the conserved element construct.

The nucleic acid encoding the full-length protein may be administered concurrently with the conserved element vaccine. In some embodiments, a full-length protein may be administered as the priming vaccine prior to administration of one or more conserved element constructs, which are administered as a boost. In preferred embodiments, one or more nucleic acids encoding conserved elements are administered as the prime and the nucleic acid encoding the full-length protein is administered as a boost. The boost is typically administered anywhere from two weeks to one, two, three, or four months, or longer, following administration of the initial vaccine.

Often, the nucleic acid constructs encoding the conserved elements and/or full-length protein are one or more purified nucleic acid molecules, for example, one or more plasmid-based vectors ("naked" DNA).

In some embodiments, the nucleic acid component may comprise vectors that encode the antigen of interest where the vector is contained within a virus. Viral delivery systems include adenovirus vectors, adeno-associated viral (AAV) vectors, herpes viral vectors, retroviral vectors, poxviral vectors, or lentiviral vectors. Methods of constructing and using such vectors are well known in the art.

Recombinant viruses in the pox family of viruses can be used for delivering the nucleic acid molecules encoding the antigens of interest. These include vaccinia viruses and avian poxviruses, such as the fowlpox and canarypox viruses. Methods for producing recombinant pox viruses are known in the art and employ genetic recombination. See, e.g., WO 91/12882; WO 89/03429; and WO 92/03545. A detailed review of this technology is found in U.S. Pat. No. 5,863,542. Representative examples of recombinant pox viruses include ALVAC, TROVAC, and NYVAC.

A number of adenovirus vectors have also been described that can be used to deliver one or more of the nucleic acid components of the vaccine. (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Retroviruses also provide a platform for gene delivery systems. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis, Semliki Forest, and Venezuelan Equine Encephalitis viruses, can also be used as viral vectors to deliver one or more nucleic acid components of the nucleic acid/protein combination vaccines of the invention. For a description of Sindbis-virus derived vectors useful for the practice of the instant methods, see, Dubensky et al., J. Virol. (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998).

Expression Constructs Encoding Fusion Polypeptides Comprising a Degradation Signal or Signal Peptide Sequence In some embodiments, a nucleic acids encoding a conserved element vaccine encodes a form in which the conserved element is fused to a sequence to enhance the immune response, such as a signal peptide sequence or a sequence that targets the protein for lysosomal degradation. Such embodiments typically results in enhanced immune responses in comparison to embodiments where the conserved element vaccine is not fused to a signal peptide or degradation signal.

Lysosomal Targeting Sequence

In other embodiments, signals that target proteins to the lysosome may also be employed. For example, the lysosome associated membrane proteins 1 and 2 (LAMP-1 and LAMP-2) include a region that targets proteins to the lysosome. Examples of lysosome targeting sequences are provided, e.g., in U.S. Pat. Nos. 5,633,234; 6,248,565; and 6,294,378.

Destabilizing sequences present in particular proteins are well known in the art. Exemplary destabilization sequences include c-myc aa 2-120; cyclin A aa 13-91; Cyclin B aa 13-91; IkBα aa 20-45; β-Catenin aa 19-44; β-Catenin aa 18-47, c-Jun aa1-67; and c-Mos aa1-35; and fragments and variants, of those segments that mediate destabilization. Such fragments can be identified using methodology well known in the art. For example, polypeptide half-life can be determined by a pulse-chase assay that detects the amount of polypeptide that is present over a time course using an antibody to the polypeptide, or to a tag linked to the polypeptide. Exemplary assays are described, e.g., in WO02/36806, which is incorporated by reference.

Variants of such sequences, e.g., that have at least 90% identity, usually at least 91%, 92%, 93%, 94%, 95%, 96%, 97%, 98%, 99%, or greater, identity to the sequences noted above, e.g., a LAMP degradation sequence, can be employed in this invention, e.g., for fusion to an HIV gag conserved element polypeptide.

Additional degradation signals that can be used to modify retroviral antigens, e.g., HIV antigens in accordance with the invention include the F-box degradation signal, such as the F-BOX signal 47 aa (182-228) from protein beta-TrCP (Liu, et al., *Biochem Biophys Res Comm.* 313:1023-1029, 2004). Accordingly, in some embodiments, an expression vector for use in the invention may encode a fusion protein where an F-box degradation signal is attached to an HIV antigen, e.g., gag.

Targeting to the Proteasome and Other Degradation Signals

Many polypeptide sequences that target a protein for degradation are known in the art. One example of destabilizing sequences are so-called PEST sequences, which are abundant in the amino acids Pro, Asp, Glu, Ser, Thr (they need not be in a particular order), and can occur in internal positions in a protein sequence. A number of proteins reported to have PEST sequence elements are rapidly targeted to the 26S proteasome. A PEST sequence typically correlates with a) predicted surface exposed loops or turns and b) serine phosphorylation sites, e.g. the motif S/TP is the target site for cyclin dependent kinases.

Additional destabilization sequences relate to sequences present in the N-terminal region. In particular the rate of ubiquitination, which targets proteins for degradation by the 26S proteasome can be influenced by the identity of the N-terminal residue of the protein. Thus, destabilization sequences can also comprise such N-terminal residues, "N-end rule" targeting (see, e.g., Tobery et al., *J. Exp. Med.* 185:909-920).

Other targeting signals include the destruction box sequence that is present, e.g., in cyclins. Such a destruction box has a motif of 9 amino acids, R1(A/T)2(A)3L4(G)5X6(I/V)7(G/T)8(N)9, in which the only invariable residues are R and L in positions 1 and 4, respectively. The residues shown in brackets occur in most destruction sequences. (see, e.g., Hershko & Ciechanover, Annu. Rev. Biochem. 67:425-79, 1998). In other instances, destabilization sequences lead to phosphorylation of a protein at a serine residue (e.g., Ixbo).

In some embodiments, a conserved element polypeptide of the invention is fused to a LAMP degradation sequence. For example, the methods of the invention may employ a polypeptide in which SEQ ID NO: 15 or SEQ ID NO: 16 is fused to a LAMP degradation sequence.

Expression Constructs that Encode Secreted Fusion Proteins

A secretory polypeptide in the context of this invention is a polypeptide signal sequence that results in secretion of the protein to which it is attached. In some embodiments, the secretory polypeptide is a chemokine, cytokine, or lymphokine, or a fragment of the chemokine, cytokine, or lymphokine that retains immunostimulatory activity. Examples of chemokines secretory polypeptides include MCP-3 and IP-10. In other embodiments, the secretory polypeptide is a polypeptide signal sequence from a secreted protein such as tissue plasminogen activator (tPA) protein, growth hormone, GM-CSF, a cytokine, or an immunoglobulin protein. Constructs encoding secretory fusion proteins are disclosed, e.g., in WO02/36806.

In some embodiments, the signal peptide is a GM-CSF sequence, e.g., a mammalian GM-CSF sequence such as a human GM-CSF signal peptide sequence.

In some embodiments, a secretory signal for use in the invention is MCP-3 amino acids 33-109, e.g., linked to IP-10 secretory peptide.

In some embodiments, a conserved element polypeptide is joined to a GM-CSF signal peptide sequence. For example, in some embodiments, the methods of the invention may employ a polypeptide comprising SEQ ID NO: 15 fused to a GM-CSF signal peptide and/or a polypeptide comprising SEQ ID NO: 16 fused to a GM-CSF signal peptide.

Similarly, an expression construct encoding a full-length polypeptide, e.g., a construct that encodes p55 gag, may also be modified with a degradation sequence and/or a secretory sequence. Moreover, more than one construct encoding the full-length polypeptide, e.g, p55gag may be administered. For example a construct in which p55 gag is fused to a signal polypeptide such as GM-CSF may be used in conjunction with a construct in which p55gag is fused to a degradation sequence, such as LAMP.

Additional Properties of Expression Constructs

Within each expression cassette, sequences encoding an antigen for use in the nucleic acid vaccines of the invention will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that promote RNA export (e.g., a constitutive transport element (CTE), a RNA transport element (RTE), or combinations thereof; sequences that enhance translation efficiency (e.g., Kozak consensus sequence);

sequences that enhance protein stability; and when desired, sequences that enhance protein secretion.

Any of the conventional vectors used for expression in eukaryotic cells may be used for directly introducing nucleic acids into tissue. Expression vectors containing regulatory elements from eukaryotic viruses are often used in eukaryotic expression vectors. Such regulatory elements include, e.g., human CMV, simian CMV, viral LTRs, and the like. Typical vectors may comprise, e.g, those with a human CMV promoter, bovine growth hormone polyA site and an antibiotic resistance gene for selective growth in bacteria.

Other expression vector components are well known in the art, including, but not limited to, the following: transcription enhancer elements, transcription termination signals, polyadenylation sequences, splice sites, sequences for optimization of initiation of translation, and translation termination sequences.

In some embodiments, the nucleic acid component may comprises one or more RNA molecules, such as viral RNA molecules or mRNA molecules that encode the antigen of interest.

In typical embodiments, the nucleic acid constructs are codon-optimized for expression.

In the present invention, a "nucleic acid" molecule can include cDNA and genomic DNA sequences, RNA, and synthetic nucleic acid sequences. Thus, "nucleic acid" also encompasses embodiments in which analogs of DNA and RNA are employed.

An immunogenic composition of the invention can be administered as one or more constructs. For example, where two sets of conserved elements are employed, e.g., conserved element polypeptides Core1 and Core2, or conserved element polypeptides p2CE1c and p24CE2c or conserved element polypeptides p2CE1d and p24CE2d, a nucleic acid construct can encode both sets, or each set may be encoded by a separate expression vector. Thus, the expression constructs administered in accordance with the invention may be administered as multiple expression vectors, or as one or more expression vectors encoding multiple expression units, e.g., a discistronic, or otherwise multicistronic, expression vectors. For example, an expression vector may be employed that encodes both SEQ ID NO:15 and SEQ ID NO:16 or multiple expression vectors may be employed where SEQ ID NO:15 is encoded by one vector and SEQ ID NO:16 is encoded by another vector.

Preparation of Immunogenic Compositions

In the methods of the invention, the nucleic acid component is often directly introduced into the cells of the individual receiving the immunogenic composition. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. The nucleic acids can be administered using ballistic delivery as described, for instance, in U.S. Pat. No. 5,204,253 or pressure (see, e.g., U.S. Pat. No. 5,922,687). Using this technique, particles comprised solely of DNA are administered, or in an alternative embodiment, the DNA can be adhered to particles, such as gold particles, for administration.

In some embodiments, e.g., where a nucleic acid component of the invention is encoded by a viral vector, the nucleic acid component can be delivered by infecting the cells with the virus containing the vector. This can be performed using any delivery technology, e.g., as described in the previous paragraph.

In some embodiments, the immunogenic compositions of the invention are administered by injection or electroporation, or a combination of injection and electroporation.

Assessment of Immunogenic Response

To assess a patient's immune system during and after treatment and to further evaluate the treatment regimen, various parameters can be measured. Measurements to evaluate vaccine response include: antibody measurements in the plasma, serum, or other body fluids; and analysis of in vitro cell proliferation in response to a specific antigen, indicating the function of CD4+ cells. Such assays are well known in the art. For example, for measuring CD4+ T cells, many laboratories measure absolute CD4+ T-cell levels in whole blood by a multi-platform, three-stage process. The CD4+ T-cell number is the product of three laboratory techniques: the white blood cell (WBC) count; the percentage of WBCs that are lymphocytes (differential); and the percentage of lymphocytes that are CD4+ T-cells. The last stage in the process of measuring the percentage of CD4+ T-lymphocytes in the whole-blood sample is referred to as "immunophenotyping by flow cytometry. Systems for measuring CD4+ cells are commercially available. For example Becton Dickenson's FACSCount System automatically measure absolutes CD4+, CD8+, and CD3+T lymphocytes.

Other measurements of immune response include assessing CD8+ responses. These techniques are well known. CD8+ T-cell responses can be measured, for example, by using tetramer staining of fresh or cultured PBMC (see, e.g., Altman, et al., *Proc. Natl. Acad. Sci. USA* 90:10330, 1993; Altman, et al., Science 274:94, 1996), or γ-interferon release assays such as ELISPOT assays (see, e.g., Lalvani, et al., *J. Exp. Med.* 186:859, 1997; Dunbar, et al., *Curr. Biol.* 8:413, 1998; Murali-Krishna, et al., *Immunity* 8:177, 1998), or by using functional cytotoxicity assays.

Viral Titer

Viremia is measured by assessing viral titer in a patient. There are a variety of methods of perform this. For example, plasma HIV RNA concentrations can be quantified by either target amplification methods (e.g., quantitative RT polymerase chain reaction [RT-PCR], Amplicor HIV Monitor assay, Roche Molecular Systems; or nucleic acid sequence-based amplification, [NASBA®], NucliSens™ HIV-1 QT assay, Organon Teknika) or signal amplification methods (e.g., branched DNA [bDNA], Quantiplex™ HIV RNA bDNA assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Administration of DNA Constructs

The DNA vectors are formulated for pharmaceutical administration. While any suitable carrier known to those of ordinary skill in the art may be employed in the pharmaceutical compositions of this invention, the type of carrier will vary depending on the mode of administration. For parenteral administration, including intranasal, intradermal, subcutaneous or intramuscular injection or electroporation, the carrier preferably comprises water, saline, and optionally an alcohol, a fat, a polymer, a wax, one or more stabilizing amino acids or a buffer. General formulation technologies are known to those of skill in the art (see, for example, Remington: The Science and Practice of Pharmacy (20th edition), Gennaro, ed., 2000, Lippincott Williams & Wilkins; Injectable Dispersed Systems: Formulation, Processing And Performance, Burgess, ed., 2005, CRC Press; and Pharmaceutical Formulation Development of Peptides and Proteins, Frkjr et al., eds., 2000, Taylor & Francis).

Naked DNA can be administered in solution (e.g., a phosphate-buffered saline solution) by injection, usually by an intra-arterial, intravenous, subcutaneous or intramuscular route. In general, the dose of a naked nucleic acid composition is from about 10 μg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA immunogenic compositions can be administered once or multiple times. DNA vaccination is performed more than once, for example, 2, 3, 4, 5, 6, 7, 8, 10, 15, 20 or more times as needed to induce the desired response (e.g., specific antigenic response or proliferation of immune cells). Multiple administrations can be administered, for example, bi-weekly, weekly, bi-monthly, monthly, or more or less often, as needed, for a time period sufficient to achieve the desired response.

The nucleic acid constructs in accordance with the invention are administered to a mammalian host. The mammalian host usually is a human or a primate. In some embodiments, the mammalian host can be a domestic animal, for example, canine, feline, lagomorpha, rodentia, *rattus*, hamster, murine. In other embodiment, the mammalian host is an agricultural animal, for example, bovine, ovine, porcine, equine, etc.

Immunogenic compositions containing the DNA expression constructs can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

In therapeutic applications, the vaccines are administered to a patient in an amount sufficient to elicit a therapeutic effect, e.g., a $CD8^+$, $CD4^+$, and/or antibody response to the HIV-1 antigens encoded by the vaccines that at least partially arrests or slows symptoms and/or complications of HIV infection. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

Suitable quantities of DNA, e.g., plasmid or naked DNA can be about 1 μg to about 100 mg, preferably 0.1 to 10 mg, but lower levels such as 1-10 μg can be employed. For example, an HIV DNA vaccine, e.g., naked DNA or polynucleotide in an aqueous carrier, can be injected into tissue, e.g., intramuscularly or intradermally, in amounts of from 10 l per site to about 1 ml per site. The concentration of polynucleotide in the formulation is usually from about 0.1 μg/ml to about 4 mg/ml.

The vaccine may be delivered in a physiologically compatible solution such as sterile PBS in a volume of, e.g., one ml. The vaccines may also be lyophilized prior to delivery. As well known to those in the art, the dose may be proportional to weight.

The compositions included in the regimen descried herein for inducing an immune response can be administered alone, or can be co-administered or sequentially administered with other immunological, antigenic, vaccine, or therapeutic compositions.

Compositions that may also be administered with the vaccines include other agents to potentiate or broaden the immune response, e.g., IL-15, IL-12, IL-2 or CD40 ligand, which can be administered at specified intervals of time, or continuously administered.

The vaccines can additionally be complexed with other components such as peptides, polypeptides and carbohydrates for delivery. For example, expression vectors, i.e., nucleic acid vectors that are not contained within a viral particle, can be complexed to particles or beads that can be administered to an individual, for example, using a vaccine gun.

Nucleic acid vaccines are administered by methods well known in the art as described in Donnelly et al. (*Ann. Rev. Immunol.* 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), each of which is incorporated herein by reference. One skilled in the art would know that the choice of a pharmaceutically acceptable carrier, including a physiologically acceptable compound, depends, for example, on the route of administration of the expression vector.

As noted above, immunogenic DNA compositions can be delivered via a variety of routes. Typical delivery routes include parenteral administration, e.g., intradermal, intramuscular or subcutaneous routes. Administration of expression vectors of the invention to muscle and by electroporation can be a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

The immunogenic compositions can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

The vaccines can be incorporated, if desired, into liposomes, microspheres or other polymer matrices (see, e.g., Felgner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer.

Liposomes include emulsions, foams, micelles, insoluble monolayers, liquid crystals, phospholipid dispersions, lamellar layers and the like.

EXAMPLES ILLUSTRATING THE INVENTION

Example 1. Core DNA Vaccination Induces Cross-Clade Specific Cellular Immune Responses in Mice Results Conserved Element DNA Vaccines A set of conserved elements (CE) was identified in $p24^{gag}$ composed of amino acids (AA) highly conserved across the entire HIV-1 group M, as determined by using the Los Alamos HIV database (www site is hiv.lanl.gov/) [32]. A refined list of 7 CE was selected based on several criteria (FIG. 1A, see Materials and Methods): a minimum length of 8 AA; inclusion of specific epitopes that have been correlated with viral control (low viral loads) in vivo; and exclusion of epitopes associated with high viral loads. The selected CE span 12-24 amino acids each, and together a total of 124 AA, thus representing 54% of $p24^{gag}$ sequence. The CE are highlighted on the $p24^{gag}$ capsid ribbon structure [97], revealing that they encompass most of the extended coiled regions of the $p24^{gag}$ protein (FIG. 1B).

We generated multiple DNA-based vaccines in which the 7 CE were collinearly arranged (FIG. 1C), and connected via short linker sequences (FIG. 1D), designed for efficient proteolytic cleavage [91, 92]. Proteolytic processing of CE peptides in vitro revealed production of optimal epitopes or slightly extended optimal epitopes from 6 of the 7 CE segments (S. Le Gall, in preparation). Therefore, the CE immunogen is predicted to be able to present a significant number of native T cell epitopes after expression. For optimal arrangement of the different segments within the p24CE immunogens, the hydrophobicity of individual CE was taken into consideration (FIG. 1C). To avoid the strongly hydrophobic N-terminus in the arrangement CE1-2-3-4-5-6-7 (left panel), which could impact the intracellular trafficking of the protein, the CE1 peptide was placed at the C-terminus (right panel).

The majority of the AA included in the p24CE immunogens are essentially invariant since they are found in >98% of HIV isolates. The length of p24CE was expanded by including some less well-conserved AA ('toggle' sites), thus expressing additional potentially immunogenic regions. This allowed the extension of the 7 CE to the length of 12-24 AA, as mentioned above, and led to two p24CE sequences differing by 7 AA, one in each CE (FIG. 1A), named p24CE1 and p24CE2. These two sequences cover >99% of all known HIV-1 group M sequences. The p24CE1 and p24CE2 sequences were RNA/codon optimized [73-75] to maximize mRNA processing, transport, stability and translation (see Material and Methods). The p24CE coding regions were cloned into the pCMVkan vaccine vector (p24CE; FIG. 1D). Additional expression plasmids were generated in order to alter the intracellular trafficking and processing of the p24CE proteins. Plasmids SP-p24CE1 and SP-p24CE2 contain the GM-CSF signal peptide at the N-terminus of p24CE to promote secretion of the p24CE proteins. Plasmids MCP3-p24CE1 and MCP3-p24CE2 express fusion proteins with the monocyte chemoattractant protein 3 (MCP-3) chemokine, previously shown to stabilize the encoded protein and to enhance trafficking to antigen presenting cells [80,81. Plasmids LAMP-p24CE1 and LAMP-p24CE2 express fusion proteins with the human lysosomal associated membrane protein 1 (LAMP-1). Fusion of Gag to LAMP was previously shown to direct it to the lysosomal compartment and to facilitate access to the MHC class II pathway as well as to the extracellular compartment [98-102].

Expression of the p24CE Proteins in Human Cells

Figure 2:
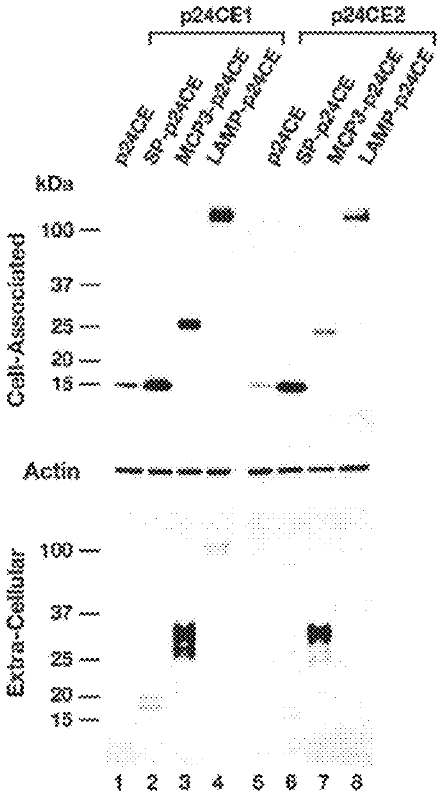
FIG. 2: Expression of the p24CE plasmids upon transient transfection in cultured cells. Plasmid DNA (1 μg) expressing different variants of either p24CE1 (left panel) or p24CE2 (right panel) proteins were transfected in HEK293 cells. The cultures were harvested 24 hrs later and proteins from equal amounts (1/250) from the cell-associated (top panel) and extra-cellular (bottom panel) fractions were resolved on a 12% NuPAGE Bis-Tris gel and analyzed by Western immunoblot using a goat anti-$p24^{gag}$ antiserum and visualized using enhanced ECL. The membrane containing the cell-associated fractions was also probed with anti-human pan actin antibody to control for equal loading of the samples.

The expression of the p24CE vectors shown in FIG. 1D was evaluated by Western immunoblots using cell extracts and supematants from transiently transfected HEK293 cells (FIG. 2). To control for equal loading, the membrane containing the cell-associated samples were probed with an antibody against human beta actin as internal control (middle panel) demonstrating that similar amounts of proteins were loaded into each lane which validates our conclusions regarding the stability and different distribution of the proteins encoded by the different transfected plasmids (see below). Very low levels of the p24CE1 and p24CE2 proteins were detected in the cell-associated fractions (lanes 1 and 5, respectively), and no proteins were found in the extracellular compartment, indicating that the p24CE proteins were unstable. We also noted that p24CE2, differing only by 7 of the 124 AA from p24CE1, produced an even less stable antigen. The presence of the GM-CSF signal peptide (SP) greatly increased the levels of both p24CE proteins (lanes 2 and 6) in both the cell-associated and the extracellular fractions. These data indicate that the signal peptide altered the trafficking of the p24CE proteins, and promoted increase in stability and secretion. We noted the presence of additional bands of the secreted p24CE proteins, likely due to posttranslational modifications related to the altered cellular trafficking (compare lane 2 and lane 1; lane 6 to lane 5). The MCP3-p24CE (lanes 3 and 7) and LAMP-p24CE fusion proteins (lanes 4 and 8) were also readily detectable, and thus these fusions greatly stabilized the p24CE proteins. MCP3-p24CE localization in the extracellular fraction (lanes 3 and 7) as several bands, was similar to our previous report on a MCP3-Gag fusion protein [81]. The LAMP-p24CE proteins accumulated primarily in the cell-associated fraction (lanes 4 and 8), although some protein could also be found in the extracellular fraction, as we previously observed for the LAMP-$p55^{gag}$ protein [101]. These data showed that altering the trafficking of the p24CE proteins, by adding the GM-CSF signal peptide or upon fusion to the MCP3 or LAMP molecules, enhanced the stability and modulated the trafficking of p24CE proteins.

Vaccination with p24CE Induces CE-Specific Cellular Immune Responses in C57BL/6 Mice We next evaluated the immunogenicity of different p24CE proteins after DNA vaccination of C57BL/6 mice. Groups of mice (N=5) were vaccinated twice (0 and 4 weeks) with the indicated p24CE plasmids or sham plasmid DNA, as negative control, by intramuscular injection followed by in vivo electroporation (EP). Two weeks after the last vaccination (week 6), the mice were sacrificed and the presence of CE-specific cellular responses was determined by polychromatic flow cytometry. Splenocytes from the individual animals from each of the vaccine groups and the sham DNA inoculated negative control group were stimulated with a Group M consensus Gag peptide pool (15-mer peptides overlapping by 11 AA) (FIG. 3A) or with a COT-M peptide pool (10-mer overlapping by 9 AA) consisting of both p24CE1 and p24CE2 sequences (FIG. 3B). The use of the 15-mer peptide pool allowed for the detection of both $CD4^+$ and $CD8^+$ T cell responses, whereas the 10-mer peptide pool favors mainly $CD8^+$ T cell responses. Vaccination with plasmids expressing p24CE or the secreted p24CE (SP-p24CE) proteins induced both CE-specific $CD4^+$ and $CD8^+$ T cell immune responses (FIG. 3A). In contrast, vaccination with the p24CE fusion proteins, MCP3-p24CE or LAMP-p24CE, elicited CE-specific responses that were almost exclusively mediated by $CD4^+$ T cells. In agreement with these results, splenocyte stimulation with 10-mer peptide pools, which are mainly associated with MHC class I antigens, induced very low responses in MCP3-p24CE DNA vaccinated mice and no responses in the LAMP-p24CE immunized mice, which verified the previous conclusions (FIG. 3B). We hypothesize that altered intracellular trafficking of the p24CE fusion antigens could be responsible for the distinct preference for $CD4^+$ or $CD8^+$ T cell responses. Responses elicited by p24CE1 proteins were in general higher than those induced by p24CE2 (FIGS. 3A and 3B, note the different scales for p24CE1 and p24CE2), likely reflecting the higher expression of p24CE as indicated by the transient transfection experiments (see FIG. 2). As expected, no cellular responses were found in splenocytes from sham DNA vaccinated mice.

The cross-reactivity of the induced responses was analyzed using peptide pools representing different HIV-1 clades (A, B, and C; see also FIG. 1A). SP-p24CE1 DNA vaccination induced cross-clade reactive $CD4^+$ and $CD8^+$ cellular responses, which were similar in magnitude to those obtained with the Group M peptide pool (FIG. 3C). Cross-clade reactivity was also obtained upon vaccination with the other p24CE plasmids (data not shown). In contrast, splenocytes from mice immunized with sham DNA failed to recognize peptides from any of the three clade-specific peptide pools.

Fine Specificity of CE-Specific T Cell Responses from Vaccinated C57BL/6 Mice

Figure 4:
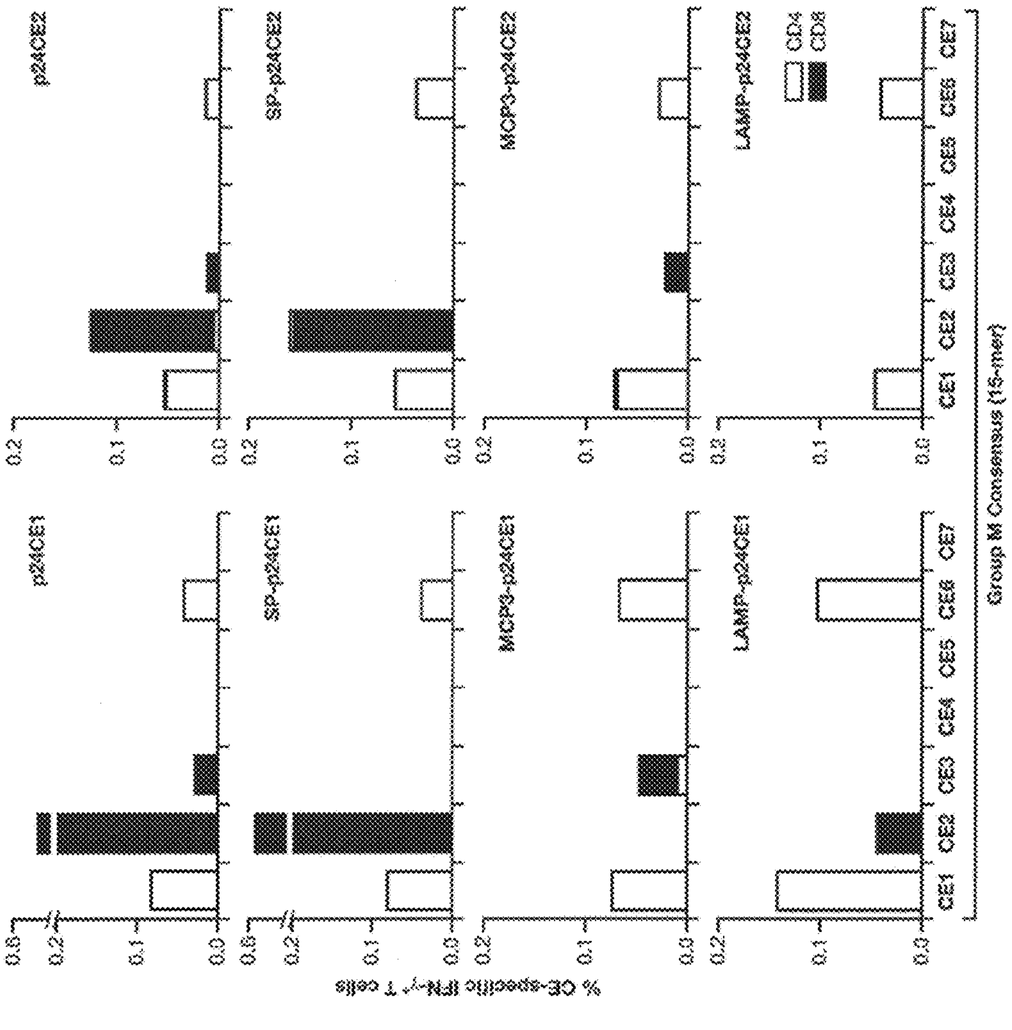
FIG. 4: Mapping of the p24CE-induced cellular immune responses. Pooled splenocytes from C57BL/6 mice (N=5) vaccinated with the indicated p24CE1 (left panels) or p24CE2 (right panels) DNAs were stimulated with the Group M Consensus peptide pools (15-mers overlapping by 11 AA) spanning the individual CEs. The frequency of CE-specific IFN-γ producing T cells was measured. $CD4^+$ (open bars) and $CD8^+$ (filled bars) Gag-specific T cells are shown.

Next, we assessed the distribution of the p24CE-induced cellular responses among the different CE (FIG. 4). Pooled splenocytes from the DNA vaccinated C57BL/6 mice (N=5/group) were stimulated with Group M consensus peptide pools (15-mer) encompassing the 7 individual CE. Polychromatic flow cytometry was used to determine the frequency of the CE-specific IFN-γ producing T cells and to discriminate between $CD4^+$ and $CD8^+$ T cell responses. Immunization with the different p24CE1 (left panels) and p24CE2 (right panels) plasmid DNAs induced cellular responses to CE1 and CE6, which were mediated almost exclusively by $CD4^+$ T cells. Interestingly, mice immunized with plasmids encoding the native p24CE protein (p24CE and SP-p24CE) developed also high $CD8^+$ mediated cellular responses to CE2. These data are in agreement with the cellular localization of the encoded proteins: the native p24CE protein remains mainly intracellular, while the SP-p24CE and MCP3-p24CE fusion are actively secreted and the LAMP-p24CE associates with the MHC class II compartment. Low levels of $CD8^+$ T cell responses to CE3 were also identified upon immunization with the p24CE and the MCP3-p24CE plasmids. In conclusion, the p24CE proteins induced responses to 4 of the 7 CE (CE1, CE2, CE3, CE6) in mice, although these responses were generally lower in animals immunized with the p24CE2 plasmids, demonstrating that vaccination induced broad $CD4^+$ and $CD8^+$ T cell responses.

p24CE Induces Broader Immune Responses than the Full-Length $p55^{gag}$

Figure 5:
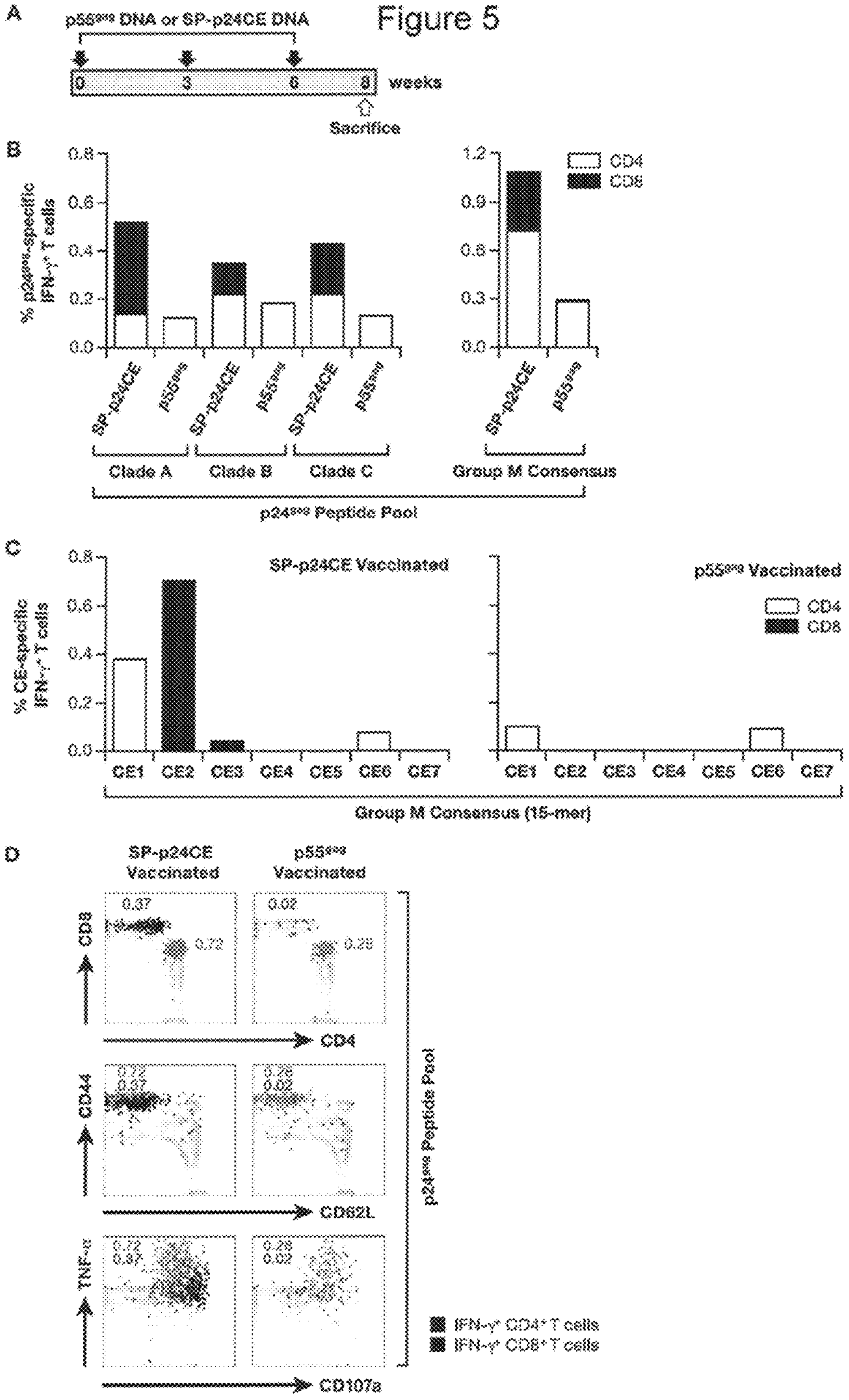
FIG. 5, A-D: Phenotypic and functional analysis of T cell responses generated by $p55^{gag}$ and p24CE DNA vaccination. (A) Mice (N=5/group) were vaccinated 3 times (week 0, 3 and 6) with 20 μg of a plasmid expressing HXB2 $p55^{gag}$ (clade B) or 20 μg of a mixture of plasmids expressing SP-p24CE1 and SP-p24CE2. The mice were sacrificed 2 weeks after the last immunization. Three independent experiments were performed and a representative experiment is shown. (B) Pooled splenocytes were stimulated with Clade A, B or C peptide pools (15-mers) spanning the $p24^{gag}$ region (left panel) and the Group M consensus peptide pool (right panel). The frequency of the $CD4^+$ (open bars) and $CD8^+$ (filled bars) $p24^{gag}$-specific IFN-γ producing T cells was determined. (C) The splenocytes from the SP-24CE (left panel) and $p55^{gag}$ (right panel) DNA vaccinated mice were stimulated with peptide pools specific for the individual CEs. The frequency of the $CD4^+$ (open bars) and $CD8^+$ (filled bars) CE-specific IFN-γ producing T cells was determined. (D) Plot overlays show the phenotypic and functional characterization of the antigen-specific T cells induced by SP-p24CE (left panels) and $p55^{gag}$ (right panels) DNA vaccines upon stimulation with $p24^{gag}$-specific peptide pool. Total T cells recovered from the spleen are shown as grey contours, and the antigen-specific IFN-γ+ T cells are overlaid as red ($CD4^+$ T cells) or black ($CD8^+$ T cells) dots. The plots show the CD4/CD8 distribution (top panel), memory phenotype as determined by CD44/CD62L staining (middle panel) and TNFα/CD107a expression (bottom panel) among the T cells from vaccinated mice. The frequency of $CD4^+$ (red) and $CD8^+$ (black) IFN-γ T lymphocytes is shown.

We compared the immune responses to the individual CE upon vaccination with a $p55^{gag}$ plasmid DNA or with a mixture of SP-p24CE1 and SP-p24CE2 DNAs. The mice (N=5/group) received 3 vaccinations (week 0, 3 and 6) and were sacrificed at week 8 (FIG. 5A). Vaccine-induced T cell responses were analyzed from pooled splenocytes (FIG. 5B) stimulated with 15-mer peptide pools specific for $p24^{gag}$ of clade A, B, or C (left panel) and the group M consensus (right panel). The overall responses induced by the $p55^{gag}$ immunogen were lower than those obtained by the p24CE immunogen, and remarkably, lacked $CD8^+$-specific T cells. Using peptide pools spanning the individual CE (FIG. 5C) showed that $p55^{gag}$ DNA elicited low responses to CE1 and CE6 only (right panel), mediated exclusively by $CD4^+$ T cells. In contrast, vaccination with SP-p24CE DNA mixture elicited higher responses towards several CE (CE1, CE2 CE3 and CE6), as also expected from the data shown in FIG. 4.

We also evaluated the quality of the cellular immune responses elicited by the different immunogens (FIG. 5D) using the $p24^{gag}$ peptide pool followed by intracellular cytokine staining and polychromatic flow cytometry. Vaccination with $p55^{gag}$ DNA induced primarily $CD4^+$ (red) T cell responses, while p24CE vaccination induced both $CD4^+$ (red) (CE1 and CE6) and $CD8^+$ (black) (CE2 and CE3) T cell responses (FIGS. 5B and 5C, top panel). Both immunogens induced effector memory T cells ($CD44^{hi}$ and $CD62L^{neg}$) (FIG. 5C, middle panel), which were mainly $CD4^+$ (0.28% of total T cells) in mice vaccinated with $p55^{gag}$ DNA, and both $CD4^+$ (0.72% of total T cells) and $CD8^+$ (0.37% of total T cells) in the mice vaccinated with the SP-p24CE DNA. Further analyses revealed that antigen-specific IFN-γ+ T cells produced TNF-α and expressed CD107a on the surface upon stimulation with antigen, indicating induction of cytotoxic T cells (FIG. 5D, bottom panel). We also noted that the $CD8^+$ T cells (black), induced only by SP-p24CE DNA vaccination, expressed higher levels of CD107a and lower levels of TNFα than the $CD4^+$ T cells (red), a phenotype consistent with the degranulation associated with CTL activity. Collectively our results show that the p24CE vaccine increased breadth and magnitude of cellular responses to $p24^{gag}$ region in DNA vaccinated mice, by inducing robust responses to several of the highly conserved elements, and that the responses are multifunctional, a desired feature for an effective HIV vaccine.

Vaccination with p24CE Induces Cross-Clade Reactive Humoral Immune Responses

Figure 6:
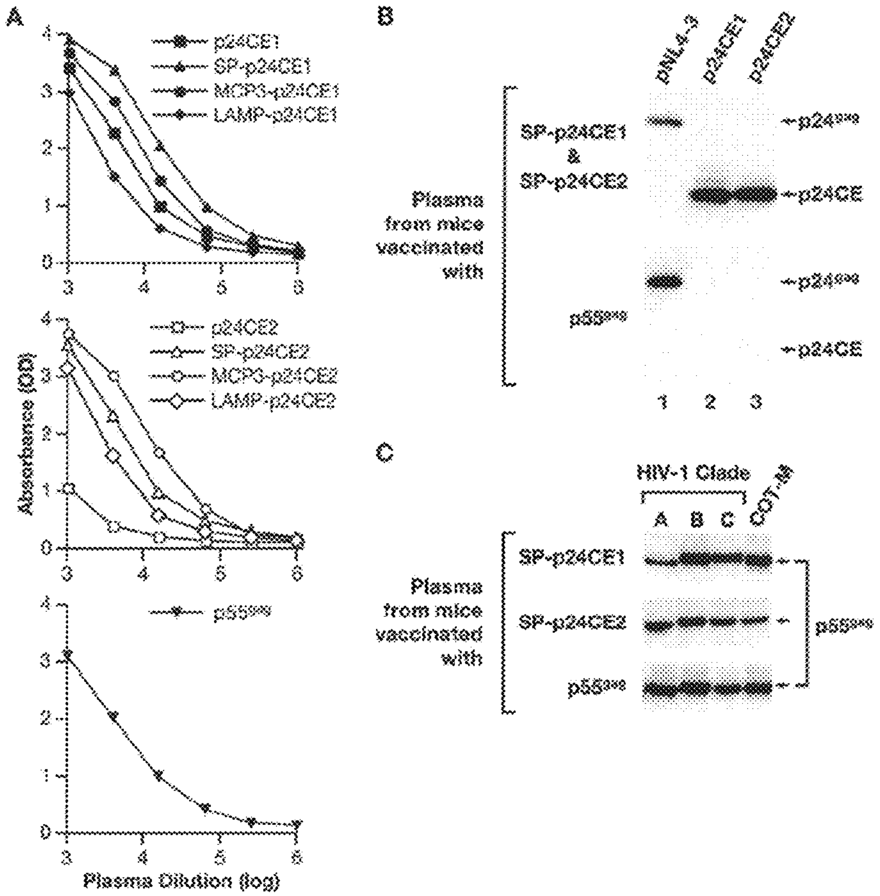
FIG. 6, A-C: Humoral immune responses in p24CE DNA vaccinated mice. (A) Anti-HIV-1 $p24^{gag}$ antibodies were measured in plasma from p24CE and $p55^{gag}$ DNA vaccinated C57BL/6 mice by a standard clade B $p24^{gag}$ ELISA.

We next examined the induction of humoral immune responses using pooled plasma samples from p24CE DNA vaccinated mice (N=5/group) by an ELISA measuring clade B $p24^{gag}$ responses (FIG. 6A). The different p24CE antigens readily induced high levels of humoral responses with titers similar or greater than those achieved in $p55^{gag}$ DNA vaccinated mice (except p24CE2, middle panel). Vaccination with p24CE DNA induced antibodies to both the p24CE proteins (FIG. 6B, top panel, lanes 2 and 3) as well as to the processed $p24^{gag}$ protein (lane 1). In contrast, the antibodies induced by $p55^{gag}$ DNA vaccination readily detected $p24^{gag}$ (FIG. 6B, bottom panel, lane 1), but failed to recognize the p24CE proteins (lanes 2 and 3). Thus, similar to the cellular immune responses (see FIG. 5), the antibodies elicited upon vaccination with full-length $p55^{gag}$ DNA were unable to recognize the conserved elements.

We also examined the cross-clade reactivity of these responses by Western immunoblot analysis (FIG. 6C). Membranes containing $p55^{gag}$ proteins from consensus clades A and C, clade B (HXB2) and COT-M, obtained from transiently transfected cells, were probed with pooled plasma samples from mice vaccinated with plasmids expressing SP-p24CE1, SP-p24CE2 or $p55^{gag}$. The Western immunoblot assays showed that the antibodies induced by the p24CE and $p55^{gag}$ DNA vaccinated mice detect the different $p55^{gag}$ proteins. These data suggest that similar to $p55^{gag}$, p24CE vaccinated mice induce cross-clade reactive antibodies.

Together, these data show that p24CE DNA vaccination induced strong humoral (FIG. 6) and cellular (FIG. 4) immune responses to the highly conserved elements in $p24^{gag}$, and that CE segments are not or only poorly immunogenic when expressed as part of the complete $p55^{gag}$ in DNA vaccinated C57BL/6 mice.

Discussion

The experiments performed in mice demonstrated that a DNA vaccine expressing 7 selected highly Conserved Elements within HIV-1 $p24^{gag}$ can be produced and that this DNA vaccine is immunogenic in comparison to DNA-encoded full-length native $p55^{gag}$. We have previously demonstrated that individuals chronically infected with HIV-1 develop cellular immune responses specific for the peptides encoded by the 7 conserved elements described in this work [34]. Furthermore, we found that the breadth, magnitude and avidity of these cellular responses to some CE were significantly higher among patients able to control HIV-1 infection, which suggests that responses against these conserved regions are clinically relevant [34].

Starting from our understanding of the rules for robust gene expression, and to avoid the escape potential of HIV, we constructed optimized DNA vectors that express maximal levels of new artificial immunogens based on highly conserved elements of the $p24^{gag}$ region. This vaccine design is based on two principles, (i) the immunogen must include critical and highly conserved elements of the virus that cannot mutate without a severe loss in viability, and (ii) the immunogen must exclude HIV epitopes that are capable of mutating without significantly affecting viral fitness. The former may induce responses against a large number of HIV isolates, and the latter avoids immunodominant competition from variable regions, which may render ineffective the vaccine-induced immune response. Not only expression, but also the stability and presentation of the artificial antigens encoded by the DNA vectors were optimized. To this end, different fusion constructs were designed. We previously noted that either addition of a signal peptide or fusion to either MCP3 or LAMP were beneficial for protein expression [81,80,94], and found that these modifications also stabilize the p24CE proteins.

Figure 3:
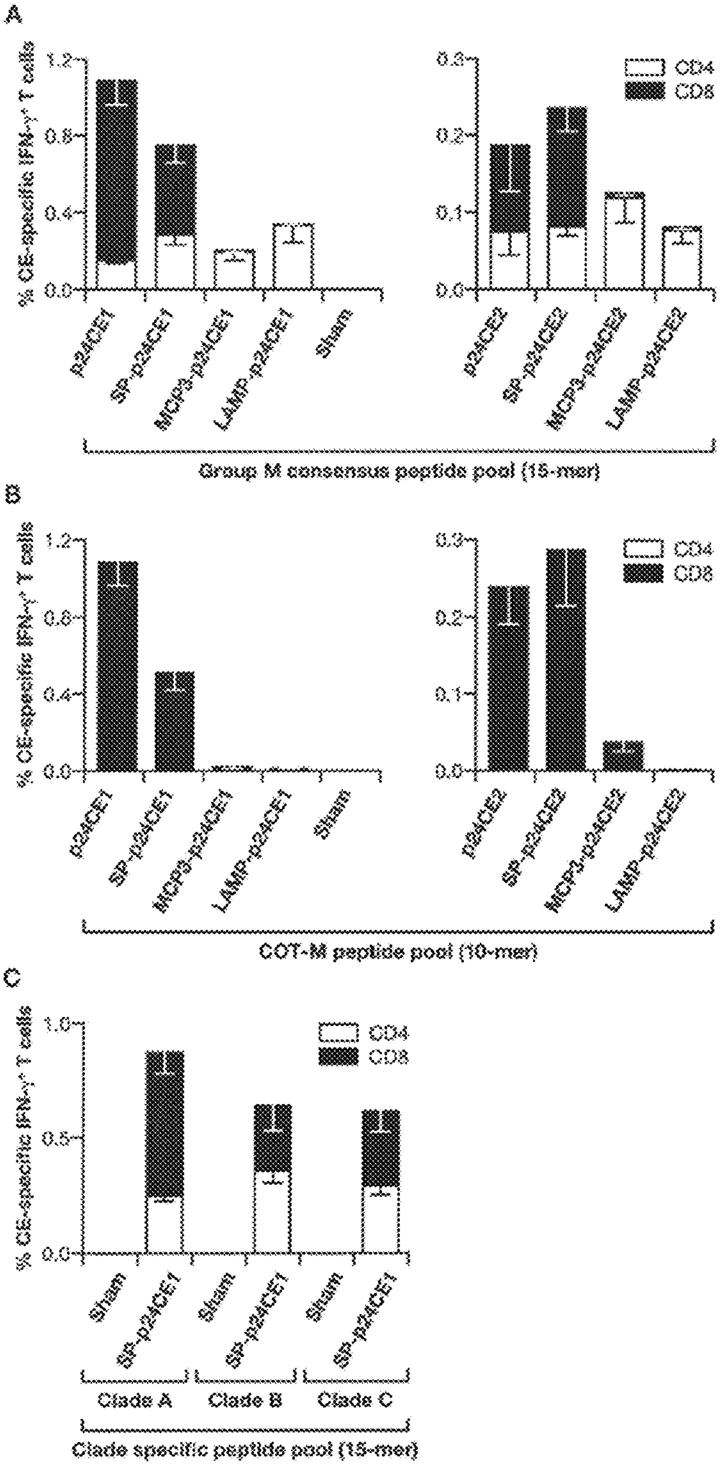
FIG. 3, A-C: Cellular responses in p24CE DNA vaccinated C57BL/6 mice. Mice were vaccinated using in vivo EP with 20 μg of the indicated p24CE1 or p24CE2 DNA plasmids or with SP-p24CE1 DNA. Splenocytes from individual animals were stimulated (A) with the Group M Consensus peptide pool (15-mer peptides overlapping by 11 AA), (B) with the COT-M peptide pool (10-mers overlapping by 9 AA) consisting of the matching peptides of p24CE1 and p24CE2 proteins, and (1 C) with peptide pools representing the clade A, B, and C $p55^{gag}$ sequences (15-mer peptides overlapping by 11 AA), as described in Materials and Methods. The frequency of CE-specific IFN-γ producing $CD4^+$ (open bars) and $CD8^+$ (filled bars) T cells was determined by polychromatic flow cytometry. The mean and SEM are shown. Three experiments were performed and data from a representative experiment are shown.

To maximize stimulation of $CD4^+$ cells in addition to $CD8^+$ T cells, we designed secreted immunogens. The p24CE antigen linked to the signal peptide of GM-CSF was expressed at high levels and also produced both $CD4^+$ and $CD8^+$ antigen-specific T cells as well as good antibody titers. In contrast, p24CE proteins fused to MCP-3 or LAMP directed the development of mostly $CD4^+$ T cell responses. These studies show that it is possible to manipulate many properties of an antigen, altering the immune response in predictable ways. Although $CD8^+$ T cell responses have been linked to control of viremia, we have also reported that cytotoxic $CD4^+$ T cell responses contribute to viral control [103]. The p24CE vaccine induced both $CD4^+$ (CE1 and CE6) as well as $CD8^+$ (CE2 and CE3) specific T cell responses in the C57BL/6 mice; these $CD8^+$ T cells had the functional phenotype of mature CTLs and were absent in mice immunized with the DNA encoding $p55^{gag}$. The molecules generated allow the selection of the most optimal combinations to achieve the best protective response for HIV prophylaxis. We have found that p24CE proteins are more immunogenic than the full-length Gag protein, expanding the quality of cellular responses to recruit $CD8^+$ T cells with the functional properties of canonical CTLs in C57BL/6 mice. These findings suggest that the peptides containing the CE regions produced from the full-length $p55^{gag}$ antigen were not recognized efficiently by the T cells. This could be due to poor antigen processing or presentation, or alternatively due to interference by immunodominant peptides from other regions within $p55^{gag}$, which are able to divert or inhibit immune response. In addition, as shown in FIGS. 3 and 4, the trafficking of the protein greatly affected its immunogenicity, with the p24CE and SP-p24CE eliciting the highest and most balanced CD4 and CD8 responses. Selection of the most optimal p24CE protein induced higher and broader immunogenicity than $p55^{gag}$. We have recently also shown that dendritic cells in vitro loaded with RNA encoding the p24CE described in this work are able to stimulate T cell responses when mixed with autologous PBMC from HIV patients or to induce de novo T cell responses in PBMC from healthy donors. The responses elicited by p24CE were usually as high as those by full-length Gag [33].

All the immunogenicity studies described in the present work were performed in C57BL/6 mice. In our experience, $p55^{gag}$ DNA immunization using the Balb/c mouse model induces higher T cell responses, but those responses are almost exclusively directed towards a single immunodominant epitope, AMQMLKETI (SEQ ID NO:45), which is present in our p24CE construct. Therefore, to avoid the restrictions imposed by this limited repertoire, we chose the C57BL/6 mouse model for the work described herein. We found very low primary immune responses to the CE regions after DNA vaccination using full-length $p55^{gag}$. It will be of interest to further examine whether other vaccine modalities, i.e. recombinant viral vectors, expressing $p55^{gag}$ are able to induce higher immune responses to the CE. To our knowledge, this study is the first comparative evaluation of immunity induced by a full-length immunogen and that induced by highly conserved elements from within the same protein. Our analysis points to the negative effect of regions outside of the defined conserved elements, which, it is important to note, are present in the full-length wild type as well as in the consensus and mosaic molecules as well as in the reported epitope immunogens. Thus, the use of the highly Conserved Element platform offers the advantage of focusing the immune responses to the invariable epitopes present in the viral proteome. Similar to the work described here, Letoumeau et al. [11] previously demonstrated that a chimeric protein containing a string of several invariable regions from the HIV-1 proteome was immunogenic, but a direct comparison with the same sequences expressed within the natural proteins was not performed. In our study, we applied more stringent criteria to define conserved elements resulting in shorter peptide sequences (12-24 AA) that exclude adjacent more variable segments. In addition, our analysis of the immune responses was performed using peptide pools strictly confined to the conserved segments defined as immunogens and, therefore, the contribution to the T cell responses of putative artificial new epitopes created by the boundaries was completely excluded. In conclusion, we showed that the p24CE DNA vaccine induced broad cross-clade reactive cellular and humoral responses in vaccinated mice. We detected robust immune responses, including $CD8^+$ T cells, to several CE upon p24CE DNA vaccination in mice, whereas only very poor ($CD4^+$ only) or no responses to the CE were obtained by DNA vaccination with vectors expressing full-length $p55^{gag}$. Thus, the inclusion of DNA vectors expressing the conserved elements is a promising vaccine strategy to induce broader immunity compared to vaccination with the $p55^{gag}$ DNA alone. These results suggest further evaluation of the p24CE antigens in macaques.

Materials and Methods $p24^{gag}$ Conserved Elements Selection

Using all HIV-1 M group $p24^{gag}$ coding sequences available in the 2009 Los Alamos database, we identified sequences of at least 8 AA in length, in which all AA were conserved in at least 98% of all sequences. This requirement was then relaxed in two ways: First, using available data that correlated epitope recognition with clinical viral load, we sought to include complete epitopes that were associated with low viral load and exclude epitopes that were associated with high viral load. Secondly, we allowed 1 toggle (variable) site/CE segment if the 2 most common AA at that site are together found in >99% of all known sequences [32]. To accommodate this variation, we created two plasmids, each with 7 CE segments from 12-24 AA in length, separated by 2-4 AA spacers (typically Ala-Ala-X) and differing only by the single toggle AA. The length and sequence of the spacers was set based on the existing knowledge of cleavage specificities and peptide availability [104], as well as to avoid fortuitous junctional homologies to HIV and the human proteome, the latter determined by searching against the HIV and human protein sequence databases.

DNA Plasmids

The p24CE and gag gene coding sequences were designed by RNA/codon optimization for efficient expression in mammalian cells [73-75] and chemically synthesized (GeneArt, Life Technologies, Grand Island, N.Y.). The genes were cloned into the pCMVkan vector [81] optimized for high gene expression. pCMVkan contains the human cytomegalovirus promoter, and the expressed transcripts contain a optimal surrounding for the AUG initiator codon from HIV-1 tat that prevents initiation of translation from internal AUGs [105], the bovine growth hormone (BGH) polyadenylation site, and the kanamycin resistance gene. This vector does not contain any splice sites or introns. The p24CE1 and p24CE2 proteins were produced from independent vectors (plasmids 164H and 182H, respectively). The secreted forms SP-p24CE1 and SP-p24CE2 contain the GM-CSF signal peptide (AA 1-17; Genbank accession Nr. NP_000749) at the N terminus (plasmids 234H and 235H). The MCP3-p24CE1 and MCP3-p24CE2 (plasmids 167H and 201H) are fusion proteins with the monocyte chemoattractant protein 3 (MCP-3) [80-81]. The LAMP-p24CE1 and LAMP-p24CE2 (plasmids 191H and 202H) are fusion proteins with the lysosomal associated membrane protein 1 (LAMP-1) [98-101]. Full-length $p55^{gag}$ proteins were produced from RNA/codon optimized genes cloned into the pCMVkan plasmid, expressing Gag from clade A (plasmid 187H, Genbank accession number AAQ98129), clade B (plasmid 114H, HXB2, Genbank accession number AAB50258), clade C (plasmid 160H, Genbank accession number AAD12096) and the center-of-tree COT-M (222H) [106]. For immunizations HXB2 $p55^{gag}$ was used. Endotoxin-free DNAs were prepared using Qiagen kit according to the manufacturer's protocol (Qiagen, Valencia, Calif.)

Transfection and Protein Analysis

DNA plasmids were transfected into $1\times10^6$ HEK-293 cells using the calcium phosphate co-precipitation technique. Culture supernatants and cells were harvested 24 or 48 hours later, and protein expression was visualized by Western immunoblot analysis. The proteins were resolved on 10% or 12% NuPAGE Bis-Tris gels (Invitrogen, Carlsbad, Calif.), transferred onto nitrocellulose membranes (Invitrogen), which were probed with a goat anti-$p24^{gag}$ antibody (dilution 1:3000, provided by L. Arthur, SAIC, NCI, Frederick) followed by anti-goat IgG-HRP labeled antibody (dilution 1:10,000; Calbiochem, EMD chemicals, Gibbstown, N.J.) or with plasma (1:200 dilution) from DNA vaccinated mice followed by anti-mouse IgG-HRP labeled (1:10,000 dilution, GE Healthcare, Piscataway, N.J.). As control, the membranes were probed with anti-human pan-actin antibody (clone C4, EMD Millipore, Billerica, Mass.) at a dilution of 1:10,000. The bands were visualized using the enhanced chemiluminescence (ECL) plus Western blotting detection system (GE HealthCare, Piscataway, N.J.).

Mouse DNA Vaccination Studies

Female C57BL/6N (6 to 8 weeks old) were obtained from Charles River Laboratories, Inc. (Frederick, Md.) and were housed at the National Cancer Institute, Frederick, Md., in a temperature-controlled, light-cycled facility. The mice were immunized with 20 μg of the vaccine DNAs by intramuscular injection followed by in vivo electroporation by ELGEN® constant current electroporation device (Inovio Pharmaceuticals, Inc, Blue Bell, Pa.). As negative controls, a group of mice received equal amount of sham DNA following the same immunization protocol. The animals were vaccinated two (0 and 4 weeks) or three times (0, 3, and 6 weeks), and were sacrificed 2 weeks after the last vaccination when spleens and blood were collected for the analysis of cellular and humoral responses.

Intracellular Cytokine Staining

The frequency of antigen specific $cytokine^+$ T cells was measured using polychromatic flow cytometry, as previously described [80]. The following set of 15-mer Gag peptide pools, overlapping by 11 AA, were used to stimulate the vaccine-induced cellular responses: HIV-1 consensus clade A (Cat #8116), consensus clade C (Cat #8118), and Group M Consensus (Cat #11057), obtained from the AIDS Research and Reference Reagent Program (Germantown, Md.); Gag 15-mer from HXB2/Clade B (Infinity Biotech Research & Resource, Inc, Aston, Pa.). Peptide pools spanning $p55^{gag}$, $p24^{gag}$ or only CE were generated. In addition, we used pools of 10-mer peptides overlapping by 9 AA from COT-M spanning the individual CE1-CE7, not including linker sequences, of p24CE1 and p24CE2 (peptide synthesis facility of the Massachusetts General Hospital, Boston). Splenocytes were cultured at 37° C. and 5% CO2 at a density of $2\times10^6$ cells/ml in complete RPMI-1640 medium containing Gag peptide pools at a final concentration of 1 μg/ml of each peptide. In all experiments, splenocytes cultured in medium without peptide pools or stimulated with phorbol myristate acetate (PMA) and calcium ionophore (Sigma, St. Louis, Mo.) were used as negative and positive control respectively. Protein secretion was blocked by the addition of monensin (GolgiStop, BD Biosciences) 1 hour after stimulation. After 12 hours incubation, the cells were harvested and cell surface staining was performed using the following antibody cocktail: CD3-APCCy7, CD4-PerCP, and CD8-Pacific Blue (BD Pharmingen, San Diego, Calif.). Splenocytes were washed twice, fixed, permeabilized with Cytofix/Cytoperm (BD Pharmingen) and staining for intracellular cytokine detection was performed using IFN-γ-FITC (BD Pharmingen). In another set of experiments, the antibody cocktail for surface staining included: CD3-AF700, CD4-PerCP, CD8-Pacific Blue, CD44-V500, CD62L-PE, CD107a-PE Cy7 (BD Pharmingen). The anti-CD107a antibody was added during the culturing of splenocytes with peptides. IFN-γ-APC and TNF-α-APC Cy7 (BD Pharmingen) were used for intracellular cytokine staining. After intracellular staining, the cells were washed twice and the samples were analyzed on an LSR II flow cytometer (BD Pharmingen). Data analysis was performed using the FlowJo platform (Tree Star, Inc., Ashland, Oreg.). All antigen specific responses are reported after subtracting values obtained from the samples without peptide stimulation. Only splenocytes giving a response more than two fold higher than the value of the sample without peptides (medium alone) were considered positive.

Antibody Assays

Serial dilutions of plasma samples were analyzed by standard HIV-1 clade B $p24^{gag}$ ELISA (Advanced Bioscience Lab, Rockville, Md.), measuring optical absorbance at 450 nm.

Example 2. Core DNA Vaccination Induces Cross-Clade Specific Cellular Immune Responses in Macaques Results Vaccination with Gag DNA Induces Poor $p24^{gag}$ Conserved Element (CE)-Specific Cellular Immune Responses in Macaques We first investigated whether vaccination of macaques with a plasmid expressing $p55^{gag}$ was able to elicit immune responses to the 7 CE [32,34] identified within the $p24^{gag}$ sequence (FIG. 7). Four animals were vaccinated twice (0, 2 month) with COT-M $p55^{gag}$ DNA by IM injection followed by in vivo electroporation (EP). Seven animals previously vaccinated with a plasmid expressing the full-length $p55^{gag}$ delivered intramuscularly (N=4) [82] or with a plasmid expressing the $p37^{gag}$ protein delivered via IM/EP (N=3) [67] were included in the analysis. Induction of Gag-specific responses was evaluated upon stimulation of PBMC with a $p24^{gag}$ specific peptide pool as well as with a CE-specific peptide pool (see Material and Methods). All 11 macaques developed readily detectable responses to the $p24^{gag}$ region, however only 5 of the 11 macaques (45%) developed responses to CE (FIG. 7B). Next, we analyzed the specificity of the responses towards the individual conserved elements in the 5 macaques that showed CE recognition (FIG. 7C). We found that 3 macaques (L985, P574, R288) recognized only 1 CE (CE3 or CE5), whereas 2 macaques (R067 and M121) developed responses to 2 CE (CE4, CE5 and CE5, CE6, respectively). Moreover, only animal L985 developed significant $CD8^+$ T cell responses against the CE, while the other 4 animals showed almost exclusively $CD4^+$ T cell mediated responses. These CE-specific T cell responses included $CD4^+$ and $CD8^+$ T cells with cytotoxic potential, as judged by the presence of antigen-specific Granzyme $B^+$ T cells in all 5 animals (FIG. 7D).

The lack of CE recognition in most of the vaccinated animals raised the concern that the immunogenicity of the CE epitopes within the Gag protein may be impaired due to either suboptimal processing and presentation of the CE-containing peptides, or immunodominance exerted by variable regions within Gag directing the CTL responses away from CE.

Vaccination with p24CE DNA Induces Cellular Immune Responses in Macaques

To test whether broader immune responses to the CE could be elicited in macaques, we vaccinated animals with a mixture of the two p24CE DNA vectors which were engineered to express the 7 CE collinearly arranged. (See Example 1). The two proteins differed by 1 AA ('toggle') per CE, (SP-p24CE1 and SP-p24CE2) (FIG. 7A). Four animals were vaccinated twice (0, 2 month) with p24CE DNA using IM/EP delivery. Cellular immune responses were measured in blood samples collected 2 weeks after the $2^{nd}$ vaccination (EP2wk2). Two additional macaques (M437, P314), previously immunized with p24CE plasmids, were also included in this analysis. All 6 macaques developed CE-specific cellular responses (FIG. 8A), as measured by the production of IFN-γ with a frequency ranging from 0.1% to 0.6% of total T cells. The overall levels of responses were non-significantly lower compared to those of the $p55^{gag}$ DNA vaccinated animals (data not shown). These responses included both $CD4^+$ and $CD8^+$ T cells, although the $CD8^+$ T cell responses were dominant in 4 of the 6 vaccinated animals (FIG. 8A). These results are in contrast to those obtained upon $p55^{gag}$ DNA vaccination, where only 5 out 11 immunized animals developed CE responses, mediated mainly by $CD4^+$ T cells (FIG. 7). Mapping of the CE-specific responses (FIG. 8B) revealed recognition of all CE except CE1 and CE7, using out-bred animals with different MHC class I haplotypes. Comparison of animals vaccinated with p24CE or Gag DNA shows that there was no apparent correlation between haplotype and ability to develop responses to CE, hence the differences could be attributed to the immunogen. Five of the 6 CE vaccinated macaques developed responses to 3 CE and only one animal (M437) showed responses to 1 CE. Phenotypic analysis of the antigen-specific T cells revealed both central (CD28+ $CD95^{+)}$ and effector memory (CD28-$CD95^+$) (FIG. 8C, top panels). A subset of the CE-specific IFN-$\gamma^+$ T cells also expressed granzyme B, indicating a cytotoxic phenotype (FIG. 8C, bottom panels), thus eliciting cytotoxic CE-specific responses. These results indicate that, similar to our observation from vaccinated mice (Example 1), the CE DNA vectors are immunogenic in all 6 macaques and that most (5 of 7) of the CE were immunogenic. These data also demonstrate that CE-containing peptides are processed and presented properly and suggest that the failure to induce CE-specific responses from $p55^{gag}$ or $p37^{gag}$ is likely the result of immunodominance exerted by epitopes located in the variable regions.

Vaccination with p24CE DNA Induces Broader and Higher Levels of Polyfunctional CE-Specific T Cell Response than Vaccination with $p55^{gag}$ DNA We further dissected CE immunogenicity by comparing the cellular responses induced by p24CE and $p55^{gag}$ DNA vaccination. First, we compared the number of CE recognized in the macaques vaccinated with DNA expressing the p24CE (N=6) or full-length $p55^{gag}$ or $p37^{gag}$ (N=1) (FIG. 9A). Immunization with p24CE induced responses to significantly more CE (p=0.0006; range 1-3 CE, median 3) than Gag DNA vaccination (range 0-2 CE) (FIG. 9A). These data demonstrate that p24CE DNA induced responses to more CE, indicating increased breadth of responses compared to $p55^{gag}$ DNA vaccination.

We also compared polyfunctionality (production of IFN-γ, TNF-α, CD107a and granzyme B) of the T cell responses upon stimulation with CE-specific peptides. FIG. 9B shows the distribution of CE-specific polyfunctional T cells from representative macaques that received either p24CE DNA (top panel) or $p55^{gag}$ DNA (middle panel). The proportion of polyfunctional T cells (1- to 4-function) is also shown as pie charts (right panels). These results demonstrate that p24CE DNA vaccination elicited higher CE-specific cytotoxic T cell levels than $p55^{gag}$ DNA vaccination. The frequency of CE-specific T cells secreting two cytokines, expressing granzyme B and able to degranulate upon antigen recognition (4-function) was also significantly higher (p=0.03) in macaques immunized with p24CE DNA (bottom panel). Together, these data show that the p24CE immunogen elicited significantly higher responses, including to more CE, and that these responses are multifunctional and have cytotoxic properties.

p55$^{gag}$ DNA Vaccination Boosts Pre-Existing CE-Specific T Cell Responses

Given that repeated vaccination with p55$^{gag}$ DNA failed or only poorly induced de novo CE-specific T cell responses (FIG. 7), we investigated whether full-length gag DNA vaccination could boost and/or broaden pre-existing CE-specific immunity. The p24CE-vaccinated macaques received an additional vaccination with a plasmid expressing COT-M p55$^{gag}$ DNA (FIG. 10A; group 1). This led to a significant increase (p=0.002) in CE-specific responses, reaching in some animals more than 1-2% of the total T cell population (FIG. 10B). Analysis of the polyfunctionality of these responses showed that the frequency of CE-specific T cells with 4 functions was also significantly boosted (p=0.002; FIG. 10C). Boosting with p55$^{gag}$ DNA also induced de novo responses to p17$^{gag}$ and C-terminal regions of Gag, thereby increasing the total Gag responses to levels similar to those obtained with the gag/p24CE DNA vaccine. Additionally, virtually the complete set of pre-existing responses to individual CE was boosted in all 6 macaques (FIG. 11A, left panel). The number of the CE found to be immunogenic upon p24CE vaccination (1-3 CE/animal) increased to 2-4 CE/animal upon Gag DNA boost. These findings confirmed that the suboptimal responses induced by priming with full-length Gag were not related to the absence of processing or presentation of CE-containing peptides, but rather to their inability to induce de novo responses in the presence of other, likely more dominant, Gag epitopes outside of CE. Thus, the immunodominance exerted by Gag epitopes outside of CE was lost in the presence of pre-existing CE-specific responses.

We also investigated whether p24CE DNA vaccination could alter the CE-specific immunity in macaques previously vaccinated with p55$^{gag}$ DNA (FIG. 10A; group 2). Vaccination with p24CE DNA minimally increased the pre-existing CE-specific responses in 3 out of 4 macaques, (FIG. 10B, group 2) and modestly increased the polyfunctional CE responses in two of the vaccinated animals (FIG. 10C, group 2), although this increase was not statistically significant. Analysis of the individual CE (FIG. 11B) showed no new CE responses upon p24CE boost. The heterologous p24CE DNA boost did not alter the pre-existing $CD4^+$ or $CD8^+$ T cell distribution. T hus, the immunodominance exerted by epitopes outside of CE could not be overcome by p24CE vaccination, as this vaccine regimen did not alter the magnitude or breadth of Gag responses.

p24CE DNA Vaccination Induces Humoral Immune Responses that Recognize p24$^{gag}$ The development of Gag-specific humoral immune responses was also monitored over the course of study (FIG. 12A) using a p24$^{gag}$ ELISA. Upon vaccination with p24CE DNAs (group 1) antibodies recognizing p24$^{gag}$ were readily detectable and peaked 2 weeks after EP2 (mean reciprocal end-point dilution titer 5.2 log). Similarly, the p24$^{gag}$ antibody titers upon COT-M p55$^{gag}$ DNA vaccination also peaked 2 weeks post EP2 (mean reciprocal end-point dilution titer 5.3 log). Thus, both vaccines elicited similar p24$^{gag}$ antibody titers.

We further assessed the ability of these antibodies to recognize the p24CE proteins as well as processed p24$^{gag}$ by Western immunoblots. The data from two representative macaques from each group are shown (group 1: L862 and M166, and group 2: P574 and R288) with similar data obtained from all animals from both vaccine groups. Plasma from macaques vaccinated with p24CE (Group 1) recognized naturally processed p24$^{gag}$ produced from a clade B molecular clone of HIV-1 (FIG. 12B, lane 1) as well as the p24CE1 (lane 2) and p24CE2 (lane 3) proteins. In contrast, vaccination with p55$^{gag}$ DNA (group 2) induced antibodies that strongly react with p24$^{gag}$ (lane 1), but failed to recognize p24CE proteins (FIG. 12B lanes 2 and 3). We conclude that only the p24CE DNA vaccination induces robust cellular and humoral responses to the conserved elements.

Lastly, we tested whether boosting with the heterologous DNA (EP3) affected the pre-existing humoral immune responses. ELISA assays showed similar increase in p24$^{gag}$ antibody levels in both groups (FIG. 12A). All Western immunoblot assays (FIG. 12B) were performed in parallel using the same plasma sample dilution and the same exposure time of the membrane to allow comparison of before and after the respective boosts. Following p55$^{gag}$ DNA boost of the p24CE DNA vaccinated animals (group 1), stronger reactivities to both p24$^{gag}$ (lane 4) as well as p24CE proteins (lanes 5 and 6) were found. These data demonstrate that p55$^{gag}$ DNA vaccination was able to substantially boost the CE-primed humoral immune responses despite its failure to induce de novo antibody responses able to recognize the CE protein. Vaccination of the p55$^{gag}$ DNA primed animals with p24CE DNA (group 2, bottom panels) showed induction of antibodies to p24CE proteins (lanes 5 and 6) and increased reactivity to p24$^{gag}$ (lane 4). Note, a significantly higher amount of plasma was used in order to detect p24CE proteins from the animals in group 2 (dilution 1:500) compared to group 1 (dilution 1:2000). Thus, these data indicate that the heterologous p24CE DNA boost induced low level CE-specific responses, rather than inducing an amnestic responses (group 2). Together, these data show that prime immunization with p24CE DNA can alter the immunodominance of both cellular and humoral immune responses and that the immunodominance of epitopes outside of CE is not overcome by boosting with CE if the animal's vaccination involved priming with p55$^{gag}$. Therefore, priming with p24CE DNA followed by the heterologous p55$^{gag}$ DNA boost is a preferred approach to achieve broad and high cellular and humoral immune responses to the highly conserved elements of HIV-1 p24$^{gag}$ protein.

Discussion

We have described DNA vectors encoding collinearly 7 highly conserved elements of the HIV-1 Group M p24$^{gag}$ protein, and we have reported that vaccination of mice with these DNAs induced both cellular and humoral responses [57]. In the current report, we demonstrated that vaccination of rhesus macaques with these DNA vectors induced CE-specific cellular and humoral immune responses. Detailed analysis of cellular immune responses showed that p24CE DNA vaccination induced cytotoxic $CD4^+$ and $CD8^+$ T cells against CE and that the elicited T cell responses were polyfunctional. Therefore, our conserved element DNA vectors show desired features for an effective vaccine. Our vaccine regimen also shows a promising approach to overcoming a problem in the HIV vaccine field, where attempts to induce both antigen-specific $CD4^+$ and $CD8^+$ T cell responses and to broaden the vaccine-induced immunity to include subdominant epitopes have been less successful, even with a reported EP DNA/Ad boost immunization strategy [83].

Importantly, we found that the p55$^{gag}$ vaccine elicits no or only poor responses to CE. We also analyzed the responses from a previous report [4], where macaques were vaccinated with consensus or mosaic p55$^{gag}$ DNA as prime followed by recombinant Adenovirus boost. We found that 5 of the 12 animals that received the consensus molecule and 6 of 12 that received the mosaic molecules developed CE responses ranging from of 0-2 (consensus) and of 0-4 (mosaic) CE responses/animal, whereas several epitopes outside the CE were immunogenic in all the animals. In the study reported herein, we found that 5 of 11 macaques vaccinated with full-length COT-M or HXB2 $p55^{gag}$ DNA developed CE-specific responses (0-2 CE/animal), whereas epitopes outside the CE were immunogenic in all the macaques. The data of the two studies are thus in good agreement, although the methods of analysis were not identical [peptide mapping [4] versus analysis with CE-specific mixture of 15-mer and 10-mer peptides (this report)]. Irrespective of the nature of Gag vaccine (consensus, mosaic or wild type), we found responses to CE in only 42-50% of the animals, and the responses were to very few CE/animal, suggesting that immunodominant epitopes within Gag focus the CTL response away from these conserved targets. In this report, we experimentally tested this hypothesis and demonstrated that immunodominance of variable regions is indeed responsible for the poor immunogenicity of the CE.

Although vaccination with either $p55^{gag}$ or $p37^{gag}$ induced strong humoral responses, we found that these antibodies fail to cross-react with the CE protein. In contrast, our engineered p24CE DNA vaccine readily induced both antibodies and cell-mediated responses to several CE, bypassing the restriction associated with full-length Gag vaccination. Importantly, immunizing with a full-length Gag greatly boosted the pre-existing CE responses. Hence, exposure to virus might also have the effect of boosting CE responses in CE-vaccinated individuals.

In a recent paper, Stephenson et al. [17] compared responses of full-length molecules to their conserved elements (Gag, Pol, and Env) vaccine and concluded that the conserved element vaccine did not provide any benefit (breadth or magnitude). In contrast, we demonstrated a clear benefit from the CE vaccine, showing increased breadth and magnitude of responses. The difference between the studies may substantively be due to our more strict definition and selection of CE, which, in contrast to others, were selected in part by their association with virus control [34], further supporting their immunological relevance.

Previous analyses of HIV-1 infected persons with different HLA haplotypes demonstrated the presence of CE-specific T cells during the chronic phase of infection [20,34]. Higher avidity CTL responses in these regions were identified in HIV controllers and detailed analysis of the responses demonstrated that, for most epitopes analyzed, controllers were able to recognize more peptide variants [34]. This indicates that TCR promiscuity could be beneficial for the recognition of epitopes with mismatched amino acids resulting in better control of viral replication and prevention of escape mutants. These data also suggest that high avidity CE-specific responses are a potential correlate of HIV control. It is not clear why vaccination with full-length Gag generates poor CE responses (in mice or macaques), while these responses are detected in chronic HIV infection. It would be of interest to study different vaccination regimens and also to examine the time of development of CE responses during natural infection. The difference in elicited immune response is reminiscent of a previous report by Ferrari et al. [84], who showed that the immunodominant $p17^{gag}$ SL9 response identified in HLA-A*0201 infected persons could not be induced upon ALVAC-gag vaccination in these haplotype-selected volunteers, although this epitope has been implicated in the Sieve effect observed in the STEP HIV vaccine trial [85]. Both studies suggest that there may be differences between vaccine-induced and infection-induced cellular responses that should be taken into consideration for successful vaccine design; they also highlight the potential immunodominant decoy effect of a full-length immunogen design.

Impaired immunogenicity of the conserved elements in the context of the natural protein sequence could be due to the presence of variable regions, which may exert an immunodominant decoy effect preventing the recognition of the conserved epitopes. This possibility is supported by a recent study where a bias was found towards less-conserved regions in HIV-1 Ad5 gag/pol/nef vaccinated human volunteers [86]. Generation of responses mainly outside of the conserved elements by full-length Gag suggested an immunodominant decoy effect. In this context, the success of our p24CE DNA prime-$p55^{gag}$ DNA boost vaccine strategy is of great importance, because it showed strong boosting of pre-existing CE-specific cellular and humoral responses in macaques. Upon gag DNA boost, we report both a robust increase of the pre-existing CE-specific responses as well as development of de novo responses to regions outside the CE. These data imply that the immunodominance exerted by Gag epitopes outside of CE was lost in the context of pre-existing CE-specific responses.

The impaired immunogenicity of the conserved elements when expressed in the context of the complete Gag could in principle be related to suboptimal processing and presentation of the CE peptides, preventing efficient priming of adaptive immune responses. However, our p24CE prime-Gag boost study clearly demonstrates that processing of the full-length Gag protein produces a collection of CE-containing peptides that are recognized by T cells. We speculate that recognition of MHC-peptide complexes is less stringent for boosting memory T cell clones than for priming naïve T cells. Similar to the observations on cellular immunity, full-length Gag boosted pre-existing B cell responses, while failing to prime the development of de novo antibodies able to recognize the CE protein. These findings support the concept that proper processing of CE-containing peptides from the native Gag protein takes place, and that these sets of CE containing peptides are able to potently augment pre-existing responses to different extents. Together, these findings point to a critical difference in T cell recognition of these peptides where a clear distinction between antigen-experienced and naïve T cells is noted.

The question then arises whether a T cell vaccine can benefit from the responses elicited by selected T cell epitopes. A previous report [87] demonstrated the potency of T cell immunity in the absence of Env. In fact, a recent paper by Mudd et al. [88] showed that a T cell vaccine that induced Mamu-B*08-restricted $CD8^+$ T-cell responses targeting 3 different viral epitopes elicited responses able to control SIVmac239 replication. Since our CE DNA vaccine was selected to highly restricted sequences and haplotype-independent, it is plausible that they too could induce such potent responses, which will be addressed in future studies.

The presented results contribute significantly to the development of improved vaccine candidates against HIV targeting the immune responses to essential highly conserved regions for the virus. We hypothesize that cellular immune responses targeting conserved regions of HIV and other highly variable pathogens, which do not allow rapid escape mutations without significant loss of viral fitness, are more likely to be protective [32-34]. Since there is evidence that vaccine-induced responses can change upon HIV infection resulting in virus escape in humans [89], a selection of strictly conserved elements is of great importance for the design of an effective vaccine. Such a selection should also avoid epitopes that may act as immunodominant decoys. Thus, a successful vaccine should be able to generate potent cross-clade specific humoral and cellular responses against conserved regions of the virus. Our results provide an effective strategy to overcome restrictions associated with immunodominance, while improving the magnitude and breadth of responses, especially those against conserved regions, minimizing the possibility of viral escape while increasing the recognition of naturally occurring divergent HIV strains. These results indicate that a vaccine candidate should be designed to extend this concept to the entire HIV proteome. Since the macaque model was in general shown to provide a similar response hierarchy to that obtained upon vaccination of humans comparing different vaccine platforms [90], our macaque study supports the evaluation of the novel CE vaccine strategies in humans.

Materials and Methods

DNA Vectors

The p24CE plasmids pSP-p24CE1 (plasmid 234H) and pSP-p24CE2 (plasmid 235H) have been described [57] and contain the human GM-CSF signal peptide at the N-terminus of the expression-optimized p24CE open reading frame. Briefly, the 7 CE were collinearly assembled in the order CE2-3-4-5-6-7-1 to avoid a strongly hydrophobic N-terminal CE1, and were connected via short linker sequences designed for efficient proteolytic cleavage [91,92]. The COT-M $p55^{gag}$ [93] DNA (plasmid 222H) expresses the full-length Gag from an RNA/codon optimized gene. The IL-12 DNA (plasmid AG157) produces the rhesus macaque IL-12 cytokine from an optimized expression vector [94,95]. The vaccine vector CMVkan [81] is comprised of a plasmid backbone optimized for growth in bacteria, the human cytomegalovirus (CMV) promoter without introns, the optimized p24CE or gag genes, the bovine growth hormone (BGH) polyadenylation site, and the kanamycin resistance gene. Endotoxin-free DNAs (Qiagen, Valencia, Calif.) were prepared according to the manufacturer's protocol.

Example 3—Additional Conserve Element Polypeptides

Alternative conserved elements were designed (FIG. 13). Briefly, CE1 was extended to provide a CE8. CE2 was extended to provide CE9. In this construct CE7 was removed. Accordingly, there are six conserve elements in the CE polypeptide. There were two variants of the conserve element polypeptide where one amino acid is changed in CE8 and CE9. Two versions were designed having different arrangements of the CEs. In the version termed "p24CEc" (p24CE1c and p24Ce2c), the order is CE8-9-2-3-4-6. In the version terms "p24CEd" (p24CE1d and p24CE2d), the order is CE9-3-4-5-6-8.

Example 4. Illustrative Data from 3 Different Vaccination Prime-Boost Schedules We tested three different vaccination strategies in which the order of conserved element vaccines and full-length gag vaccine was varied. The three protocols are shown in FIG. 20:

1. p24CE prime followed by p55gag boost
2. p55gag prime followed by p24CE boost
3. combination of p24CE and p55gag in all vaccinations.

The animals received 1 mg of each DNA. For p24CE, SP-p24CE1 and SPp24CE2 were used. The DNA was administered via the intramuscular route followed by in vivo electroporation. FIG. 21 shows the cellular immune responses before and after the boost. Cellular immune responses were measured with peptides (15-mer overlapping by 11 amino acids) spanning the complete p24gag. This analysis showed responses in all the vaccinated animals.

The animals were also analyzed for CE-specific responses using a peptide pool (mixture of 10-mer peptide overlapping by 9 amino acids and 15-mer overlapping by 11 amino acids) spanning the 7 CE. All the p24CE vaccinated animals showed positive responses. In contrayst, Only 5 of the 11 gag DNA vaccinated animals showed responses (data shown). Three of 4 animals with the combination vaccine ($p24CE+p55^{gag}$) showed positive responses. After boosting by p55gag DNA, the p24CE primed animals significantly increased CE-specific responses. p24CE DNA boost increased the responses of the gag vaccinated animals (no significant increase). A third vaccination of the animals vaccinated by the combination ($p24CE+p55^{gag}$) did not consistently further increase responses.

FIG. 22 shows the analysis of the responses to individual CE. The responses to each CE were mapped in all the animals using CE-specific peptides (mixture of 10-mer peptide overlapping by 9 amino acids and 15-mer peptides overlapping by 11 amino acids) for each CE. The number of CE that showed positive responses per animal are shown. The p24CE primed animals had 100% response rates with a range of 1-3 CE/animal and median of 3 CE per animal. The gag DNA primed animals have a response rate of 45% with a range of 0-2 CE/animal. The animals that received the combination vaccine are more similar to the CE primed animals.

FIG. 23 shows that different vaccine strategies induced similar levels of p27gag antibody responses. Binding antibody titers were measured in the plasma of macaques by ELISA.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

REFERENCES CITED IN APPLICATION BY NUMBER

1. Nickle D C, Rolland M, Jensen M A, Pond S L, Deng W, et al. (2007) Coping with viral diversity in HIV vaccine design. PLoS Comput Biol 3: e75.
2. Nickle D C, Jojic N, Heckerman D, Jojic V, Kirovski D, et al. (2008) Comparison of immunogen designs that optimize peptide coverage: reply to Fischer et al. PLoS Comput Biol 4: e25.
3. Barouch D H, O'Brien K L, Simmons N L, King S L, Abbink P, et al. (2010) Mosaic HIV-1 vaccines expand the breadth and depth of cellular immune responses in rhesus monkeys. Nat Med 16: 319-323.
4. Santra S, Liao H X, Zhang R, Muldoon M, Watson S, et al. (2010) Mosaic vaccines elicit CD8+T lymphocyte responses that confer enhanced immune coverage of diverse HIV strains in monkeys. Nat Med 16: 324-328.

5. Fischer W, Perkins S, Theiler J, Bhattacharya T, Yusim K, et al. (2007) Polyvalent vaccines for optimal coverage of potential T-cell epitopes in global HIV-1 variants. Nat Med 13: 100-106.
6. Fischer W, Liao H X, Haynes B F, Letvin N L, Korber B (2008) Coping with viral diversity in HIV vaccine design: a response to Nickle et al. PLoS Comput Biol 4: el5; author reply e25.
7. Doria-Rose N A, Learn G H, Rodrigo A G, Nickle D C, Li F, et al. (2005) Human immunodeficiency virus type 1 subtype B ancestral envelope protein is functional and elicits neutralizing antibodies in rabbits similar to those elicited by a circulating subtype B envelope. J Virol 79: 11214-11224.
8. Mullins J I, Nickle D C, Heath L, Rodrigo A G, Learn G H (2004) Immunogen sequence: the fourth tier of AIDS vaccine design. Expert Rev Vaccines 3: S151-159.
9. Nickle D C, Jensen M A, Gottlieb G S, Shriner D, Learn G H, et al. (2003) Consensus and ancestral state HIV vaccines. Science 299: 1515-1518; author reply 1515-1518.
10. Dahirel V, Shekhar K, Pereyra F, Miura T, Artyomov M, et al. (2011) Coordinate linkage of HIV evolution reveals regions of immunological vulnerability. Proc Natl Acad Sci USA 108: 11530-11535.
11. Letourneau S, Im E J, Mashishi T, Brereton C, Bridgeman A, et al. (2007) Design and pre-clinical evaluation of a universal HIV-1 vaccine. *PLoS One* 2: e984.
12. Rosario M, Bridgeman A, Quakkelaar E D, Quigley M F, Hill B J, et al. (2010) Long peptides induce polyfunctional T cells against conserved regions of HIV-1 with superior breadth to single-gene vaccines in macaques. Eur J Immunol 40: 1973-1984.
13. De Groot A S, Rivera D S, McMurry J A, Buus S, Martin W (2008) Identification of immunogenic HLA-B7 "Achilles' heel" epitopes within highly conserved regions of HIV. Vaccine 26: 3059-3071.
14. Wilson C C, McKinney D, Anders M, MaWhinney S, Forster J, et al. (2003) Development of a DNA vaccine designed to induce cytotoxic T lymphocyte responses to multiple conserved epitopes in HIV-1. J Immunol 171: 5611-5623.
15. Kaufman D R, Li F, Cruz A N, Self S G, Barouch D H (2012) Focus and breadth of cellular immune responses elicited by a heterologous insert prime-boost vaccine regimen in rhesus monkeys. Vaccine 30: 506-509.
16. Almeida R R, Rosa D S, Ribeiro S P, Santana V C, Kallas E G, et al. (2012) Broad and cross-clade CD4+ T-cell responses elicited by a DNA vaccine encoding highly conserved and promiscuous HIV-1 M-group consensus peptides. PloS One 7: e45267.
17. Stephenson K E, SanMiguel A, Simmons N L, Smith K, Lewis M G, et al. (2012) Full-length HIV-1 immunogens induce greater magnitude and comparable breadth of T lymphocyte responses to conserved HIV-1 regions compared with conserved-region-only HIV-1 immunogens in rhesus monkeys. J Virol 86: 11434-11440.
18. Lichterfeld M, Yu X G, Le Gall S, Altfeld M (2005) Immunodominance of HIV-1-specific CD8(+) T-cell responses in acute HIV-1 infection: at the crossroads of viral and host genetics. Trends Immunol 26: 166-171.
19. Friedrich T C, Valentine L E, Yant L J, Rakasz E G, Piaskowski S M, et al. (2007) Subdominant C D8+ T-cell responses are involved in durable control of AIDS virus replication. J Virol 81: 3465-3476.
20. Liu Y, McNevin J, Rolland M, Zhao H, Deng W, et al. (2009) Conserved HIV-1 epitopes continuously elicit subdominant cytotoxic T-lymphocyte responses. J Infect Dis 200: 1825-1833.
21. Liu J, Ewald B A, Lynch D M, Nanda A, Sumida S M, et al. (2006) Modulation of DNA vaccine-elicited CD8+ T-lymphocyte epitope immunodominance hierarchies. J Virol 80: 11991-11997.
22. Frahm N, Kiepiela P, Adams S, Linde C H, Hewitt H S, et al. (2006) Control of human immunodeficiency virus replication by cytotoxic T lymphocytes targeting subdominant epitopes. Nat Immunol 7: 173-178.
23. Bockl K, Wild J, Bredl S, Kindsmuller K, Kostler J, et al. (2012) Altering an Artificial Gagpolnef Polyprotein and Mode of ENV Co-Administration Affects the Immunogenicity of a Clade C HIV DNA Vaccine. *PLoS One* 7: e34723.
24. Iversen A K, Stewart-Jones G, Learn G H, Christie N, Sylvester-Hviid C, et al. (2006) Conflicting selective forces affect T cell receptor contacts in an immunodominant human immunodeficiency virus epitope. Nat Immunol 7: 179-189.
25. Schneidewind A, Brumme Z L, Brumme C J, Power K A, Reyor L L, et al. (2009) Transmission and long-term stability of compensated CD8 escape mutations. J Virol 83: 3993-3997.
26. Altfeld M, Kalife E T, Qi Y, Streeck H, Lichterfeld M, et al. (2006) HLA Alleles Associated with Delayed Progression to AIDS Contribute Strongly to the Initial CD8 (+) T Cell Response against HIV-1. PLoS Med 3: e403.
27. Friedrich D, Jalbert E, Dinges W L, Sidney J, Sette A, et al. (2011) Vaccine-induced HIV-specific CD8+ T cells utilize preferential HLA alleles and target-specific regions of HIV-1. J Acquir Immune Defic Syndr 58: 248-252.
28. Maurer K, Harrer E G, Goldwich A, Eismann K, Bergmann S, et al. (2008) Role of cytotoxic T-lymphocyte-mediated immune selection in a dominant human leukocyte antigen-B8-restricted cytotoxic T-lymphocyte epitope in Nef. J Acquir Immune Defic Syndr 48: 133-141.
29. Toapanta F R, Craigo J K, Montelaro R C, Ross T M (2007) Reduction of anti-HIV-1 Gag immune responses during co-immunization: immune interference by the HIV-1 envelope. Current HIV research 5: 199-209.
30. Morozov V A, Morozov A V, Semaan M, Denner J (2012) Single mutations in the transmembrane envelope protein abrogate the immunosuppressive property of HIV-1. Retrovirology 9: 67.
31. Hovav A H, Santosuosso M, Bivas-Benita M, Plair A, Cheng A, et al. (2009) X4 human immunodeficiency virus type 1 gp120 down-modulates expression and immunogenicity of codelivered antigens. Journal of virology 83: 10941-10950.
32. Rolland M, Nickle D C, Mullins J I (2007) HIV-1 group M conserved elements vaccine. PLoS Pathog 3: e157.
33. Niu L, Termini J M, Kanagavelu S K, Gupta S, Rolland M M, et al. (2011) Preclinical evaluation of HIV-1 therapeutic ex vivo dendritic cell vaccines expressing consensus Gag antigens and conserved Gag epitopes. Vaccine 29: 2110-2119.
34. Mothe B, Llano A, Ibarrondo J, Zamarreno J, Schiaulini M, et al. (2012) CTL responses of high functional avidity and broad variant cross-reactivity are associated with HIV control. PLoS One 7: e29717.
35. Herbeck J T, Nickle D C, Learn G H, Gottlieb G S, Curlin M E, et al. (2006) Human immunodeficiency virus type 1 env evolves toward ancestral states upon transmission to a new host. J Virol 80: 1637-1644.
36. Duda A, Lee-Turner L, Fox J, Robinson N, Dustan S, et al. (2009) HLA-associated clinical progression correlates with epitope reversion rates in early human immunodeficiency virus infection. J Virol 83: 1228-1239.
37. Kent S J, Fernandez C S, Dale C J, Davenport M P (2005) Reversion of immune escape HIV variants upon transmission: insights into effective viral immunity. Trends Microbiol 13: 243-246.
38. Li B, Gladden A D, Altfeld M, Kaldor J M, Cooper D A, et al. (2007) Rapid reversion of sequence polymorphisms dominates early human immunodeficiency virus type 1 evolution. J Virol 81: 193-201.
39. Martinez-Picado J, Prado J G, Fry E E, Pfafferott K, Leslie A, et al. (2006) Fitness cost of escape mutations in p24 Gag in association with control of human immunodeficiency virus type 1. J Virol 80: 3617-3623.
40. Peyerl F W, Bazick H S, Newberg M H, Barouch D H, Sodroski J, et al. (2004) Fitness costs limit viral escape from cytotoxic T lymphocytes at a structurally constrained epitope. J Virol 78: 13901-13910.
41. Liu Y, McNevin J, Zhao H, Tebit D M, Troyer R M, et al. (2007) Evolution of human immunodeficiency virus type 1 cytotoxic T-lymphocyte epitopes: fitness-balanced escape. J Virol 81: 12179-12188.
42. Troyer R M, Collins K R, Abraha A, Fraundorf E, Moore D M, et al. (2005) Changes in human immunodeficiency virus type 1 fitness and genetic diversity during disease progression. J Virol 79: 9006-9018.
43. Kiepiela P, Ngumbela K, Thobakgale C, Ramduth D, Honeybome I, et al. (2007) CD8+ T-cell responses to different HIV proteins have discordant associations with viral load. Nat Med 13: 46-53.
44. Honeyborne I, Prendergast A, Pereyra F, Leslie A, Crawford H, et al. (2007) Control of human immunodeficiency virus type 1 is associated with HLA-B*13 and targeting of multiple gag-specific CD8+ T-cell epitopes. J Virol 81: 3667-3672.
45. Schneidewind A, Brockman M A, Yang R, Adam R I, Li B, et al. (2007) Escape from the dominant HLA-B27-restricted cytotoxic T-lymphocyte response in Gag is associated with a dramatic reduction in human immunodeficiency virus type 1 replication. J Virol 81: 12382-12393.
46. Ngumbela K C, Day C L, Mncube Z, Nair K, Ramduth D, et al. (2008) Targeting of a CD8 T cell env epitope presented by HLA-B*5802 is associated with markers of HIV disease progression and lack of selection pressure. AIDS Res Hum Retroviruses 24: 72-82.
47. Rolland M, Heckerman D, Deng W, Rousseau C M, Coovadia H, et al. (2008) Broad and Gag-biased HIV-1 epitope repertoires are associated with lower viral loads. *PLoS One* 3: e1424.
48. Masemola A, Mashishi T, Khoury G, Mohube P, Mokgotho P, et al. (2004) Hierarchical targeting of subtype C human immunodeficiency virus type 1 proteins by CD8+ T cells: correlation with viral load. J Virol 78: 3233-3243.
49. Mothe B, Ibarrondo J, Llano A, Brander C (2009) Virological, immune and host genetics markers in the control of HIV infection. Dis Markers 27: 105-120.
50. Zuniga R, Lucchetti A, Galvan P, Sanchez S, Sanchez C, et al. (2006) Relative dominance of Gag p24-specific cytotoxic T lymphocytes is associated with human immunodeficiency virus control. J Virol 80: 3122-3125.
51. Mothe B, Llano A, Ibarrondo J, Daniels M, Miranda C, et al. (2011) Definition of the viral targets of protective HIV-1-specific T cell responses. J Transl Med 9: 208.
52. Assarsson E, Sidney J, Oseroff C, Pasquetto V, Bui H H, et al. (2007) A quantitative analysis of the variables affecting the repertoire of T cell specificities recognized after vaccinia virus infection. J Immunol 178: 7890-7901.
53. Altfeld M, Allen T M (2006) Hitting HIV where it hurts: an alternative approach to HIV vaccine design. Trends Immunol 27: 504-510.
54. Rosario M, Borthwick N, Stewart-Jones G B, Mbewe-Mvula A, Bridgeman A, et al. (2012) Prime-boost regimens with adjuvanted synthetic long peptides elicit T cells and antibodies to conserved regions of HIV-1 in macaques. AIDS 26: 275-284.
55. Ribeiro S P, Rosa D S, Fonseca S G, Mairena E C, Postol E, et al. (2010) A vaccine encoding conserved promiscuous HIV CD4 epitopes induces broad T cell responses in mice transgenic to multiple common HLA class II molecules. PloS One 5: e11072.
56. Rosa D S, Ribeiro S P, Almeida R R, Mairena E C, Postol E, et al. (2011) A DNA vaccine encoding multiple HIV CD4 epitopes elicits vigorous polyfunctional, long-lived CD4+ and CD8+ T cell responses. PloS One 6: e16921.
57. Kulkami V, Rosati M, Valentin A, Ganneru B, Singh A K, et al. An HIV-1 p24gag derived conserved element DNA vaccine increased the breadth of immune response in mice. submitted.
58. Winstone N, Wilson A J, Morrow G, Boggiano C, Chiuchiolo M J, et al. (2011) Enhanced control of pathogenic SIVmac239 replication in macaques immunized with a plasmid IL12 and a DNA prime, viral vector boost vaccine regimen. J Virol 85: 9578-9587.
59. Aihara H, Miyazaki J (1998) Gene transfer into muscle by electroporation in vivo. Nat Biotechnol 16: 867-870.
60. Mathiesen I (1999) Electropermeabilization of skeletal muscle enhances gene transfer in vivo. Gene Ther 6: 508-514.
61. Prud'homme G J, Glinka Y, Khan A S, Draghia-Akli R (2006) Electroporation-enhanced nonviral gene transfer for the prevention or treatment of immunological, endocrine and neoplastic diseases. Curr Gene Ther 6: 243-273.
62. Rizzuto G, Cappelletti M, Maione D, Savino R, Lazzaro D, et al. (1999) Efficient and regulated erythropoietin production by naked DNA injection and muscle electroporation. Proc Natl Acad Sci USA 96: 6417-6422.
63. Wang Z, Troilo P J, Wang X, Griffiths T G, Pacchione S J, et al. (2004) Detection of integration of plasmid DNA into host genomic DNA following intramuscular injection and electroporation. Gene Ther 11: 711-721.
64. Widera G, Austin M, Rabussay D, Goldbeck C, Barnett S W, et al. (2000) Increased DNA vaccine delivery and immunogenicity by electroporation in vivo. J Immunol 164: 4635-4640.
65. Otten G, Schaefer M, Doe B, Liu H, Srivastava I, et al. (2004) Enhancement of DNA vaccine potency in rhesus macaques by electroporation. Vaccine 22: 2489-2493.
66. Otten G R, Schaefer M, Doe B, Liu H, Megede J Z, et al. (2006) Potent immunogenicity of an HIV-1 gag-pol fusion DNA vaccine delivered by in vivo electroporation. Vaccine 24: 4503-4509.
67. Rosati M, Valentin A, Jalah R, Patel V, von Gegerfelt A, et al. (2008) Increased immune responses in rhesus macaques by DNA vaccination combined with electroporation. Vaccine 26: 5223-5229.
68. Luckay A, Sidhu M K, Kjeken R, Megati S, Chong S Y, et al. (2007) Effect of plasmid DNA vaccine design and in vivo electroporation on the resulting vaccine-specific immune responses in rhesus macaques. J Virol 81: 5257-5269.
69. Hirao L A, Wu L, Khan A S, Hokey D A, Yan J, et al. (2008) Combined effects of IL-12 and electroporation enhances the potency of DNA vaccination in macaques. Vaccine 26: 3112-3120.
70. Rosati M, Bergamaschi C, Valentin A, Kulkami V, Jalah R, et al. (2009) DNA vaccination in rhesus macaques induces potent immune responses and decreases acute and chronic viremia after SIVmac251 challenge. Proc Natl Acad Sci USA 06: 15831-15836.
71. Patel V, Valentin A, Kulkami V, Rosati M, Bergamaschi C, et al. (2010) Long-lasting humoral and cellular immune responses and mucosal dissemination after intramuscular DNA immunization. Vaccine 28: 4827-4836.
72. Vasan S, Schlesinger S J, Chen Z, Hurley A, Lombardo A, et al. (2010) Phase 1 safety and immunogenicity evaluation of ADMVA, a multigenic, modified vaccinia Ankara-HIV-1 B'/C candidate vaccine. PLoS One 5: e8816.
73. Nasioulas G, Zolotukhin A S, Tabernero C, Solomin L, Cunningham C P, et al. (1994) Elements distinct from human immunodeficiency virus type 1 splice sites are responsible for the Rev dependence of env mRNA. J Virol 68: 2986-2993.
74. Schneider R, Campbell M, Nasioulas G, Felber B K, Pavlakis G N (1997) Inactivation of the human immunodeficiency virus type 1 inhibitory elements allows Rev-independent expression of Gag and Gag/protease and particle formation. J Virol 71: 4892-4903.
75. Schwartz S, Campbell M, Nasioulas G, Harrison J, Felber B K, et al. (1992) Mutational inactivation of an inhibitory sequence in human immunodeficiency virus type 1 results in Rev-independent gag expression. J Virol 66: 7176-7182.
76. Schwartz S, Felber B K, Pavlakis G N (1992) Distinct RNA sequences in the gag region of human immunodeficiency virus type 1 decrease RNA stability and inhibit expression in the absence of Rev protein. J Virol 66: 150-159.
77. Andre S, Seed B, Eberle J, Schraut W, Bultmann A, et al. (1998) Increased immune response elicited by DNA vaccination with a synthetic gp120 sequence with optimized codon usage. J Virol 72: 1497-1503.
78. Wagner R, Graf M, Bieler K, Wolf H, Grunwald T, et al. (2000) Rev-independent expression of synthetic gag-pol genes of human immunodeficiency virus type 1 and simian immunodeficiency virus: implications for the safety of lentiviral vectors. Hum Gene Ther 11: 2403-2413.
79. Graf M, Deml L, Wagner R (2004) Codon-optimized genes that enable increased heterologous expression in mammalian cells and elicit efficient immune responses in mice after vaccination of naked DNA. Methods Mol Med 94: 197-210.
80. Kulkami V, Jalah R, Ganneru B, Bergamaschi C, Alicea C, et al. (2011) Comparison of immune responses generated by optimized DNA vaccination against SIV antigens in mice and macaques. Vaccine 29: 6742-6754.
81. Rosati M, von Gegerfelt A, Roth P, Alicea C, Valentin A, et al. (2005) DNA vaccines expressing different forms of simian immunodeficiency virus antigens decrease viremia upon SIVmac251 challenge. J Virol 79: 8480-8492.
82. Valentin A, Chikhlikar P, Patel V, Rosati M, Maciel M, et al. (2009) Comparison of DNA vaccines producing HIV-1 Gag and LAMP/Gag chimera in rhesus macaques reveals antigen-specific T-cell responses with distinct phenotypes. Vaccine 27: 4840-4849.
83. Vojnov L, Bean A T, Peterson E J, Chiuchiolo M J, Sacha J B, et al. (2011) DNA/Ad5 vaccination with SIV epitopes induced epitope-specific CD4 T cells, but few subdominant epitope-specific CD8 T cells. Vaccine 29: 7483-7490.
84. Ferrari G, Neal W, Ottinger J, Jones A M, Edwards B H, et al. (2004) Absence of immunodominant anti-Gag p17 (SL9) responses among Gag CTL-positive, HIV-uninfected vaccine recipients expressing the HLA-A*0201 allele. J Immunol 173: 2126-2133.
85. Rolland M, Tovanabutra S, deCamp A C, Frahm N, Gilbert P B, et al. (2011) Genetic impact of vaccination on breakthrough HIV-1 sequences from the STEP trial. Nat Med 17: 366-371.
86. Li F, Finnefrock A C, Dubey S A, Korber B T, Szinger J, et al. Mapping HIV-1 vaccine induced T-cell responses: bias towards less-conserved regions and potential impact on vaccine efficacy in the Step study. *PLoS One* 6: e20479.
87. Wilson N A, Keele B F, Reed J S, Piaskowski S M, MacNair C E, et al. (2009) Vaccine-induced cellular responses control simian immunodeficiency virus replication after heterologous challenge. J Virol 83: 6508-6521.
88. Mudd P A, Martins M A, Ericsen A J, Tully D C, Power K A, et al. (2012) Vaccine-induced CD8+ T cells control AIDS virus replication. Nature 491: 129-133.
89. Betts M R, Exley B, Price D A, Bansal A, Camacho Z T, et al. (2005) Characterization of functional and phenotypic changes in anti-Gag vaccine-induced T cell responses and their role in protection after HIV-1 infection. Proc Natl Acad Sci USA 102: 4512-4517.
90. Bett A J, Dubey S A, Mehrotra D V, Guan L, Long R, et al. (2010) Comparison of T cell immune responses induced by vectored HIV vaccines in non-human primates and humans. Vaccine 28: 7881-7889.
91. Le Gall S, Stamegna P, Walker B D (2007) Portable flanking sequences modulate CTL epitope processing. J Clin Invest 117: 3563-3575.
92. Zhang S C, Martin E, Shimada M, Godfrey S B, Fricke J, et al. (2012) Aminopeptidase Substrate Preference Affects HIV Epitope Presentation and Predicts Immune Escape Patterns in HIV-Infected Individuals. J Immunol 188: 5924-5934.
93. Rolland M, Jensen M A, Nickle D C, Yan J, Learn G H, et al. (2007) Reconstruction and function of ancestral center-of-tree human immunodeficiency virus type 1 proteins. J Virol 81: 8507-8514.
94. Jalah R, Patel V, Kulkami V, Rosati M, Alicea C, et al. (2012) IL-12 DNA as molecular vaccine adjuvant increases the cytotoxic T cell responses and breadth of humoral immune responses in SIV DNA vaccinated macaques. Hum Vaccin Immunother 8: 1620-1629.
95. Jalah R, Rosati M, Ganneru B, Pilkington G R, Valentin A, et al. (2013) The p40 Subunit of IL-12 Promotes Stabilization and Export of the p35 Subunit: Implications for Improved IL-12 Cytokine Production. J Biol Chem in press.
96. Hanke T, McMichael A (1999) Pre-clinical development of a multi-CTL epitope-basedDNA prime MVA boost vaccine for AIDS. Immunol Lett 66: 177-181.
97. Pomillos O, Ganser-Pomillos B K, Kelly B N, Hua Y, Whitby F G, et al. (2009) X-ray structures of the hexameric building block of the HIV capsid. Cell 137: 1282-1292.

98. Chikhlikar P, de Arruda L B, Maciel M, Silvera P, Lewis M G, et al. (2006) DNA encoding an HIV-1 Gag/human lysosome-associated membrane protein-1 chimera elicits a broad cellular and humoral immune response in Rhesus macaques. PLoS ONE 1: e135.
99. de Arruda L B, Chikhlikar P R, August J T, Marques E T (2004) DNA vaccine encoding human immunodeficiency virus-1 Gag, targeted to the major histocompatibility complex II compartment by lysosomal-associated membrane protein, elicits enhanced long-term memory response. Immunology 112: 126-133.
100. Marques E T, Jr., Chikhlikar P, de Arruda L B, Leao I C, Lu Y, et al. (2003) HIV-1 p55Gag encoded in the lysosome-associated membrane protein-1 as a DNA plasmid vaccine chimera is highly expressed, traffics to the major histocompatibility class II compartment, and elicits enhanced immune responses. J Biol Chem 278: 37926-37936.
101. Valentin A, Chikhlikar P, Patel V, Rosati M, Maciel M, et al. (2009) Comparison of DNA vaccines producing HIV-1 Gag and LAMP/Gag chimera in rhesus macaques reveals antigen-specific T-cell responses with distinct phenotypes. Vaccine 27: 4840-4849.
102. Qiu J T, Song R, Dettenhofer M, Tian C, August T, et al. (1999) Evaluation of novel human immunodeficiency virus type 1 Gag DNA vaccines for protein expression in mammalian cells and induction of immune responses. J Virol 73: 9145-9152.
103. von Gegerfelt A, Valentin A, Alicea C, Van Rompay K K, Marthas M L, et al. (2010) Emergence of simian immunodeficiency virus-specific cytotoxic CD4+ T cells and increased humoral responses correlate with control of rebounding viremia in CD8-depleted macaques infected with Rev-independent live-attenuated simian immunodeficiency virus. J Immunol 185: 3348-3358.
104. Lazaro E, Kadie C, Stamegna P, Zhang S C, Gourdain P, et al. (2011) Variable HIV peptide stability in human cytosol is critical to epitope presentation and immune escape. J Clin Invest 121: 2480-2492.
105. Schwartz S, Felber B K, Pavlakis G N (1992) Mechanism of translation of monocistronic and multicistronic human immunodeficiency virus type 1 mRNAs. Mol Cell Biol 12: 207-219.
106. Rolland M, Jensen M A, Nickle D C, Yan J, Learn G H, et al. (2007) Reconstruction and function of ancestral center-of-tree human immunodeficiency virus type 1 proteins. J Virol 81: 8507-8514.

| Table of Illustrative Conserved Element Sequences |
|---|
| p24 Gag conserved elements for p24CE1 vaccine ("also referred to as "Core1"): |
| SEQ ID NO: 1 conserved element 1 (CE1)<br>ISPRTLNAWVKV |
| SEQ ID NO: 2 conserved element 2 (CE2)<br>VIPMFSALSEGATPQDLN |
| SEQ ID NO: 3 conserved element 3 (CE3)<br>VGGHQAAMQMLKDTINEEAAEWDR |
| SEQ ID NO: 4 conserved element 4 (CE4)<br>PRGSDIAGTTSTLQEQIGW |
| SEQ ID NO: 5 conserved element 5 (CE5)<br>KRWIILGLNKIVRMYSPTSI |
| SEQ ID NO: 6 conserved element 6 (CE6)<br>YVDRFYKTLRAEQA |
| SEQ ID NO: 7 conserved element 7 (CE7)<br>LEEMMTACQGVGGPGHK |
| p24 Gag conserved elements for p24CE2 vaccine ("also referred to as "Core2"): |
| SEQ ID NO: 8 conserved element 1 (CE1)<br>LSPRTLNAWVKV |
| SEQ ID NO: 9 conserved element 2 (CE2)<br>VIPMFTALSEGATPQDLN |
| SEQ ID NO: 10 conserved element 3 (CE3)<br>VGGHQAAMQMLKETINEEAAEWDR |
| SEQ ID NO: 11 conserved element 4 (CE4)<br>PRGSDIAGTTSTLQEQIAW |
| SEQ ID NO: 12 conserved element 5 (CE5)<br>KRWIILGLNKIVRMYSPVSI |
| SEQ ID NO: 13 conserved element 6 (CE6)<br>YVDRFFKTLRAEQA |
| SEQ ID NO: 14 conserved element 7 (CE7)<br>LEEMMTACQGVGGPSHK |

-continued

Table of Illustrative Conserved Element Sequences

SEQ ID NO: 15 p24 Gag conserved elements for p24CE1 vaccine ("also referred to as "Core1"):
VIPMFSALSEGATPQDLNAAVGGHQAAMQMLKDTINEEAAEWDRAAAEPRGSDIAGTTSTLQEQIGWAAAKRWIILGLNKIVRMYSPTSIAA
KYVDRFYKTLRAEQAAGLEEMMTACQGVGGPGHKAAISPRTLNAWVKV SEQ ID NO: 16 p24 Gag conserved elements for p24CE2 vaccine ("also referred to as "Core2"):
VIPMFTALSEGATPQDLNAAVGGHQAAMQMLKETINEEAAEWDRAAAEPRGSDIAGTTSTLQEQIAWAAAKRWIILGLNKIVRMYSPVSIAA
KYVDRFFKTLRAEQAAGLEEMMTACQGVGGPSHKAALSPRTLNAWVKV SEQ ID NO: 17 Nucleic acid construct encoding Core1 plus Core 2 (p24CE1 + p24CE2)
(306H) (genes underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGATGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGCGGGcgcgcgtcgacaagaaATGTGGCTCCAGAGCCTGCTACTCCTGGGGACGGTGGCCTGCAGCATCTCGGTCATCCCG
ATGTTCTCGGCGCTCAGCGAGGGAGCGACGCCGCAGGACCTGAACGCGGCCGTCGGAGGTCACCAGGCAGCGATGCAGATGCTGAAGGACAC
GATCAACGAGGAGGCGGCCGAGTGGGACCGGGCGGCAGCCGAGCCACGCGGTTCCGACATCGCGGGCACCACCTCGACGCTCCAGGAGCAGA
TCGGGTGGGCCGCAGCTAAGCGCTGGATCATCCTCGGGCTGAACAAGATCGTCCGGATGTACAGCCCGACGTCGATCGCTGCTAAGTACGTT
GACCGGTTCTACAAGACCCTGAGGGCCGAGCAGGCGGCCGGACTGGAGGAGATGATGACCGCGTGCCAGGGGGTCGGTGGACCAGGGCACAA
GGCCGCGATCTCGCCGCGCACGCTGAACGCGTGGGTGAAGGTCTGATAAgaattcgctagcggcgcgccagatctgatatcggatctGCTGT
GCCTTCTAGTTGCCAGCCATCTGTTGTTTGCCCCTCCCCCGTGCCTTCCTTGACCCTGGAAGGTGCCACTCCCACTGTCCTTTCCTAATAAA
ATGAGGAAATTGCATCGCATTGTCTGAGTAGGTGTCATTCTATTCTGGGGGGTGGGGTGGGGCAGGACAGCAAGGGGGAGGATTGGGAAGAC
AATAGCAGGCATGCTGGGGATGCGGTGGGCTCTATGGGTACCCAGGTGCTGAAGAATTGACCCGGTTCCTCCTGGGCCAGAAAGAAGCAGGC
ACATCCCCTTCTCTGTGACACACCCTGTCCACGCCCCTGGTTCTTAGTTCCAGCCCCACTCATAGGACACTCATAGCTCAGGAGGGCTCCGC
CTTCAATCCCACCCGCTAAAGTACTTGGAGCGGTCTCTCCCTCCCTCATCAGCCCACCAAACCAAACCTAGCCTCCAAGAGTGGGAAGAAAT
TAAAGCAAGATAGGCTATTAAGTGCAGAGGGAGAGAAAATGCCTCCAACATGTGAGGAAGTAATGAGAGAAATCATAGAATTTCTTCCGCTT
CCTCGCTCACTGACTCGCTGCGCTCGGTCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCGTTCATCCATAGTTGCCTGACTCGGGGGGGG
GGGGCGCTGAGGTCTGCCTCGTGAAGAAGGTGTTGCTGACTCATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTTTGCTTTGCCACGGAACGGTCTGCGTTGTCGGGAAGATGCGTG
ATCTGATCCTTCAACTCAGCAAAAGTTCGATTTATTCAACAAAGCCGCCGTCCCGTCAAGTCAGCGTAATGCTCTGCCAGTGTTACAACCAA
TTAACCAATTCTGATTAGAAAAACTCATCGAGCATCAAATGAAACTGCAATTTATTCATATCAGGATTATCAATACCATATTTTTGAAAAAG
CCGTTTCTGTAATGAAGGAGAAAACTCACCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGTGACGACTGAATCCGGTGAGAATGGCAAA
AGCTTATGCATTTCTTTCCAGACTTGTTCAACAGGCCAGCCATTACGCTCGTCATCAAAATCACTCGCATCAACCAAACCGTTATTCATTCG
TGATTGCGCCTGAGCGAGACGAAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATCGCAGTGGTGAGTAACCATGCA
TCATCAGGAGTACGGATAAAATGCTTGATGGTCGGAAGAGGCATAAATTCCGTCAGCCAGTTTAGTCTGACCATCTCATCTGTAACATCATT
GGCAACGCTACCTTTGCCATGTTTCAGAAACAACTCTGGCGCATCGGGCTTCCCATACAATCGATAGATTGTCGCACCTGATTGCCCGACAT
TATCGCGAGCCCATTTATACCCATATAAATCAGCATCCATGTTGGAATTTAATCGCGGCCTCGAGCAAGACGTTTCCCGTTGAATATGGCTC
ATAACACCCCTTGTATTACTGTTTATGTAAGCAGACAGTTTTATTGTTCATGATGATATATTTTTATCTTGTGCAATGTAACATCAGAGATT
TTGAGACACAACGTGGATCATCCAGACATGATAAGATACATTGATGAGTTTGGACAAACCACAACTAGAATGCAGTGAAAAAAATGCTTTAT
TTGTGAAATTTGTGATGCTATTGCTTTATTTGTAACCATTATAAGCTGCAATAAACAAGTTAACAACAACAATTGCATTCATTTTATGTTTC
AGGTTCAGGGGGAGGTGTGGGAGGTTTTTTAAAGCAAGTAAAACCTCTACAAATGTGGTATGGCTGATTATGATCgtcgaggatccggcgTT
ATCAGACCTTCACCCAGGCGTTGAGGGTGCGAGGCGAGAGGGCCGCCTTGTGCGACGGTCCTCCGACTCCCTGGCAGGCTGTCATCATCTCC
TCGAGACCCGCGGCCTGCTCTGCCCTCAGCGTCTTGAAGAAGCGGTCTACGTATTTGGCCGCGATGCTGACTGGGCTGTACATCCTGACGAT
CTTGTTGAGGCCCAGGATGATCCAGCGCTTGGCTGCAGCCCAGGCGATCTGCTCCTGGAGGGTGCTGGTCGTGCCTGCGATGTCGCTACCCC
TTGGCTCAGCTGCTGCCCTGTCCCACTCGGCTGCCTCCTCGTTGATGGTCTCCTTGAGCATCTGCATTGCCGCCTGGTGTCCACCGACCGCG
GCGTTGAGGTCCTGCGGTGTCGCACCCTCACTGAGTGCGGTGAACATGGGGATGACCGAGATCGAGCACGCCACGGTCCCGAGTAGCAGGAG
CGACTGCAGCCACATttcttccgtttaaacgtcgacagatccaaacGCTCCTCCGACGTCCCCAGGCAGAATGGCGGTTCCCTAAACGAGCA
TTGCTTATATAGACCTCCCATTAGGCACGCCTACCGCCCATTTACGTCAATGGAACGCCCATTTGCGTCATTGCCCCTCCCCATTGACGTCA
ATGGGGATGTACTTGGCAGCCATCGCGGGCCATTTACCGCCATTGACGTCAATGGGAGTACTGCCAATGTACCCTGGCGTACTTCCAATAGT
AATGTACTTGCCAAGTTACTATTAATAGATATTGATGTACTGCCAAGTGGGCCATTTACCGTCATTGACGTCAATAGGGGGCGTGAGAACGG
ATATGAATGGGCAATGAGCCATCCCATTGACGTCAATGGTGGGTGGTCCTATTGACGTCAATGGGCATTGAGCCAGGCGGGCCATTTACCGT
AATTGACGTCAATGGGGGAGGCGCCATATACGTCAATAGGACCGCCCATATGACGTCAATAGGTAAGACCATGAGGCCCTTTCGTCTCGCGC
GTTTCGGTGATGACGGTGAAAACCTCTGACACATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACTATGCGGCATCAGAGCAGATTGTACTGAGAGTGCACCATATGCG
GTGTGAAATACCGCACAGATGCGTAAGGAGAAAATACCGCATCAGATTGGCTATTGGCATTATGCC SEQ ID NO: 18 p24CE1 encoded by SEQ ID NO: 17 (includes a GM-CSF signal peptide)
MWLQSLLLLGTVACSISVIPMFSALSEGATPQDLNAAVGGHQAAMQMLKDTINEEAAEWDRAAAEPRGSDIAGTTSTLQEQIGWAAAKRWII
LGLNKIVRMYSPTSIAAKYVDRFYKTLRAEQAAGLEEMMTACQGVGGPGHKAAISPRTLNAWVKV -continued

| Table of Illustrative Conserved Element Sequences |
|---|

SEQ ID NO: 19 p24CE2 encoded by SEQ ID NO: 17 (includes a GM-CSF signal peptide)
MWLQSLLLLGTVACSISVIPMFTALSEGATPQDLNAAVGGHQAAMQMLKETINEEAAEWDRAAAEPRGSDIAGTTSTLQEQIAWAAAKRWII
LGLNKIVRMYSPVSIAAKYVDRFFKTLRAEQAAGLEEMMTACQGVGGPSHKAALSPRTLNAWVKV SEQ ID NO: 20 LAMP-p24CE2 (202H) (gene underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGACGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGcgggcgcgcgtcgactagcATGGCGCCCCGCAGCGCCCGGCGACCCCTGCTGCTACTGCTGTTGCTGCTGCTCGGCC
TCATGCATTGTGCGTCAGCAGCAATGTTTATGGTGAAAAATGGCAACGGGACCGCGTGCATAATGGCCAACTTCTCTGCTGCCTTCTCAGTG
AACTACGACACCAAGAGTGGCCCTAAGAACATGACCCTTGACCTGCCATCAGATGCCACAGTGGTGCTCAACCGCAGCTCCTGTGGAAAAGA
GAACACTTCTGACCCCAGTCTCGTGATTGCTTTTGGAAGAGGACATACACTCACTCTCAATTTCACGAGAAATGCAACACGTTACAGCGTTC
AGCTCATGAGTTTTGTTTATAACTTGTCAGACACACACCTTTTCCCCAATGCGAGCTCCAAAGAAATCAAGACTGTGGAATCTATAACTGAC
ATCAGGGCAGATATAGATAAAAAATACAGATGTGTTAGTGGCACCCAGGTCCACATGAACAACGTGACCGTAACGCTCCATGATGCCACCAT
CCAGGCGTACCTTTCCAACAGCAGCTTCAGCAGGGGAGAGACACGCTGTGAACAAGACAGGCCTTCCCCAACCACAGCGCCCCCTGCGCCAC
CCAGCCCCTCGCCCTCACCCGTGCCCAAGAGCCCCTCTGTGGACAAGTACAACGTGAGCGGCACCAACGGGACCTGCCTGCTGGCCAGCATG
GGGCTGCAGCTGAACCTCACCTATGAGAGGAAGGACAACACGACGGTGACAAGGCTTCTCAACATCAACCCCAACAAGACCTCGGCCAGCGG
GAGCTGCGGCGCCCACCTGGTGACTCTGGAGCTGCACAGCGAGGGCACCACCGTCCTGCTCTTCCAGTTCGGGATGAATGCAAGTTCTAGCC
GGTTTTTCCTACAAGGAATCCAGTTGAATACAATTCTTCCTGACGCCAGAGACCCTGCCTTTAAAGCTGCCAACGGCTCCCTGCGAGCGCTG
CAGGCCACAGTCGGCAATTCCTACAAGTGCAACGCGGAGGAGCACGTCCGTGTCACGAAGGCGTTTTCAGTCAATATATTCAAAGTGTGGGT
CCAGGCTTTCAAGGTGGAAGGTGGCCAGTTTGGCTCTGTGGAGGAGTGTCTGCTGGACGAGAACAGCCTCGAGGATATCGTCATCCCGATGT
TCACGGCGCTCAGCGAGGGAGCGACGCCGCAGGACCTGAACGCGGCCGTCGGAGGTCACCAGGCAGCGATGCAGATGCTGAAGGAGACGATC
AACGAGGAGGCGGCCGAGTGGGACCGGGCGGCAGCCGAGCCACGCGGTTCCGACATCGCGGGCACCACCTCGACGCTCCAGGAGCAGATCGC
GTGGGCCGCAGCTAAGCGCTGGATCATCCTGGGCTGAACAAGATCGTCCGGATGTACAGCCCGGTCTCGATCGCTGCTAAGTACGTTGACC
GGTTCTTCAAGACCCTGAGGGCCGAGCAGGCGGCCGGACTGGAGGAGATGATGACCGCGTGCCAGGGGGTCGGTGGACCATCGCACAAGGCC
GCGCTCTCGCCGCGCACGCTGAACGCGTGGGTGAAGGTCGGATCCGAATTCACGCTGATCCCCATCGCTGTGGGTGGTGCCCTGGCGGGGCT
GGTCCTCATCGTCCTCATCGCCTACCTCGTCGGCAGGAAGAGGAGTCACGCAGGCTACCAGACTATCTAGggtacctctagGATCTGCTGTG
CCTTCTAGTTGCCAGCCATCTGTTGTTTGCCCCTCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGGCAGGACAGCAAGGGGGAGGATTGGGAAGACA
ATAGCAGGCATGCTGGGGATGCGGTGGGCTCTATGGGTACCCAGGTGCTGAAGAATTGACCCGGTTCCTCCTGGGCCAGAAAGAAGCAGGCA
CATCCCCTTCTCTGTGACACACCCTGTCCACGCCCCTGGTTCTTAGTTCCAGCCCCACTCATAGGACACTCATAGCTCAGGAGGGCTCCGCC
TTCAATCCCACCCGCTAAAGTACTTGGAGCGGTCTCTCCCTCCCTCATCAGCCCACCAAACCAAACCTAGCCTCCAAGAGTGGGAAGAAATT
AAAGCAAGATAGGCTATTAAGTGCAGAGGGAGAGAAAATGCCTCCAACATGTGAGGAAGTAATGAGAGAAATCATAGAATTTCTTCCGCTTC
CTCGCTCACTGACTCGCTGCGCTCGGTCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTCCGCCTTTCTCCCTTCGGGAAGCGTGGCGCTTTCTCAAT
GCTCACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGTTGCCTGACTCGGGGGGGG
GGGGCGCTGAGGTCTGCCTCGTGAAGAAGGTGTTGCTGACTCATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTTTGCTTTGCCACGGAACGGTCTGCGTTGTCGGGAAGATGCGTG
ATCTGATCCTTCAACTCAGCAAAAGTTCGATTTATTCAACAAAGCCGCCGTCCCGTCAAGTCAGCGTAATGCTCTGCCAGTGTTACAACCAA
TTAACCAATTCTGATTAGAAAAACTCATCGAGCATCAAATGAAACTGCAATTTATTCATATCAGGATTATCAATACCATATTTTTGAAAAAG
CCGTTTCTGTAATGAAGGAGAAAACTCACCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGTGACGACTGAATCCGGTGAGAATGGCAAA
AGCTTATGCATTTCTTTCCAGACTTGTTCAACAGGCCAGCCATTACGCTCGTCATCAAAATCACTCGCATCAACCAAACCGTTATTCATTCG
TGATTGCGCCTGAGCGAGACGAAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATCGCAGTGGTGAGTAACCATGCA
TCATCAGGAGTACGGATAAAATGCTTGATGGTCGGAAGAGGCATAAATTCCGTCAGCCAGTTTAGTCTGACCATCTCATCTGTAACATCATT
GGCAACGCTACCTTTGCCATGTTTCAGAAACAACTCTGGCGCATCGGGCTTCCCATACAATCGATAGATTGTCGCACCTGATTGCCCGACAT
TATCGCGAGCCCATTTATACCCATATAAATCAGCATCCATGTTGGAATTTAATCGCGGCCTGGAGCAAGACGTTTCCCGTTGAATATGGCTC
ATAACACCCCTTGTATTACTGTTTATGTAAGCAGACAGTTTTATTGTTCATGATGATATATTTTTATCTTGTGCAATGTAACATCAGAGATT
TTGAGACACAACGTGGCTTTCCCCCCCCCCCCATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCATTATTATCATGACATTAACCTAT
AAAAATAGGCGTATCACGAGGCCCTTTCGTCTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTTGGCGGGTGTCGGGGCTGGCTTAACTATGCGG
CATCAGAGCAGATTGTACTGAGAGTGCACCATATGCGGTGTGAAATACCGCACAGATGCGTAAGGAGAAAATACCGCATCAGATTGGCTATT
GG SEQ ID NO: 21 LAMP-p24CE2 fusion (p24CE2 underlined) encoded by SEQ ID NO: 20
MAPRSARRPLLLLLLLLLLGLMHCASAAMFMVKNGNGTACIMANFSAAFSVNYDTKSGPKNMTLDLPSDATVVLNRSSCGKENTSDPSLVIA
FGRGHTLTLNFTRNATRYSVQLMSFVYNLSDTHLFPNASSKEIKTVESITDIRADIDKKYRCVSGTQVHMNNVTVTLHDATIQAYLSNSSFS
RGETRCEQDRPSPTTAPPAPPSPSPSPVPKSPSVDKYNVSGTNGTCLLASMGLQLNLTYERKDNTTVTRLLNINPNKTSASGSCGAHLVTLE
LHSEGTTVLLFQFGMNASSSRFFLQGIQLNTILPDARDPAFKAANGSLRALQATVGNSYKCNAEEHVRVTKAFSVNIFKVWVQAFKVEGGQF -continued Table of Illustrative Conserved Element Sequences GSVEECLLDENSLEDIVIPMFTALSEGATPQDLNAAVGGHQAAMQMLKETINEEAAEWDRAAAEPRGSDIAGTTSTLQEQIAWAAAKRWIIL
GLNKIVRMYSPVSIAAKYVDRFFKTLRAEQAAGLEEMMTACQGVGGPSHKAALSPRTLNAWVKVGSEFTLIPIAVGGALAGLVLIVLIAYLV
GRKRSHAGYQTI.

SEQ ID NO: 22 LAMP-p24CE1 (191H) (gene underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGATGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGCgggcgcgcgtcgactagcATGGCGCCCCGCAGCGCCCGGCGACCCCTGCTGCTGCTACTGCTGTTGCTGCTGCTCGGCC
TCATGCATTGTGCGTCAGCAGCAATGTTTATGGTGAAAAATGGCAACGGGACCGCGTGCATAATGGCCAACTTCTCTGCTGCCTTCTCAGTG
AACTACGACACCAAGAGTGGCCCTAAGAACATGACCCTTGACCTGCCATCAGATGCCACAGTGGTGCTCAACCGCAGCTCCTGTGGAAAAGA
GAACACTTCTGACCCCAGTCTCGTGATTGCTTTTGGAAGAGGACATACACTCACTCTCAATTTCACGAGAAATGCAACACGTTACAGCGTTC
AGCTCATGAGTTTTGTTTATAACTTGTCAGACACACACCTTTTCCCCAATGCGAGCTCCAAAGAAATCAAGACTGTGGAATCTATAACTGAC
ATCAGGGCAGATATAGATAAAAAATACAGATGTGTTAGTGGCACCCAGGTCCACATGAACAACGTGACCGTAACGCTCCATGATGCCACCAT
CCAGGCGTACCTTTCCAACAGCAGCTTCAGCAGGGGAGAGACACGCTGTGAACAAGACAGGCCTTCCCCAACCACAGCGCCCCCTGCGCCAC
CCAGCCCCTCGCCCTCACCCGTGCCCAAGAGCCCCTCTGTGGACAAGTACAACGTGAGCGGCACCAACGGGACCTGCCTGCTGGCCAGCATG
GGGCTGCAGCTGAACCTCACCTATGAGAGGAAGGACAACACGACGGTGACAAGGCTTCTCAACATCAACCCCAACAAGACCTCGGCCAGCGG
GAGCTGCGGCGCCCACCTGGTGACTCTGGAGCTGCACAGCGAGGGCACCACCGTCCTGCTCTTCCAGTTCGGGATGAATGCAAGTTCTAGCC
GGTTTTTCCTACAAGGAATCCAGTTGAATACAATTCTTCCTGACGCCAGAGACCCTGCCTTTAAAGCTGCCAACGGCTCCCTGCGAGCGCTG
CAGGCCACAGTCGGCAATTCCTACAAGTGCAACGCGGAGGAGCACGTCCGTGTCACGAAGGCGTTTTCAGTCAATATATTCAAAGTGTGGGT
CCAGGCTTTCAAGGTGGAAGGTGGCCAGTTTGGCTCTGTGGAGGAGTGTCTGCTGGACGAGAACAGCCTCGAGGATATCGTCATCCCGATGT
TCTCGGCGCTCAGCGAGGGAGCGACGCCGCAGGACCTGAACGCGGCCGTCGGAGGTCACCAGGCAGCGATGCAGATGCTGAAGGACACGATC
AACGAGGAGGCGGCCGAGTGGGACCGGGCGGCAGCCGAGCCACGCGGTTCCGACATCGCGGGCACCACCTCGACGCTCCAGGAGCAGATCGG
GTGGGCCGCAGCTAAGCGCTGGATCATCCTCGGGCTGAACAAGATCGTCCGGATGTACAGCCCGACGTCGATCGCTGCTAAGTACGTTGACC
GGTTCTACAAGACCCTGAGGGCCGAGCAGGCGGCCGGACTGGAGGAGATGATGACCGCGTGCCAGGGGGTCGGTGGACCAGGGCACAAGGCC
GCGATCTCGCCGCGCACGCTGAACGCGTGGGTGAAGGTCGGATCCGAATTCACGCTGATCCCCATCGCTGTGGGTGGTGCCCTGGCGGGGCT
GGTCCTCATCGTCCTCATCGCCTACCTCGTCGGCAGGAAGAGGAGTCACGCAGGCTACCAGACTATCTAGggtacctctagGATCTGCTGTG
CCTTCTAGTTGCCAGCCATCTGTTGTTTGCCCCTCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGGCAGGACAGCAAGGGGGAGGATTGGGAAGACA
ATAGCAGGCATGCTGGGGATGCGGTGGGCTCTATGGGTACCCAGGTGCTGAAGAATTGACCCGGTTCCTCCTGGGCCAGAAAGAAGCAGGCA
CATCCCCTTCTCTGTGACACACCCTGTCCACGCCCCTGGTTCTTAGTTCCAGCCCCACTCATAGGACACTCATAGCTCAGGAGGGCTCCGCC
TTCAATCCCACCCGCTAAAGTACTTGGAGCGGTCTCTCCCTCCCTCATCAGCCCACCAAACCAAACCTAGCCTCCAAGAGTGGGAAGAAATT
AAAGCAAGATAGGCTATTAAGTGCAGAGGGAGAGAAAATGCCTCCAACATGTGAGGAAGTAATGAGAGAAATCATAGAATTTCTTCCGCTTC
CTCGCTCACTGACTCGCTGCGCTCGGTCGTTCGGCTGCGGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTCCGCCTTTCTCCCTTCGGGAAGCGTGGCGCTTTCTCAAT
GCTCACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGTTGCCTGACTCGGGGGGGG
GGGGCGCTGAGGTCTGCCTCGTGAAGAAGGTGTTGCTGACTCATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTTTGCTTTGCCACGGAACGGTCTGCGTTGTCGGGAAGATGCGTG
ATCTGATCCTTCAACTCAGCAAAAGTTCGATTTATTCAACAAAGCCGCCGTCCCGTCAAGTCAGCGTAATGCTCTGCCAGTGTTACAACCAA
TTAACCAATTCTGATTAGAAAAACTCATCGAGCATCAAATGAAACTGCAATTTATTCATATCAGGATTATCAATACCATATTTTTGAAAAAG
CCGTTTCTGTAATGAAGGAGAAAACTCACCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGTGACGACTGAATCCGGTGAGAATGGCAAA
AGCTTATGCATTTCTTTCCAGACTTGTTCAACAGGCCAGCCATTACGCTCGTCATCAAAATCACTCGCATCAACCAAACCGTTATTCATTCG
TGATTGCGCCTGAGCGAGACGAAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATCGCAGTGGTGAGTAACCATGCA
TCATCAGGAGTACGGATAAAATGCTTGATGGTCGGAAGAGGCATAAATTCCGTCAGCCAGTTTAGTCTGACCATCTCATCTGTAACATCATT
GGCAACGCTACCTTTGCCATGTTTCAGAAACAACTCTGGCGCATCGGGCTTCCCATACAATCGATAGATTGTCGCACCTGATTGCCCGACAT
TATCGCGAGCCCATTTATACCCATATAAATCAGCATCCATGTTGGAATTTAATCGCGGCCTGGAGCAAGACGTTTCCCGTTGAATATGGCTC
ATAACACCCCTTGTATTACTGTTTATGTAAGCAGACAGTTTTATTGTTCATGATGATATATTTTTATCTTGTGCAATGTAACATCAGAGATT
TTGAGACACAACGTGGCTTTCCCCCCCCCCCCATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCATTATTATCATGACATTAACCTAT
AAAAATAGGCGTATCACGAGGCCCTTTCGTCTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTTGGCGGGTGTCGGGGCTGGCTTAACTATGCGG
CATCAGAGCAGATTGTACTGAGAGTGCACCATATGCGGTGTGAAATACCGCACAGATGCGTAAGGAGAAAATACCGCATCAGATTGGCTATT
GG SEQ ID NO: 23 LAMP-p24CE1 (p24CE1 underlined)
MAPRSARRPLLLLLLLLLLGLMHCASAAMFMVKNGNGTACIMANFSAAFSVNYDTKSGPKNMTLDLPSDATVVLNRSSCGKENTSDPSLVIA
FGRGHTLTLNFTRNATRYSVQLMSFVYNLSDTHLFPNASSKEIKTVESITDIRADIDKKYRCVSGTQVHMNNVTVTLHDATIQAYLSNSSFS
RGETRCEQDRPSPTTAPPAPPSPSPSPVPKSPSVDKYNVSGTNGTCLLASMGLQLNLTYERKDNTTVTRLLNINPNKTSASGSCGAHLVTLE
LHSEGTTVLLFQFGMNASSSRFFLQGIQLNTILPDARDPAFKAANGSLRALQATVGNSYKCNAEEHVRVTKAFSVNIFKVWVQAFKVEGGQF
GSVEECLLDENSLEDIVIPMFSALSEGATPQDLNAAVGGHQAAMQMLKDTINEEAAEWDRAAAEPRGSDIAGTTSTLQEQIGWAAAKRWIIL
GLNKIVRMYSPTSIAAKYVDRFYKTLRAEQAAGLEEMMTACQGVGGPGHKAAISPRTLNAWVKVGSEFTLIPIAVGGALAGLVLIVLIAYLV
GRKRSHAGYQTI.

-continued

Table of Illustrative Conserved Element Sequences

SEQ ID NO: 24 SP-p24CE2 (235H) (gene underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGATGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGCGGGcgcgcgtcgacaagaaATGTGGCTCCAGAGCCTGCTACTCCTGGGGACGGTGGCCTGCAGCATCTCGGTCATCCCG
ATGTTCACGGCGCTCAGCGAGGGAGCGACGCCGCAGGACCTGAACGCGGCCGTCGGAGGTCACCAGGCAGCGATGCAGATGCTGAAGGAGAC
GATCAACGAGGAGGCGGCCGAGTGGGACCGGGCGGCAGCCGAGCCACGCGGTTCCGACATCGCGGGCACCACCTCGACGCTCCAGGAGCAGA
TCGCGTGGGCCGCAGCTAAGCGCTGGATCATCCTCGGGCTGAACAAGATCGTCCGGATGTACAGCCCGGTCTCGATCGCTGCTAAGTACGTT
GACCGGTTCTTCAAGACCCTGAGGGCCGAGCAGGCGGCCGGACTGGAGGAGATGATGACCGCGTGCCAGGGGGTCGGTGGACCATCGCACAA
GGCCGCGCTCTCGCCGCGCACGCTGAACGCGTGGGTGAAGGTCTGATAAgaattcgcggatatcggttaacggatccAGATCTGCTGTGCCT
TCTAGTTGCCAGCCATCTGTTGTTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAGGGGGAGGATTGGGAAGACAATA
GCAGGCATGCTGGGGATGCGGTGGGCTCTATGGGTACCCAGGTGCTGAAGAATTGACCCGGTTCCTCCTGGGCCAGAAAGAAGCAGGCACAT
CCCCTTCTCTGTGACACACCCTGTCCACGCCCCTGGTTCTTAGTTCCAGCCCCACTCATAGGACACTCATAGCTCAGGAGGGCTCCGCCTTC
AATCCCACCCGCTAAAGTACTTGGAGCGGTCTCTCCCTCCCTCATCAGCCCACCAAACCAAACCTAGCCTCCAAGAGTGGGAAGAAATTAAA
GCAAGATAGGCTATTAAGTGCAGAGGGAGAGAAAATGCCTCCAACATGTGAGGAAGTAATGAGAGAAATCATAGAATTTCTTCCGCTTCCTC
GCTCACTGACTCGCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTGACTCGGGGGGGGGGGG
CGCTGAGGTCTGCCTCGTGAAGAAGGTGTTGCTGACTCATACCAGGCCTGAATCGCCCCATCATCCAGCCAGAAAGTGAGGGAGCCACGGTT
GATGAGAGCTTTGTTGTAGGTGGACCAGTTGGTGATTTTGAACTTTTGCTTTGCCACGGAACGGTCTGCGTTGTCGGGAAGATGCGTGATCT
GATCCTTCAACTCAGCAAAAGTTCGATTTATTCAACAAAGCCGCCGTCCCGTCAAGTCAGCGTAATGCTCTGCCAGTGTTACAACCAATTAA
CCAATTCTGATTAGAAAAACTCATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGATTCCGACTCGTCCAACATCAAT
ACAACCTATTAATTTCCCCTCGTCAAAAATAAGGTTATCAAGTGAGAAATCACCATGAGTGACGACTGAATCCGGTGAGAATGGCAAAAGCT
TATGCATTTCTTTCCAGACTTGTTCAACAGGCCAGCCATTACGCTCGTCATCAAAATCACTCGCATCAACCAAACCGTTATTCATTCGTGAT
TGCGCCTGAGCGAGACGAAATACGCGATCGCTGTTAAAAGGACAATTACAAACAGGAATCGAATGCAACCGGCGCAGGAACACTGCCAGCGC
ATCAACAATATTTTCACCTGAATCAGGATATTCTTCTAATACCTGGAATGCTGTTTTCCCGGGGATCGCAGTGGTGAGTAACCATGCATCAT
CAGGAGTACGGATAAAATGCTTGATGGTCGGAAGAGGCATAAATTCCGTCAGCCAGTTTAGTCTGACCATCTCATCTGTAACATCATTGGCA
ACGCTACCTTTGCCATGTTTCAGAAACAACTCTGGCGCATCGGGCTTCCCATACAATCGATAGATTGTCGCACCTGATTGCCCGACATTATC
GCGAGCCCATTTATACCCATATAAATCAGCATCCATGTTGGAATTTAATCGCGGCCTCGAGCAAGACGTTTCCCGTTGAATATGGCTCATAA
CACCCCTTGTATTACTGTTTATGTAAGCAGACAGTTTTATTGTTCATGATGATATATTTTTATCTTGTGCAATGTAACATCAGAGATTTTGA
GACACAACGTGGCTTTCCCCCCCCCCCCATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTATCATGACATTAACCTATAAAA
ATAGGCGTATCACGAGGCCCTTTCGTCTCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTGTCGGGGCTGGCTTAACTATGCGGCATC
AGAGCAGATTGTACTGAGAGTGCACCATATGCGGTGTGAAATACCGCACAGATGCGTAAGGAGAAAATACCGCATCAGATTGGCTATTGG SEQ ID NO: 25 SP-p24CE2 (p24CE2 underlined) encoded by SEQ ID NO: 24
MWLQSLLLLGTVACSISVIPMFTALSEGATPQDLNAAVGGHQAAMQMLKETINEEAAEWDRAAAEPRGSDIAGTTSTLQEQIAWAAAKRWII
LGLNKIVRMYSPVSIAAKYVDRFFKTLRAEQAAGLEEMMTACQGVGGPSHKAALSPRTLNAWVKV SEQ ID NO: 26 MCP3-p24CE1 (230H) (gene underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGATGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGCGGGcgcgcgtcgacaagaaATGTGGAAGCCGATGCCCTCGCCAAGCAACATGAAGGCGTCCGCCGCGCTCCTGTGCCTG
CTCCTCACGGCCGCGGCTTTCAGCCCCCAGGGGCTCGCGCAGCCGGTCGGGATCAACACGAGCACGACCTGCTGCTACCGGTTCATCAACAA
GAAGATCCCGAAGCAGCGTCTGGAGAGCTACCGCCGGACCACGTCGAGCCACTGCCCGCGGGAGGCGGTCATCTTCAAGACGAAGCTGGACA
AGGAGATCTGCGCCGACCCGACGCAGAAGTGGGTTCAGGACTTCATGAAGCACCTGGACAAGAAGACGCAGACGCCGAAGCTGGTCATCCCG
ATGTTCTCGGCGCTCAGCGAGGGAGCGACGCCGCAGGACCTGAACGCGGCCGTCGGAGGTCACCAGGCAGCGATGCAGATGCTGAAGGACAC
GATCAACGAGGAGGCGGCCGAGTGGGACCGGGCGGCAGCCGAGCCACGCGGTTCCGACATCGCGGGCACCACCTCGACGCTCCAGGAGCAGA
TCGGGTGGGCCGCAGCTAAGCGCTGGATCATCCTCGGGCTGAACAAGATCGTCCGGATGTACAGCCCGACGTCGATCGCTGCTAAGTACGTT
GACCGGTTCTACAAGACCCTGAGGGCCGAGCAGGCGGCCGGACTGGAGGAGATGATGACCGCGTGCCAGGGGGTCGGTGGACCAGGGCACAA
GGCCGCGATCTCGCCGCGCACGCTGAACGCGTGGGTGAAGGTCTGATAAgaattcgcggatatcggttaacggatccaGATCTGCTGTGCCT
TCTAGTTGCCAGCCATCTGTTGTTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAGGGGGAGGATTGGGAAGACAATA
GCAGGCATGCTGGGGATGCGGTGGGCTCTATGGGTACCCAGGTGCTGAAGAATTGACCCGGTTCCTCCTGGGCCAGAAAGAAGCAGGCACAT -continued Table of Illustrative Conserved Element Sequences CCCCTTCTCTGTGACACACCCTGTCCACGCCCCTGGTTCTTAGTTCCAGCCCCACTCATAGGACACTCATAGCTCAGGAGGGCTCCGCCTTC
AATCCCACCCGCTAAAGTACTTGGAGCGGTCTCTCCCTCCCTCATCAGCCCACCAAACCAAACCTAGCCTCCAAGAGTGGGAAGAAATTAAA
GCAAGATAGGCTATTAAGTGCAGAGGGAGAGAAAATGCCTCCAACATGTGAGGAAGTAATGAGAGAAATCATAGAATTTCTTCCGCTTCCTC
GCTCACTGACTCGCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTGACTCGGGGGGGGGGGG
CGCTGAGGTCTGCCTCGTGAAGAAGGTGTTGCTGACTCATACCAGGCCTGAATCGCCCCATCATCCAGCCAGAAAGTGAGGGAGCCACGGTT
GATGAGAGCTTTGTTGTAGGTGGACCAGTTGGTGATTTTGAACTTTTGCTTTGCCACGGAACGGTCTGCGTTGTCGGGAAGATGCGTGATCT
GATCCTTCAACTCAGCAAAAGTTCGATTTATTCAACAAAGCCGCCGTCCCGTCAAGTCAGCGTAATGCTCTGCCAGTGTTACAACCAATTAA
CCAATTCTGATTAGAAAAACTCATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGATTCCGACTCGTCCAACATCAAT
ACAACCTATTAATTTCCCCTCGTCAAAAATAAGGTTATCAAGTGAGAAATCACCATGAGTGACGACTGAATCCGGTGAGAATGGCAAAAGCT
TATGCATTTCTTTCCAGACTTGTTCAACAGGCCAGCCATTACGCTCGTCATCAAAATCACTCGCATCAACCAAACCGTTATTCATTCGTGAT
TGCGCCTGAGCGAGACGAAATACGCGATCGCTGTTAAAAGGACAATTACAAACAGGAATCGAATGCAACCGGCGCAGGAACACTGCCAGCGC
ATCAACAATATTTTCACCTGAATCAGGATATTCTTCTAATACCTGGAATGCTGTTTTCCCGGGGATCGCAGTGGTGAGTAACCATGCATCAT
CAGGAGTACGGATAAAATGCTTGATGGTCGGAAGAGGCATAAATTCCGTCAGCCAGTTTAGTCTGACCATCTCATCTGTAACATCATTGGCA
ACGCTACCTTTGCCATGTTTCAGAAACAACTCTGGCGCATCGGGCTTCCCATACAATCGATAGATTGTCGCACCTGATTGCCCGACATTATC
GCGAGCCCATTTATACCCATATAAATCAGCATCCATGTTGGAATTTAATCGCGGCCTCGAGCAAGACGTTTCCCGTTGAATATGGCTCATAA
CACCCCTTGTATTACTGTTTATGTAAGCAGACAGTTTTATTGTTCATGATGATATATTTTTATCTTGTGCAATGTAACATCAGAGATTTTGA
GACACAACGTGGCTTTCCCCCCCCCCCCATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTATCATGACATTAACCTATAAAA
ATAGGCGTATCACGAGGCCCTTTCGTCTCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTGTCGGGGCTGGCTTAACTATGCGGCATC
AGAGCAGATTGTACTGAGAGTGCACCATATGCGGTGTGAAATACCGCACAGATGCGTAAGGAGAAAATACCGCATCAGATTGGCTATTGG SEQ ID NO: 27 MCP3-p24CE1 (p24CE1 underlined) encoded by SEQ ID NO: 26
MWKPMPSPSNMKASAALLCLLLTAAAFSPQGLAQPVGINTSTTCCYRFINKKIPKQRLESYRRTTSSHCPREAVIFKTKLDKEICADPTQKW
VQDFMKHLDKKTQTPKLVIPMFSALSEGATPQDLNAAVGGHQAAMQMLKDTINEEAAEWDRAAAEPRGSDIAGTTSTLQEQIGWAAAKRWII
LGLNKIVRMYSPTSIAAKYVDRFYKTLRAEQAAGLEEMMTACQGVGGPGHKAAISPRTLNAWVKV..

SEQ ID NO: 28 MCP3-p24CE2 (231H) (gene underlined)
CCTGGCCATTGCATACGTTGTATCCATATCATAATATGTACATTTATATTGGCTCATGTCCAACATTACCGCCATGTTGACATTGATTATTG
ACTAGTTATTAATAGTAATCAATTACGGGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGCCCCCTATTGACGTCAATGATGGTAAA
TGGCCCGCCTGGCATTATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGACGCAAATGGGCGGTAGGCGTGTACGGTGGGAG
GTCTATATAAGCAGAGCTCGTTTAGTGAACCGTCAGATCGCCTGGAGACGCCATCCACGCTGTTTTGACCTCCATAGAAGACACCGGGACCG
ATCCAGCCTCCGCGGGcgcgcgtcgacaagaaATGTGGAAGCCGATGCCCTCGCCAAGCAACATGAAGGCGTCCGCCGCGCTCCTGTGCCTG
CTCCTCACGGCCGCGGCTTTCAGCCCCCAGGGGCTCGCGCAGCCGGTCGGGATCAACACGAGCACGACCTGCTGCTACCGGTTCATCAACAA
GAAGATCCCGAAGCAGCGTCTGGAGAGCTACCGCCGGACCACGTCGAGCCACTGCCCGCGGGAGGCGGTCATCTTCAAGACGAAGCTGGACA
AGGAGATCTGCGCCGACCCGACGCAGAAGTGGGTTCAGGACTTCATGAAGCACCTGGACAAGAAGACGCAGACGCCGAAGCTGGTCATCCCG
ATGTTCACGGCGCTCAGCGAGGGAGCGACGCCGCAGGACCTGAACGCGGCCGTCGGAGGTCACCAGGCAGCGATGCAGATGCTGAAGGAGAC
GATCAACGAGGAGGCGGCCGAGTGGGACCGGGCGGCAGCCGAGCCACGCGGTTCCGACATCGCGGGCACCACCTCGACGCTCCAGGAGCAGA
TCGCGTGGGCCGCAGCTAAGCGCTGGATCATCCTCGGGCTGAACAAGATCGTCCGGATGTACAGCCCGGTCTCGATCGCTGCTAAGTACGTT
GACCGGTTCTTCAAGACCCTGAGGGCCGAGCAGGCGGCCGGACTGGAGGAGATGATGACCGCGTGCCAGGGGGTCGGTGGACCATCGCACAA
GGCCGCGCTCTCGCCGCGCACGCTGAACGCGTGGGTGAAGGTCTGATAAgaattcgcggatatcggttaacggatccaGATCTGCTGTGCCT
TCTAGTTGCCAGCCATCTGTTGTTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAGGGGGAGGATTGGGAAGACAATA
GCAGGCATGCTGGGGATGCGGTGGGCTCTATGGGTACCCAGGTGCTGAAGAATTGACCCGGTTCCTCCTGGGCCAGAAAGAAGCAGGCACAT
CCCCTTCTCTGTGACACACCCTGTCCACGCCCCTGGTTCTTAGTTCCAGCCCCACTCATAGGACACTCATAGCTCAGGAGGGCTCCGCCTTC
AATCCCACCCGCTAAAGTACTTGGAGCGGTCTCTCCCTCCCTCATCAGCCCACCAAACCAAACCTAGCCTCCAAGAGTGGGAAGAAATTAAA
GCAAGATAGGCTATTAAGTGCAGAGGGAGAGAAAATGCCTCCAACATGTGAGGAAGTAATGAGAGAAATCATAGAATTTCTTCCGCTTCCTC
GCTCACTGACTCGCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTGACTCGGGGGGGGGGGG
CGCTGAGGTCTGCCTCGTGAAGAAGGTGTTGCTGACTCATACCAGGCCTGAATCGCCCCATCATCCAGCCAGAAAGTGAGGGAGCCACGGTT
GATGAGAGCTTTGTTGTAGGTGGACCAGTTGGTGATTTTGAACTTTTGCTTTGCCACGGAACGGTCTGCGTTGTCGGGAAGATGCGTGATCT
GATCCTTCAACTCAGCAAAAGTTCGATTTATTCAACAAAGCCGCCGTCCCGTCAAGTCAGCGTAATGCTCTGCCAGTGTTACAACCAATTAA
CCAATTCTGATTAGAAAAACTCATCGAGCATCAAATGAAACTGCAATTTATTCATATCAGGATTATCAATACCATATTTTTGAAAAAGCCGT -continued Table of Illustrative Conserved Element Sequences TTCTGTAATGAAGGAGAAAACTCACCGAGGCAGTTCCATAGGATGGCAAGATCCTGGTATCGGTCTGCGATTCCGACTCGTCCAACATCAAT
ACAACCTATTAATTTCCCCTCGTCAAAAATAAGGTTATCAAGTGAGAAATCACCATGAGTGACGACTGAATCCGGTGAGAATGGCAAAAGCT
TATGCATTTCTTTCCAGACTTGTTCAACAGGCCAGCCATTACGCTCGTCATCAAAATCACTCGCATCAACCAAACCGTTATTCATTCGTGAT
TGCGCCTGAGCGAGACGAAATACGCGATCGCTGTTAAAAGGACAATTACAAACAGGAATCGAATGCAACCGGCGCAGGAACACTGCCAGCGC
ATCAACAATATTTTCACCTGAATCAGGATATTCTTCTAATACCTGGAATGCTGTTTTCCCGGGGATCGCAGTGGTGAGTAACCATGCATCAT
CAGGAGTACGGATAAAATGCTTGATGGTCGGAAGAGGCATAAATTCCGTCAGCCAGTTTAGTCTGACCATCTCATCTGTAACATCATTGGCA
ACGCTACCTTTGCCATGTTTCAGAAACAACTCTGGCGCATCGGGCTTCCCATACAATCGATAGATTGTCGCACCTGATTGCCCGACATTATC
GCGAGCCCATTTATACCCATATAAATCAGCATCCATGTTGGAATTTAATCGCGGCCTCGAGCAAGACGTTTCCCGTTGAATATGGCTCATAA
CACCCCTTGTATTACTGTTTATGTAAGCAGACAGTTTTATTGTTCATGATGATATATTTTTATCTTGTGCAATGTAACATCAGAGATTTTGA
GACACAACGTGGCTTTCCCCCCCCCCCCATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTATCATGACATTAACCTATAAAA
ATAGGCGTATCACGAGGCCCTTTCGTCTCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTGTCGGGGCTGGCTTAACTATGCGGCATC
AGAGCAGATTGTACTGAGAGTGCACCATATGCGGTGTGAAATACCGCACAGATGCGTAAGGAGAAAATACCGCATCAGATTGGCTATTGG SEQ ID NO: 29 MCP3-p24CE2 (p24CE2 is underlined) encoded by SEQ ID NO: 28
MWKPMPSPSNMKASAALLCLLLTAAAFSPQGLAQPVGINTSTTCCYRFINKKIPKQRLESYRRTTSSHCPREAVIFKTKLDKEICADPTQKW
VQDFMKHLDKKTQTPKLVIPMFTALSEGATPQDLNAAVGGHQAAMQMLKETINEEAAEWDRAAAEPRGSDIAGTTSTLQEQIAWAAAKRWII
LGLNKIVRMYSPVSIAAKYVDRFFKTLRAEQAAGLEEMMTACQGVGGPSHKAALSPRTLNAWVKV.

SEQ ID NO: 30 SP-p24CE1c-alternative conserved element nucleic acid construct
ATGTGGCTCCAGAGCCTGCTACTCCTGGGGACGGTGGCCTGCAGCATCTCGCAGGGGCAGATGGTCCACCAGGCGATCTCGCCGCGCACGCT
GAACGCGTGGGTGAAGGTCCTGGCGAAGGAGGAGAAGGCGTTCAGCCCGGAGGTCATCCCGATGTTCTCGGCGCTCAGCGAGGGAGCGACGC
CGCAGGACCTGAACGCGGCCAAGGTCGGAGGTCACCAGGCAGCGATGCAGATGCTGAAGGAGACGATCAACGAGGAGGCGGCCGAGTGGGAC
CGGGCGGCAGCCGAGCCACGCGGTTCCGACATCGCGGGCACCACCTCGACGCTCCAGGAGCAGATCGGGTGGGCCGCAGCTAAGCGCTGGAT
CATCCTCGGGCTGAACAAGATCGTCCGGATGTACAGCCCGACGTCGATCGCTGCTAAATACGTTGACCGGTTCTACAAGACCCTGAGGGCCG
AGCAGGCGGATTACAAGGACGATGACGACAAGCTGTGATAA SEQ ID NO: 31 SP-p24CE1c (p24CE1c underlined) encoded by SEQ ID NO: 30. Includes GM-CSF signal peptide. CE1 and CE2 replaced by CE8 and CE9, respectively (relative to p24 CE "Core1"); lacks CE7; arranged in the configuration of conserved elements: CE 8-9-3-4-5-6
MWLQSLLLLGTVACSISQGQMVHQAISPRTLNAWVKVLAKEEKAFSPEVIPMFSALSEGATPQDLNAAKVGGHQAAMQMLKETINEEAAEWD
RAAAEPRGSDIAGTTSTLQEQIGWAAAKRWIILGLNKIVRMYSPTSIAAKYVDRFYKTLRAEQADYKDDDDKL SEQ ID NO: 32 conserved element 8 (CE8)
QGQMVHQAISPRTLNAWVKV SEQ ID NO: 33 conserved element 9 (CE9)
EEKAFSPEVIPMFSALSEGATPQDLN SEQ ID NO: 34 SP-p24CE2c-alternative
ATGTGGCTCCAGAGCCTGCTACTCCTGGGGACGGTGGCCTGCAGCATCTCGCAGGGGCAGATGGTCCACCAGGCGCTGTCGCCGCGCACGCT
GAACGCGTGGGTGAAGGTCCTGGCGAAGGAGGAGAAGGGGTTCAACCCGGAGGTCATCCCGATGTTCACGGCGCTCAGCGAGGGAGCGACGC
CGCAGGACCTGAACGCGGCCAAGGTCGGAGGTCACCAGGCAGCGATGCAGATGCTGAAGGACACGATCAACGAGGAGGCGGCCGAGTGGGAC
CGGGCGGCAGCCGAGCCACGCGGTTCCGACATCGCGGGCACCACCTCGACGCTCCAGGAGCAGATCGCGTGGGCCGCAGCTAAGCGCTGGAT
CATCCTCGGGCTGAACAAGATCGTCCGGATGTACAGCCCGGTCTCGATCGCTGCTAAATACGTTGACCGGTTCTTCAAGACCCTGAGGGCCG
AGCAGGCGTGATAA SEQ ID NO: 35 SP-p24CE2c (p24CE2c underlined)
MWLQSLLLLGTVACSISQGQMVHQALSPRTLNAWVKVLAKEEKGFNPEVIPMFTALSEGATPQDLNAAKVGGHQAAMQMLKDTINEEAAEWD
RAAAEPRGSDIAGTTSTLQEQIAWAAAKRWIILGLNKIVRMYSPVSIAAKYVDRFFKTLRAEQA SEQ ID NO: 36 SP-p24CE2d alternative nucleic acid conserved element nucleic acid construct; in order CE9-3-4-5-6-8
ATGTGGCTCCAGAGCCTGCTACTCCTGGGGACGGTGGCCTGCAGCATCTCGGAGGAGAAGGGGTTCAACCCGGAGGTCATCCCGATGTTCAC
GGCGCTCAGCGAGGGAGCGACGCCGCAGGACCTGAACGCGGCCAAGGTCGGAGGTCACCAGGCAGCGATGCAGATGCTGAAGGACACGATCA
ACGAGGAGGCGGCCGAGTGGGACCGGGCGGCAGCCGAGCCACGCGGTTCCGACATCGCGGGCACCACCTCGACGCTCCAGGAGCAGATCGCG
TGGGCCGCAGCTAAGCGCTGGATCATCCTCGGGCTGAACAAGATCGTCCGGATGTACAGCCCGGTCTCGATCGCTGCTAAATACGTTGACCG
GTTCTTCAAGACCCTGAGGGCCGAGCAGGCGGCGCTGCAGGGGCAGATGGTCCACCAGGCGCTGTCGCCGCGCACGCTGAACGCGTGGGTGA
AGGTCTGATAA SEQ ID NO: 37 p24CE2d (protein underlined) encoded by SEQ ID NO: 36
MWLQSLLLLGTVACSISEEKGFNPEVIPMFTALSEGATPQDLNAAKVGGHQAAMQMLKDTINEEAAEWDRAAAEPRGSDIAGTTSTLQEQIA
WAAAKRWIILGLNKIVRMYSPVSIAAKYVDRFFKTLRAEQAALQGQMVHQALSPRTLNAWVKV SEQ ID NO: 38 SP-24CE1d-conserved element nucleic acid construct; in order CE9-3-4-5-6-8
ATGTGGCTCCAGAGCCTGCTACTCCTGGGGACGGTGGCCTGCAGCATCTCGGAGGAGAAGGCGTTCAGCCCGGAGGTCATCCCGATGTTCTC
GGCGCTCAGCGAGGGAGCGACGCCGCAGGACCTGAACGCGGCCAAGGTCGGAGGTCACCAGGCAGCGATGCAGATGCTGAAGGAGACGATCA
ACGAGGAGGCGGCCGAGTGGGACCGGGCGGCAGCCGAGCCACGCGGTTCCGACATCGCGGGCACCACCTCGACGCTCCAGGAGCAGATCGGG
TGGGCCGCAGCTAAGCGCTGGATCATCCTCGGGCTGAACAAGATCGTCCGGATGTACAGCCCGACGTCGATCGCTGCTAAATACGTTGACCG
GTTCTACAAGACCCTGAGGGCCGAGCAGGCGGCGCTGCAGGGGCAGATGGTCCACCAGGCGATCTCGCCGCGCACGCTGAACGCGTGGGTGA
AGGTCTGATAA SEQ ID NO: 39 SP-24CE1d encoded by SEQ ID NO: 38
MWLQSLLLLGTVACSISEEKAFSPEVIPMFSALSEGATPQDLNAAKVGGHQAAMQMLKETINEEAAEWDRAAAEPRGSDIAGTTSTLQEQIG
WAAAKRWIILGLNKIVRMYSPTSIAAKYVDRFYKTLRAEQAALQGQMVHQAISPRTLNAWVKV -continued

| Table of Illustrative Conserved Element Sequences |
|---|
| p24CE1d has 6 CE (is identical to p24CE1c except for the CE arrangement within the protein)<br>GM-CSF signal peptide<br>CE1 and C2 replaced by CE8 and CE9 respectively, lacks CE7 and has the CE arranged in the configuration CE9-3-4-5-6-8 |
| SEQ ID NO: 40 conserved element 8 (CE8-variant for CE2 constructs)<br>QGQMVHQALSPRTLNAWVKV |
| SEQ ID NO: 41 conserved element 9 (CE9)<br>EEKGFNPEVIPMFTALSEGATPQDLN |

Differences between CE for p24 CE polypeptides and variant p24CE polypeptides is one amino acid per CE except CE9, which differs by 3 amino acids

What is claimed is:

1. A nucleic acid comprising a nucleotide sequence encoding a fusion polypeptide comprising the conserved element amino acid sequences of SEQ ID NO:1, SEQ ID NO:2, SEQ ID NO:3, SEQ ID NO:4, SEQ ID NO:5, SEQ ID NO:6, and SEQ ID NO:7, wherein the conserved elements are separated by alanine-containing peptide linker amino acid sequences.

2. The nucleic acid of claim 1, wherein the fusion polypeptide comprises the amino acid sequence SEQ ID NO:15.

3. The nucleic acid of claim 2, comprising the region of the nucleic acid sequence of SEQ ID NO:17 that encodes p24CE1.

4. The nucleic acid of claim 2, wherein the fusion polypeptide comprises a GM-CSF signal peptide.

5. The nucleic acid of claim 4, wherein the fusion polypeptide comprises the amino acid sequence of SEQ ID NO:18.

6. The nucleic acid of claim 2, wherein the fusion polypeptide comprises the amino acid sequence of SEQ ID NO:23 or the amino acid sequence of SEQ ID NO:27.

7. The nucleic acid of claim 1, wherein the nucleic acid is an RNA molecule.

8. The nucleic acid of claim 1, wherein the nucleic acid is a DNA molecule.

9. An expression vector comprising the nucleic acid sequence of claim 1.

10. The expression vector of claim 9, further comprising a nucleic acid encoding a second fusion polypeptide comprising the conserved element amino acid sequences of SEQ ID NO:8, SEQ ID NO:9, SEQ ID NO:10, SEQ ID NO:11, SEQ ID NO:12, SEQ ID NO:13, and SEQ ID NO:14 separated by alanine-containing peptide linker amino acid sequences.

11. The expression vector of claim 10, wherein the second fusion polypeptide comprises the amino acid sequence SEQ ID NO:16.

12. The expression vector of claim 11, wherein the nucleic acid encoding the second fusion polypeptide comprises the region of the nucleic acid sequence of SEQ ID NO:17 that encodes p24CE2.

13. The expression vector of claim 11, wherein the second fusion polypeptide comprises a GM-CSF signal peptide.

14. The expression vector of claim 13, wherein the second fusion polypeptide comprises the amino acid sequence of SEQ ID NO:19.

15. The expression vector of claim 11, wherein the second fusion polypeptide comprises the amino acid sequence of SEQ ID NO:21 or comprises the amino acid sequence of SEQ ID NO:29.

16. A nucleic acid construct comprising the nucleic acid of claim 1, and further comprising a nucleic acid encoding a second fusion polypeptide comprising the conserved element amino acid sequences of SEQ ID NO:8, SEQ ID NO:9, SEQ ID NO:10, SEQ ID NO:11, SEQ ID NO:12, SEQ ID NO:13, and SEQ ID NO:14, wherein the conserved elements are separated by alanine-containing peptide linker amino acid sequences.

17. A nucleic acid construct comprising the nucleic acid of claim 2, further comprising a nucleic acid encoding a second fusion polypeptide comprising the amino acid sequence of SEQ ID NO:16.

18. The nucleic acid construct of claim 17, comprising the nucleic acid sequence of SEQ ID NO:17.

19. The nucleic acid construction of claim 17, wherein the construct is an RNA molecule.

* * * * *